US011718637B2

(12) United States Patent
Byun et al.

(10) Patent No.: US 11,718,637 B2
(45) Date of Patent: Aug. 8, 2023

(54) PRODRUGS OF 4'-C-SUBSTITUTED-2-HALO-2'-DEOXYADENOSINE NUCLEOSIDES AND METHODS OF MAKING AND USING THE SAME

(71) Applicant: Gilead Sciences, Inc., Foster City, CA (US)

(72) Inventors: Daniel H. Byun, Foster City, CA (US); Byoung-Kwon Chun, Pleasanton, CA (US); Michael O. Clarke, Redwood City, CA (US); Petr Jansa, Foster City, CA (US); Richard L. Mackman, Millbrae, CA (US); Devan Naduthambi, San Bruno, CA (US); Neil H. Squires, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 18 days.

(21) Appl. No.: 17/207,161

(22) Filed: Mar. 19, 2021

(65) Prior Publication Data
US 2022/0363708 A1    Nov. 17, 2022

Related U.S. Application Data

(60) Provisional application No. 62/992,733, filed on Mar. 20, 2020.

(51) Int. Cl.
| | | |
|---|---|---|
| A01N 43/04 | (2006.01) |
| A61K 31/70 | (2006.01) |
| C07H 19/16 | (2006.01) |
| A61P 31/18 | (2006.01) |
| A61K 31/7076 | (2006.01) |
| A61K 45/06 | (2006.01) |
| C07H 19/20 | (2006.01) |

(52) U.S. Cl.
CPC ......... *C07H 19/16* (2013.01); *A61K 31/7076* (2013.01); *A61K 45/06* (2013.01); *A61P 31/18* (2018.01); *C07H 19/20* (2013.01)

(58) Field of Classification Search
None
See application file for complete search history.

(56) References Cited

U.S. PATENT DOCUMENTS

| | | | |
|---|---|---|---|
| 4,963,662 A | 10/1990 | Matthes et al. |
| 8,569,478 B2 | 10/2013 | Du et al. |
| 8,835,615 B2 | 9/2014 | Chang |
| 9,815,864 B2 | 11/2017 | Beigelman et al. |
| 10,953,029 B2 | 3/2021 | Girijavallabhan |
| 2005/0215512 A1 | 9/2005 | Kohgo et al. |
| 2015/0051167 A1 | 2/2015 | Wang et al. |
| 2015/0366887 A1 | 12/2015 | Blatt et al. |
| 2015/0366888 A1 | 12/2015 | Blatt et al. |
| 2019/0177326 A1 | 6/2019 | Alexandre et al. |
| 2019/0185508 A1 | 6/2019 | Alexandre et al. |
| 2021/0060051 A1 | 3/2021 | Schinazi et al. |

FOREIGN PATENT DOCUMENTS

| | | |
|---|---|---|
| CA | 2502109 A1 | 9/2005 |
| CN | 101177442 A | 5/2008 |
| EP | 1589026 A1 | 10/2005 |
| EP | 2177527 A1 | 4/2010 |
| EP | 2402358 A2 | 1/2012 |
| JP | 2004107329 A | 4/2004 |
| JP | 2017/057200 A | 3/2017 |
| KR | 101718242 B1 | 3/2017 |
| WO | WO-0069876 A1 | 11/2000 |
| WO | WO-2005011709 A1 | 2/2005 |
| WO | WO-2005090349 A1 | 9/2005 |
| WO | WO-2007038507 A2 | 4/2007 |
| WO | WO-2008100447 A2 | 8/2008 |
| WO | WO-2009009951 A1 | 1/2009 |
| WO | WO-2009067409 A1 | 5/2009 |
| WO | WO-2009084655 A1 | 7/2009 |
| WO | WO-2009119785 A1 | 10/2009 |
| WO | WO-2009125841 A1 | 10/2009 |
| WO | WO-2009152095 A2 | 12/2009 |
| WO | WO-2010026153 A1 | 3/2010 |
| WO | WO-2010108140 A1 | 9/2010 |
| WO | WO-2011099443 A1 | 8/2011 |
| WO | WO-2013096679 A1 | 6/2013 |
| WO | WO-20131142525 A1 | 9/2013 |
| WO | WO-2014209979 A1 | 12/2014 |
| WO | WO-2015038596 A1 | 3/2015 |
| WO | WO-2015054465 A1 | 4/2015 |
| WO | WO-2015148746 A1 | 10/2015 |
| WO | WO-2015200205 A1 | 12/2015 |

(Continued)

OTHER PUBLICATIONS

Franchetti et al., "Synthesis and evaluation fo the anti-HIV activity of aza and deaza analogues of isodda and their phosphates as prodrugs," 37 J. Med Chem 3534-3541 (1994).

International Search Report for related International Application No. PCT/US2021/023252 (published as WO 2021/188959), dated Sep. 23, 2021.

Singh et al., "A divergent approach for the synthesis of D- and L-4'-ethynyl dioxalane nucleosides with potent anti-HIV activity," Synthesis 2016, 48, 3050-3056.

Written Opinion of the International Searching Authority for related International Application No. PCT/US2021/023252 (published as WO 2021/188959), dated Sep. 23, 2021.

Search Report dated Dec. 9, 2021 for ROC (Taiwan) Patent Application No. 110110091.

(Continued)

*Primary Examiner* — Patrick T Lewis

(57) ABSTRACT

The present disclosure provides prodrugs of 4'-C-substituted-2-halo-2'-deoxyadenoside nucleosides, and compositions, methods, and kits thereof. Such compounds can be useful for treating viral infections including, but not limited to, human immunodeficiency virus.

34 Claims, No Drawings

(56) References Cited

FOREIGN PATENT DOCUMENTS

| | | | |
|---|---|---|---|
| WO | WO-2015200219 A1 | 12/2015 | |
| WO | WO-2016100569 A1 | 6/2016 | |
| WO | WO-2016145142 A1 | 9/2016 | |
| WO | WO-2017053216 A2 | 3/2017 | |
| WO | WO-2019133712 A1 | 7/2019 | |
| WO | WO-2019140365 A1 | 7/2019 | |
| WO | WO-2019171285 A1 * | 9/2019 | ............. A61P 31/18 |
| WO | WO-2020007070 A1 | 1/2020 | |
| WO | WO-2020031131 A1 | 2/2020 | |
| WO | WO-2020044257 A1 * | 3/2020 | ............. A61P 31/18 |
| WO | WO-2020178767 A1 * | 9/2020 | ............. A61K 31/70 |
| WO | WO-2021021717 A1 | 2/2021 | |
| WO | WO-2021038509 A1 | 3/2021 | |
| WO | WO-2021050956 A1 | 3/2021 | |
| WO | WO-2021050961 A1 | 3/2021 | |

OTHER PUBLICATIONS

International Preliminary Report on Patentability and Written Opinion of the International Searching Authority, dated Sep. 29, 2022 for Intl. Appl. No. PCT/US2021/023252.
Office Action in Taiwan Application No. 110110091, dated Nov. 15, 2022, (3 pages of English Translation) .

* cited by examiner

PRODRUGS OF 4'-C-SUBSTITUTED-2-HALO-2'-DEOXYADENOSINE NUCLEOSIDES AND METHODS OF MAKING AND USING THE SAME

CROSS-REFERENCE TO RELATED APPLICATIONS

This application claims the benefit of priority to U.S. Provisional Patent Application No. 62/992,733 filed 20 Mar. 2020, titled "PRODRUGS OF 4'-C-SUBSTITUTED-2-HALO-2'DEOXYADENOSINE NUCLEOSIDES AND METHODS OF MAKING AND USING THE SAME," the entirety of which is incorporated herein by reference.

TECHNICAL FIELD

The present disclosure relates to compounds, compositions, and methods for treating viral infections.

BACKGROUND

Human immunodeficiency virus (HIV) infection is a life-threatening and serious disease of major public health significance affecting tens of millions of people worldwide. No cure is known, and accordingly those affected by HIV can require life-long treatments, which can include taking one or more treatments per day and can have various side effects. Improved treatments for HIV and other viral infections are desirable.

SUMMARY

Disclosed herein are, for instance, compounds of formula (I):

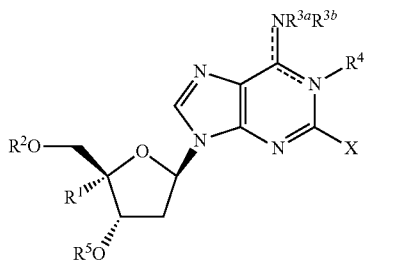

(I)

wherein
a dashed line ( ---- ), in conjunction with the solid line to which it is parallel, represents an optional double bond;
X represents halogen;
$R^1$ represents $(C_1-C_6)$alkynyl;
$R^2$ represents H, —C(═O)($R^a$), —C(═O)(O—$R^a$), —C(═O)($R^b$), —P(═O)(O—$R^b$)($R^{c1}$), —P(═O)($R^{c1}$)($R^{c2}$), —C(═O)(O—$R^d$), —C(═O)($R^h$), —C(═O)(O—$R^h$), or —C(═O)(L-$R^h$);
$R^{3a}$ represents H or $R^e$;
$R^{3b}$ represents H or is absent;
$R^4$ represents $R^d$ or is absent;
$R^5$ represents H, —C(═O)($R^a$), —C(═O)(O—$R^a$), —C(═O)($R^b$), —C(═O)(O—$R^d$), —P(═O)(O—$R^b$)($R^{c1}$), —C(═O)($R^h$), —C(═O)(O—$R^h$), or —C(═O)(L-$R^h$);

each $R^a$ represents $(C_1-C_{25})$alkyl, which can be the same or different;
  wherein each $R^a$ is optionally substituted with one $R^b$;
each $R^b$ represents phenyl or cyclohexyl,
  wherein each $R^b$ is optionally substituted with from one to three groups independently chosen from $R^f$, —$CH_2$—O—C(═O)($R^f$), and —O—C(═O)($R^f$);
each $R^{c1}$ and $R^{c2}$ represents —NH-L-C(═O)(O—$R^f$) and —NH-L-C(═O)(O—$R^g$), which can be the same or different;
each $R^d$ independently represents or

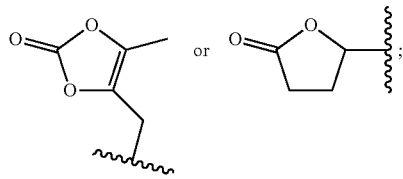

$R^e$ represents H, —C(═O)($R^a$), —C(═O)(O—$R^a$), —C(═O)-L-O—$R^f$, —C(═O)-L-O—C(═O)($R^f$), —C(═O)—O-L-C(═O)(O—$R^f$), —C(═O)-L-S—C(═O)($R^f$), —C(═O)($R^b$), —C(═O)(O—$R^b$), —C(═O)—O-L-C(═O)(O—$R^d$), —C(═O)($R^d$), —C(═O)($R^h$), or —C(═O)(O—$R^b$);
each $R^f$ independently represents $(C_1-C_{18})$alkyl;
each L independently represents $(C_1-C_{18})$alkylenyl;
$R^g$ represents cyclohexyl; and
each $R^h$ independently represents a steroid derivative or a bridged, spirocyclic, or fused polycyclic $(C_7-C_{18})$ carbocycle,
  wherein the steroid derivative is optionally substituted with one to four groups independently selected from —OH and $(C_1-C_{12})$alkyl;
when $R^5$ is H, then $R^2$ is not —P(═O)(O—$R^b$)($R^{c1}$) or —P(═O)($R^{c1}$)($R^{c2}$),
when $R^{3a}$ is H, $R^{3b}$ is H, and $R^5$ is H, then $R^2$ is not H, —C(═O)(($C_1-C_5$)alkyl), or —C(═O)(Z-butyl-Z'),
  wherein Z represents a bond, $(C_1-C_{10})$alkyl, C($R^x$)($R^z$),
  $R^x$ and $R^z$ are independently chosen from H, $(C_1-C_6)$alkyl, and $(C_6-C_{10})$cycloalkyl,
  each of $R^x$ and $R^z$ are independently optionally substituted with $(C_1-C_6)$alkyl, oxo, or $(C_1-C_6)$alkoxy; and
  Z' represents H, $(C_1-C_{10})$alkyl, or $(C_1-C_{10})$alkoxy, and wherein Z' is optionally substituted with $(C_1-C_6)$alkyl, oxo, or $(C_1-C_6)$alkoxy;
when
  $R^{3a}$ is $R^e$ and $R^{3b}$ is H,
  $R^e$ is H or —C(═O)(O—$(C_1-C_6)$alkyl) or —C(═O)$(C_1-C_{25})$alkyl, and
  $R^5$ is H or —C(═O)(O—$(C_1-C_{25})$alkyl),
then $R^2$ is not —C(═O)(O—$(C_1-C_{25})$alkyl); and
when
  $R^2$ is H or —C(═O)(O—$(C_1-C_{10})$alkyl), and
  $R^5$ is —C(═O)(($C_1-C_{18}$)alkyl optionally substituted with oxo or $(C_1-C_6)$alkyl), —C(═O)-(cyclohexyl optionally substituted with $(C_1-C_{18})$alkyl), or —C(═O)(phenyl optionally substituted with $(C_1-C_6)$alkyl or —O—C(═O)(($C_1-C_6$)alkyl)),
then $R^e$ is not (a) H, (b) —C(═O)(O—$(C_1-C_{10})$alkyl), or
(c) —C(═O)(($C_1-C_{15}$)alkyl);

or a pharmaceutically acceptable salt thereof. Also disclosed herein are sub-formulas Ia and Ib. Also disclosed herein are methods of making and using the same.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

I. Definitions

The term "about" or "approximately," used in connection with a quantity, is inclusive of the stated value and has the meaning dictated by the context (e.g., includes the degree of error associated with measurement of the particular quantity).

As used herein, the term "administering" or "administration" typically refers to the administration of a composition to a subject to achieve delivery of an agent that is, or is included, in a composition to a target site or a site to be treated. Those of ordinary skill in the art will be aware of a variety of routes that may, in appropriate circumstances, be utilized for administration to a subject, for example a human. For example, in some embodiments, administration may be parenteral. In some embodiments, administration may be by injection (e.g., intramuscular, intravenous, or subcutaneous injection). In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time). In some embodiments, administration may involve continuous dosing (e.g., perfusion) for at least a selected period of time.

"Alkyl" is hydrocarbon containing normal, secondary or tertiary atoms. For example, an alkyl group can have 1 to 25 carbon atoms (i.e., ($C_1$-$C_{25}$)alkyl), 1 to 10 carbon atoms (i.e., ($C_1$-$C_{10}$)alkyl), 1 to 8 carbon atoms (i.e., ($C_1$-$C_8$)alkyl) or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ ($CH_2CH_2CH_3$)), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$, and octyl (—$(CH_2)_7CH_3$) "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., ($C_1$-$C_{10}$) alkyl), or 1 to 6 carbon atoms (i.e., ($C_1$-$C_6$)alkyl) or 1-3 carbon atoms (i.e., ($C_1$-$C_3$)alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

The term "($C_{1-n}$)alkyl" (also described as "($C_1$-$C_n$)alkyl") as used herein, wherein n is an integer, either alone or in combination with another radical, is intended to mean acyclic, straight or branched chain alkyl radicals containing from 1 to n carbon atoms. "($C_{1-6}$)alkyl" includes, but is not limited to, methyl, ethyl, propyl (n-propyl), butyl (n-butyl), 1-methylethyl (iso-propyl), 1-methylpropyl (.sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

"Alkylene" (including those which are part of other groups) refers to branched and unbranched divalent "alkyl" groups. As used herein, alkylene can have 1 to 25 carbon atoms (i.e., $C_{1-25}$alkylene), 1 to 8 carbon atoms (i.e., $C_{1-8}$ alkylene), 1 to 6 carbon atoms (i.e., Cu 6 alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethylethylene.

"Alkenyl" is a straight or branched hydrocarbon containing normal, secondary or tertiary carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—$CH$=$CH_2$), allyl (—$CH_2CH$=$CH_2$), cyclopentenyl (—$C_5H_7$), and 5-hexenyl (—$CH_2CH_2CH_2CH_2CH$=$CH_2$).

The term "($C_{2-n}$)alkenyl," as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "($C_{2-n}$)alkenyl" is understood to encompass individual stereoisomers where possible, including but not limited to (E) and (Z) isomers, and mixtures thereof. When a ($C_{2-n}$)alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

"Alkynyl" is a straight or branched hydrocarbon containing normal, secondary or tertiary carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—CH$_2$C≡CH), and the like.

The term "($C_{2-n}$)alkynyl," as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a ($C_{2-n}$)alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho, spiro or bridged bicyclic or multicyclic radical having about 9 to 14 atoms in which at least one ring is aromatic (e.g., an aryl fused to one or more aryl or carbocycle). Such bicyclic or multicyclic rings may be optionally substituted with one or more (e.g., 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1, 2, 3, 4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl- moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "aryl-($C_{1-n}$)alkyl-" as used herein, wherein n is an integer, either alone or in combination with another radical, is intended to mean an alkyl radical having 1 to n carbon atoms as defined above which is itself substituted with an aryl radical as defined above. Examples of aryl-($C_{1-n}$)alkyl- include, but are not limited to, phenylmethyl (benzyl), 1-phenylethyl, 2-phenylethyl and phenylpropyl. When an aryl-($C_{1-n}$)alkyl- group is substituted, it is understood that substituents may be attached to either the aryl or the alkyl portion thereof or both, unless specified otherwise, such that the substitution would give rise to a chemically stable compound, such as are recognized by those skilled in the art.

The term "carbocycle" or "carbocyclyl" refers to a saturated (i.e., cycloalkyl) or partially unsaturated (e.g., cycloalkenyl, cycloalkadienyl, etc.) ring having 3 to 7 carbon atoms as a monocycle or a mutlicyclic ring system. In one embodiment the carbocycle is a monocycle comprising 3-6 ring carbons (i.e. ($C_3$-$C_6$)carbocycle). Carbocycle includes multicyclic carbocyles having 7 to 12 carbon atoms as a bicycle, and up to about 20 carbon atoms as a polycycle provided that the largest single ring of a multicyclic carbocycle is 7 carbon atoms. The term "spiro carbocycle" refers to a carbocycle ring system wherein the rings of the ring system are connected to a single carbon atom (e.g., spiropentane, spiro[4,5]decane, spiro[4.5]decane, etc). The term "fused carbocycle" refers to a carbocycle ring system wherein the rings of the ring system are connected to two adjacent carbon atoms such as a bicyclo[4,5], [5,5], [5,6] or [6,6] system, or 9 or 10 ring atoms arranged as a bicyclo[5,6] or [6,6] system (e.g., decahydronaphthalene, norsabinane, norcarane). The term "bridged carbocycle" refers to a carbocycle ring system wherein the rings of the ring system are connected to two non-adjacent carbon (e.g., norbornane, bicyclo[2.2.2]octane, etc). The "carbocycle" or "carbocyclyl" may be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl- moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-CH$_2$—, carbocyclyl-CH(CH$_3$)—, carbocyclyl-CH$_2$CH$_2$—, 2-(carbocyclyl)ethan-1-yl, and the like, wherein the "carbocyclyl" portion includes any of the carbocyclyl groups described above.

The term "chiral" refers to molecules which have the property of non-superimposability of the mirror image partner, while the term "achiral" refers to molecules which are superimposable on their mirror image partner.

"Cycloalkyl" refers to a non-aromatic hydrocarbon ring consisting of carbon and hydrogen atoms, having from three to fifteen carbon atoms, in certain embodiments having from three to ten carbon atoms or from three to seven carbon atoms, and which is saturated or partially unsaturated and attached to the rest of the molecule by a single bond. Cycloalkyl rings include, for example, cyclopropyl, cyclobutyl, cyclopentyl, cyclopentenyl, cyclohexyl, cyclohexenyl, 1,3-cyclohexadienyl, 1,4-cyclohexadienyl, cycloheptyl, cycloheptenyl, and cyclooctyl.

The term "($C_3$-m)cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "($C_{3-m}$)cycloalkyl-($C_{1-n}$)alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of ($C_{3-7}$)cycloalkyl-($C_{1-6}$)alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise, such that the substitution would give rise to a chemically stable compound, such as are recognized by those skilled in the art.

As used herein, the term "combination therapy" refers to those situations in which a subject is simultaneously exposed to two or more therapeutic or prophylactic regimens (e.g., two or more therapeutic or prophylactic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc., to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Unless the context requires otherwise, throughout the present disclosure and claims, the word "comprise" and variations thereof, such as, "comprises" and "comprising" are to be construed in an open, inclusive sense, that is as "including, but not limited to."

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

As used herein, the term "dosage form" refers to a physically discrete unit of an active agent (e.g., a therapeutic, prophylactic, or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a prophylactic or therapeutic dosing regimen). Those of ordinary skill in the art appreciate that the total amount of a composition or agent administered to a particular subject is determined by one or more attending physicians and may involve administration of multiple dosage forms.

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Enantiomers" refer to two stereoisomers of a compound which are non-superimposable mirror images of one another.

"Halo" or "halogen" refers to bromo, chloro, fluoro or iodo.

The term "inhibitor of HIV replication" as used herein is intended to mean an agent capable of reducing or eliminating the ability of HIV to replicate in a host cell, whether in vitro, ex vivo, or in vivo.

The term "inhibitor of HBV replication" as used herein is intended to mean an agent capable of reducing or eliminating the ability of HBV to replicate in a host cell, whether in vitro, ex vivo, or in vivo.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution. It is to be understood that when a variable is substituted, for example, as described by the phrase "$(C_1-C_6)$alkyl, either alone or as part of a group, is optionally substituted," the phrase means that the variable $(C_1-C_6)$alkyl can be substituted when it is alone and that it can also be substituted when the variable "$(C_1-C_6)$alkyl" is part of a larger group such as for example an aryl$(C_1-C_6)$alkyl or a —$(C_1-C_6)$alkyl-$SO_2$— $(C_1-C_6)$alkyl-$(C_3-C_7)$carbocycle group. Similarly, when stated, other variables (e.g., $(C_1-C_6)$alkenyl, $(C_1-C_6)$alkynyl, aryl, heteroaryl, heterocycle, etc.) can also be substituted "either alone or as part of a group."

The term "oxo" as used herein is intended to mean an oxygen atom attached to a carbon atom as a substituent by a double bond (=O).

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or other pharmacologically inactive substance that is formulated in combination with a pharmacologically active ingredient of a pharmaceutical composition and is compatible with the other ingredients of the formulation and suitable for use in humans or domestic animals without undue toxicity, irritation, allergic response, and the like.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts of a nitrogen atom or an amino group include, for example, salts of organic carboxylic acids such as acetic, trifluoroacetic, adipic, ascorbic, aspartic, butyric, camphoric, cinnamic, citric, digluconic, glutamic, glycolic, glycerophosphoric, formic, hexanoic, benzoic, lactic, fumaric, tartaric, maleic, hydroxymaleic, malonic, malic, mandelic, isethionic, lactobionic, nicotinic, oxalic, pamoic, pectinic, phenylacetic, 3-phenylpropionic, pivalic, propionic, pyruvic, salicylic, stearic, sulfanilic, tartaric, undecanoic, and succinic acids; organic sulfonic acids, such as methanesulfonic, ethanesulfonic, camphorsulfonic, mesitylenesulfonic, benzenesulfonic, p-toluenesulfonic acids, naphthalenesulfonic, and 2-naphthalenesulfonic; and inorganic acids, such as hydrochloric, hydrobromic, sulfuric, phosphoric, nitric, and sulfamic acids. Pharmaceutically acceptable salts of a compound of a hydroxy group include the anion of said compound in combination with a suitable cation such as $Na^+$ and $NX_4^+$ (wherein X is independently selected from H or a $C_{1-4}$alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compounds of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

As used herein, the terms "preventing" and "prevention" refer to the administration of a compound, composition, or pharmaceutically salt according to the present disclosure pre- or post-exposure of the human to the virus but before the appearance of symptoms of the disease, and/or prior to the detection of the virus in the blood. In some embodiments, the terms refer to prevention of the appearance of symptoms of the disease and/or to prevent the virus from reaching detectible levels in the blood. The terms "also encompass the administration of a compound or composition according to the present embodiments disclosed herein before the exposure of the individual to the virus (also called pre-exposure prophylaxis or PrEP), to prevent HIV infection from taking hold if the individual is exposed to the virus and/or to keep the virus from establishing a permanent infection and/or to prevent the appearance of symptoms of the disease and/or to prevent the virus from reaching detectable levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby, by administration to the mother before giving birth and to the child within the first days of life. The terms also refer to prevention of transmission of HIV through blood transfusion.

"Spiro" or "spirocyclic" refers to an aryl, carbocyclic or heterocyclic ring structure described herein which is connected to an existing ring structure in the compounds disclosed herein via a single atom that is shared by the spiro ring structure and the existing ring structure. For example, the bicyclic compounds below incorporate spiro cyclopropane (i.e., a cyclopropane ring that is spirocyclic to a cyclohexane ring), spiro 1,3-dithiolane (i.e., a 1,3-dithiolane ring that is spirocyclic to a cycloheptane ring), and spiro cyclopentene (i.e., a cyclopentene ring that is spirocyclic to a cyclohexene ring), respectively:

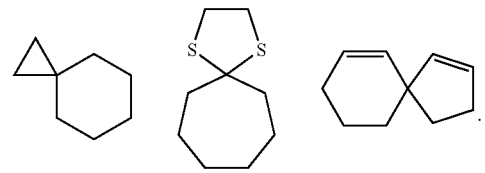

The term "stereoisomer(s)" refers to compounds which have identical chemical constitution, but differ with regard to the arrangement of the atoms or groups in space. For example, a stereoisomer refers to a compound made up of the same atoms bonded by the same bonds as another compound, but the two compounds have different three-dimensional structures, which are not interchangeable. The present disclosure contemplates various stereoisomers and mixtures thereof and includes diastereomers, enantiomers and the like. In any of the embodiments disclosed herein, compounds disclosed herein may be in the form of a stereoisomer thereof.

The term "steroid" as used herein, either alone or in combination with another radical, is intended to mean a tetracyclic hydrocarbon ring (hexadecahydro-1H-cyclopenta[a]phenanthrene) that is optionally substituted with one to six groups independently selected from —OH and ($C_1$-$C_{12}$)alkyl; "steroid" includes, but is not limited to, cholic acid, glycocholic acid, taurocholic acid, deoxycholic acid, chenodeoxycholic acid, glycochenodeoxycholic acid, taurochenodeoxycholic acid, lithocholic acid, β-sitosterol, campesterol, cholesterol, stigmasterol, stigmastanol, campestanol, brassicasterol, ergosterol, lupeol, cycloartenol.

As used herein, the term "subject" refers to an organism, typically a mammal (e.g., a human). In some embodiments, a subject is suffering from a relevant disease, disorder or condition. In some embodiments, a human subject is an adult, adolescent, or pediatric subject. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy and/or prophylaxis is and/or has been administered.

As used herein, "therapeutically effective amount" is an amount that produces the desired effect for which it is administered. In some embodiments, the term "therapeutically effective amount" or "therapeutically effective dose" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "treating" with respect to the treatment of a disease-state in a patient include (i) inhibiting or ameliorating the disease-state in a patient, e.g., arresting or slowing its development; or (ii) relieving the disease-state in a patient, i.e., causing regression or cure of the disease-state. In the case of HIV, treatment includes reducing the level of HIV viral load in a patient.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The terms "treating" and "treatment" as used herein are intended to mean the administration of a compound or composition according to the embodiments disclosed herein to alleviate or eliminate one or more symptoms of HIV or HBV infection and/or to reduce viral load in a patient. In certain embodiments, the terms "treating" and "treatment" also encompass the administration of a compound or composition according to the embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed herein to prevent perinatal transmission of, for example, HIV from mother to baby, by administration to the mother before giving birth and to the child within the first days of life. The terms "treating" and "treatment" also encompass the administration of a compound or composition according to the present embodiments disclosed herein both before and after the exposure of the individual to the virus.

The embodiments disclosed herein are also meant to encompass all pharmaceutically acceptable compounds of formula disclosed herein being isotopically labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. In certain embodiments, these radiolabeled compounds are useful to help determine or measure the effectiveness of the compounds, by characterizing, for example, the site or mode of action, or binding affinity to pharmacologically important site of action. Certain isotopically labeled compounds of formulas disclosed herein for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

In certain embodiments, substitution with heavier isotopes such as deuterium, i.e., $^2$H, may afford certain therapeutic advantages resulting from greater metabolic stability. For example, in vivo half-life may increase, or dosage requirements may be reduced. Thus, heavier isotopes may be preferred in some circumstances.

Substitution with positron emitting isotopes, such as $^{11}$C, $^{18}$F, $^{15}$O, and $^{13}$N, can be useful in Positron Emission Topography (PET) studies for examining substrate receptor occupancy. Isotopically labeled compounds of formulas disclosed herein can be prepared by techniques known to those skilled in the art or by processes analogous to those described in the Examples as set out below using an appropriate isotopically labeled reagent in place of the non-labeled reagent previously employed.

The methods, compositions, kits and articles of manufacture provided herein use or include compounds disclosed herein or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Foster, "Deuterium Isotope Effects in Studies of Drug Metabolism," *Trends Pharmacol. Sci.*, 5(12):524-527 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. EFdA is not intended to be included in the embodiments disclosed herein. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Unless specifically disclosed, the present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

II. Compounds

Provided herein are compounds that function as antiviral agents, (in some embodiments, anti-HIV agents), pharmaceutical compositions comprising such compounds, optionally in combination with one or more (e.g., two, three, or four) additional therapeutic agents, and method of using such compounds and compositions. All compound embodiments described herein include any pharmaceutically acceptable salt, stereoisomer, or mixture of stereoisomers thereof.

In one embodiment, a compound of formula (I) is provided:

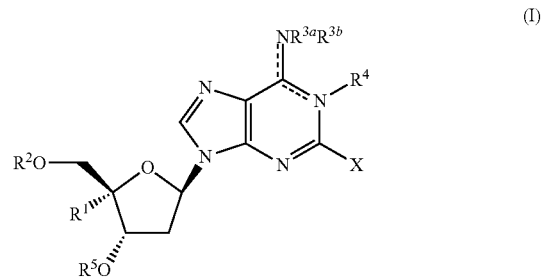

(I)

wherein
a dashed line ( ---- ), in conjunction with the solid line to which it is parallel, represents an optional double bond;
X represents halogen;
$R^1$ represents $(C_1-C_6)$alkynyl;
$R^2$ represents H, $-C(=O)(R^a)$, $-C(=O)(O-R^a)$, $-C(=O)(R^b)$, $-P(=O)(O-R^b)(R^{c1})$, $-P(=O)(R^{c1})(R^{c2})$, $-C(=O)(O-R^d)$, $-C(=O)(R^h)$, $-C(=O)(O-R^h)$, or $-C(=O)(L-R^h)$;
$R^{3a}$ represents H or $R^e$;
$R^{3b}$ represents H or is absent;
$R^4$ represents $R^d$ or is absent;
$R^5$ represents H, $-C(=O)(R^a)$, $-C(=O)(O-R^a)$, $-C(=O)(R^b)$, $-C(=O)(O-R^d)$, $-P(=O)(O-R^b)(R^{c1})$, $-C(=O)(R^h)$, $-C(=O)(O-R^h)$, or $-C(=O)(L-R^h)$;
each $R^a$ represents $(C_1-C_{25})$alkyl, which can be the same or different;
wherein each $R^a$ is optionally substituted with one $R^b$;
each $R^b$ represents phenyl or cyclohexyl,
wherein each $R^b$ is optionally substituted with from one to three groups independently chosen from $R^f$, $-CH_2-O-C(=O)(R^f)$, and $-O-C(=O)(R^f)$;
each $R^{c1}$ and $R^{c2}$ represents $-NH-L-C(=O)(O-R^f)$ and $-NH-L-C(=O)(O-R^g)$, which can be the same or different;
each $R^d$ independently represents

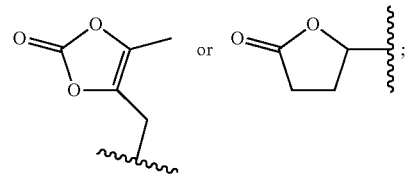

$R^e$ represents H, $-C(=O)(R^a)$, $-C(=O)(O-R^a)$, $-C(=O)-L-O-R^f$, $-C(=O)-L-O-C(=O)(R^f)$, $-C(=O)-O-L-C(=O)(O-R^f)$, $-C(=O)-L-S-C(=O)(R^f)$, $-C(=O)(R^b)$, $-C(=O)(O-R^b)$, $-C(=O)-O-L-C(=O)(O-R^d)$, $-C(=O)(R^d)$, $-C(=O)(R^h)$, or $-C(=O)(O-R^h)$;
each $R^f$ independently represents $(C_1-C_{18})$alkyl;
each L independently represents $(C_1-C_{18})$alkylenyl;
$R^g$ represents cyclohexyl; and
each $R^h$ independently represents a steroid derivative or a bridged, spirocyclic, or fused polycyclic $(C_7-C_{18})$ carbocycle,
wherein the steroid derivative is optionally substituted with one to four groups independently selected from $-OH$ and $(C_1-C_{12})$alkyl;

when $R^5$ is H, then $R^2$ is not —P(=O)(O—$R^b$)($R^{c1}$) or —P(=O)($R^{c1}$)($R^{c2}$), when $R^{3a}$ is H, $R^{3b}$ is H, and $R^5$ is H, then $R^2$ is not H, —C(=O)(($C_1$-$C_5$)alkyl), or —C(=O)(Z-butyl-Z'),
wherein Z represents a bond, ($C_1$-$C_{10}$)alkyl, C($R^x$)($R^z$),
$R^x$ and $R^z$ are independently chosen from H, ($C_1$-$C_6$)alkyl, and ($C_6$-$C_{10}$)cycloalkyl,
each of $R^x$ and $R^z$ are independently optionally substituted with ($C_1$-$C_6$)alkyl, oxo, or ($C_1$-$C_6$)alkoxy; and
Z' represents H, ($C_1$-$C_{10}$)alkyl, or ($C_1$-$C_{10}$)alkoxy, and wherein Z' is optionally substituted with ($C_1$-$C_6$)alkyl, oxo, or ($C_1$-$C_6$)alkoxy;

when
$R^{3a}$ is $R^e$ and $R^{3b}$ is H,
$R^e$ is H or —C(=O)(O—($C_1$-$C_6$)alkyl) or —C(=O)($C_1$-$C_{25}$)alkyl, and
$R^5$ is H or —C(=O)(O—($C_1$-$C_{25}$)alkyl),
then $R^2$ is not —C(=O)(O—($C_1$-$C_{25}$)alkyl); and when
$R^2$ is H or —C(=O)(O—($C_1$-$C_{10}$)alkyl), and
$R^5$ is —C(=O)(($C_1$-$C_{18}$)alkyl optionally substituted with oxo or ($C_1$-$C_6$)alkyl), —C(=O)-(cyclohexyl optionally substituted with ($C_1$-$C_{18}$)alkyl), or —C(=O)(phenyl optionally substituted with ($C_1$-$C_6$)alkyl or —O—C(=O)(($C_1$-$C_6$)alkyl)),
then $R^e$ is not (a) H, (b) —C(=O)(O—($C_1$-$C_{10}$)alkyl), or
(c) —C(=O)(($C_1$-$C_{15}$)alkyl);
or a pharmaceutically acceptable salt thereof.

A compound of the following formula (Ia):

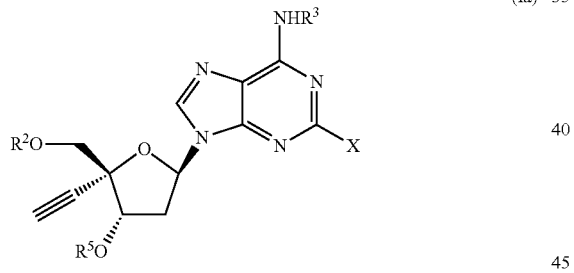

(Ia)

wherein
X represents F or Cl;
$R^2$ represents H, —C(=O)($R^a$), —C(=O)($R^b$), or —P(=O)(O—$R^b$)($R^{c1}$),
$R^3$ represents H, —C(=O)($R^a$), or —C(=O)(O—$R^a$);
$R^5$ represents H, —C(=O)($R^a$), or —P(=O)(O—$R^b$)($R^{c1}$);
each $R^a$ independently represents ($C_1$-$C_{25}$)alkyl; wherein each $R^a$ is independently optionally substituted with one $R^b$;
each $R^b$ independently represents phenyl optionally substituted with one to three groups independently chosen from $R^f$ and —O—C(=O)($R^f$);
$R^{c1}$ represents —NH-L-C(=O)(O—$R^g$);
each $R^f$ independently represents ($C_1$-$C_{18}$)alkyl;
L represents ($C_1$-$C_{18}$)alkylenyl; and
$R^g$ represents cyclohexyl;
provided that
when $R^5$ is H, then $R^2$ is not —P(=O)(O—$R^b$)($R^{c1}$),
when $R^3$ and $R^5$ are H, then $R^2$ is not H, —C(=O)(($C_1$-$C_5$)alkyl), or —C(=O)(Z-butyl-Z'),
wherein Z represents a bond, ($C_1$-$C_{10}$)alkyl, C($R^x$)($R^z$),
$R^x$ and $R^z$ are independently chosen from H, ($C_1$-$C_6$)alkyl, and ($C_6$-$C_{10}$)cycloalkyl,
wherein each of $R^x$ and $R^z$ are independently optionally substituted with ($C_1$-$C_6$)alkyl, oxo, or ($C_1$-$C_6$)alkoxy; and
wherein Z' represents H, ($C_1$-$C_{10}$)alkyl, or ($C_1$-$C_{10}$)alkoxy, and Z' is optionally substituted with ($C_1$-$C_6$)alkyl, oxo, or ($C_1$-$C_6$)alkoxy;
when
$R^3$ is H or —C(=O)(O—($C_1$-$C_6$)alkyl) or —C(=O)($C_1$-$C_{25}$)alkyl, and
$R^5$ is H,
then $R^2$ is not —C(=O)(O—($C_1$-$C_{25}$)alkyl); and
when
$R^2$ is H, and
$R^5$ is —C(=O)(($C_1$-$C_{18}$)alkyl),
$R^3$ is not H, —C(=O)(O—($C_1$-$C_{10}$)alkyl)), or —C(=O)(($C_1$-$C_{15}$)alkyl);
or a pharmaceutically acceptable salt thereof.

A compound of the following formula (Ib):

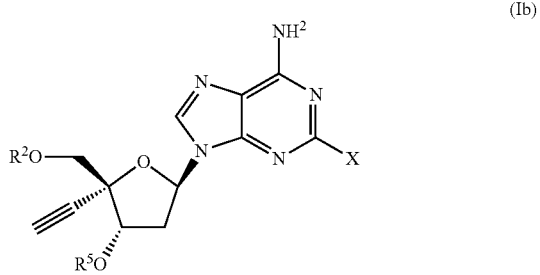

(Ib)

wherein
X represents F or Cl;
$R^2$ represents —C(=O)($R^a$),
$R^5$ represents H or —C(=O)($R^a$),
each $R^a$ independently represents ($C_1$-$C_{25}$)alkyl optionally substituted with one $R^b$;
each $R^b$ independently represents phenyl optionally substituted with from one to three groups independently chosen from —$CH_3$ and —O—C(=O)—$CH_3$; and
provided that
when $R^5$ is H, then $R^2$ is not —C(=O)($C_1$-$C_5$alkyl), or —C(=O)(Z-butyl-Z'),
wherein Z represents a bond, ($C_1$-$C_{10}$)alkyl, C($R^x$)($R^z$),
$R^x$ and $R^z$ are independently chosen from H and ($C_1$-$C_6$)alkyl, and
each of $R^x$ and $R^z$ is independently optionally substituted with ($C_1$-$C_6$)alkyl, oxo, or ($C_1$-$C_6$)alkoxy; and
wherein Z' represents H, ($C_1$-$C_{10}$)alkyl, or ($C_1$-$C_{10}$)alkoxy, and Z' is optionally substituted with ($C_1$-$C_6$)alkyl, oxo, or ($C_1$-$C_6$)alkoxy;
or a pharmaceutically acceptable salt thereof.

The following description applies to one or more of the formulas disclosed herein (formulas I, Ia, and Ib). X can be selected from a halogen. In some embodiments, X is Cl. In some embodiments, X is F. In some embodiments, X is Br. In some embodiments, X is I.

$R^1$ can be selected from ($C_1$-$C_6$)alkynyl. In some embodiments, $R^1$ is ethynyl. In some embodiments, $R^1$ is propynyl.

In some embodiments, $R^1$ is butynyl. In some embodiments, $R^1$ is pentynyl. In some embodiments, $R^1$ is hexynyl.

$R^2$ can be selected from H, —C(=O)($R^a$), —C(=O)(O—$R^a$), —C(=O)($R^b$), —P(=O)(O—$R^b$)($R^{c1}$), —P(=O)($R^{c1}$)($R^{c2}$), —C(=O)(O—$R^d$), —C(=O)($R^h$), —C(=O)(O—$R^h$), and —C(=O)(L-$R^h$). A person of ordinary skill in the art would recognize the structures represented herein in this nomenclature. For instance, a person of ordinary skill in the art would recognize that groups of nomenclature —P(=O)($R^{c1}$)($R^{c2}$) and the like could also be represented as follows:

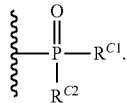

Similarly, a person of ordinary skill in the art would recognize that groups of nomenclature —P(=O)(O—$R^b$)($R^{c1}$) and the like could also be represented as follows:

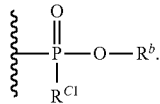

Similarly, a person of ordinary skill in the art would recognize that groups of nomenclature —C(=O)($R^a$) and the like could also be represented as follows:

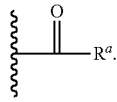

Similarly, a person of ordinary skill in the art would recognize that groups of nomenclature —C(=O)(O—$R^a$) and the like could also be represented as follows:

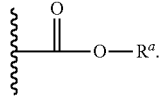

In some embodiments, $R^2$ is H. In some embodiments, $R^2$ is —C(=O)($R^a$). In some embodiments, $R^2$ is —C(=O)(($C_1$-$C_{25}$)alkyl). In some embodiments, $R^2$ is —C(=O)(($C_1$-$C_{18}$)alkyl). In some embodiments, $R^2$ is —C(=O)(($C_1$-$C_{12}$)alkyl). In some embodiments, $R^2$ is —C(=O)(($C_1$-$C_6$)alkyl). In some embodiments, $R^2$ is —C(=O)(($C_1$-$C_4$)alkyl). In some embodiments, $R^2$ is —C(=O)(methyl). In some embodiments, $R^2$ is —C(=O)(isopropyl). In some embodiments, $R^2$ is —C(=O)(($C_1$-$C_4$)alkyl substituted with phenyl). In some embodiments, $R^2$ is —C(=O)(($C_1$-$C_4$) alkyl substituted with phenyl), wherein the phenyl is substituted with —$CH_3$. In some embodiments, $R^2$ is —C(=O)(($C_1$-$C_4$)alkyl substituted with phenyl), wherein the phenyl is substituted with acetoxy. In some embodiments, $R^2$ is —C(=O)(($C_1$-$C_4$)alkyl substituted with phenyl), wherein the phenyl is substituted with —$CH_3$ and acetoxy.

In some embodiments, $R^2$ is —C(=O)(O—$R^a$). In some embodiments, $R^2$ is —C(=O)(($C_1$-$C_{16}$)alkoxy). In some embodiments, $R^2$ is —C(=O)(($C_1$-$C_{12}$)alkoxy).

In some embodiments, $R^2$ is —C(=O)($R^b$). In some embodiments, $R^2$ is —C(=O)(aryl). In some embodiments, $R^2$ is —C(=O)(cycloalkyl). In some embodiments, $R^2$ is —C(=O)(phenyl group that is substituted with a ($C_1$-$C_4$) alkyl). In some embodiments, $R^2$ is —C(=O)(phenyl). In some embodiments, $R^2$ is —C(=O)(cyclohexyl). In some embodiments, $R^2$ is —C(=O)(phenyl substituted with an ester). In some embodiments, $R^2$ is —C(=O)(cyclohexyl substituted with ($C_1$-$C_4$)alkyl). In some embodiments, $R^2$ is —C(=O)(phenyl substituted with —$CH_2$—C(=O)—($C_1$-$C_6$)alkyl). In some embodiments, $R^2$ is —C(=O)(phenyl substituted with —$CH_2$—C(=O)—($C_1$-$C_4$)alkyl). In some embodiments, $R^2$ is —C(=O)(phenyl substituted with an ester). In some embodiments, $R^2$ is —C(=O)(phenyl substituted with an ester), wherein the ester moiety is a ($C_1$-$C_{16}$)alkyl ester, a ($C_1$-$C_{12}$)alkyl ester, a ($C_1$-$C_6$)alkyl ester, a ($C_6$-$C_{12}$)alkyl ester, or a ($C_{12}$-$C_{16}$)alkyl ester.

In some embodiments, $R^2$ is —C(=O)(O—$R^d$). In some embodiments, $R^5$ is —C(=O)(O—$R^d$), where $R^d$ is

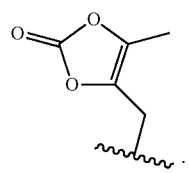

In some embodiments, $R^2$ is —C(=O)(O—$R^d$), where $R^d$ is

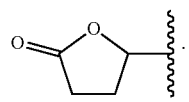

In some embodiments, $R^2$ is —P(=O)(O—$R^b$)($R^{c1}$). In some embodiments, $R^2$ is —P(=O)(O-phenyl)($R^{c1}$). In some embodiments, $R^2$ is —P(=O)(O-phenyl)(—NH—CH(CH$_3$)—C(=O)—O—($C_1$-$C_6$)alkyl). In some embodiments, $R^2$ is —P(=O)(O—$R^b$)(—NH—CH(CH$_3$)—C(=O)—O—($C_1$-$C_6$)alkyl). In some embodiments, $R^2$ is —P(=O)(O-phenyl)(—NH—CH(CH$_3$)—C(=O)—O—($C_1$-$C_6$)alkyl). In some embodiments, $R^2$ is —P(=O)(O—$R^b$)(—NH—CH(CH$_3$)—C(=O)—O—($C_1$-$C_3$)alkyl). In some embodiments, $R^2$ is —P(=O)(O-phenyl)(—NH—CH(CH$_3$)—C(=O)—O—($C_1$-$C_3$)alkyl). In some embodiments, $R^2$ is —P(=O)(O-phenyl)(—NH—CH(CH$_3$)—C(=O)—O—($C_4$-$C_8$)cycloalkyl). In some embodiments, $R^2$ is —P(=O)(O-phenyl)(—NH—CH(CH$_3$)—C(=O)—O-cyclohexyl). In some embodiments, $R^2$ is —P(=O)($R^{c1}$)($R^{c2}$). In some embodiments, $R^2$ is —P(=O)(—NH—CH(CH$_3$)—C(=O)—O—($C_1$-$C_6$)alkyl)$^2$. In some embodiments, $R^2$ is —P(=O)(—NH—CH(CH$_3$)—C(=O)—O—($C_1$-$C_3$)alkyl)$^2$.

In some embodiments, $R^2$ comprises a phosphate residue. In some embodiments, $R^2$ comprises a phosphate derivative residue. In some embodiments, $R^2$ comprises a monophosphate residue. In some embodiments, $R^2$ comprises a diphosphate residue. In some embodiments, $R^2$ comprises a triphosphate residue. In some embodiments, $R^2$ comprises a phosphonate. In some embodiments, $R^2$ comprises a phosphate polyester. In some embodiments, $R^2$ comprises a phosphate diester. In some embodiments, $R^2$ comprises a phosphate triester. In some embodiments, $R^2$ comprises a phosphate amidate. In some embodiments, $R^2$ comprises a phosphate monoamidite. In some embodiments, R² comprises a phosphate diamidate. In some embodiments, R² comprises a phsophorothioate. In some embodiments, R² comprises a phsphoroselenoate. In some embodiments, R² comprises a phosphoboranoate.

In some embodiments, R² is —C(=O)(R$^h$). In some embodiments, R² is —C(=O)(O—R$^h$). In some embodiments, R² is —C(=O)((C$_7$-C$_{10}$) carbocycle). In some embodiments, R² is —C(=O)(bridged-bicyclic (C$_7$-C$_{10}$) carbocycle). In some embodiments, R² is —C(=O)(bicyclo[2.2.2]octane). In some embodiments, R² is —C(=O)(spiro-bicyclic (C$_7$-C$_{10}$) carbocycle). In some embodiments, R² is —C(=O)(spiro[5.3]nonane). In some embodiments, R² is —C(=O)(spiro[5.3]nonane). In some embodiments, R² is —C(=O)(spiro[3.3]heptane). In some embodiments, R² is —C(=O)(O-bridged-bicyclic (C$_7$-C$_{10}$) carbocycle). In some embodiments, R² is —C(=O)(O-bicyclo[2.2.2]octane). In some embodiments, R² is —C(=O)(O-spiro-bicyclic (C$_7$-C$_{10}$) carbocycle). In some embodiments, R² is —C(=O)(O-spiro[5.3]nonane). In some embodiments, R² is —C(=O)(O-spiro[5.3]nonane). In some embodiments, R² is —C(=O)(O-spiro[3.3]heptane).

In some embodiments, R² is —C(=O)(L-R$^h$). In some embodiments, R² is

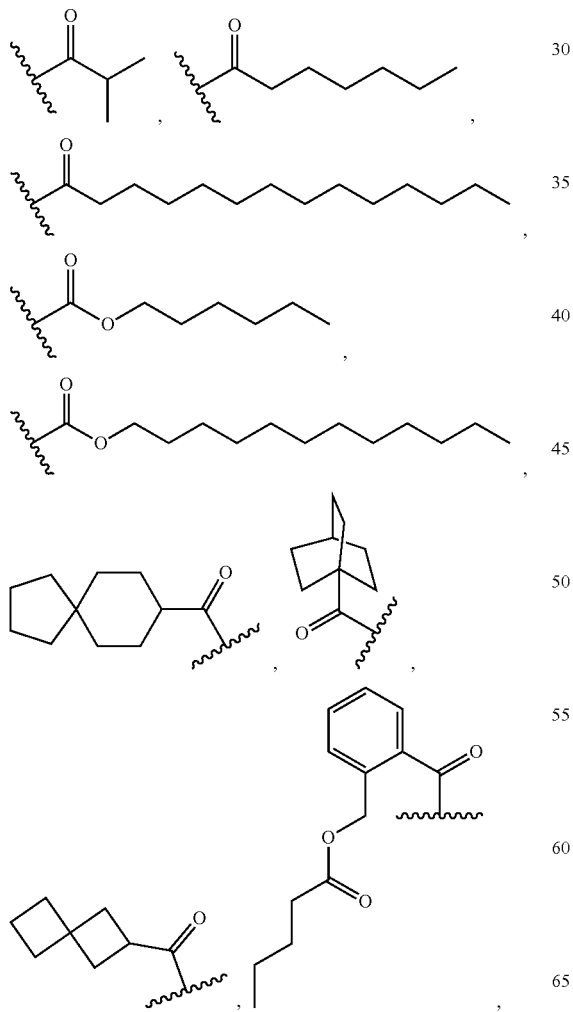

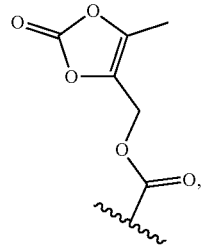

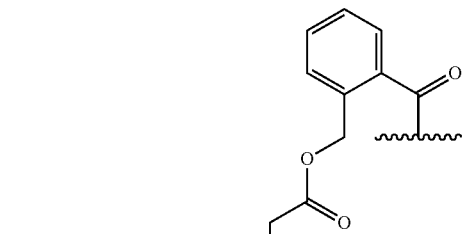

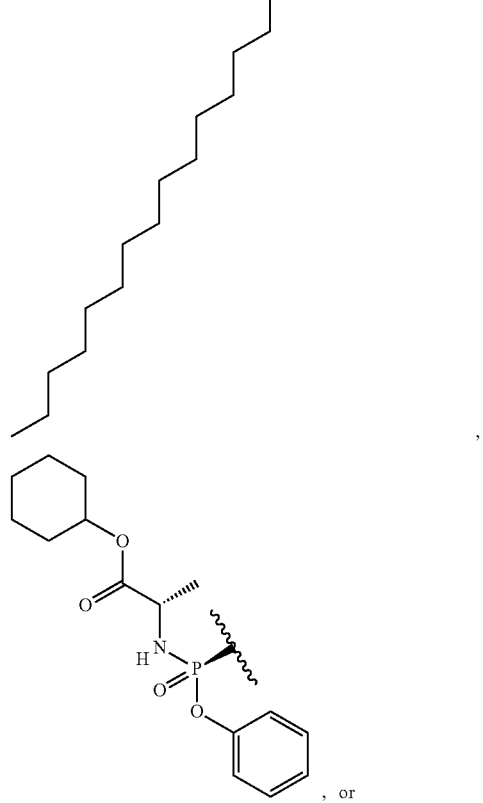

, or

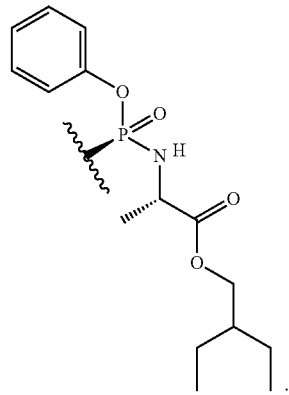

.

In formula I, $R^{3a}$ can be selected from H and $R^e$, and $R^{3b}$ represents H or is absent. In some embodiments, $R^{3a}$ is H. In some embodiments, $R^{3a}$ is $R^e$. In some embodiments, $R^{3b}$ is H. In some embodiments, $R^{3b}$ is absent. In some embodiments, $R^{3a}R^{3b}$ is the same as $R^2$. In some embodiments, $R^{3a}R^{3b}$ is different than $R^2$. In some embodiments, $R^{3a}R^{3b}$ can be any of the possible substituents listed for $R^2$.

In some embodiments, $R^4$ is absent. In some embodiments, $R^4$ is $R^d$. In some embodiments, $R^4$ is the same as $R^{3a}$. In some embodiments, $R^4$ is different than $R^{3a}$. In some embodiments, $R^4$ is the same as $R^{3a}R^{3b}$. In some embodiments, $R^4$ is different than $R^{3a}R^{3b}$. In some embodiments, $R^4$ can be any of the possible substituents listed for $R^{3a}R^{3b}$.

$R^5$ can be H, —C(=O)($R^a$), —C(=O)(O—$R^a$), —C(=O)($R^b$), —C(=O)(O—$R^d$), —P(=O)(O—$R^b$)($R^{c1}$), —C(=O)($R^h$), —C(=O)(O—$R^h$), or —C(=O)(L-$R^h$). In some embodiments, $R^5$ is the same as $R^{3a}R^{3b}$. In some embodiments, $R^5$ is the same as $R^{3a}$. In some embodiments, $R^5$ is the same as $R^2$. In some embodiments, $R^5$ is different than $R^{3a}R^{3b}$. In some embodiments, $R^5$ is different than $R^{3a}$. In some embodiments, $R^5$ is different than $R^2$. In some embodiments, $R^5$ can be any of the possible substituents listed for $R^2$. In some embodiments, $R^5$ can be any of the possible substituents listed for $R^{3a}R^{3b}$. In some embodiments, $R^5$ can be any of the possible substituents listed for $R^{3a}$. In some embodiments, $R^2$, $R^5$ and $R^{3a}R^{3b}$ are the same. In some embodiments, $R^2$, $R^5$ and $R^{3a}$ are the same. In some embodiments, $R^2$, $R^5$ and $R^{3a}R^{3b}$ are not all the same. In some embodiments, $R^2$, $R^5$ and $R^{3a}$ are not all the same.

In some embodiments, $R^5$ is H. In some embodiments, $R^5$ is —C(=O)($R^a$). In some embodiments, $R^5$ is —C(=O)(isopropyl). In some embodiments, $R^5$ is —C(=O)(O—$R^a$). In some embodiments, $R^5$ is —C(=O)(O—$R^a$). In some embodiments, $R^5$ is —C(=O)(($C_1$-$C_{16}$)alkoxy). In some embodiments, $R^5$ is —C(=O)(($C_1$-$C_{12}$)alkoxy). In some embodiments, $R^5$ is —C(=O)(($C_1$-$C_4$)alkoxy). In some embodiments, $R^5$ is —C(=O)(($C_1$-$C_4$)alkyl substituted with phenyl), wherein the phenyl is substituted with —$CH_3$. In some embodiments, $R^5$ is —C(=O)(($C_1$-$C_4$)alkyl substituted with phenyl), wherein the phenyl is substituted with acetoxy. In some embodiments, $R^5$ is —C(=O)(($C_1$-$C_4$)alkyl substituted with phenyl), wherein the phenyl is substituted with —$CH_3$ and acetoxy.

In some embodiments, $R^5$ is —C(=O)($R^b$). In some embodiments, $R^5$ is —C(=O)(phenyl substituted with ($C_1$-$C_4$)alkyl). In some embodiments, $R^5$ is —C(=O)(cyclohexyl substituted with ($C_1$-$C_4$)alkyl). In some embodiments, $R^5$ is —C(=O)(phenyl substituted with —$CH_2$—C(=O)—($C_1$-$C_6$)alkyl). In some embodiments, $R^5$ is —C(=O)(phenyl substituted with —$CH_2$—C(=O)—($C_1$-$C_4$)alkyl).

In some embodiments, $R^5$ is —C(=O)(O—$R^d$). In some embodiments, $R^5$ is —C(=O)(O—$R^d$), where $R^d$ is

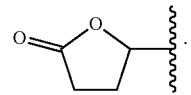

In some embodiments, $R^5$ is —C(=O)(O—$R^d$), where $R^d$ is

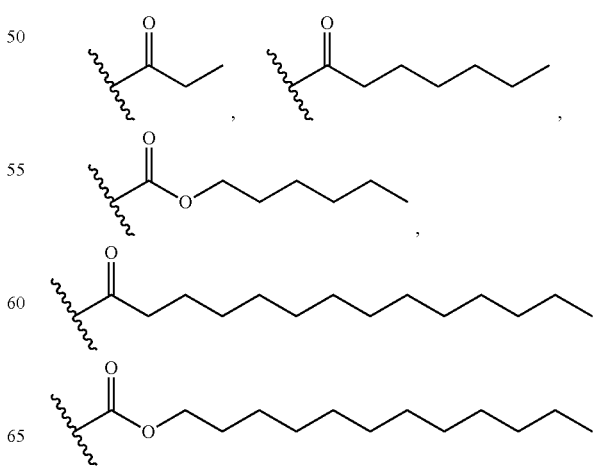

In some embodiments, $R^5$ is —P(=O)(O—$R^b$)($R^{c1}$). In some embodiments, $R^5$ is —P(=O)(O-phenyl)(—NH—CH(CH$_3$)—C(=O)—O—($C_1$-$C_6$)alkyl). In some embodiments, $R^5$ is —P(=O)(O—$R^b$)(—NH—CH(CH$_3$)—C(=O)—O—($C_1$-$C_6$)alkyl). In some embodiments, $R^5$ is —P(=O)(O-phenyl)(—NH—CH(CH$_3$)—C(=O)—O—($C_1$-$C_6$)alkyl). In some embodiments, $R^5$ is —P(=O)(O—$R^b$)(—NH—CH(CH$_3$)—C(=O)—O—($C_1$-$C_3$)alkyl). In some embodiments, $R^5$ is —P(=O)(O-phenyl)(—NH—CH(CH$_3$)—C(=O)—O—($C_1$-$C_3$)alkyl). In some embodiments, $R^5$ is —P(=O)(—NH—CH(CH$_3$)—C(=O)—O—($C_1$-$C_6$)alkyl)$^2$. In some embodiments, $R^5$ is —P(=O)(—NH—CH(CH$_3$)—C(=O)—O—($C_1$-$C_3$)alkyl)$^2$.

In some embodiments, $R^5$ comprises a phosphate residue. In some embodiments, $R^5$ comprises a phosphate derivative residue. In some embodiments, $R^5$ comprises a monophosphate residue. In some embodiments, $R^5$ comprises a diphosphate residue. In some embodiments, $R^5$ comprises a triphosphate residue. In some embodiments, $R^5$ comprises a phosphonate. In some embodiments, $R^5$ comprises a phosphate polyester. In some embodiments, $R^5$ comprises a phosphate diester. In some embodiments, $R^5$ comprises a phosphate triester. In some embodiments, $R^5$ comprises a phosphate amidate. In some embodiments, $R^5$ comprises a phosphate monoamidite. In some embodiments, $R^5$ comprises a phosphate diamidate. In some embodiments, $R^5$ comprises a phosphorothioate. In some embodiments, $R^5$ comprises a phosphoroselenoate. In some embodiments, $R^5$ comprises a phosphoboranoate.

In some embodiments, $R^5$ is —C(=O)($R^h$). In some embodiments, $R^5$ is —C(=O)(O—$R^h$). In some embodiments, $R^5$ is —C(=O)(L-$R^h$). In some embodiments, $R^5$ is —C(=O)(O-spiro-bicyclic ($C_7$-$C_{10}$) carbocycle). In some embodiments, $R^5$ is —C(=O)(O-spiro[5.3]nonane). In some embodiments, $R^5$ is —C(=O)(O-spiro[5.3]nonane). In some embodiments, $R^5$ is —C(=O)(O-spiro[3.3]heptane). In some embodiments, $R^5$ is —C(=O)(O-spiro[5.3]nonane). In some embodiments, $R^5$ is —C(=O)(bridged-bicyclic ($C_7$-$C_{10}$) carbocycle). In some embodiments, $R^5$ is —C(=O)(bicyclo[2.2.2]octane). In some embodiments, $R^5$ is -continued

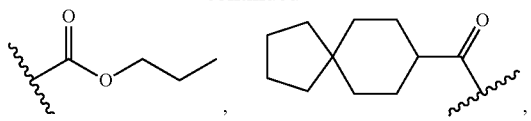

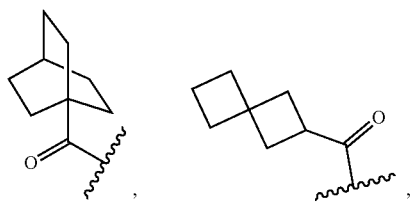

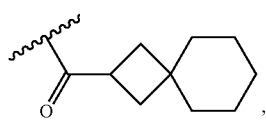

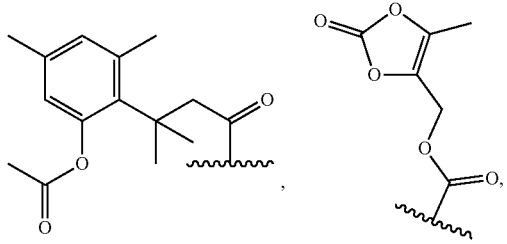

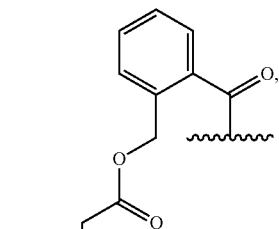

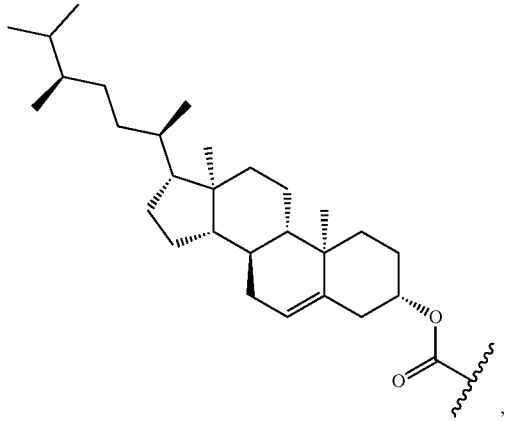

-continued

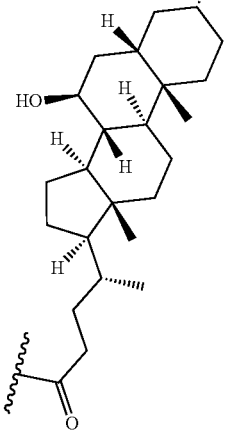

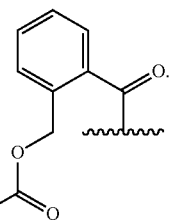

In some embodiments, at least one $R^a$ is $(C_1-C_{25})$alkyl. In some embodiments, at least one $R^a$ is $(C_1-C_{18})$alkyl. In some embodiments, at least one $R^a$ is $(C_1-C_6)$alkyl. In some embodiments, at least one $R^a$ is $(C_1-C_4)$alkyl. In some embodiments, at least one $R^a$ is substituted with one $R^b$.

In some embodiments, at least one $R^b$ is phenyl. In some embodiments, at least one $R^b$ is cyclohexyl. In some embodiments, at least one $R^b$ is substituted with $R^f$. In some embodiments, at least one $R^b$ is substituted with —CH$_2$—O—C(=O)(R$^f$). In some embodiments, at least one $R^b$ is substituted with —O—C(=O)(R$^f$). In some embodiments, at least one $R^b$ is phenyl substituted with two independently chosen $R^f$ groups and one —O—C(=O)(R$^f$). In some embodiments, at least one $R^b$ is phenyl substituted with —CH$_3$, —CH$_3$, and —O—C(=O)(CH$_3$).

In some embodiments, at least one of $R^{c1}$ and $R^{c2}$ is —NH-L-C(=O)(O—R$^f$). In some embodiments, at least one $R^{c1}$ and $R^{c2}$ is —NH-L-C(=O)(O—R$^b$). In some embodiments, $R^{c1}$ and $R^{c2}$ are the same. In some embodiments, $R^{c1}$ and $R^{c2}$ are different.

In some embodiments, at least one $R^d$ comprises a dioxolane. In some embodiments, $R^d$ comprises a dioxolane. In some embodiments, $R^d$ comprises a 1,3-dioxolane. In some embodiments, $R^d$ comprises a dioxolane substituted with one to three additional groups selected from $(C_1-C_6)$alkyl and oxo. In some embodiments, $R^d$ comprises a 1,3-dioxolane substituted with oxo. In some embodiments, $R^d$ comprises a 1,3-dioxolane substituted with oxo and methyl. In some embodiments, $R^d$ is —$(C_1-C_6)$alkyl-dioxolane. In some embodiments, $R^d$ is —$CH_2$-dioxolane. In some embodiments, $R^d$ is —$CH_2$-dioxolane, wherein the dioxolane is substituted with oxo and methyl. In some embodiments, at least one $R^d$ is

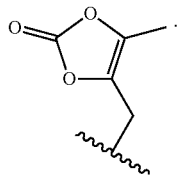

In some embodiments, at least one $R^d$ is


In some embodiments, $R^e$ is H. In some embodiments, $R^e$ is —C(=O)($R^a$). In some embodiments, $R^e$ is —C(=O)(O—$R^a$). In some embodiments, $R^e$ is —C(=O)-L-O—$R^f$. In some embodiments, $R^e$ is —C(=O)-L-O—C(=O)($R^f$).

In some embodiments, $R^e$ is —C(=O)—O-L-C(=O)(O—$R^f$). In some embodiments, $R^e$ is —C(=O)-L-S—C(=O)($R^f$). In some embodiments, $R^e$ is —C(=O)($R^b$). In some embodiments, $R^e$ is —C(=O)(O—$R^b$).

In some embodiments, $R^e$ is —C(=O)—O-L-C(=O)(O—$R^d$). In some embodiments, $R^e$ is —C(=O)($R^d$). In some embodiments, $R^e$ is —C(=O)($R^h$). In some embodiments, $R^e$ is —C(=O)(O—$R^h$). In some embodiments, $R^e$ is

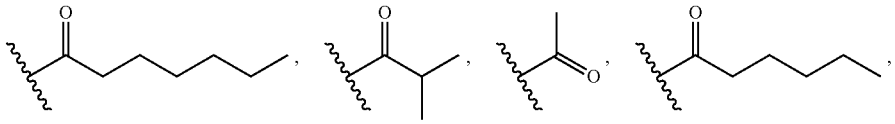

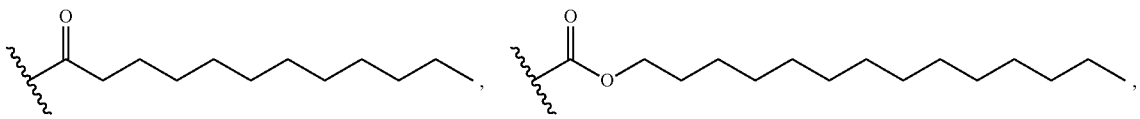

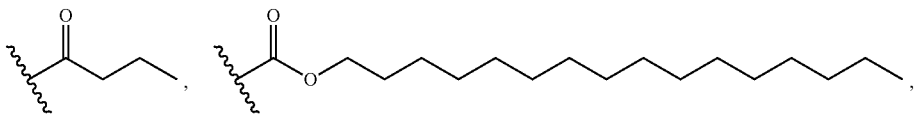

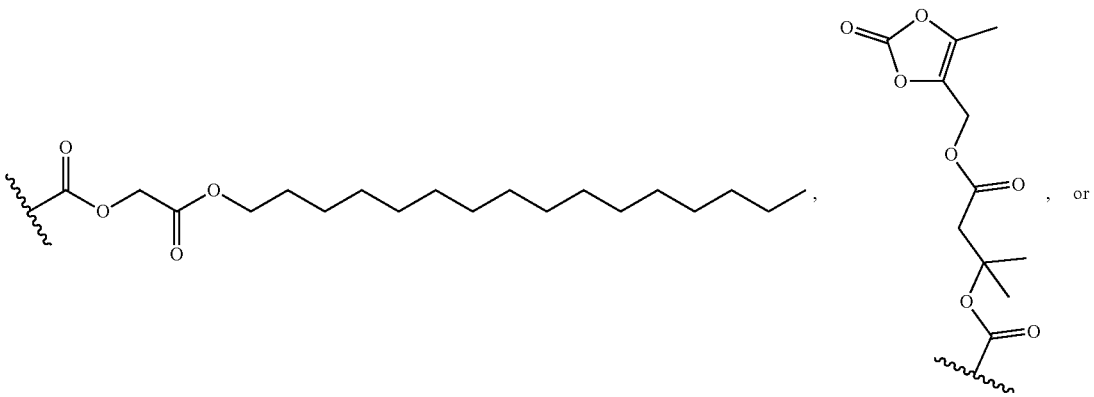

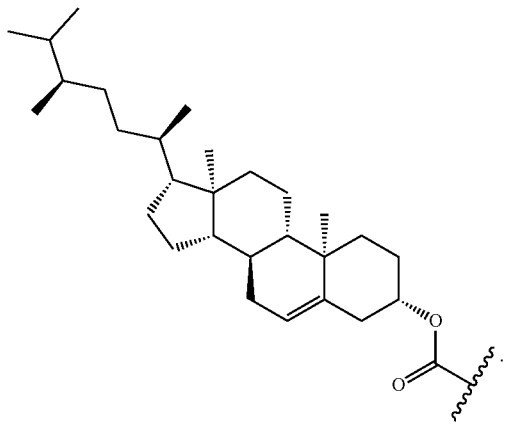

In some embodiments, $R^f$ is $(C_1-C_6)$alkyl. In some embodiments, $R^f$ is $(C_1-C_3)$alkyl.

In some embodiments, at least one L is $(C_1-C_6)$ alkylenyl. In some embodiments, at least one L is $(C_1-C_4)$ alkylenyl. In some embodiments, at least one $R^h$ is a spiro-bicyclic $(C_7-C_{10})$ carbocycle. In some embodiments, at least one $R^h$ is a bridged-bicyclic $(C_7-C_{10})$carbocycle. In some embodiments, at least one $R^h$ is a fused-polycyclic carbocycle.

In some embodiments, at least one $R^h$ is a steroid derivative optionally substituted with one to four groups independently selected from —OH and $(C_1-C_{12})$alkyl. In some embodiments, $R^h$ comprises a bile acid conjugate. In some embodiments, $R^h$ comprises a sterol.

In some embodiments, each —C(=O)($R^h$) is independently chosen from

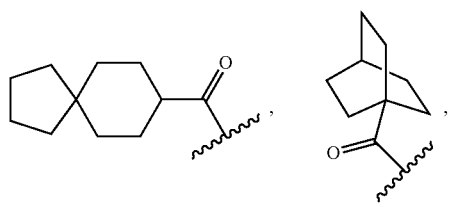

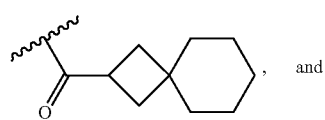

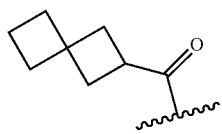

In some embodiments, —C(=O)(O—$R^h$) is

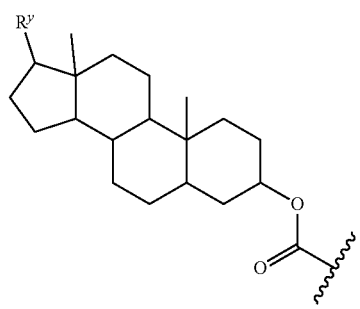

wherein $R^y$ is independently chosen from H, $(C_1-C_8)$alkyl, and $(C_1-C_8)$alkenyl, and each $R^y$ is independently optionally substituted with $(C_1-C_6)$alkyl.

In some embodiments, each —C(=O)(L-$R^h$) is independently chosen from

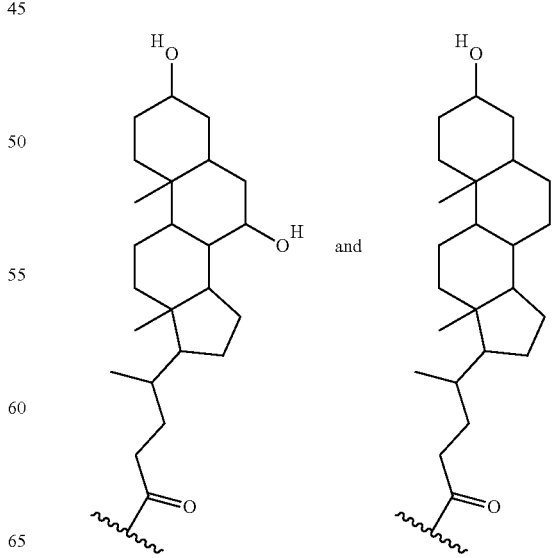

In some embodiments, the compounds disclosed herein have the formula:
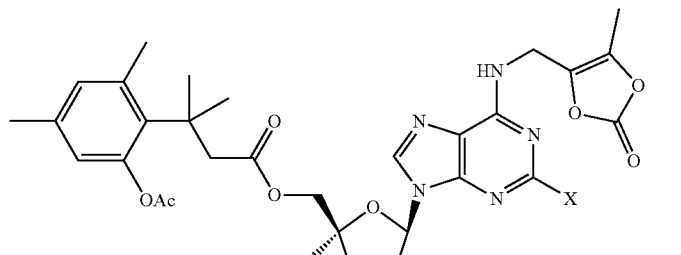
X = F, Cl
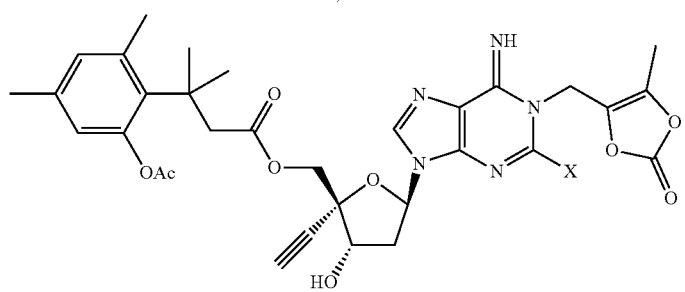
X = F, Cl
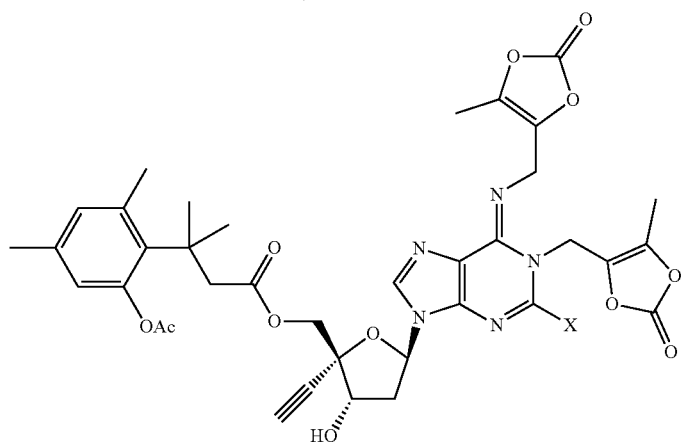
X = F, Cl
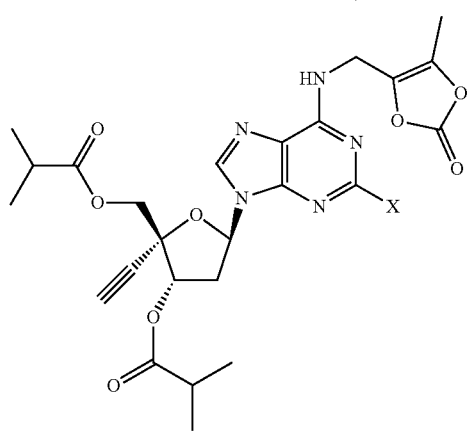
X = F, Cl

31
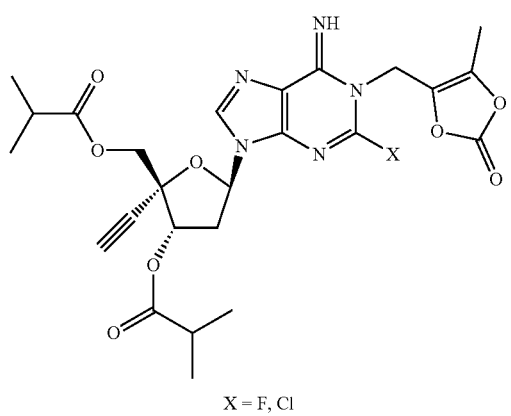
X = F, Cl
32
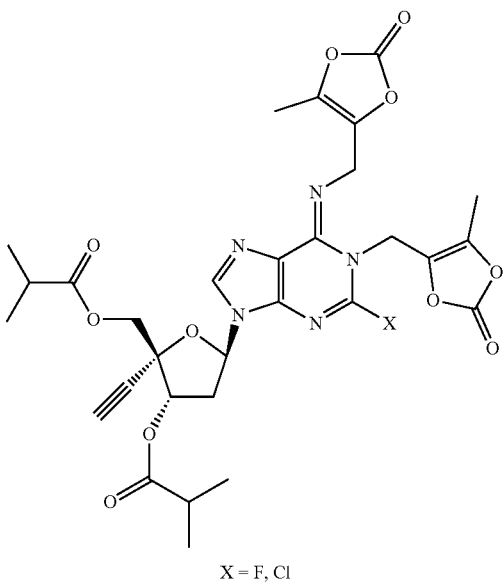
X = F, Cl
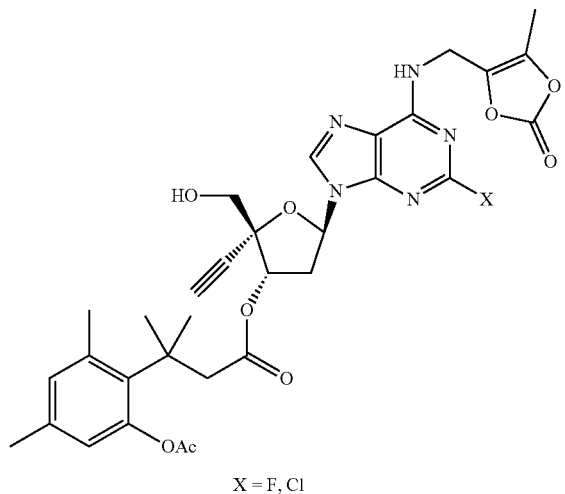
X = F, Cl
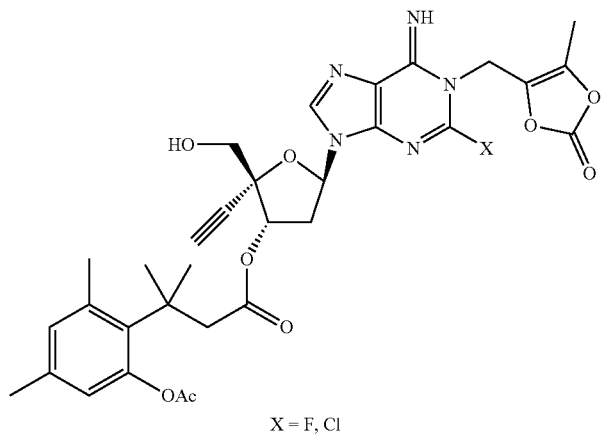
X = F, Cl

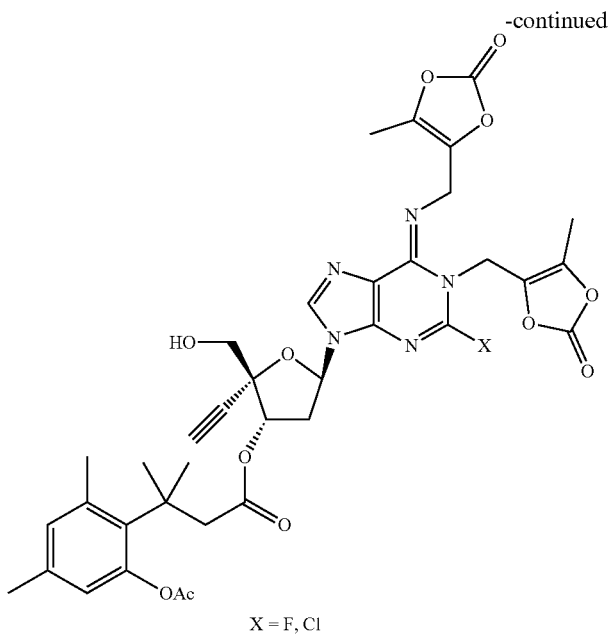
X = F, Cl
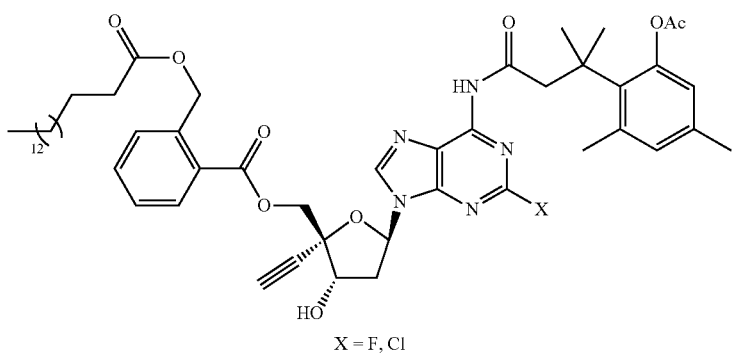
X = F, Cl
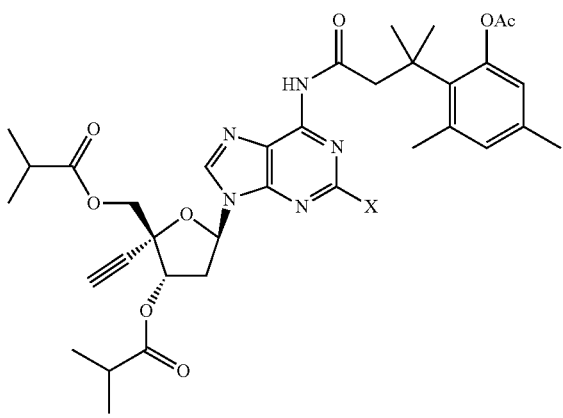
X = F, Cl

-continued
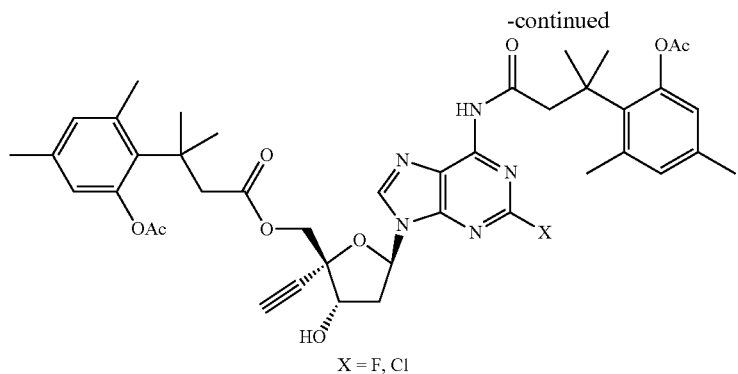
X = F, Cl
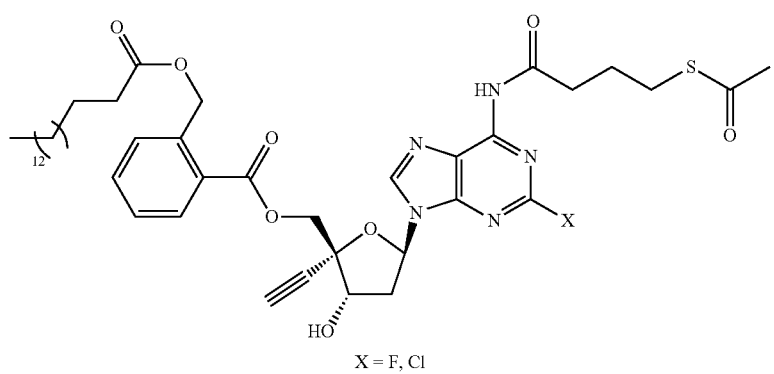
X = F, Cl
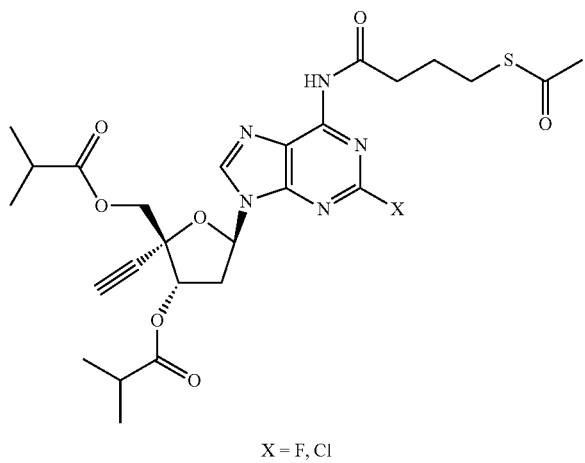
X = F, Cl
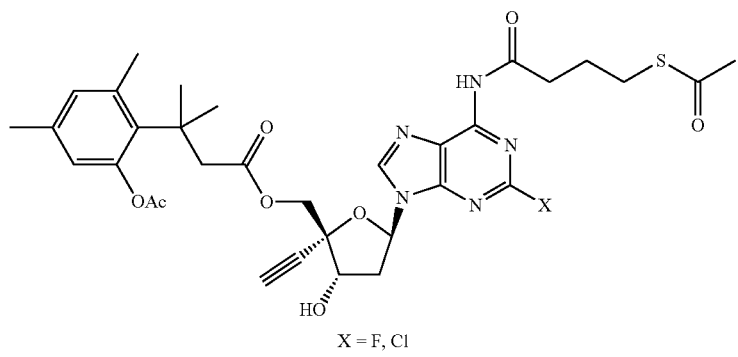
X = F, Cl

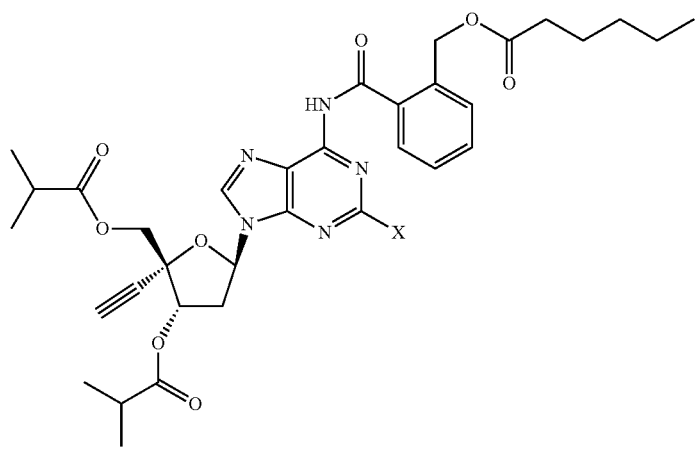
X = F, Cl
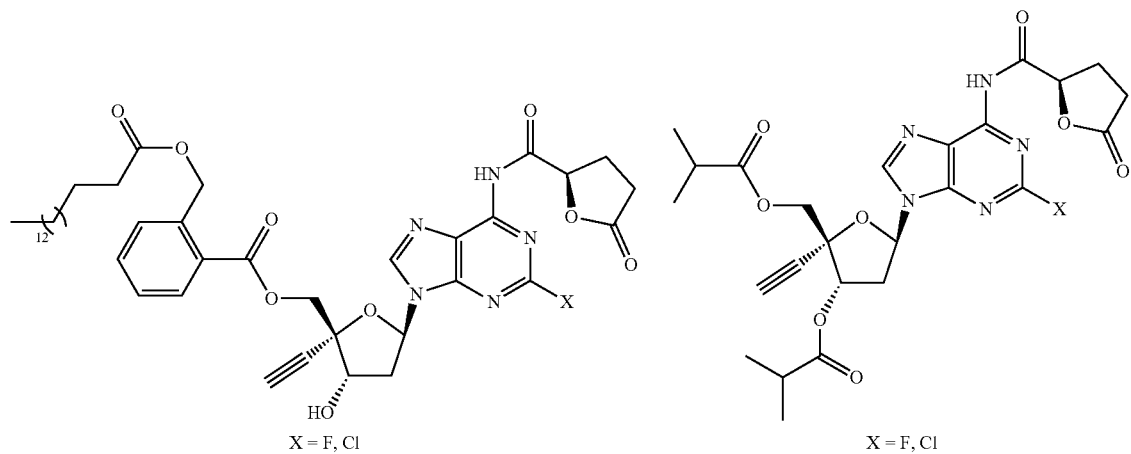
X = F, Cl
X = F, Cl
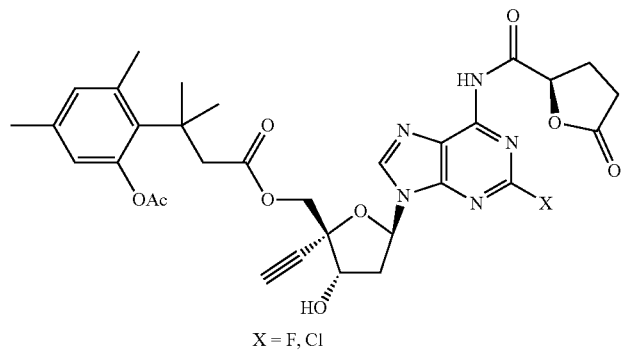
X = F, Cl

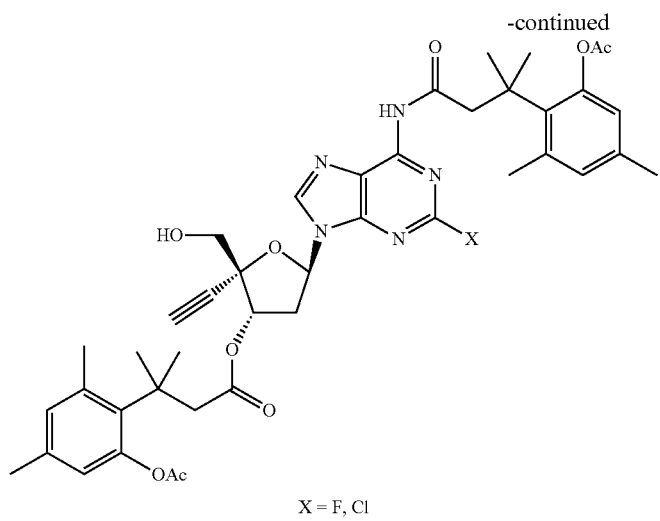
X = F, Cl
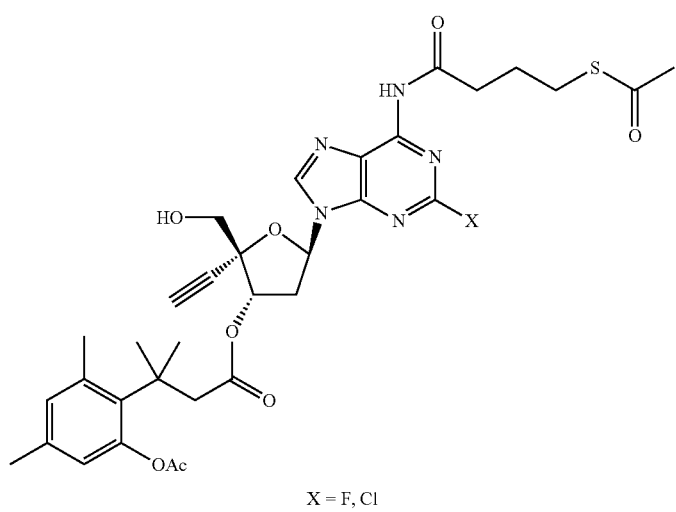
X = F, Cl
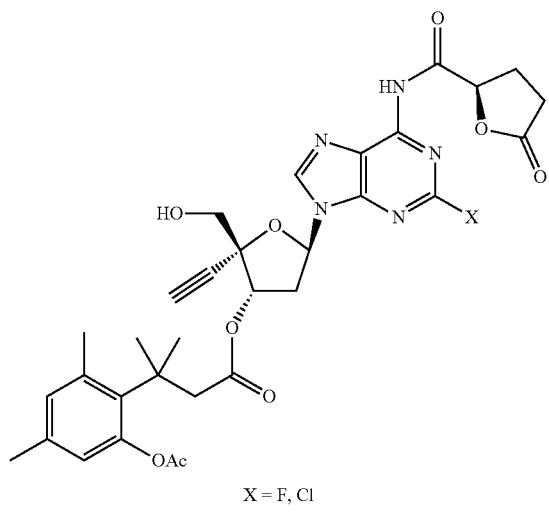
X = F, Cl

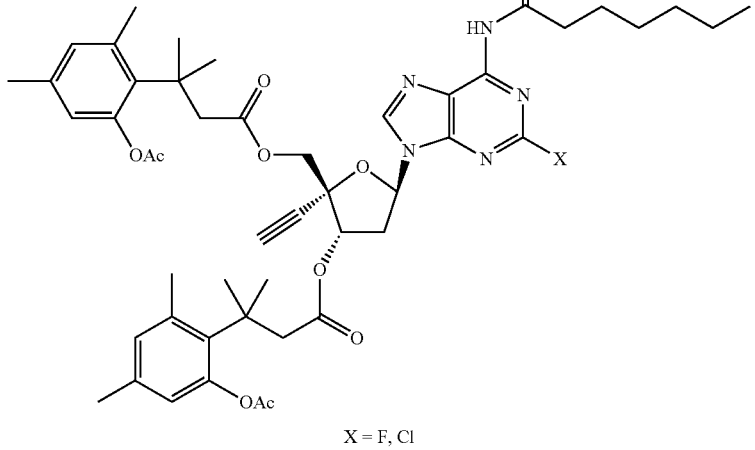
X = F, Cl
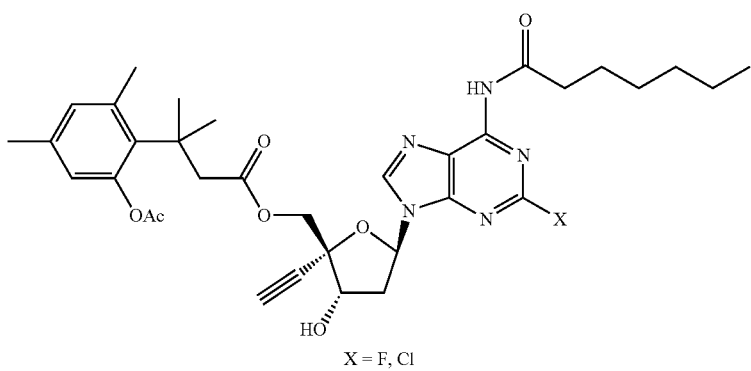
X = F, Cl
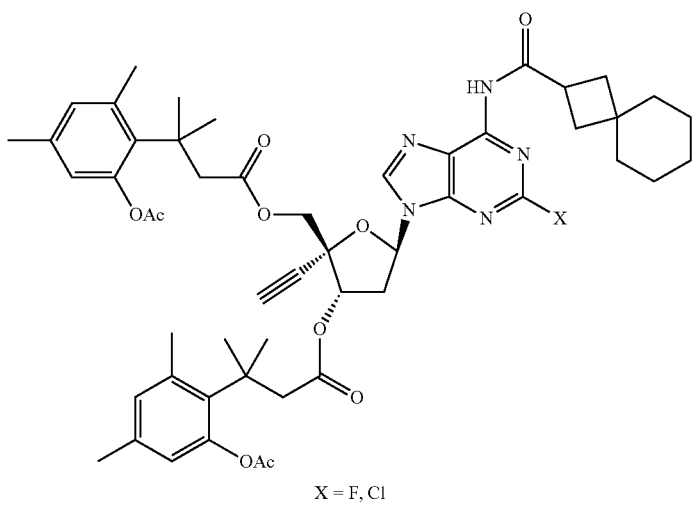
X = F, Cl

-continued
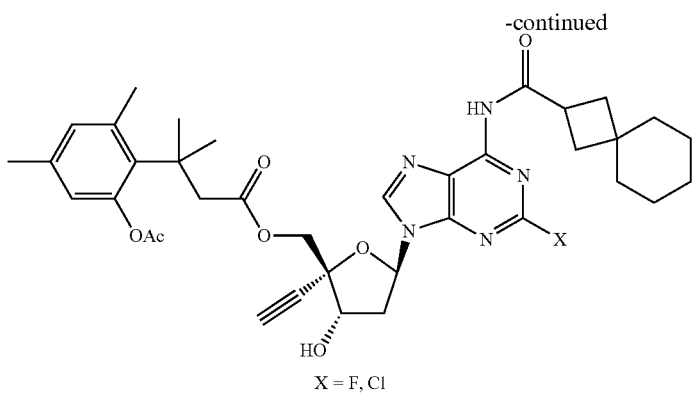
X = F, Cl
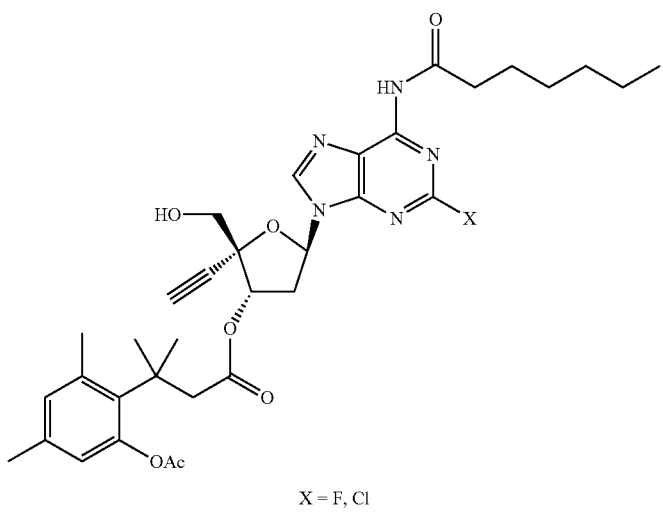
X = F, Cl
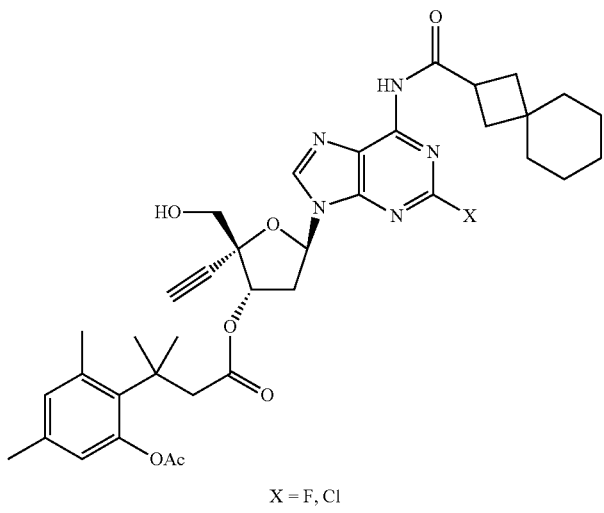
X = F, Cl

-continued
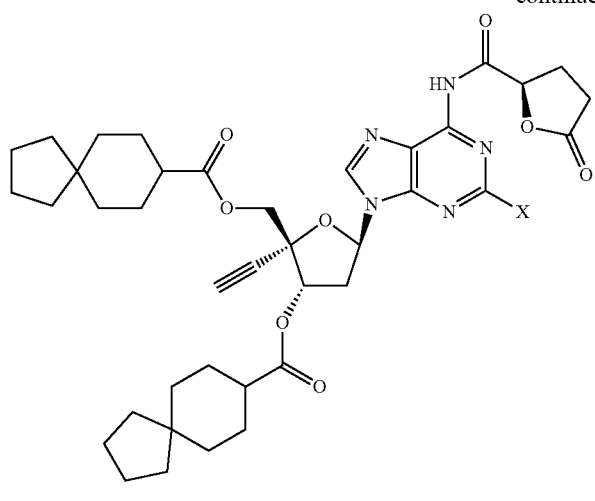
X = F, Cl
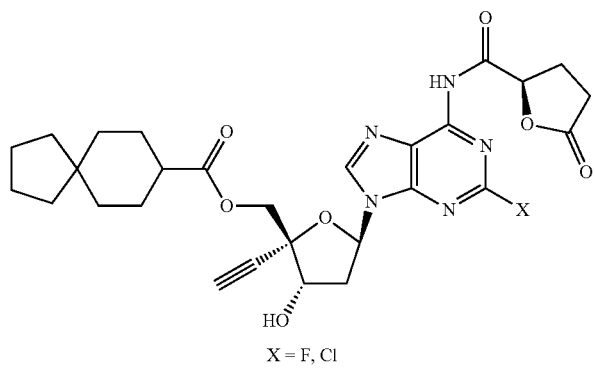
X = F, Cl
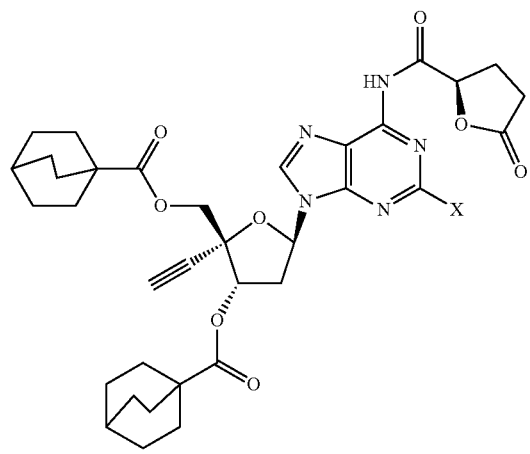
X = F, Cl
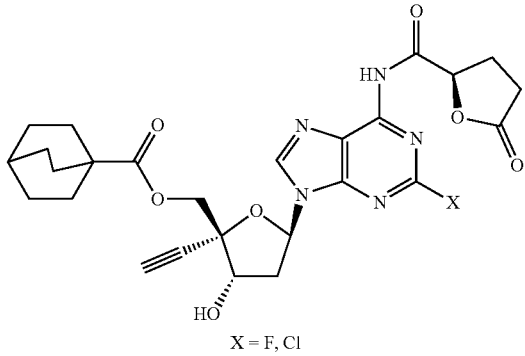
X = F, Cl -continued
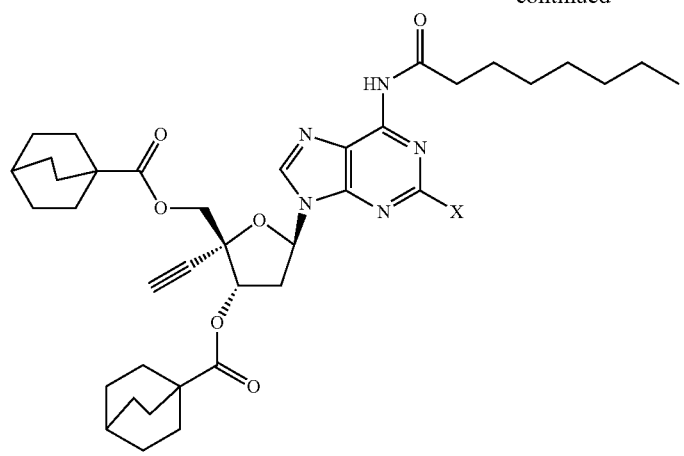
X = F, Cl
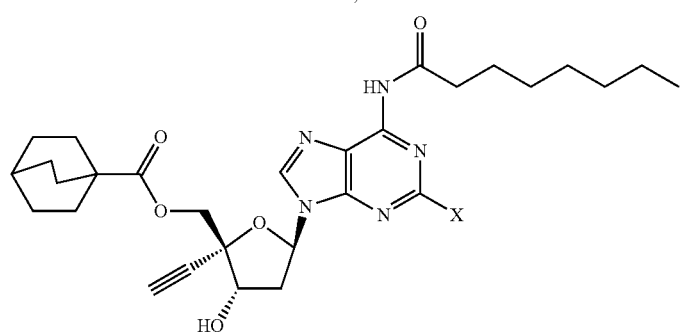
X = F, Cl
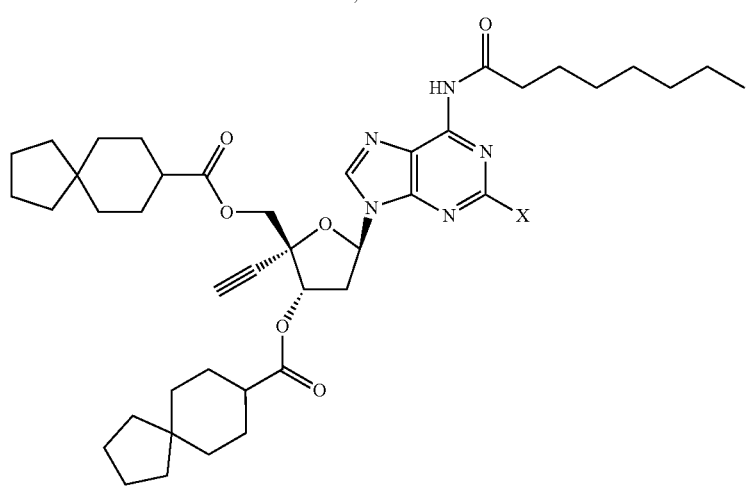
X = F, Cl
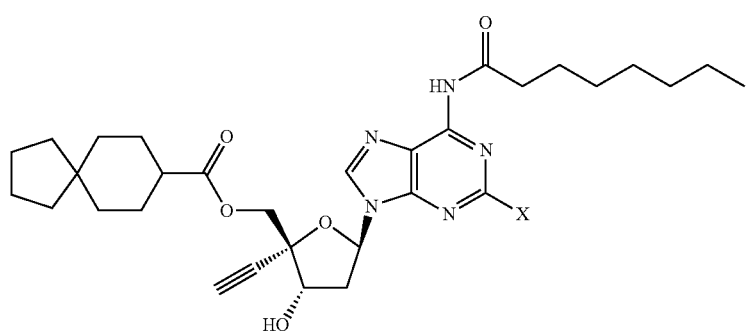
X = F, Cl 49 50
-continued
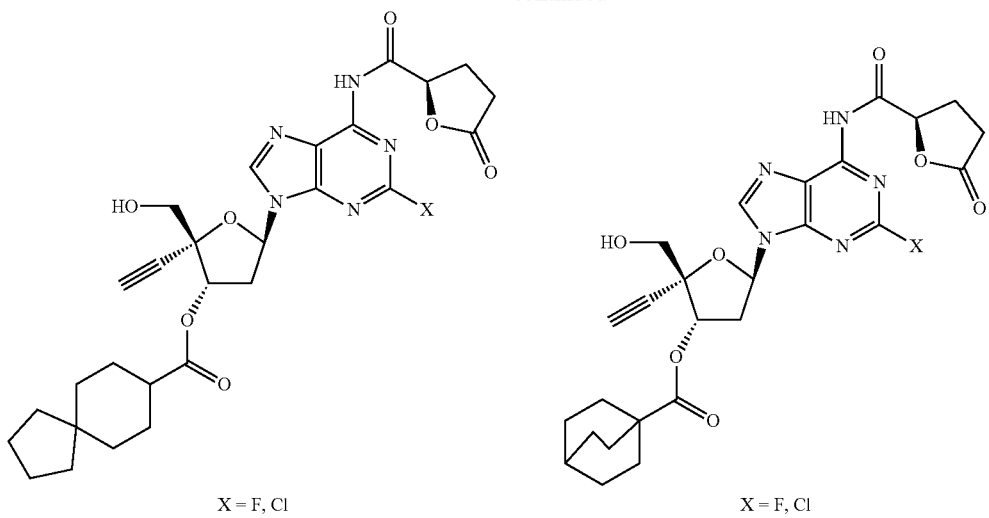
X = F, Cl    X = F, Cl
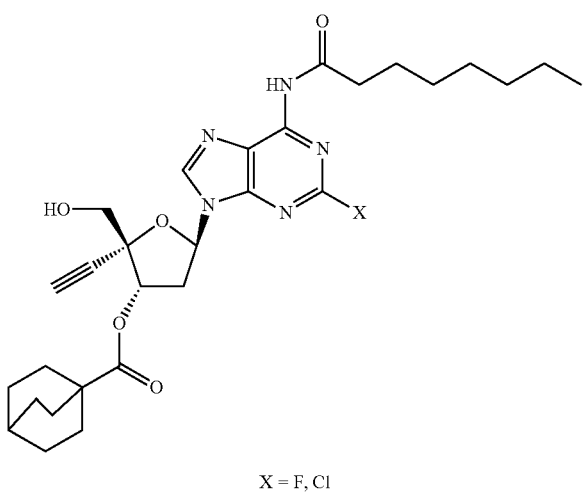
X = F, Cl
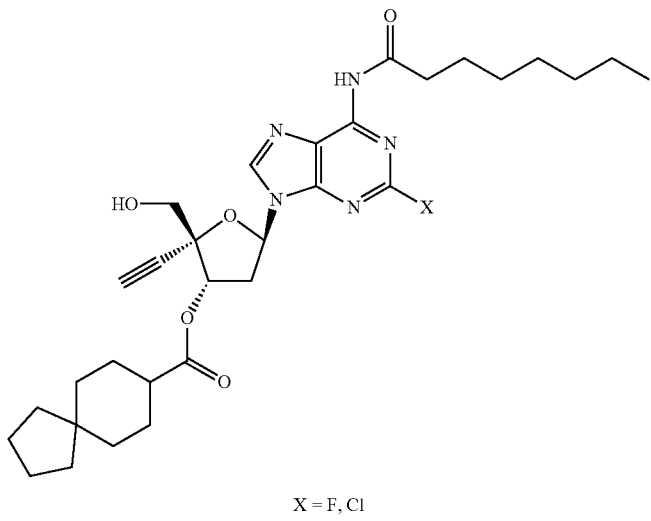
X = F, Cl

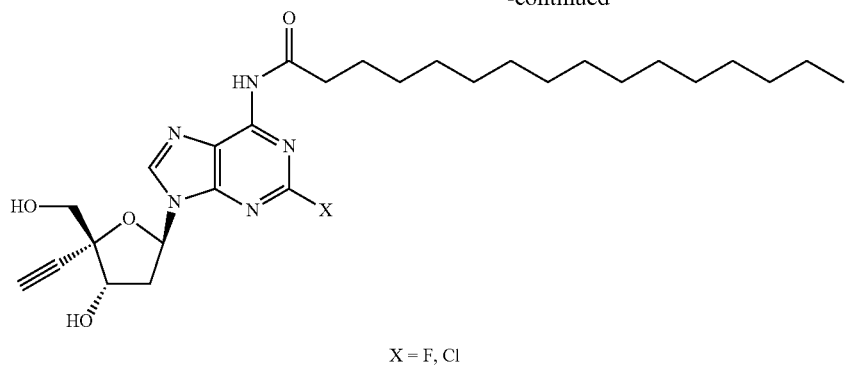
X = F, Cl
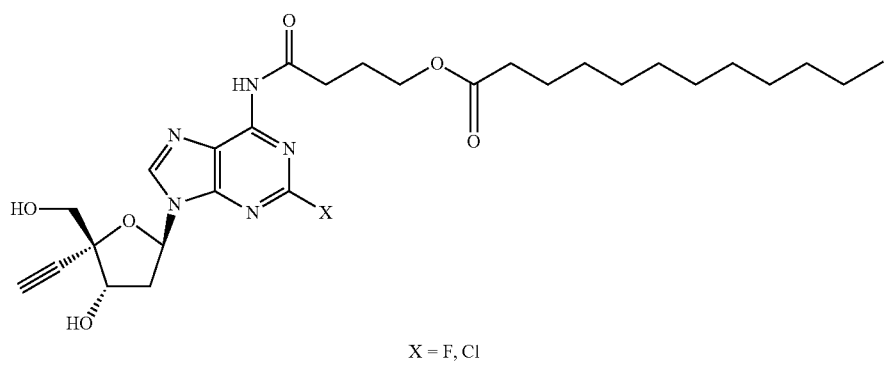
X = F, Cl
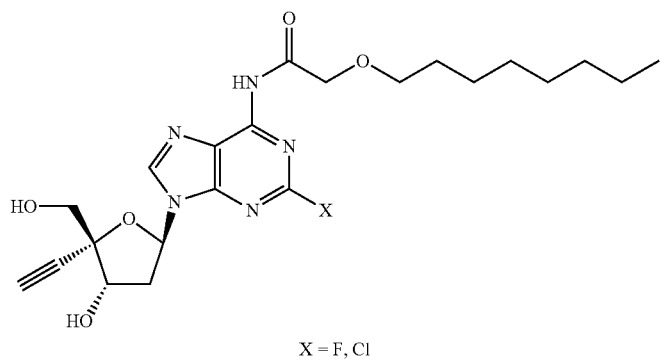
X = F, Cl
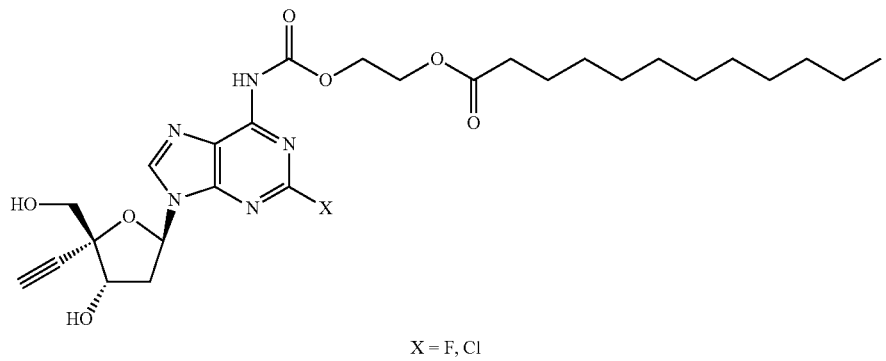
X = F, Cl

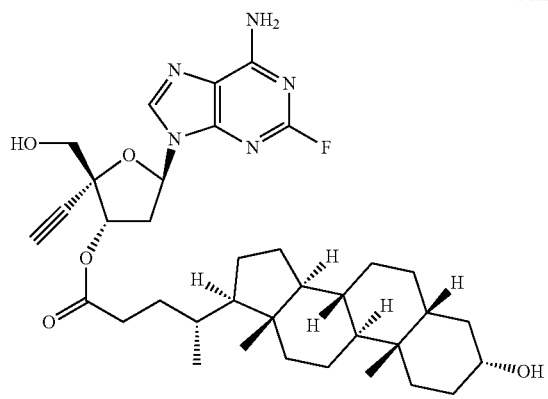
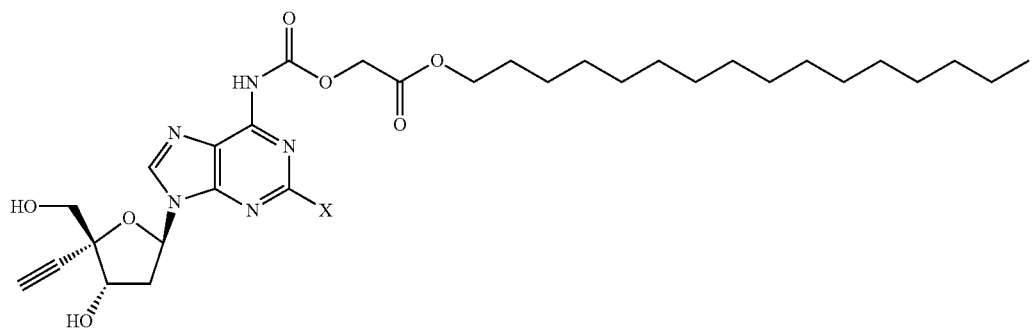
X = F, Cl
P-Kx6
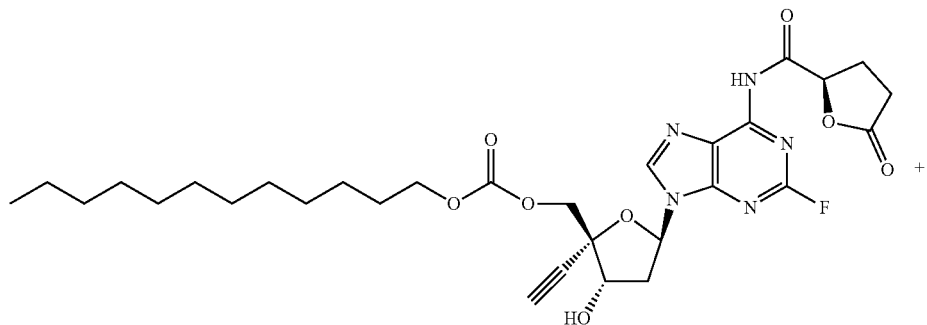
P-Lx6
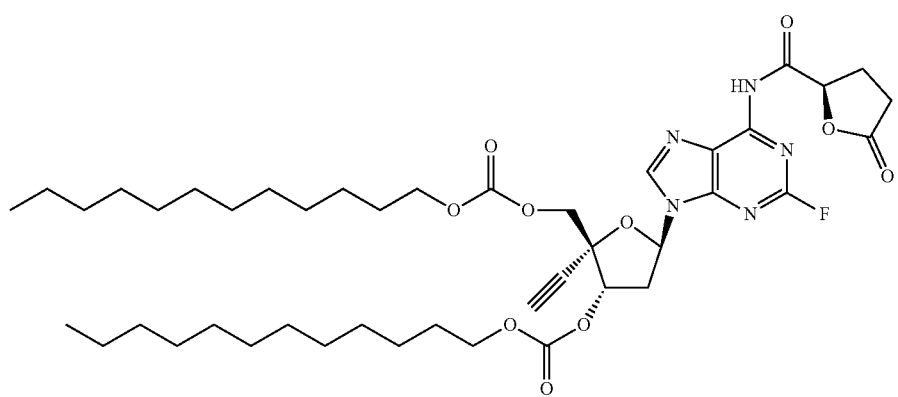

-continued
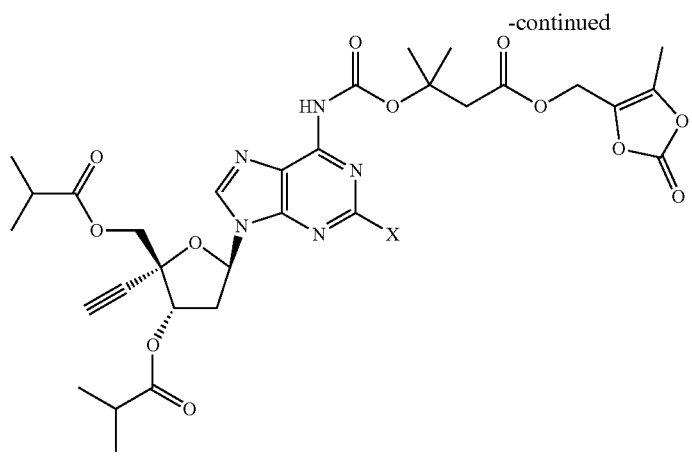
X = F, Cl
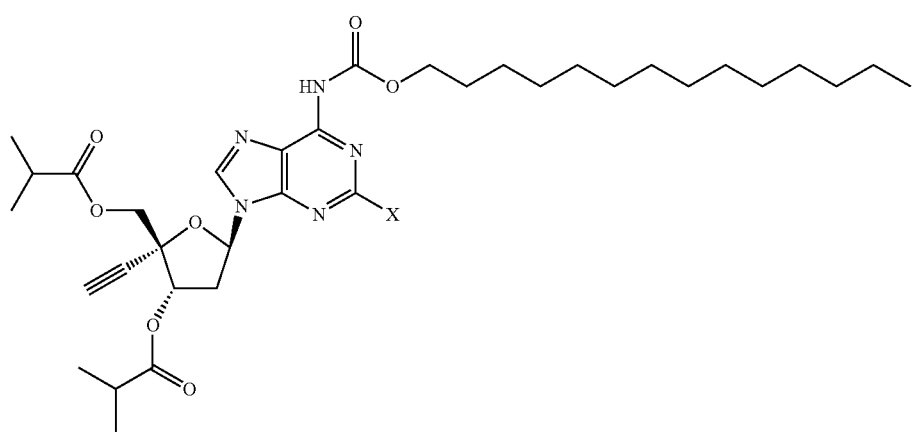
X = F, Cl
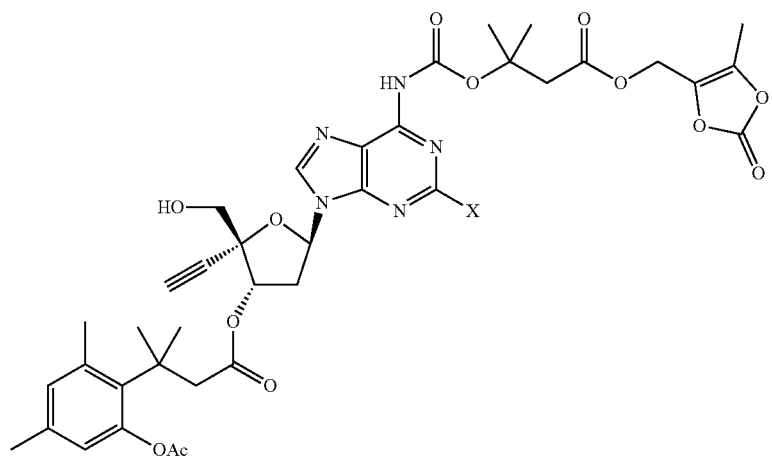
X = F, Cl

-continued
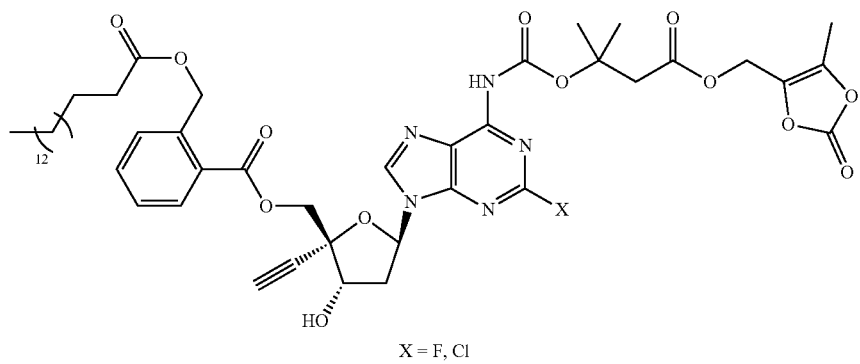
X = F, Cl
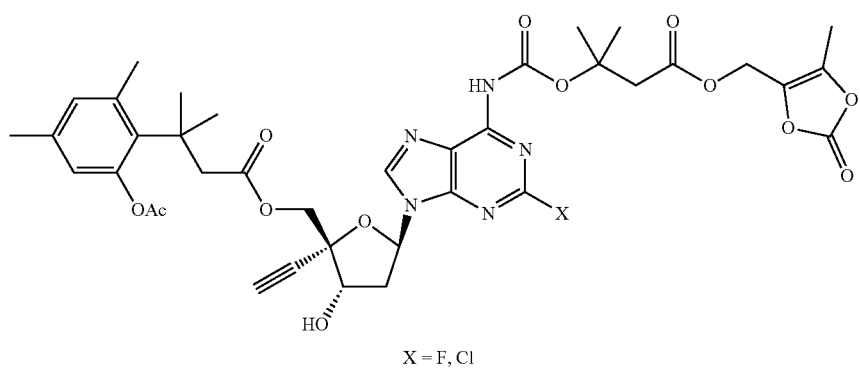
X = F, Cl
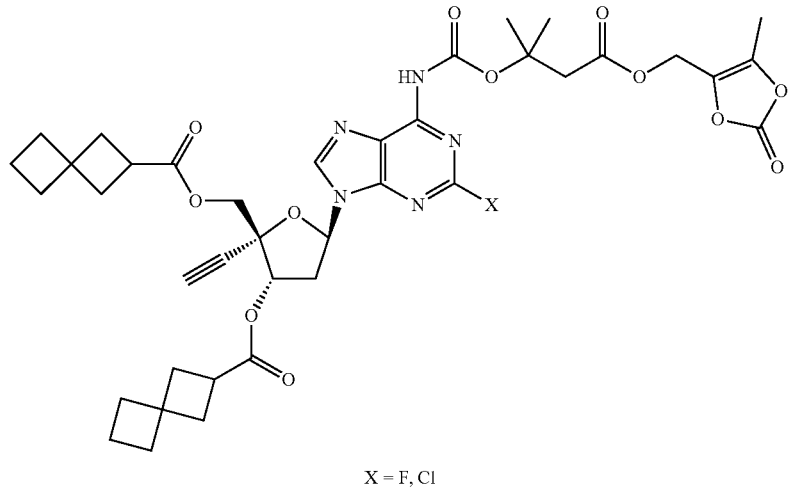
X = F, Cl
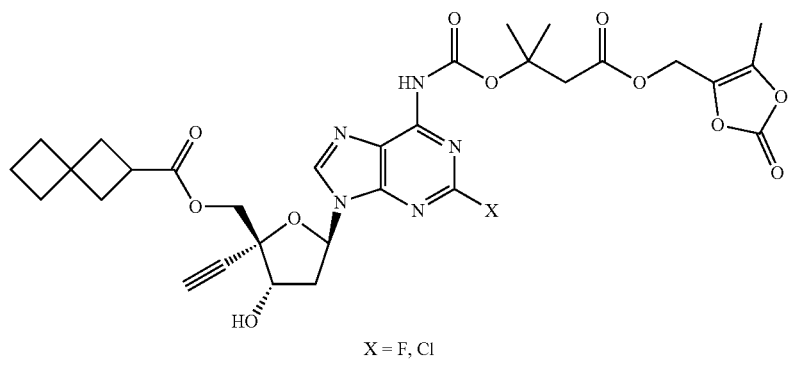
X = F, Cl -continued
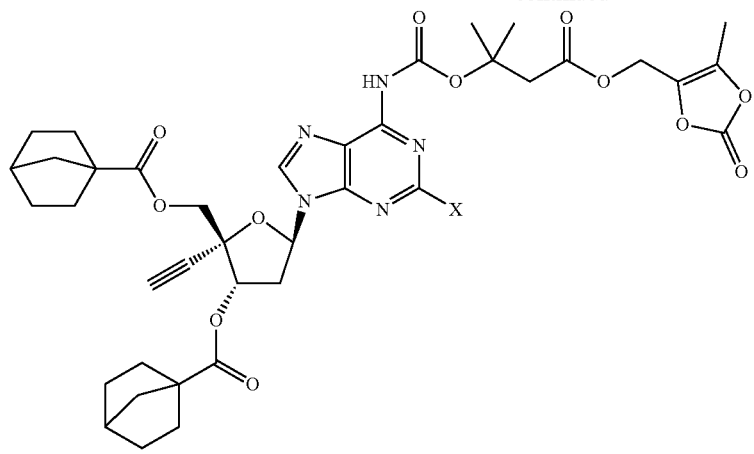
X = F, Cl
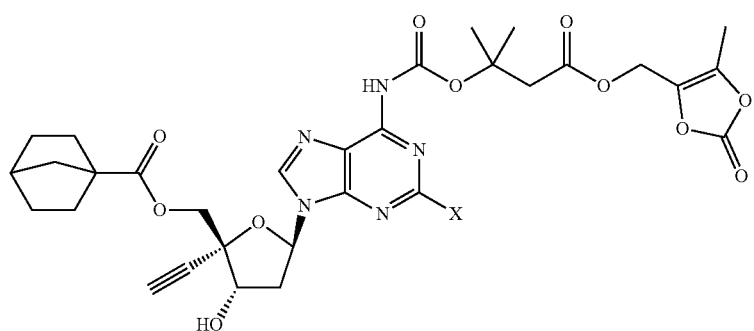
X = F, Cl
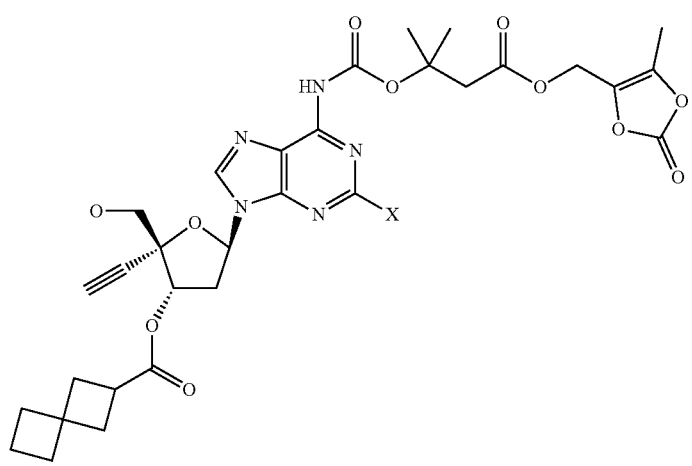
X = F, Cl -continued
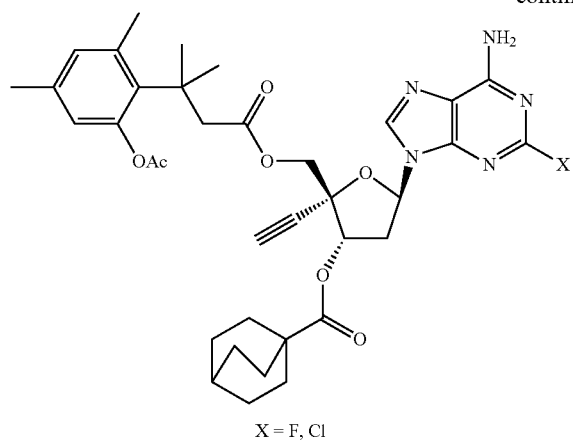
X = F, Cl
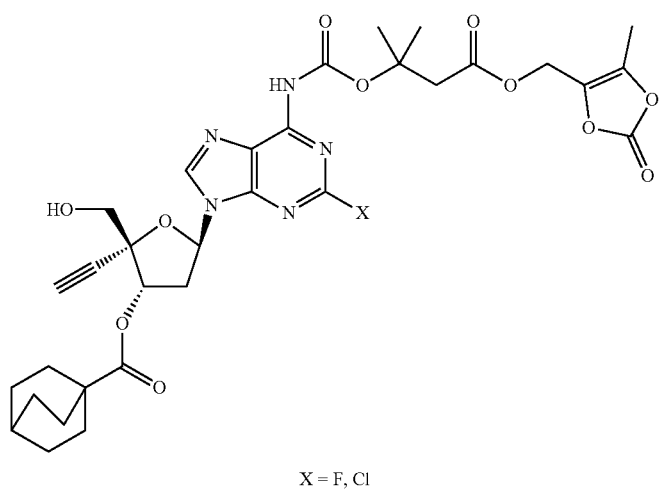
X = F, Cl
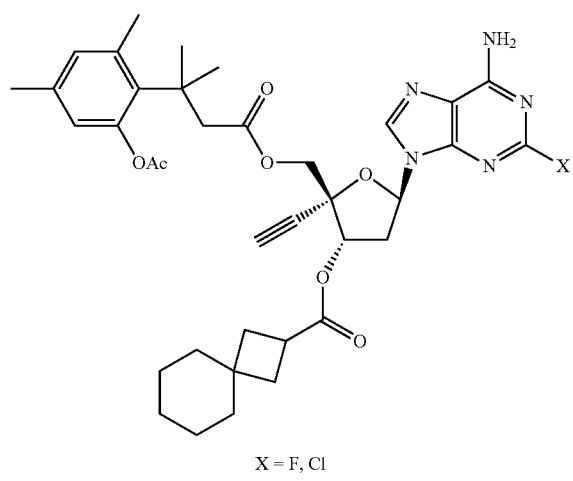
X = F, Cl 63   64
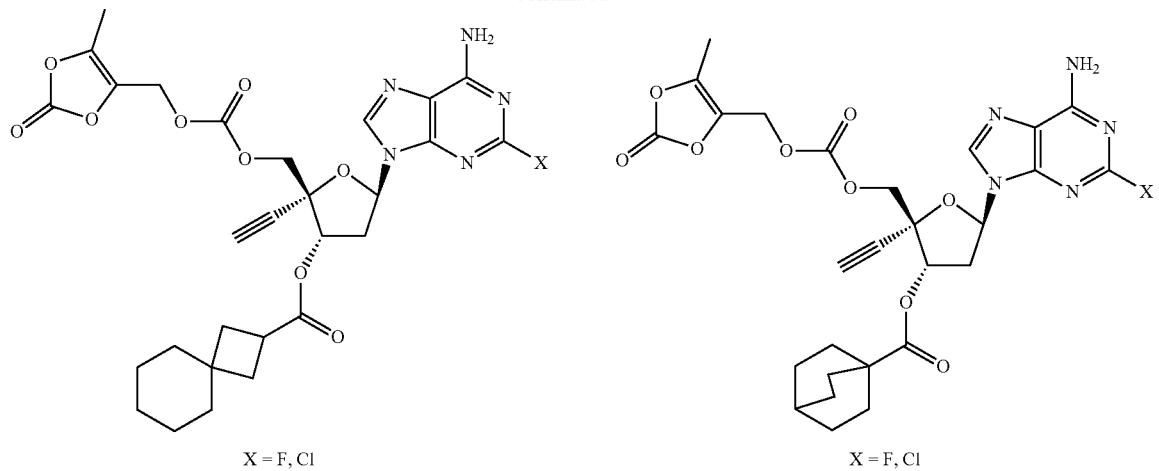
X = F, Cl
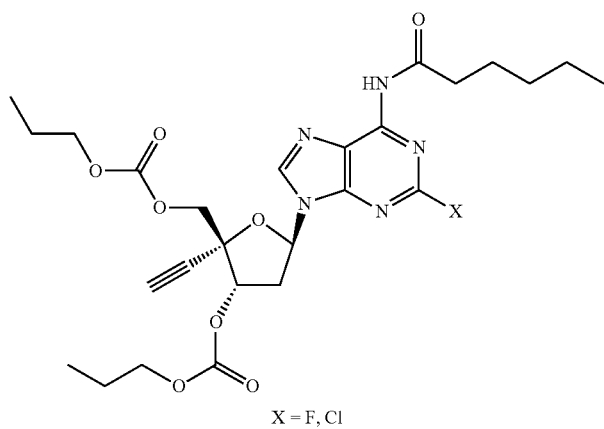
X = F, Cl
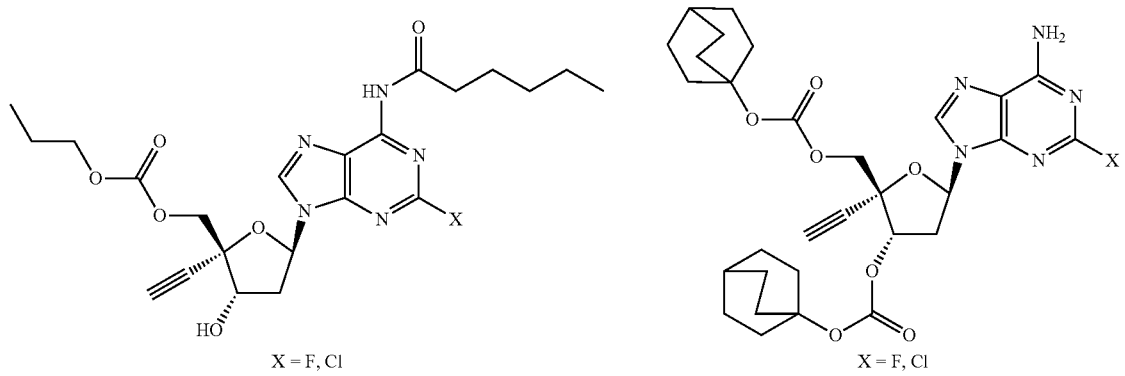
X = F, Cl 65
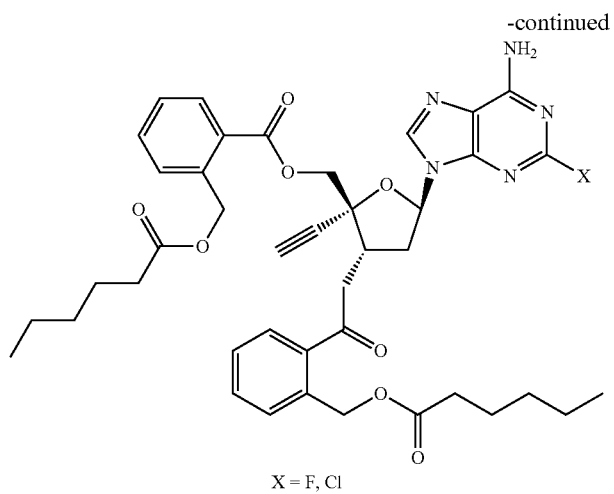
X = F, Cl
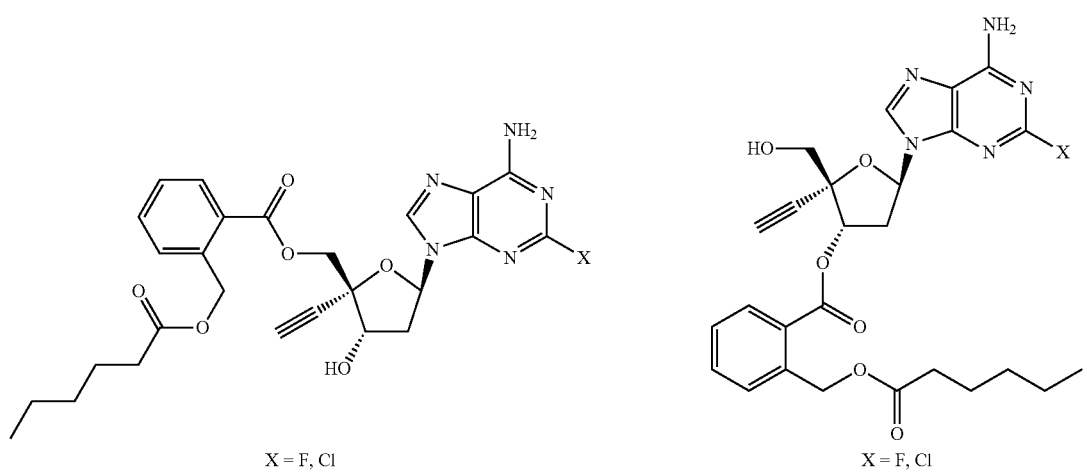
66
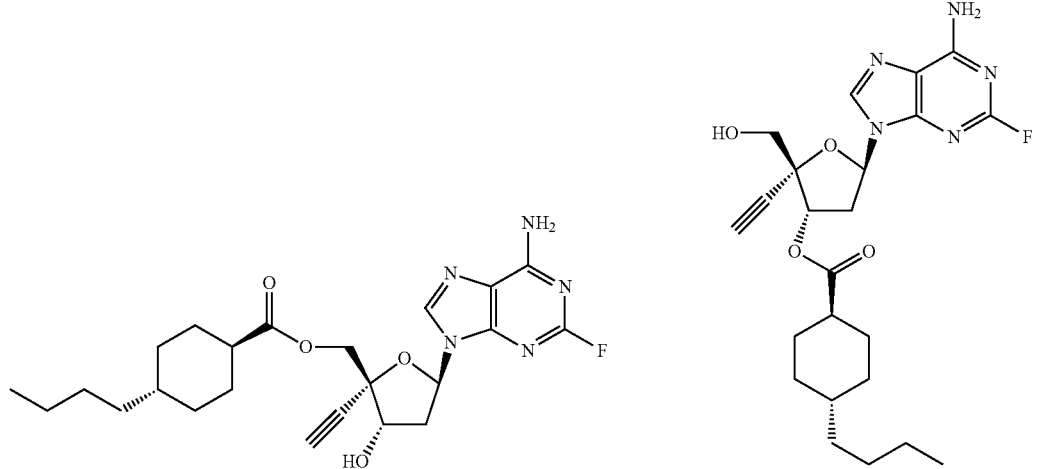

-continued
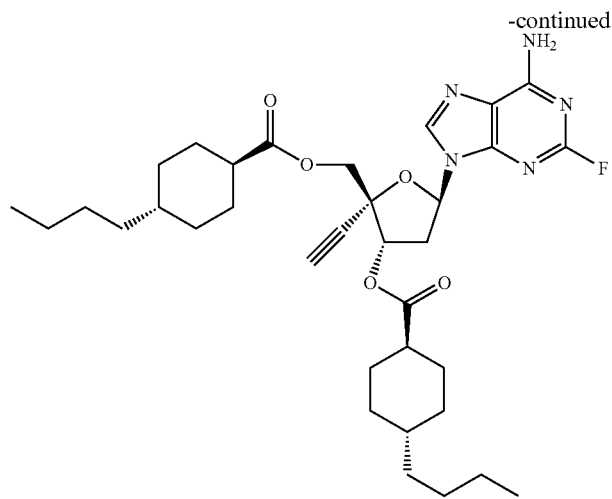
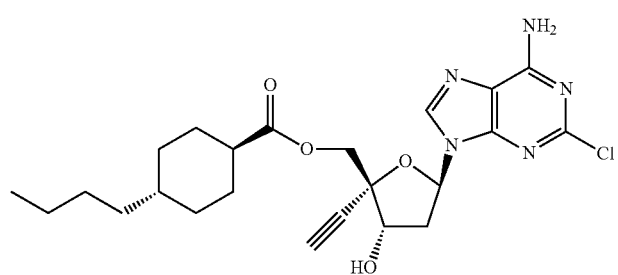
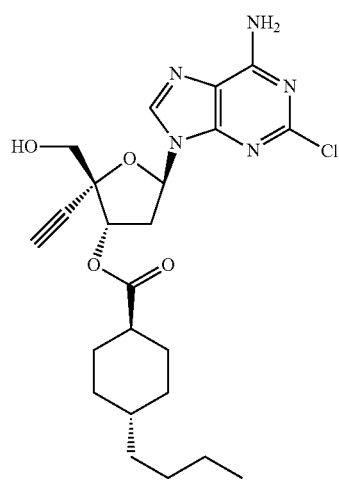
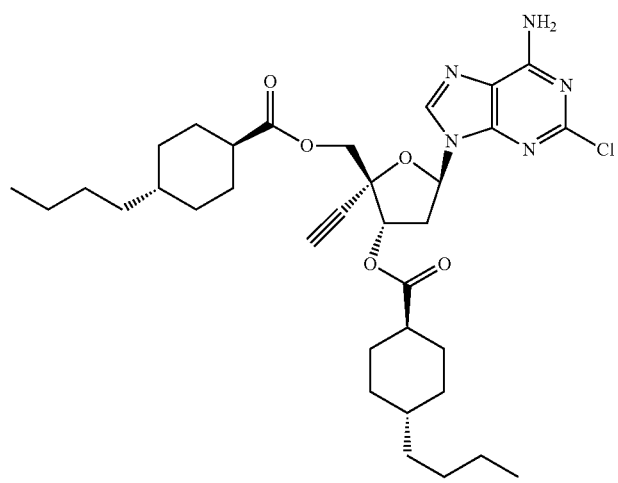

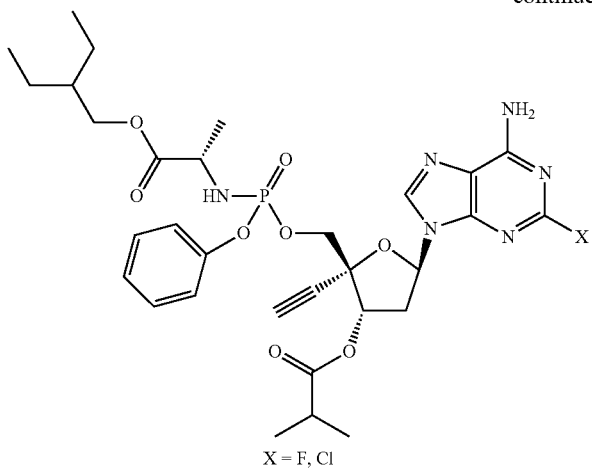
X = F, Cl
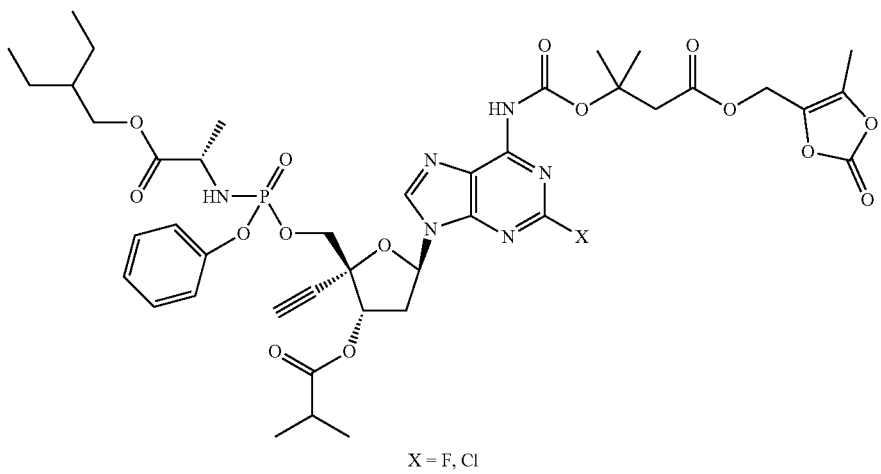
X = F, Cl
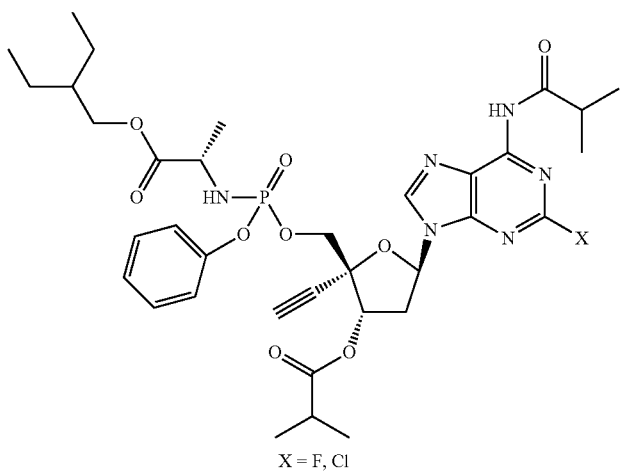
X = F, Cl

-continued
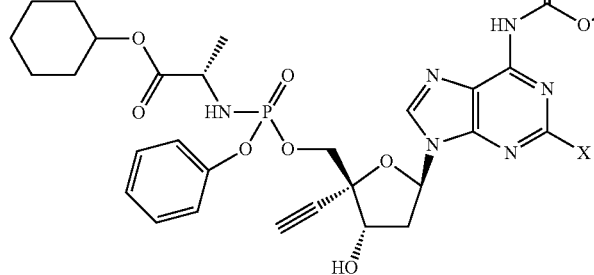
X = F, Cl
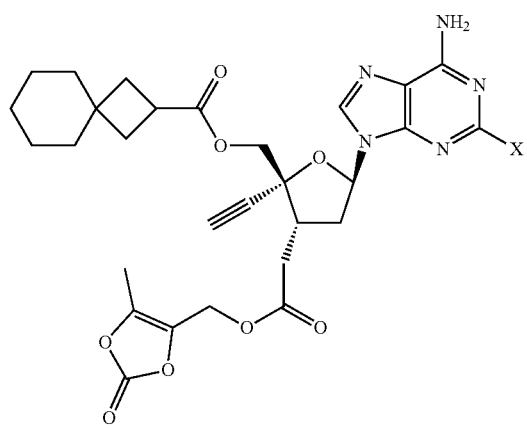
X = F, Cl
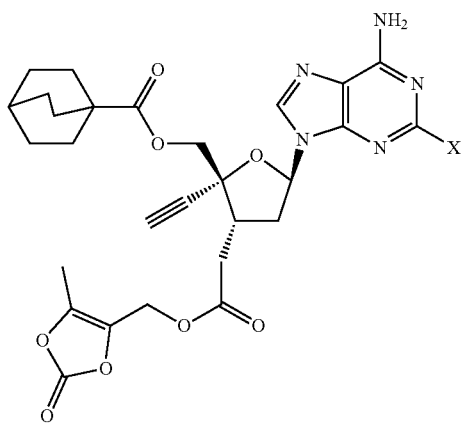
X = F, Cl
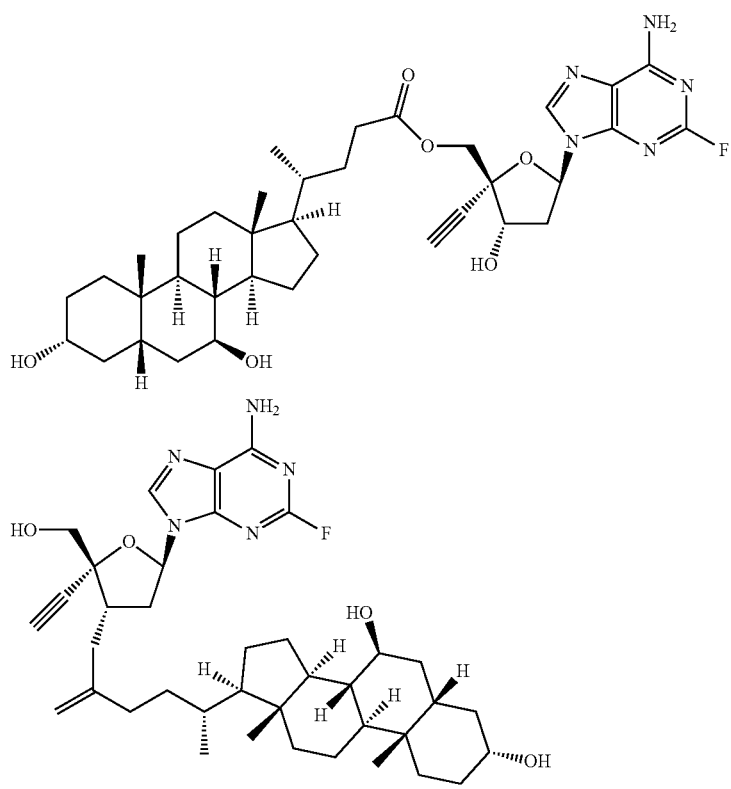

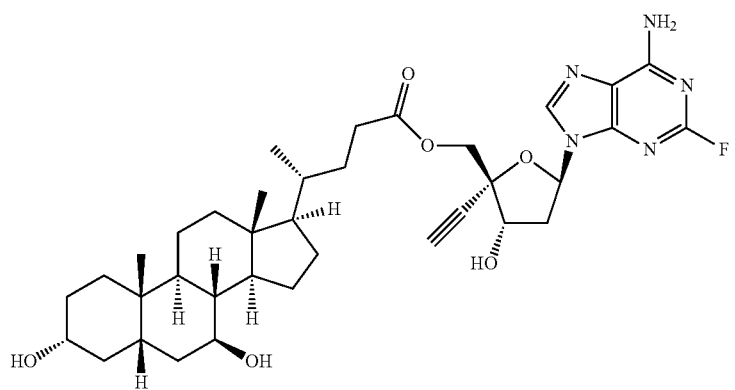
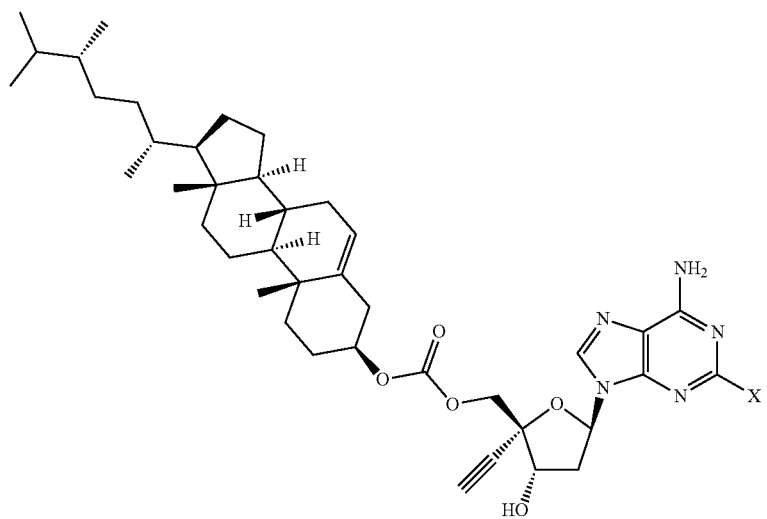
X = F, Cl
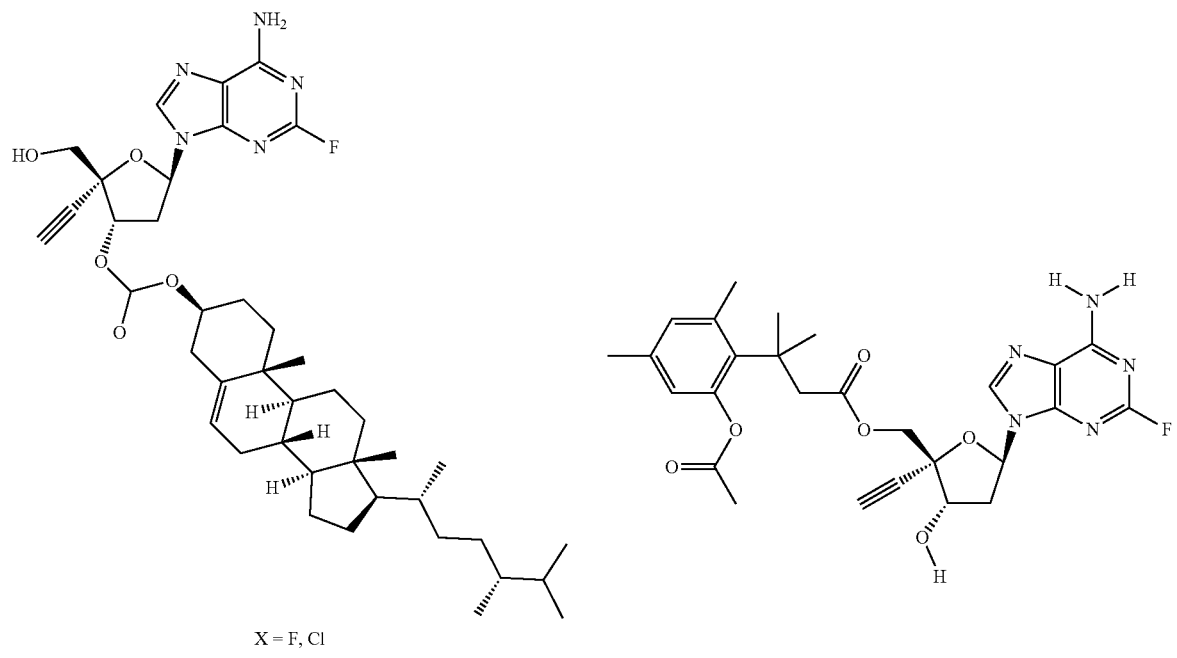
X = F, Cl

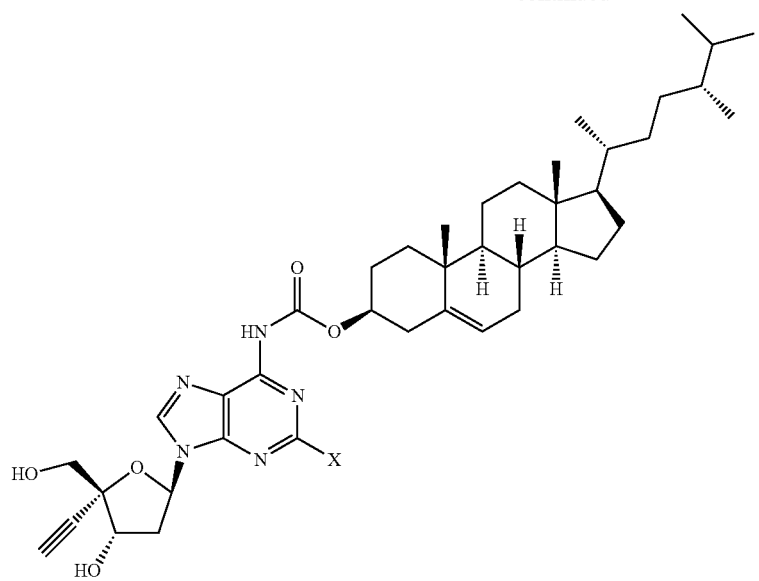
X = F, Cl
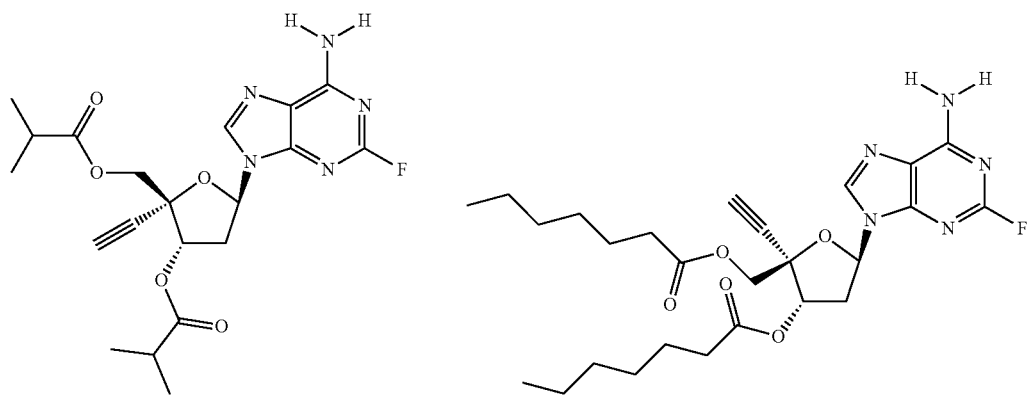
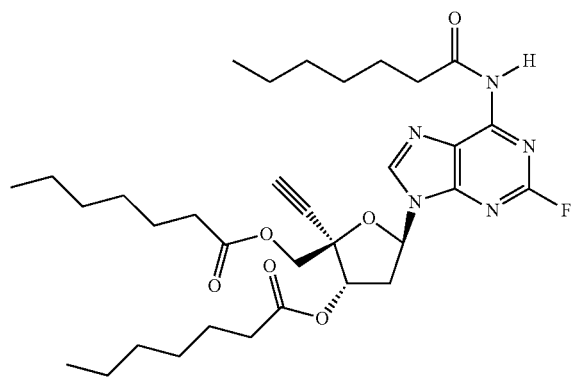

-continued
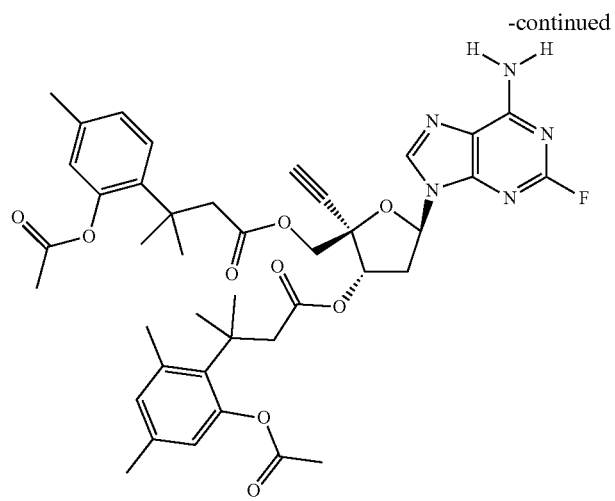
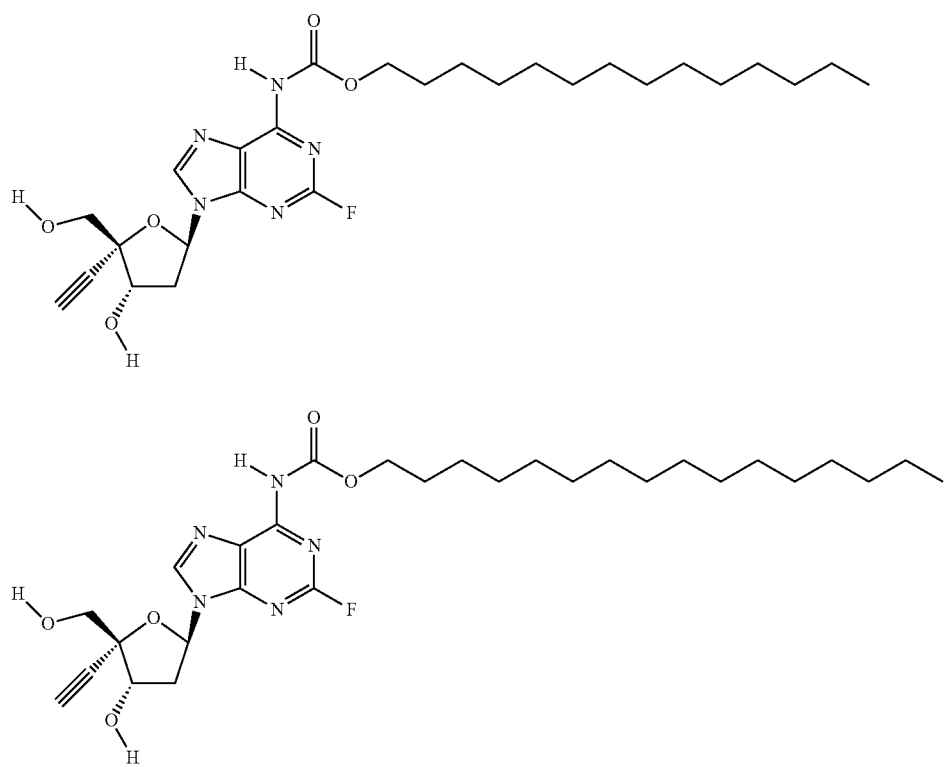
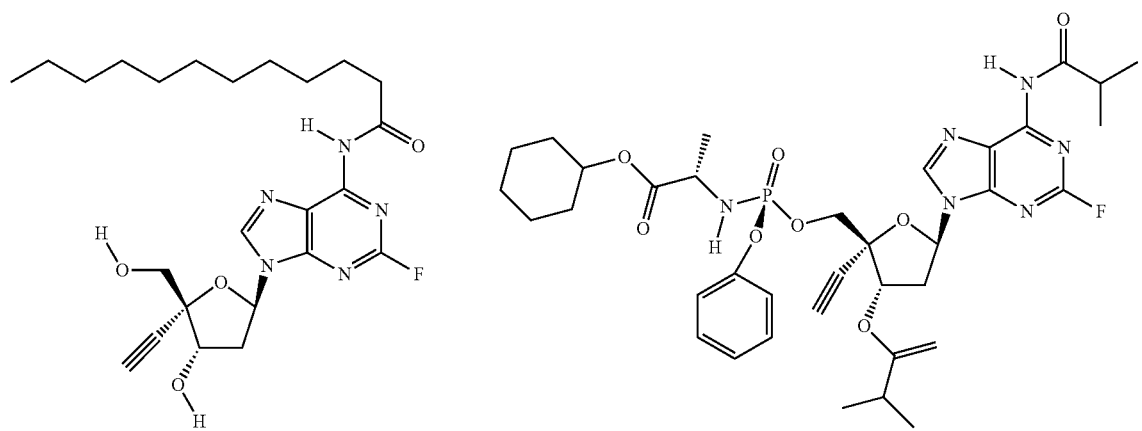

-continued
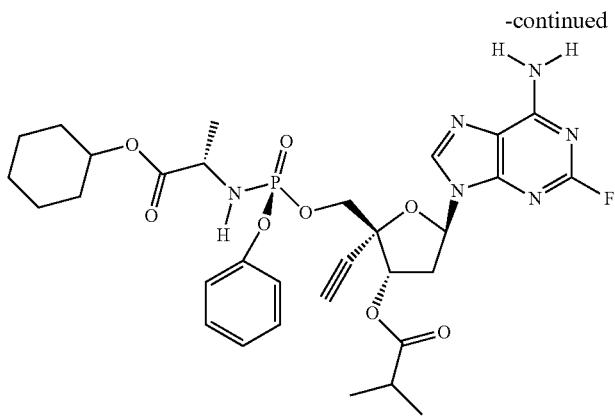
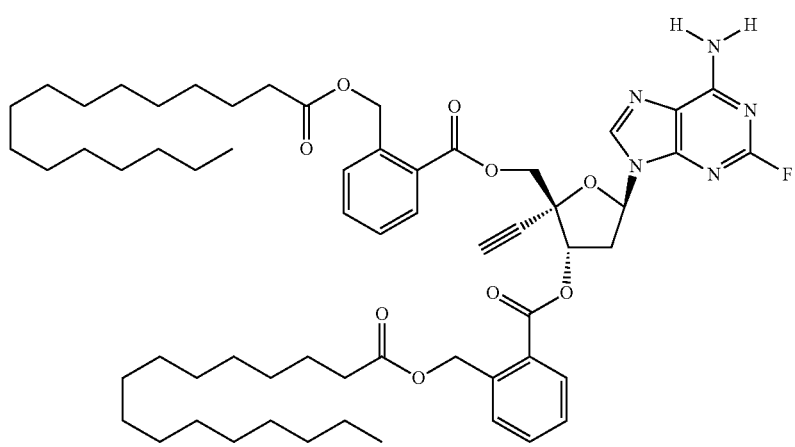
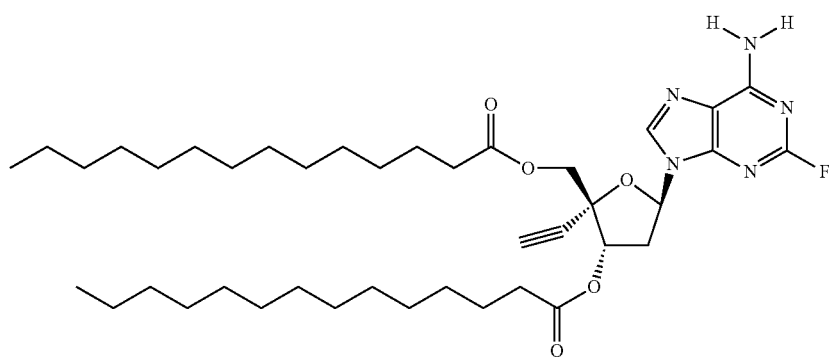
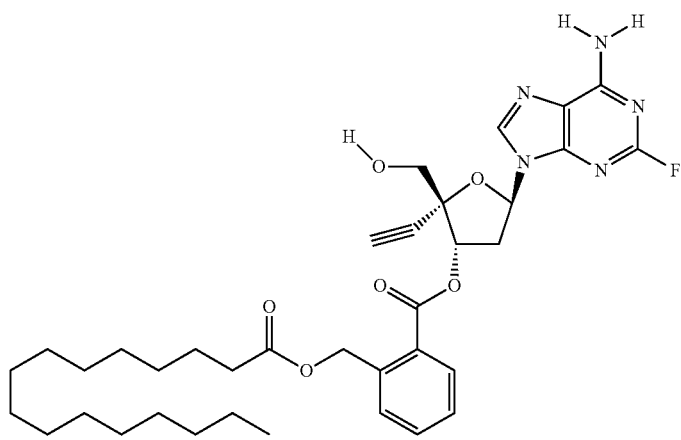

-continued
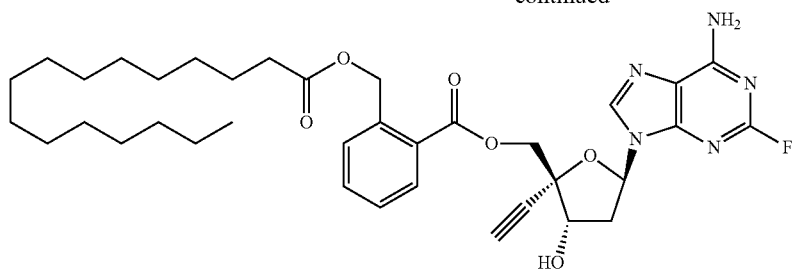
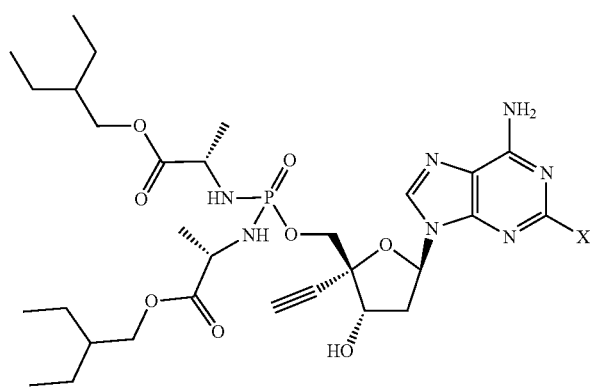
X = F, Cl
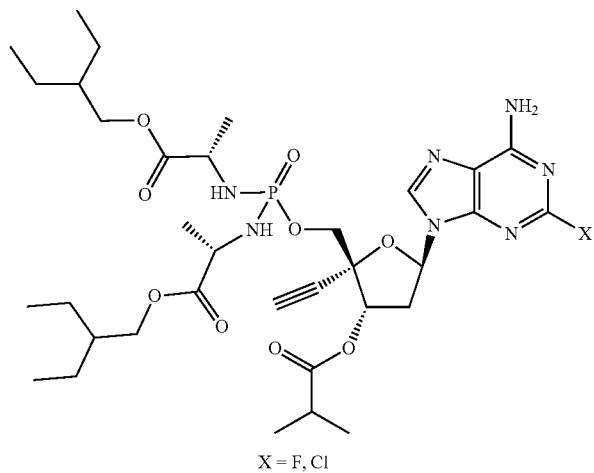
X = F, Cl
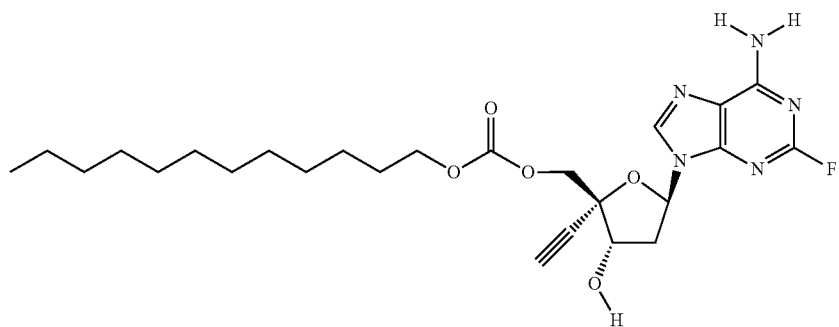

83
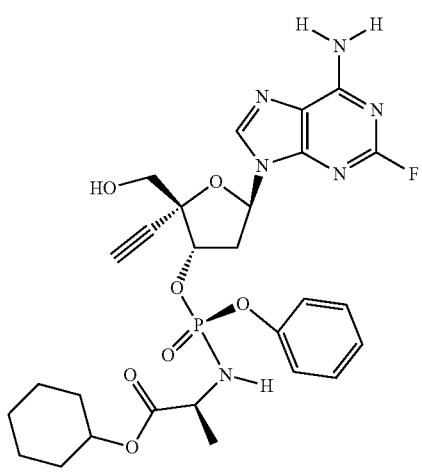
84
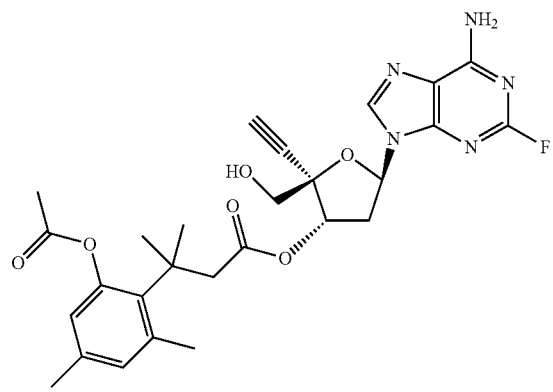
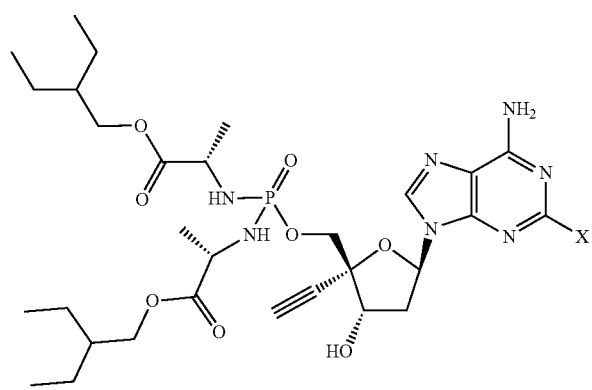
X = F, Cl
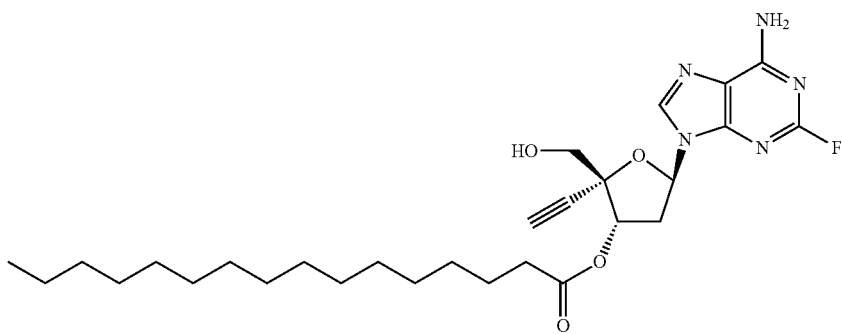
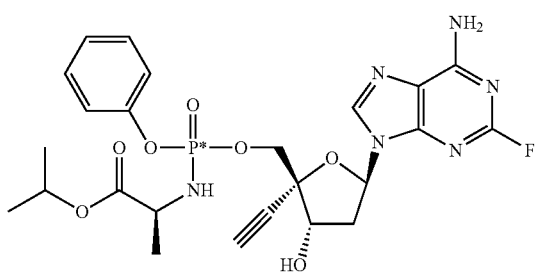

-continued
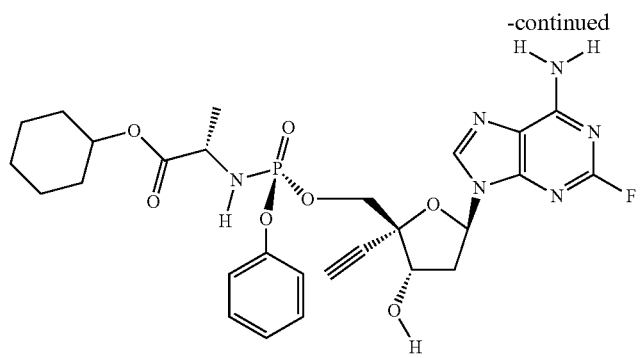
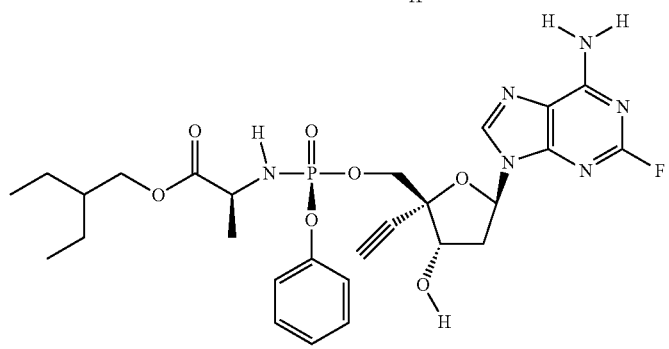
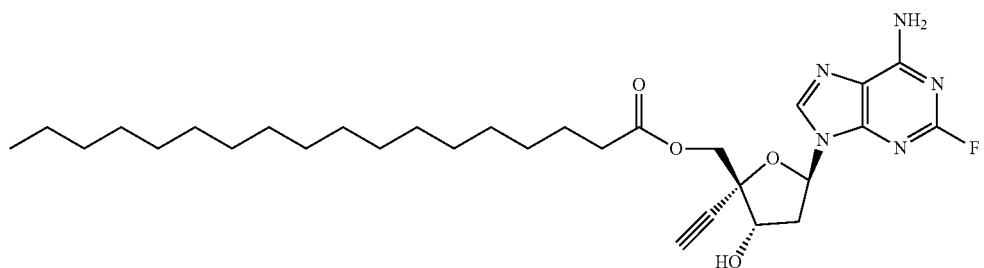
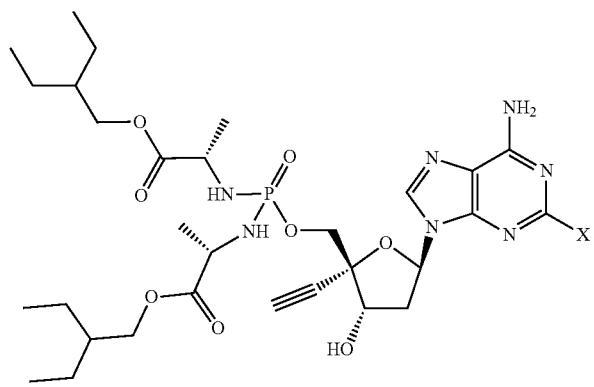
X = F, Cl
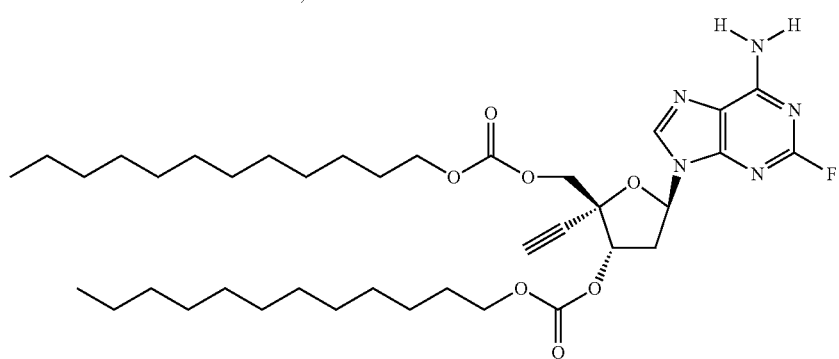

-continued
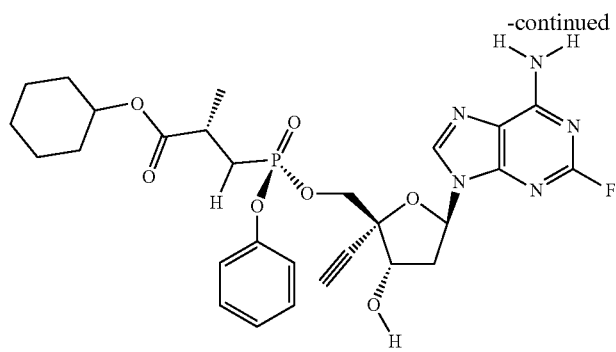
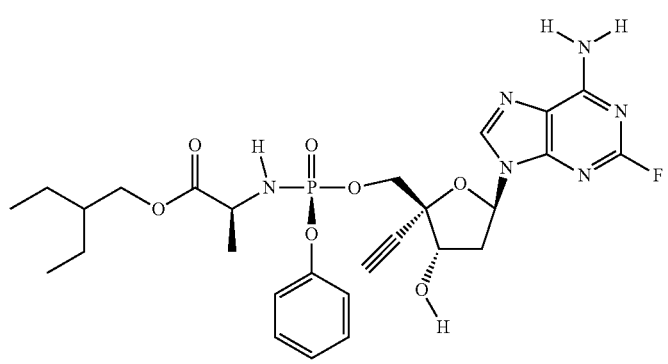
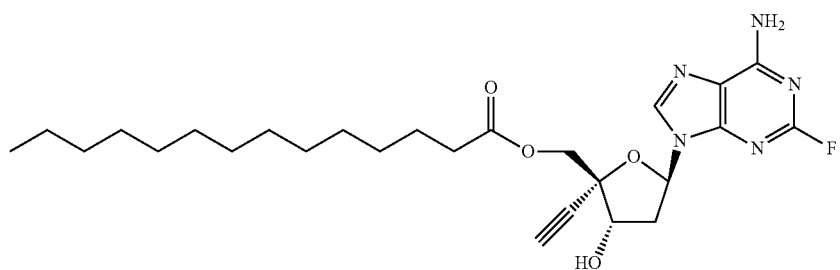
or
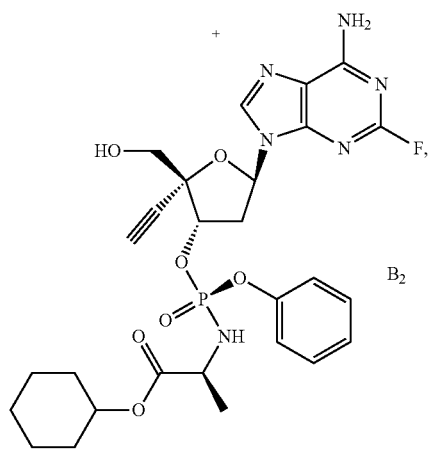
B₂
or a pharmaceutically acceptable salt thereof. For the compounds above with "X=F, Cl" language, this intended to be the same as explicitly disclosing each compound (one where X=F and a separate one where X=Cl) individually.

In some embodiments, the compound is
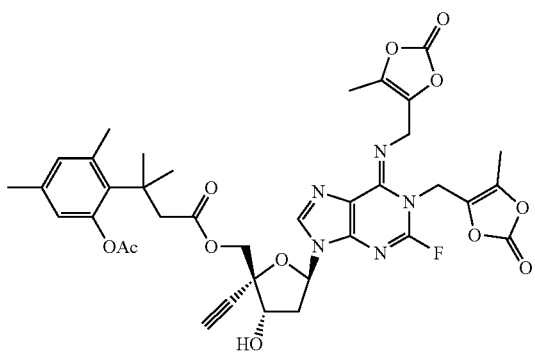
or a pharmaceutically acceptable salt thereof.
In some embodiments, the compound is
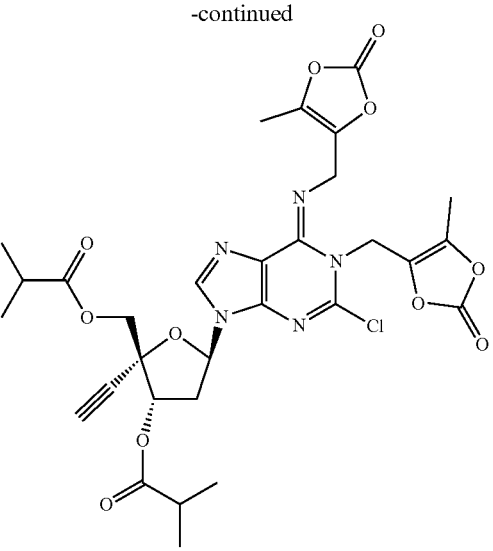
or
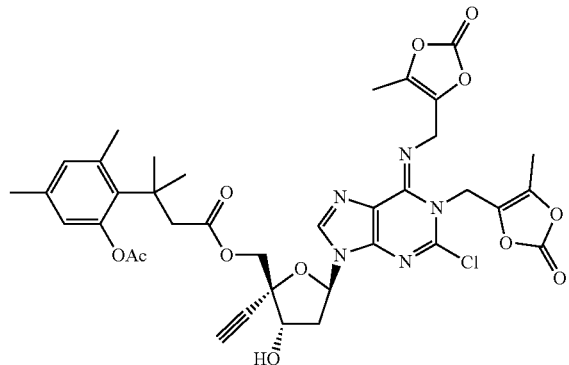
or a pharmaceutically acceptable salt thereof.
In some embodiments, the compound is
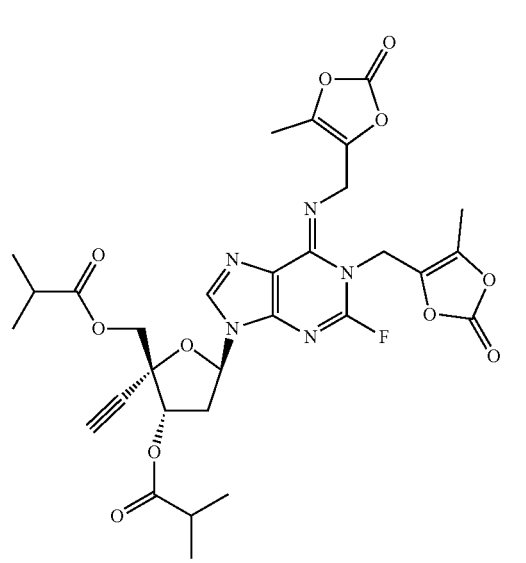
or
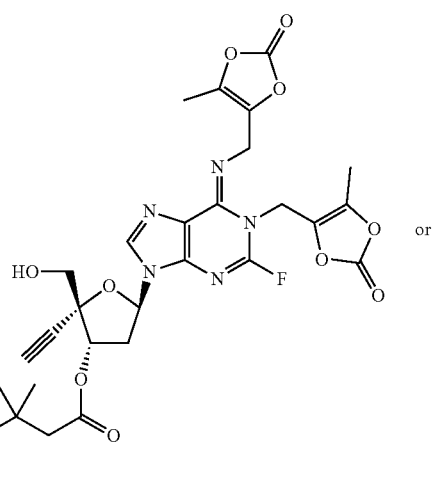
or a pharmaceutically acceptable salt thereof.

III. Pharmaceutical Compositions

In some embodiments, the present disclosure provides a pharmaceutical composition comprising a compound of the present disclosure, and a pharmaceutically acceptable excipient.

In some embodiments, the pharmaceutical composition comprises one or more additional therapeutic agents, as more fully set forth below.

Pharmaceutical compositions comprising the compounds disclosed herein, or pharmaceutically acceptable salts thereof, may be prepared with one or more pharmaceutically acceptable excipients that may be selected in accord with ordinary practice. Tablets may contain excipients including glidants, fillers, binders and the like. Aqueous compositions may be prepared in sterile form, and when intended for delivery by other than oral administration generally may be isotonic. In some embodiments, compositions may contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In some embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if desired, shaping the product. Techniques and formulations generally are found in Remington: The Science and Practice of Pharmacy, 21$^{st}$ Edition, Lippincott Williams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5 to about 95% of the total compositions (weight:weight).

In some embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition that can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of the present disclosure as a second or other active ingredient having a synergistic effect with other active ingredients in known drugs, or administration of the compound of the present disclosure together with such drugs.

The compound of the present disclosure may also be used in the form of a prodrug or other suitably modified form that releases the active ingredient in vivo.

IV. Methods of Treatment

HIV Infection

The present disclosure provides methods of treating and/or preventing human immunodeficiency virus (HIV) infection in a subject in need thereof. In some embodiments, a method of treating and/or preventing HIV infection in a subject in need thereof comprises administering to the subject a composition provided herein. In some embodiments, the method is for treating and/or preventing HIV-1 infection. In some embodiments, the method is for treating and/or preventing HIV-2 infection.

In some embodiments, a method of treating HIV infection in a subject in need thereof comprises administering to the subject a composition provided herein. In some such embodiments, the subject is HIV positive. In some such embodiments, the subject is of unknown HIV status. In some such embodiments, the subject is not HIV negative.

In some embodiments, a method of preventing HIV infection in a subject in need thereof comprises administering to the subject a composition provided herein. In some such embodiments, the subject is HIV negative. In some embodiments, the subject is at risk of acquiring HIV infection.

In some embodiments, the present disclosure provides compositions for use in the treatment and/or prevention of HIV infection in a subject.

In some embodiments, the present disclosure provides compositions for the manufacture of a medicament for treating and/or preventing HIV infection in a subject.

In some embodiments, the present disclosure provides a method of treating and/or preventing HIV infection in a subject in need thereof, comprising administering to the subject a combination therapy comprising a composition provided herein and one or more (e.g., one, two, three, one or two, or one to three) additional therapeutic agents. In some embodiments, a method for treating an HIV infection in a human subject having or at risk of having the infection is provided, comprising administering to the human subject a therapeutically effective amount of a composition disclosed herein, in combination with a therapeutically effective amount of one or more (e.g., one, two, three, one or two, or one to three) additional therapeutic agents. In some embodiments, the subject is receiving or has received one or more additional therapeutic agents. In some embodiments, the additional therapeutic agents are selected from the same class of therapeutic agents. In some embodiments, the additional therapeutic agents are selected from a different class of therapeutic agents. In some embodiments, the additional therapeutic agent is suitable for treating and/or preventing HIV infection. In some embodiments, the additional therapeutic agent is not for treating and/or preventing HIV infection.

In some embodiments, the combination therapy comprises administering a composition provided herein and one, two, three, four, or more additional therapeutic agents. In some embodiments, the combination therapy comprises co-administering a composition provided herein and two additional therapeutic agents. In some embodiments, the combination therapy comprises administering a composition provided herein and three additional therapeutic agents. In some embodiments, the combination therapy comprises administering a composition provided herein and four additional therapeutic agents.

The additional therapeutic agent can be any additional therapeutic agent disclosed herein. In some embodiments, the additional therapeutic agent is disclosed in the HIV Combination Therapy sections herein. In some embodiments, the additional therapeutic agent is disclosed in the HBV Combination Therapy sections herein.

In some embodiments, the additional therapeutic agent is an anti-HIV agent. For example, in some embodiments, the additional therapeutic agent is selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, HIV Tat or Rev inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, HIV-1 Nef modulators, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for treating and/or preventing HIV infection, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a combination drug treating and/or preventing HIV infection. Examples of combination drugs for treating and/or preventing HIV infection include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC);

EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY (bictegravir+emtricitabine+tenofovir alafenamide), DOVATO, TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; cabotegravir+rilpivirine; elpida (elsulfavirine; VM-1500; VM-1500A).

In some embodiments, the additional therapeutic agent is a drug for treating and/or preventing HIV infection. Examples of other drugs for treating and/or preventing HIV infection include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

In some embodiments, the additional therapeutic agent is a HIV protease inhibitor. Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

In some embodiments, the additional therapeutic agent is a reverse transcriptase inhibitor. Reverse transcriptase inhibitors can be non-nucleoside/non-nucleotide inhibitors or nucleoside/nucleotide inhibitors.

In some embodiments, the additional therapeutic agent is non-nucleoside or non-nucleotide reverse transcriptase inhibitors. Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and elsulfavirine (VM-1500.).

In some embodiments, the additional therapeutic agent is a nucleoside or nucleotide reverse transcriptase inhibitor. Examples of nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-8583, VM-2500 and KP-1461.

In some embodiments, the additional therapeutic agent is a HIV integrase inhibitor. Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

In some embodiments, a HIV integrase inhibitor is a non-catalytic site (i.e., allosteric) integrase inhibitor (NCINI). Examples of NCINIs include CX-05045, CX-05168, and CX-1442.

In some embodiments, the additional therapeutic agent is a HIV entry (fusion) inhibitor. Examples of HIV entry (fusion) inhibitors include cenicriviroc, CCR5 inhibitors, gp41 inhibitors, CD4 attachment inhibitors, gp120 inhibitors, and CXCR4 inhibitors.

In some embodiments, the additional therapeutic agent is a CCR5 inhibitor. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

In some embodiments, the additional therapeutic agent is a gp41 inhibitor. Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

In some embodiments, the additional therapeutic agent is a CD4 attachment inhibitor. Examples of CD4 attachment inhibitors include ibalizumab and CADA analogs.

In some embodiments, the additional therapeutic agent is a gp120 inhibitor. Examples of gp120 inhibitors include Radha-108 (receptol) 3B3-PE38, BanLec, bentonite-based nanomedicine, fostemsavir tromethamine, IQP-0831, and BMS-663068.

In some embodiments, the additional therapeutic agent is a CXCR4 inhibitor. Examples of CXCR4 inhibitors include plerixafor, ALT-1188, N15 peptide, and vMIP (Haimipu).

In some embodiments, the additional therapeutic agent is a HIV maturation inhibitor. Examples of HIV maturation inhibitors include BMS-955176, GSK-3640254 and GSK-2838232.

In some embodiments, the additional therapeutic agent is a latency reversing agent. Examples of latency reversing agents include toll-like receptor (TLR) agonists (including TLR7 agonists, e.g., GS-9620), histone deacetylase (HDAC) inhibitors, proteasome inhibitors such as velcade, protein kinase C (PKC) activators, Smyd2 inhibitors, BET-bromodomain 4 (BRD4) inhibitors, ionomycin, IAP antagonists (inhibitor of apoptosis proteins, such as APG-1387, LBW-242), SMAC mimetics (including TL32711, LCL161, GDC-0917, HGS1029, AT-406), PMA, SAHA (suberanilohydroxamic acid, or suberoyl, anilide, and hydroxamic acid), NIZ-985, IL-15 modulating antibodies (including IL-15, IL-15 fusion proteins and IL-15 receptor agonists), JQ1, disulfiram, amphotericin B, and ubiquitin inhibitors such as largazole analogs, APH-0812, and GSK-343.

In some embodiments, the additional therapeutic agent is a HDAC (e.g., histone deacetylase 9 (HDAC9, HD7, HD7b, HD9, HDAC, HDAC7, HDAC7B, HDAC9B, HDAC9FL, HDRP, MITR; Gene ID: 9734) inhibitor. Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, romidepsin, SHP-141, valproic acid (VAL-001), vorinostat, tinostamustine, remetinostat, and entinostat.

In some embodiments, the additional therapeutic agent is a PKC activator. Examples of PKC activators include indolactam, prostratin, ingenol B, and DAG-lactones.

In some embodiments, the additional therapeutic agent is a capsid inhibitor. Examples of capsid inhibitors include include capsid polymerization inhibitors or capsid disrupting compounds, HIV nucleocapsid p7 (NCp7) inhibitors such as azodicarbonamide, HIV p24 capsid protein inhibitors, GS-6207, GS-CA1, AVI-621, AVI-101, AVI-201, AVI-301, and AVI-CAN1-15 series, and compounds described in this patent, GSK WO2019/087016.

In some embodiments, the additional therapeutic agent is selected from one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune checkpoints can augment the effect of immune checkpoint inhibitors in infective therapeutics. In some embodiments, the immune checkpoint proteins or receptors regulate T cell responses (e.g., reviewed in Xu, et al., *J Exp Clin Cancer Res*. (2018) 37:110). In various embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the additional therapeutic agent is a blocker or inhibitor of one or more T-cell inhibitory immune checkpoint proteins or receptors. Examples of T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278);

inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res.* (2018) 37:110.

In some embodiments, the additional therapeutic agent is a blocker or inhibitor of one or more NK-cell inhibitory immune checkpoint proteins or receptors. Examples of NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

In some embodiments, the additional therapeutic agent is an inhibitor of CLTA4. Examples of inhibitors of CLTA4 include ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

In some embodiments, the additional therapeutic agent is an inhibitors of PD-L1 (CD274) or PD-1 (PDCD1). Examples of inhibitors of PD-L1 (CD274) or PD-1 (PDCD1) include pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In some embodiments, the additional therapeutic agent is an anti-TIGIT antibody. Examples of anti-TIGIT antibodies include BMS-986207, RG-6058, and AGEN-1307.

In some embodiments, the additional therapeutic agent is an agonist of one or more TNF receptor superfamily (TNFRSF) members, e.g., an agonist of one or more of TNFRSF1A (NCBI Gene ID: 7132), TNFRSF IB (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

In some embodiments, the additional therapeutic agent is an anti-TNFRSF4 (OX40) antibody. Examples of anti-TNFRSF4 (OX40) antibodies include MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

In some embodiments, the additional therapeutic agent is an anti-TNFRSF5 (CD40) antibody. Examples of anti-TNFRSF5 (CD40) antibodies include RG7876, SEA-CD40, APX-005M, and ABBV-428.

In some embodiments, the additional therapeutic agent is an anti-TNFRSF7 (CD27) antibody. An example of an anti-TNFRSF7 (CD27) antibody is varlilumab (CDX-1127).

In some embodiments, the additional therapeutic agent is an anti-TNFRSF9 (4-IBB, CD137) antibody. Examples of anti-TNFRSF9 (4-1BB, CD137) antibodies include urelumab, utomilumab (PF-05082566), AGEN2373 and ADG-106.

In some embodiments, the additional therapeutic agent is an anti-TNFRSF18 (GITR) antibody. Examples of anti-TNFRSF18 (GITR) antibodies include MEDI1873, FPA-154, INCAGN-1876, TRX-518, BMS-986156, MK-1248, GWN-323, and those described in WO2017096179, WO2017096276, WO2017096189, and WO2018089628.

In some embodiments, the additional therapeutic agent is an antibody, or fragment thereof, co-targeting TNFRSF4 (OX40) and TNFRSF18 (GITR). Such antibodies are described, e.g., in WO2017096179 and WO2018089628.

In some embodiments, the additional therapeutic agent is a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers include those that target CD16 and one or more HIV-associated antigens. BiKEs and TriKEs are described, e.g., in Felices et al., *Methods Mol Biol*. (2016) 1441:333-346; Fang et al., *Semin Immunol*. (2017) 31:37-54. Examples of a trispecific NK cell engager (TRiKE) include OXS-3550, and CD16-IL-15-B7H3 TriKe.

In some embodiments, the additional therapeutic agent is an inhibitor of indoleamine 2,3-dioxygenase 1 (IDO1; NCBI Gene ID: 3620). Examples of IDO1 inhibitors include BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

In some embodiments, the additional therapeutic agent is an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists include AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An example of a TLR7/TLR8 agonist is NKTR-262, telratolimod and BDB-001. Examples of TLR8 agonists include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and U.S. Pat. No. 2,013,025 1673 (Novira Therapeutics). Example TLR9 agonists include AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PEIL-042. Examples of TLR3 agonists include rintatolimod, poly-ICLC, RIBOXXON®, Apoxxim, RIBOXXIM®, IPH-33, MCT-465, MCT-475, and ND-1.1. Examples of TLR4 agonists include G-100, and GSK-1795091.

In some embodiments, the additional therapeutic agent is a stimulator of interferon genes (STING) agonist or activator. Examples of STING receptor agonists or activators include ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

In some embodiments, the additional therapeutic agent is a RIG-I modulator such as RGT-100, or a NOD2 modulator, such as SB-9200, and IR-103.

In some embodiments, the additional therapeutic agent is an anti-TIM-3 antibody, such as TSR-022, LY-3321367, MBG-453, INCAGN-2390.

In some embodiments, the additional therapeutic agent is an anti LAG-3 (Lymphocyte-activation) antibody, such as relatlimab (ONO-4482), LAG-525, MK-4280, REGN-3767, INCAGN2385.

In some embodiments, the additional therapeutic agent is an interleukin agonist, such as IL-2, IL-7, IL-15, IL-10, IL-12 agonists; examples of IL-2 agonists such as proleukin (aldesleukin, IL-2); pegylated IL-2 (eg NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include CYT-107.

In some embodiments, the additional therapeutic agent is an immune-based therapy selected from include interferon alfa; interferon alfa-2b; interferon alfa-n3; pegylated interferon alfa; interferon gamma; Flt3 agonists; gepon; normferon, peginterferon alfa-2a, peginterferon alfa-2b, and RPI-MN.

In some embodiments, the additional therapeutic agent is a phosphatidylinositol 3-kinase (PI3K) inhibitor. Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

In some embodiments, the additional therapeutic agent is an integrin alpha-4/beta-7 antagonist. Examples of integrin alpha-4/beta-7 antagonists include PTG-100, TRK-170, abrilumab, etrolizumab, carotegrast methyl, and vedolizumab.

In some embodiments, the additional therapeutic agent is a HIV antibody, bispecific antibody, or "antibody-like" therapeutic protein. Examples of HIV antibodies, bispecific antibodies, and "antibody-like" therapeutic proteins include DARTs®, DUOBODIES®, BITES®, XmAbs®, TandAbs®, Fab derivatives, bNAbs (broadly neutralizing HIV-1 antibodies), TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

In some embodiments, the additional therapeutic agent is a bNAbs. Examples include those described in U.S. Pat. Nos. 8,673,307, 9,493,549, 9,783,594, WO2014/063059, WO2012/158948, WO2015/117008, and PCT/US2015/41272, and WO2017/096221, including antibodies 12A12, 12A21, NIH45-46, bANC131, 8ANC134, IB2530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid, et al., Nature, 458:636-640 (2009), Eroshkin et al, Nucleic Acids Res., 42 (Database issue):Dl 133-9 (2014), Mascola et al., Immunol Rev, 254(l):225-44 (2013), such as 2F5, 4E10, M66.6, CAP206-CH12, 10E81 (all of which bind the MPER of gp41); PG9, PG16, CHOI-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

In some embodiments, the additional therapeutic agent is a broadly neutralizing antibody, such as those described in e.g., U.S. Pat. Nos. 8,673,307; 9,493,549; 9,783,594; and WO 2012/154312; WO2012/158948; WO 2013/086533; WO 2013/142324; WO2014/063059; WO 2014/089152; WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include those described in Sajadi, et al., Cell. (2018) 173(7): 1783-1795; Sajadi et al., J Infect Dis. (2016) 213(1): 156-64; Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid et al., Nature, 458:636-640 (2009), Eroshkin et al., Nucleic Acids Res., 42 (Database issue):Dl 133-9 (2014), Mascola et al., Immunol Rev., 254(l):225-44 (2013), such as 2F5, 4E10, M66.6, CAP206-CH12, 10E8, 10E8v4, 10E8-5R-100cF, DH511.11P, 7b2, and LN01 (all of which bind the MPER of gp41).

Additional antibodies that can be used as the additional therapeutic agent include bavituximab, UB-421, BF520.1, CHOI, CH59, C2F5, C4E10, C2F5+C2G12+C4E10, 3BNC117, 3BNC117-LS, 3BNC60, DH270.1, DH270.6, D1D2, 10-1074-LS, GS-9722, DH411-2, BG18, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

Examples of HIV bispecific and trispecific antibodies include MGD014, B12BiTe, TMB-bispecific, SAR-441236, VRC-01/PGDM-1400/10E8v4, 10E8.4/iMab, 10E8v4/PGT121-VRC01.

Examples of in vivo delivered bnabs such as AAV8-VRC07; mRNA encoding anti-HIV antibody VRC01; and engineered B-cells encoding 3BNC117 (Hartweger et al, J. Exp. Med. 2019, 1301).

In some embodiments, the additional therapeutic agent is a pharmacokinetic enhancer. Examples pharmacokinetic enhancers include cobicistat and ritonavir.

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

In some embodiments, the additional therapeutic agent is a HIV vaccine. Examples of HIV vaccines include peptide vaccines, recombinant subunit protein vaccines, live vector vaccines, DNA vaccines, CD4-derived peptide vaccines, vaccine combinations, adenoviral vector vaccines (an adenoviral vector such as Ad5, Ad26 or Ad35), simian adenovirus (chimpanzee, gorilla, rhesus, i.e., rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, Venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replicating RNA/self-amplifying RNA vaccines.

Examples of vaccines include: rgp120 (AIDSVAX), ALVAC HIV (vCP1521)/AIDSVAXB/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3 S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, AD VAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MV A mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HI-VADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based vaccines (Vaxwave, TheraT), MVA-BN HIV-1 vaccine regimen, UBI HIV gp120, mRNA based prophylactic vaccines, and TBL-1203HI.

In some embodiments, the additional therapeutic agent is birth control (i.e., a contraceptive). Examples of birth control include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In some embodiments, a provided composition is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, a provided composition is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In some embodiments, a provided composition is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In some embodiments, a provided composition is combined with tenofovir, tenofovir disoproxil, tenofovir disoproxil fumarate, tenofovir alafenamide, or tenofovir alafenamide hemifumarate.

In some embodiments, a provided composition is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In some embodiments, a provided composition is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In some embodiments, a provided composition is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In some embodiments, the additional therapeutic agent is gene therapy or cell therapy. Gene therapy and cell therapy include genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of dendritic cell therapy include AGS-004. CCR5 gene editing agents include SB-728T. CCR5 gene inhibitors include Cal-1. In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

In some embodiments, the additional therapeutic agent is a gene editor (e.g., an HIV targeted gene editor). In some embodiments a genome editing system is selected from the group consisting of a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

In some embodiments, the additional therapeutic agent is CAR-T cell therapy. CAR-T cell therapy comprises a population of immune effector cells engineered to express a chimeric antigen receptor (CAR), wherein the CAR comprises an HIV antigen-binding domain. The HIV antigen includes an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include VC-CAR-T, CMV-N6-CART, anti-CD4 CART-cell therapy, CD4 CAR+C34-CXCR4+CCR5 ZFN T-cells, autologous hematopoietic stem cells genetically engineered to express a CD4 CAR and the C46 peptide.

In some embodiments, the additional therapeutic agent is TCR-T cell therapy. TCR-T cell therapy comprises TCR-T cells engineered to target HIV derived proteins present on the surface of virus-infected cells, for example ImmTAV.

In some embodiments, the antibodies or antigen-binding fragments described herein are combined with a population of B cells genetically modified to express broadly neutralizing antibodies, such as 3BNC117 (Hartweger et al, J. Exp. Med. 2019, 1301, Moffett et al., Sci. Immunol. 4, eaax0644 (2019) 17 May 2019).

HBV Infection

The present disclosure provides methods of treating and/or preventing hepatitis B virus (HBV) infection in a subject in need thereof. In some embodiments, a method of treating and/or preventing HBV infection in a subject in need thereof comprises administering to the subject a composition provided herein.

In some embodiments, a method of treating HBV infection in a subject in need thereof comprises administering to the subject a composition provided herein.

In some embodiments, a method of preventing HBV infection in a subject in need thereof comprises administering to the subject a composition provided herein. In some such embodiments, the subject is at risk of acquiring HBV infection.

In some embodiments, the present disclosure provides compositions for use in the treatment and/or prevention of HBV infection in a subject.

In some embodiments, the present disclosure provides compositions for the manufacture of a medicament for treating and/or preventing HBV infection in a subject.

In some embodiments, the present disclosure provides a method of treating and/or preventing HBV infection in a subject in need thereof, comprising administering to the subject a combination therapy comprising a composition provided herein and one or more additional therapeutic agents. In some embodiments, the subject is receiving or has received one or more additional therapeutic agents. In some embodiments, the additional therapeutic agents are selected from the same class of therapeutic agents. In some embodiments, the additional therapeutic agents are selected from a different class of therapeutic agents. In some embodiments, the additional therapeutic agent is for treating and/or preventing HBV infection. In some embodiments, the additional therapeutic agent is not for treating and/or preventing HBV infection.

In some embodiments, the present disclosure provides a method for treating an HBV infection, comprising administering to a subject in need thereof a therapeutically effective amount of a composition disclosed herein, in combination with a therapeutically effective amount of one or more (e.g., one, two, three, four, one or two, one to three, or one to four) additional therapeutic agents which are suitable for treating an HBV infection.

In some embodiments, a composition disclosed herein is combined with one, two, three, four, or more additional therapeutic agents. In some embodiments, a composition disclosed herein is combined with two additional therapeutic agents. In some embodiments, a composition disclosed herein is combined with three additional therapeutic agents. In some embodiments, a composition disclosed herein is combined with four additional therapeutic agents. The one, two, three, four, or more additional therapeutic agents can be different therapeutic agents selected from the same class of therapeutic agents, and/or they can be selected from different classes of therapeutic agents.

The compositions described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In some embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NODI, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In some embodiments, provided compositions are combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-di oxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

In some embodiments, the additional therapeutic agent is a HBV combination drug. Examples of HBV combination drugs include TRUVADA® (tenofovir disoproxil fumarate and emtricitabine); ABX-203, lamivudine, and PEG-IFN-alpha; ABX-203 adefovir, andPEG-IFNalpha; and INO-1800 (INO-9112 and RG7944).

In some embodiments, the additional therapeutic agent is another HBV drug. Examples of other drugs for the treatment of HBV infection include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16/28335A1 (Roche), WO16/20186A1 (Roche), US2016237090A (Roche), WO16/07833A1 (Roche), WO16/07832A1 (Roche), US2016176899A (Roche), WO16/02438A1 (Roche), WO16012470A1 (Roche), US2016220586A (Roche), and US2015031687A (Roche).

In some embodiments, the additional therapeutic agent is an HBV vaccine. In some embodiments, the HBV vaccine is a prophylactic HBV vaccine. Examples of prophylactic HBV vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV- 001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

In some embodiments, the HBV vaccine is a therapeutic HBV vaccine. Examples of therapeutic HBV vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, Altra-HepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

In some embodiments, the additional therapeutic agent is an HBV DNA polymerase inhibitor. Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

In some embodiments, the additional therapeutic agent is an immunomodulatory. Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, AIC-649, and IR-103.

In some embodiments, the additional therapeutic agent is a toll-like receptor (TLR) modulator. TLR modulators include modulators of TLR1, TLR2, TLR3, TLR4, TLR5, TLR6, TLR7, TLR8, TLR9, TLR10, TLR11, TLR12, and TLR13.

In some embodiments, the TLR modulator is a TLR3 modulator. Examples of TLR3 modulators include rintatolimod, poly-ICLC, RIBOXXON®, Apoxxim, RIBOXXIM®, IPH-33, MCT-465, MCT-475, GS-9688 and ND-1.1.

In some embodiments, the TLR modulator is a TLR7 modulator. Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences).

In some embodiments, the TLR modulator is a TLR8 modulator. Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

In some embodiments, the TLR modulator is a TLR9 modulator. Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

In some embodiments, the additional therapeutic agent is an interferon alpha receptor ligand. Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

In some embodiments, the additional therapeutic agent is a hyaluronidase inhibitor. An example of a hyaluronidase inhibitor is astodrimer.

In some embodiments, the additional therapeutic agent is a hepatitis B surface antigen (HBsAg) inhibitor. Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP- 2163, REP-2165, REP-2053, REP-2031 and REP-006, and REP-9 AC'. An example of HBsAg secretion inhibitor is BM601.

In some embodiments, the additional therapeutic agent is a cytotoxic T-lymphocyte-associated protein 4 (ipi4) inhibitor. Examples of cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

In some embodiments, the additional therapeutic agent is a cyclophilin inhibitor. Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

In some embodiments, the additional therapeutic agent is a HBV viral entry inhibitor. An example of an HBV viral entry inhibitor is Myrcludex B.

In some embodiments, the additional therapeutic agent is an antisense oligonucleotide targeting viral mRNA. Examples of antisense oligonucleotide targeting viral mRNA include ISIS-HBVRx, IONIS-HBVRx, IONIS-GSK6-LRx, GSK-3389404, RG-6004.

In some embodiments, the additional therapeutic agent is a short interfering RNA (siRNA). Examples of siRNA include TKM-HBV (TKM-HepB), ALN-HBV, SR-008, HepB-nRNA, and ARC-520, ARC-521, ARB-1740, ARB-1467.

In some embodiments, the additional therapeutic agent is a DNA-directed RNA interference (ddRNAi). An example of ddRNAi is BB-HB-331.

In some embodiments, the additional therapeutic agent is an endonuclease modulator. An example of an endonuclease modulator is PGN-514.

In some embodiments, the additional therapeutic agent is a ribonucleotide reductase inhibitor. An example of a ribonucleotide reductase inhibitor is Trimidox.

In some embodiments, the additional therapeutic agent is an HBV E antigen inhibitor. An example of a HBV E antigen inhibitor is wogonin.

In some embodiments, the additional therapeutic agent is a covalently closed circular DNA (cccDNA) inhibitor. Examples of cccDNA inhibitors include BSBI-25 and CHR-101.

In some embodiments, the additional therapeutic agent is a farnesoid x receptor agonist. An example of a farnesoid x receptor agonist is EYP-001.

In some embodiments, the additional therapeutic agent is an HBV antibody. Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed). Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088). Fully human monoclonal antibodies such as HBC-34.

In some embodiments, the additional therapeutic agent is a CCR2 chemokine antagonist. An example of a CCR2 chemokine antagonist is propagermanium.

In some embodiments, the additional therapeutic agent is a thymosin agonist. An example of a thymosin agonist is Thymalfasin, recombinant thymosin alpha 1 (GeneScience).

In some embodiments, the additional therapeutic agent is a cytokine. Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

In some embodiments, the additional therapeutic agent is a nucleoprotein modulator. In some embodiments, the nucleoprotein modulator is a HBV core or capsid protein inhibitor. Examples of nucleoprotein modulators include AB-423, AT-130, GLS4, NVR-1221, NVR-3778, BAY 41-4109, morphothiadine mesilate, JNJ-379, RG-7907, ABI-H0731, ABI-H2158 and DVR-23. Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

In some embodiments, the additional therapeutic agent is a stimulator of retinoic acid-inducible gene 1. Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

In some embodiments, the additional therapeutic agent is a stimulator of NOD2. An example of a stimulator of NOD2 is SB-9200.

In some embodiments, the additional therapeutic agent is a phosphatidylinositol 3-kinase (PI3K) inhibitor. Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

In some embodiments, the additional therapeutic agent is an indoleamine-2, 3-dioxygenase (IDO) pathway inhibitor. Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

In some embodiments, the additional therapeutic agent is a PD-1 inhibitor. Examples of PD-1 inhibitors include nivolumab, pembrolizumab, pidilizumab, BGB-108, SHR-1210, PDR-001, PF-06801591, IBI-308, GB-226, STI-1110, and mDX-400.

In some embodiments, the additional therapeutic agent is a PD-L1 inhibitor. Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

In some embodiments, provided compositions are combined with compounds such as those disclosed in WO2018026971, US20180044329, US20180044305, US20180044304, US20180044303, US20180044350, US20180057455, US20180057486, US20180045142, WO20180044963, WO2018044783, WO2018009505, WO20180044329, WO2017066227, WO2017087777, US20170145025, WO2017079669, WO2017070089, US2017107216, WO2017222976, US20170262253, WO2017205464, US20170320875, WO2017192961, WO2017112730, US20170174679, WO2017106634, WO2017202744, WO2017202275, WO2017202273, WO2017202274, WO2017202276, WO2017180769, WO2017118762, WO2016041511, WO2016039749, WO2016142835, WO2016142852, WO2016142886, WO2016142894, and WO2016142833.

In some embodiments, the additional therapeutic agent is a recombinant thymosin alpha-1. Examples of recombinant thymosin alpha-1 include NL-004 and PEGylated thymosin alpha-1.

In some embodiments, the additional therapeutic agent is a Bruton's tyrosine kinase (BTK) inhibitor. Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

In some embodiments, the additional therapeutic agent is a KDM inhibitor. In some embodiments, the KDM inhibitor is a KDM5 inhibitor. Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel). In some embodiments, the KDM inhibitor is a KDM1 inhibitor. Examples of KDM1 inhibitors include the compounds disclosed in U.S. Pat. No. 9,186,337B2 (Oryzon Genomics), and GSK-2879552, RG-6016, ORY-2001.

In some embodiments, the additional therapeutic agent is a hepatitis B virus replication inhibitor. Examples of hepatitis B virus replication inhibitors include isothiafludine, IQP-HBV, RM-5038, and Xingantie.

In some embodiments, the additional therapeutic agent is an arginase inhibitor. Examples of arginase inhibitors include CB-1158, C-201, and resminostat.

In some embodiments, combination therapy described herein comprises gene therapy and/or cell therapy. Gene therapy and cell therapy includes: genetic modification to silence a gene; genetic approaches to directly kill infected cells; infusion of immune cells designed to replace most of the subject's own immune system to enhance the immune response to infected cells, or activate the patient's own immune system to kill infected cells, or find and kill the infected cells; and genetic approaches to modify cellular activity to further alter endogenous immune responsiveness against the infection.

In some embodiments, combination therapy described herein comprises gene editors. The genome editing system can by selected from the group consisting of: a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreS1, PreS2, S, P and/or SP gene(s) is performed by targeting the gene(s) within HBV cccDNA and/or integrated HBV DNA.

In some embodiments, combination therapy described herein comprises CAR-T cell therapy. CAR-T cell therapy can comprise a population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

In some embodiments, combination therapy described herein comprises TCR-T cell therapy. TCR-T cell therapy can comprise: T cells expressing HBV-specific T cell receptors. TCR-T cells are engineered to target HBV derived peptides presented on the surface of virus-infected cells. T-Cells expressing HBV surface antigen (HBsAg)-specific TCR. TCR-T therapy directed to treatment of HBV, such as LTCR-H2-1.

In some embodiments, a method of treating and/or preventing HBV infection comprises administering combination therapy comprising a provided composition and one, two, three, or four additional therapeutic agents selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®).

In some embodiments, a method of treating and/or preventing HBV infection comprises administering combination therapy comprising a provided composition and a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®).

In some embodiments, a method of treating and/or preventing HBV infection comprises administering combination therapy comprising a provided composition and an HBV DNA polymerase inhibitor. In some embodiments, a method of treating and/or preventing HBV infection comprises administering combination therapy comprising a provided composition, an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NODI, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In some embodiments, a method of treating and/or preventing HBV infection comprises administering combination therapy comprising (i) a provided composition, (ii) an HBV DNA polymerase inhibitor, (iii) one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In some embodiments, a method of treating and/or preventing HBV infection comprises administering combination therapy comprising a provided composition, an HBV DNA polymerase inhibitor, and at least a second additional therapeutic agent selected from the group consisting of immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In some embodiments, a method of treating and/or preventing HBV infection comprises administering combination therapy comprising a provided composition, an HBV DNA polymerase inhibitor, and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In some embodiments, a method of treating and/or preventing HBV infection comprises administering combination therapy comprising (i) a provided composition; (ii) a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES® BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NODI, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In some embodiments, a method of treating and/or preventing HBV infection comprises administering combination therapy comprising (i) a provided composition; (ii) a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®); and (iii) at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In some embodiments, a method of treating and/or preventing HBV infection comprises administering combination therapy comprising (i) a provided composition; (ii) a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and (iii) at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES® BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In some embodiments, a method of treating and/or preventing HBV infection comprises administering combination therapy comprising (i) a provided composition; (ii) a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and (iii) at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In some embodiments, a method of treating and/or preventing HBV infection comprises administering combination therapy comprising (i) a provided composition; (ii) a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); (iii) one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES® BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and (iv) one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In some embodiments, a method of treating and/or preventing HBV infection comprises administering combination therapy comprising (i) a provided composition; (ii) a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); (iii) one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and (iv) one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In some embodiments, a method of treating and/or preventing HBV infection comprises administering combination therapy comprising (i) a provided composition; (ii) a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and (iii) one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In some embodiments, a method of treating and/or preventing HBV infection comprises administering combination therapy comprising a provided composition and one or more compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, provided compositions may be combined with one or more (e.g., one, two, three, four, one or two, one to three, or one to four) additional therapeutic agents in any dosage amount of the provided composition.

In some embodiments, a provided composition is combined with tenofovir alafenamide fumarate, tenofovir alafenamide hemifumarate, or tenofovir alafenamide. In some embodiments, a provided composition is combined with 5-30 mg tenofovir alafenamide fumarate, tenofovir alafenamide hemifumarate, or tenofovir alafenamide. In some embodiments, a provided composition is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In some embodiments, a provided composition is combined with 10 mg tenofovir alafenamide fumarate, tenofovir alafenamide hemifumarate, or tenofovir alafenamide. In some embodiments, a provided composition is combined with 25 mg tenofovir alafenamide fumarate, tenofovir alafenamide hemifumarate, or tenofovir alafenamide. A provided composition may be combined with agents provided herein in any dosage amount of the composition, the same as if each combination of dosages were specifically and individually listed.

In some embodiments, a provided composition is combined with 100-400 mg tenofovir disoproxil fumarate, tenofovir disoproxil hemifumarate, or tenofovir disoproxil. In some embodiments, a provided composition is combined with 100 mg to 150 mg; 100 mg to 200 mg; 100 mg to 250 mg; 100 mg to 300 mg; 100 mg to 350 mg; 150 mg to 200 mg; 150 mg to 250 mg; 150 mg to 300 mg; 150 mg to 350 mg; 150 mg to 400 mg; 200 mg to 250 mg; 200 mg to 300 mg; 200 mg to 350 mg; 200 mg to 400 mg; 250 mg to 350 mg; 250 mg to 400 mg; 350 mg to 400 or 300 mg to 400 mg tenofovir disoproxil fumarate, tenofovir disoproxil hemifumarate, or tenofovir disoproxil. In some embodiments, a provided composition is combined with 300 mg tenofovir disoproxil fumarate, tenofovir disoproxil hemifumarate, or tenofovir disoproxil. In some embodiments, a provided composition is combined with 250 mg tenofovir disoproxil fumarate, tenofovir disoproxil hemifumarate, or tenofovir disoproxil. In some embodiments, a provided composition is combined with 150 mg tenofovir disoproxil fumarate, tenofovir disoproxil hemifumarate, or tenofovir disoproxil. A provided composition may be combined with agents provided herein in any dosage amount of the provided composition, the same as if each combination of dosages were specifically and individually listed.

In some embodiments, kits comprising a composition disclosed herein in combination with one or more (e.g., one, two, three, four, one or two, or one to three, or one to four) additional therapeutic agents are provided. Provided compositions may be used in the kits, the same as if each and every composition were specifically and individually listed for use in a kit.

HIV Combination Therapy

In certain embodiments, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one, two, three, or four additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one, two, three, or four additional therapeutic agents.

In certain embodiments, a method for treating an HIV infection is provided, comprising administering to the human a therapeutically effective amount of a compound disclosed herein, or a pharmaceutically acceptable salt thereof, in combination with a therapeutically effective amount of one, two, three, or four additional therapeutic agents.

In one embodiment, pharmaceutical compositions comprising a compound disclosed herein, or a pharmaceutically acceptable salt thereof, in combination with one, two, three, or four additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one, two, three, or four additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In certain embodiments, a compound disclosed herein, or a pharmaceutically acceptable salt thereof, is combined with one, two, three, or four additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one, two, three, or four additional therapeutic agents. Co-administration of a compound disclosed herein with one, two, three, or four additional therapeutic agents generally refers to simultaneous or sequential administration of a compound disclosed herein and one, two, three, or four additional therapeutic agents, such that therapeutically effective amounts of the compound disclosed herein and the one, two, three, or four additional therapeutic agents are both present in the body of the patient. When administered sequentially, the combination may be administered in two or more administrations.

Co-administration includes administration of unit dosages of the compounds disclosed herein before or after administration of unit dosages of one, two, three, or four additional therapeutic agents. For example, the compound disclosed herein may be administered within seconds, minutes, or hours of the administration of the one, two, three, or four additional therapeutic agents. In some embodiments, a unit dose of a compound disclosed herein is administered first, followed within seconds or minutes by administration of a unit dose of one, two, three, or four additional therapeutic agents. Alternatively, a unit dose of one, two, three, or four additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one, two, three, or four additional therapeutic agents. In yet other embodiments, a unit dose of one, two, three, or four additional therapeutic agents is administered first, followed, after a period of hours (e.g., 1-12 hours), by administration of a unit dose of a compound disclosed herein.

In certain embodiments, a compound disclosed herein is combined with one, two, three, or four additional therapeutic agents in a unitary dosage form for simultaneous administration to a patient, for example as a solid dosage form for oral administration.

In certain embodiments, a kit comprising a compound disclosed herein, or a pharmaceutically acceptable salt thereof, in combination with one or more (e.g., one, two, three, or four) additional therapeutic agents is provided.

In certain embodiments, a compound of any formula disclosed herein is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In a specific embodiment, the kit includes a compound disclosed herein, or a pharmaceutically acceptable salt thereof, an HIV nucleoside or nucleotide inhibitor of reverse transcriptase, and an HIV capsid inhibitor or an HIV capsid polymerization inhibitor.

In certain embodiments, such tablets are suitable for once daily dosing.

HIV Combination Therapy

In certain embodiments, the compounds or pharmaceutically acceptable salts thereof described herein are combined with at least one HIV combination therapy. In the above embodiments, the additional therapeutic agent or agents may be an anti-HIV agent. In the above embodiments, the additional therapeutic agent or agents may be an anti-HIV agent selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), latency reversing agents, compounds that target the HIV capsid, capsid polymerization inhibitors, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof. In some embodiments, the additional therapeutic agent can be chosen from HIV capsid inhibitors, HIV Tat or Rev inhibitors, engineered B cells, fatty acid synthase inhibitors, HIV-1 Nef modulators, TNF alpha ligand inhibitors, HIV Nef inhibitors, IFN antagonists, CD3 antagonists, CDK-4 inhibitors, CDK-6 inhibitors, Cytochrome P450 3 inhibitors, CXCR4 modulators, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T-cell and NK cell recruiting bispecific antibodies, chimeric T-cell receptors targeting HIV antigens, pharmacokinetic enhancers, and other drugs for treating HIV, and combinations thereof.

In some embodiments, the additional therapeutic agent or agents are chosen from dolutegravir, cabotegravir, islatravir, darunavir, bictegravir, elsulfavirine, rilpivirine, and lenacapavir, and combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

In certain embodiments, the compounds or pharmaceutically acceptable salts thereof described herein are combined with at least one HIV combination drug. Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide, emtricitabine, and cobicistat); BIKTARVY® (bictegravir, tenofovir alafenamide, and emtricitabine); bictegravir, tenofovir disoproxil and emtricitabine; bictegravir, tenofovir alafenamide and lamivudine; bictegravir, tenofovir disoproxil and lamivudine; bictegravir, abacavir and lamivudine; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); JULUCA® (dolutegravir, ripilvirine); TRIZIVIR® (abacavir sulfate, zidovudine, and lamivudine; ABC+AZT+3TC); dolutegravir and lamivudine; dolutegravir and abacavir; cabotegravir and lamivudine; cabotegravir and abacavir; cabotegravir and rilpivirine; atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride. In some embodiments, the additional agent is a tenofovir analog, lopinavir, ritonavir, zidovudine, lopinavir+ritonavir+abacavir+lamivudine, lamivudine, cabotegravir+rilpivirine, 3-BNC117+albuvirtide, elpida (elsulfavirine, VM-1500), and VM-1500A, or combinations thereof.

Other HIV Drugs

In certain embodiments, the compounds or pharmaceutically acceptable salts thereof described herein are combined with at least one other HIV drug. Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, MazF gene therapy, BlockAide, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576. Additional examples of other drugs for treating HIV include, but are not limited to, AAV-eCD4-Ig gene therapy, bevirimat derivatives, ABBV-382, APH0202, bryostatin-1, bryostatin analogs, BG-HIV, BRII-732, CS-TATI-1, fluoro-beta-D-arabinose nucleic acid (FANA)-modified antisense oligonucleotides, FX-101, griffithsin, GSK-3739937, GSK-3739937 (long-acting), hydroxychloroquine, IMB-10035, JL-18008, LADAVRU, MK-8558, OB-002H, ODE-Bn-TFV, PC-707, QF-036, S-648414, DIACC-1010, Fasnall, 2-CLIPS peptide, HRF-4467, thrombospondin analogs, TBL-1004HI, VG-1177, xl-081, AVI-CO-004, rfhSP-D, [18F]-MC-225, URMC-099-C, RES-529, Verdinexor, IMC-M113V, IML-106, antiviral fc conjugate (AVC), WP-1096, WP-1097, Gammora, ISR-C048, ISR-48, ISR-49, MK-8527, cannabinoids, ENOB-HV-32, HiviCide-I, T-1144, and combinations thereof.

HIV Protease Inhibitors

In certain embodiments, the compounds or pharmaceutically acceptable salts thereof described herein are combined with at least one HIV protease inhibitor. Examples of HIV protease inhibitors include amprenavir, atazanavir, brecanavir, darunavir, fosamprenavir, fosamprenavir calcium, indinavir, indinavir sulfate, lopinavir, nelfinavir, nelfmavir mesylate, ritonavir, saquinavir, saquinavir mesylate, tipranavir, DG-17, TMB-657 (PPL-100), T-169, BL-008, MK-8122, TMB-607, and TMC-310911. Additional examples of HIV protease inhibitors include, but are not limited to, ASC-09+ritonavir, AEBL-2, GS-1156, GRL-02031, and combinations thereof.

Additional examples of HIV protease inhibitors are described, e.g., in U.S. Pat. No. 10,294,234, and U.S. Patent Application Publication Nos. US2020030327 and US2019210978.

HIV Reverse Transcriptase Inhibitors

In certain embodiments, the compounds or pharmaceutically acceptable salts thereof described herein are combined with at least one HIV reverse transcriptase inhibitor. Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and elsulfavirine (VM-1500). Additional examples of HIV non-nucleoside or non-nucleotide inhibitors of reverse transcriptase include, but are not limited to, ACC-008, AIC-292, F-18, KM-023, PC-1005, M1-TFV, M2-TFV, VM-1500A-LAI, PF-3450074, elsulfavirine (sustained release oral, HIV infection), doravirine+islatravir (fixed dose combination/oral tablet formulation, HIV-1 infection), elsulfavirine (long acting injectable nanosuspension, HIV infection), or combinations thereof.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-858, VM-2500 and KP-1461. Additional examples of HIV nucleoside or nucleotide inhibitors of reverse transcriptase include, but are not limited to, tenofovir octadecyloxyethyl ester (AGX-1009), MK-8583, and combinations thereof.

Additional examples of HIV nucleoside or nucleotide inhibitors of reverse transcriptase include, but are not limited to, those described in patent publications US2007049754, US2016250215, US2016237062, US2016251347, US2002119443, US2013065856, US2013090473, US2014221356, and WO04096286.

HIV Integrase Inhibitors

In certain embodiments, the compounds or pharmaceutically acceptable salts thereof described herein are combined with at least one HIV integrase inhibitor. Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

Examples of HIV non-catalytic site, or allosteric, integrase inhibitors (NCINI) include CX-05045, CX-05168, and CX-14442. Additional examples of HIV integrase inhibitors include, but are not limited to, elvitegravir (extended-release microcapsules), PEGylated raltegravir, cabotegravir (long acting injectable), STP-0404, or combinations thereof.

Additional examples of HIV capsid inhibitors include, but are not limited to, those described in U.S. Patent Application Publication Nos. US2014221356 and US2016016973.

HIV Viral Injectivity Factor Inhibitors

In certain embodiments, the compounds or pharmaceutically acceptable salts thereof described herein are combined with at least one HIV viral infectivity factor inhibitor. Examples of HIV viral infectivity factor inhibitors include, but are not limited to, 2-amino-N-(2-methoxyphenyl)-6-((4-nitrophenyl)thio)benzamide derivatives.

HIV Entry Inhibitors

In certain embodiments, the compounds or pharmaceutically acceptable salts thereof described herein are combined with at least one HIV entry (fusion) inhibitor. Examples of HIV entry (fusion) inhibitors include cenicriviroc, CCR5 inhibitors, gp41 inhibitors, CD4 attachment inhibitors, gp120 inhibitors, and CXCR4 inhibitors. Additional examples of HIV entry (fusion) inhibitors include, but are not limited to, AAR-501, LBT-5001, gp160 inhibitors, and combinations thereof.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Additional examples of CCR5 inhibitors include, but are not limited to, maraviroc (long acting injectable nanoemulsion), thioraviroc, and combinations theoreof.

Examples of gp41 inhibitors include albuvirtide, enfuvirtide, BMS-986197, enfuvirtide biobetter, enfuvirtide biosimilar, HIV fusion inhibitors (P26-Bapc), ITV-1, ITV-2, ITV-3, ITV-4, PIE-12 trimer and sifuvirtide. Examples of gp41 inhibitors include, but are not limited to, griffithsin (gp41/gp120/gp160 inhibitor), CPT-31, C13hmAb, lipuvirtide, HIV-1 fusion inhibitors (P26-Bapc), and combinations thereof.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068. Additional examples of gp120 inhibitors include, but are not limited to, anti-HIV microbicide, BMS818251, VVX-004, and combinations thereof.

Examples of gp160 inhibitors include, but are not limited to, fangchinoline.

Examples of CXCR4 inhibitors include plerixafor, ALT-1188, N15 peptide, and vMIP (Haimipu).

HIV Maturation Inhibitors

In certain embodiments, the compounds or pharmaceutically acceptable salts thereof described herein are combined with at least one HIV maturation inhibitor. Examples of HIV maturation inhibitors include BMS-955176, GSK-3640254 and GSK-2838232.

Latency Reversing Agents

In certain embodiments, the compounds or pharmaceutically acceptable salts thereof described herein are combined with at least one latency reversing agent. Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), IL-15 modulating antibodies, JQ1, disulfiram, amphotericin B, and ubiquitin inhibitors such as largazole analogs, APH-0812, GSK-343, and toll-like receptor modulators. Additional examples of latency reversing agents include, but are not limited to, toll-like receptor (TLR) agonists (including TLR7 agonists, e.g., GS-9620, TLR8 agonists, and TLR9 agonists), (such as ZL-0580, apabetalone), IAP antagonists (inhibitor of apoptosis proteins, such as APG-1387, LBW-242), SMAC mimetics (including TL32711, LCL161, GDC-0917, HGS1029, AT-406, Debio-1143), NIZ-985, IL-15 modulating antibodies (including IL-15, IL-15 fusion proteins, and IL-15 receptor agonists), and combinations thereof.

Examples of HDAC inhibitors include romidepsin, vorinostat, and panobinostat.

Examples of PKC activators include indolactam, prostratin, ingenol B, and DAG-lactones.

Additional examples of TLR7 agonists include, but are not limited to, those described in U.S. Patent Application Publication No. US2010143301.

Additional examples of TLR8 agonists include, but are not limited to, those described in U.S. Patent Application Publication No. US2017071944.

Histone Deacetylase (HDAC) Inhibitors

In some embodiments, the compounds or pharmaceutically acceptable salts thereof as described herein are combined with an inhibitor of a histone deacetylase, e.g., histone deacetylase 1, histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HB1-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Capsid Inhibitors

In certain embodiments, the compounds or pharmaceutically acceptable salts thereof described herein are combined with at least one capsid inhibitor. Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207, AVI-621, AVI-101, AVI-201, AVI-301, and AVI-CAN1-15 series. In some embodiments, the at least one compound presently disclosed is combined with GS-6207. Additional examples of capsid inhibitors include, but are not limited to, lenacapavir, GS-CA1, PF-3450074, HIV-1 capsid inhibitors (HIV-1 infection, Shandong University), compounds described in GSK patent publication WO2019/087016, and combinations thereof.

Additional examples of capsid inhibitors include, but not limited to, those described in U.S. Patent Application Publication Nos. US2018051005 and US2016108030.

Cytochrome P450 3 Inhibitors

In certain embodiments, the compounds or pharmaceutically acceptable salts thereof described herein are combined with at least one cytochrome P450 3 inhibitor. Examples of Cytochrome P450 3 inhibitors include, but are not limited to, those described in U.S. Pat. No. 7,939,553.

RNA Polymerase Modulators

In certain embodiments, the compounds or pharmaceutically acceptable salts thereof described herein are combined with at least one RNA polymerase modulator. Examples of RNA polymerase modulators include, but are not limited to, those described in U.S. Pat. Nos. 10,065,958; 8,008,264.

Immune Checkpoint Modulators

In various embodiments, the compounds or pharmaceutically acceptable salts thereof as described herein are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu et al., *JExp Clin Cancer Res.* (2018) 37:110). In various embodiments, the immune checkpoint proteins or receptors regulate NK cell responses (e.g., reviewed in Davis et al., *Semin Immunol.* (2017) 31:64-75 and Chiossone et al., *Nat Rev Immunol.* (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In various embodiments, the compounds or pharmaceutically acceptable salts thereof described herein are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu et al., *J Exp Clin Cancer Res*. (2018) 37:110.

In various embodiments, the compounds or pharmaceutically acceptable salts thereof as described herein are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis et al., *Semin Immunol*. (2017) 31:64-75; Fang et al., *Semin Immunol*. (2017) 31:37-54; and Chiossone et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181(budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155), KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multispecific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In various embodiments, the agents as described herein are combined with anti-TIGIT antibodies, such as BMS-986207, RG-6058, and AGEN-1307.

TNF Receptor Superfamily (TNFRSF) Member Agonists or Activators

In various embodiments, the compounds or pharmaceutically acceptable salts thereof as described herein are combined with an agonist of one or more TNF receptor superfamily (TNFRSF) members, e.g., an agonist of one or more of TNFRSF1A (NCBI Gene ID: 7132), TNFRSF IB (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-IBB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Examples of anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples of anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In various embodiments, the compounds or pharmaceutically acceptable salts thereof as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices et al., *Methods Mol Biol.* (2016) 1441:333-346; Fang et al., *Semin Immunol.* (2017) 31:37-54. Examples of trispecific NK cell engagers (TRiKE) include, but are not limited to, OXS-3550, HIV-TriKE, and CD16-IL-15-B7H3 TriKe.

Indoleamine-Pyrrole-2,3-Dioxygenase (IDO1) Inhibitors

In various embodiments, the compounds or pharmaceutically acceptable salts thereof as described herein are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, shIDO-ST, EOS-200271, KHK-2455, and LY-3381916.

Immune-Based Therapies

In certain embodiments, the compounds or pharmaceutically acceptable salts thereof described herein are combined with at least one immune-based therapy. Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (PDL-1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, normferon, peginterferon alfa-2a, peginterferon alfa-2b, recombinant interleukin-15, RPI-MN, STING modulators, RIG-I modulators, NOD2 modulators, SB-9200, and IR-103.

Examples of TLR agonists include vesatolimod (GS-9620), lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, and telratolimod.

Toll-Like Receptor (TLR) Agonists

In various embodiments, the compounds or pharmaceutically acceptable salts thereof as described herein are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR7/TLR8 agonists include without limitation NKTR-262, telratolimod and BDB-001. TLR8 agonists include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR9 agonists include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. TLR4 agonists include, but are not limited to, G-100 and GSK-1795091.

CDK Inhibitors or Antagonists

In some embodiments, the compounds or pharmaceutically acceptable salts thereof described herein are combined with an inhibitor or antagonist of CDK. In some embodiments, the CDK inhibitor or antagonist is selected from the group consisting of VS2-370.

STING Agonists, RJG-I and NOD2 Modulators

In some embodiments, the compounds or pharmaceutically acceptable salts thereof described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, STING agonist (latent HIV), 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In certain embodiments, the compounds or pharmaceutically acceptable salts thereof as described herein are combined with an anti-TIM-3 antibody, such as TSR-022, LY-3321367, MBG-453, INCAGN-2390.

In certain embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In certain embodiments, the compounds or pharmaceutically acceptable salts thereof described herein are combined with at least one interleukin agonist. In certain embodiments, the agents described herein are combined with an interleukin agonist, such as IL-2, IL-7, IL-15, IL-10, IL-12 agonists; examples of IL-2 agonists such as proleukin (aldesleukin, IL-2); BC-IL (Cel-Sci), pegylated IL-2 (e.g., NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include without limitation CYT-107.

Examples of additional immune-based therapies that can be combined with an agent of this disclosure include, but are not limited to, interferon alfa, interferon alfa-2b, interferon alfa-n3, pegylated interferon alfa, interferon gamma; FLT3 agonists such as CDX-301, GS-3583, gepon, normferon, peginterferon alfa-2a, peginterferon alfa-2b, and RPI-MN.

Phosphatidylinositol 3-Kinase (PI3K) Inhibitors

In certain embodiments, the compounds or pharmaceutically acceptable salts thereof described herein are combined with at least one PI3K inhibitor. Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

In certain embodiments, the compounds or pharmaceutically acceptable salts thereof described herein are combined with at least one alpha-4/beta-7 antagonist. Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-like" Therapeutic Proteins

In certain embodiments, the compounds or pharmaceutically acceptable salts thereof described herein are combined with at least one HIV antibody, bispecific antibody, and "antibody-like" therapeutic protein. Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bNAbs (broadly neutralizing HIV antibodies), BMS-936559, TMB-360, and those targeting HIV gp120 or gp41, antibody-recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66. Additional examples of HIV antibodies, bispecific antibodies, and "antibody-like" therapeutic proteins include, but are not limited to, gp120 bispecific monoclonal antibody, PCT121.414.LS, ibalizumab (second generation), clone 3 human monoclonal antibody targeting KLIC (HIV infection), GS-9721, BG-HIV, VRC-HIVMAB091-00-AB, and combinations thereof.

Various bNAbs may be used. Examples include, but are not limited to, those described in U.S. Pat. Nos. 8,673,307, 9,493,549, 9,783,594, 10,239,935, US2018371086, US2020223907, WO2014/063059, WO2012/158948, WO2015/117008, and PCT/US2015/41272, and WO2017/096221, including antibodies 12A12, 12A21, NIH45-46, bANC131, 8ANC134, IB2530, INC9, 8ANC195, 8ANC196, 10-259, 10-303, 10-410, 10-847, 10-996, 10-1074, 10-1121, 10-1130, 10-1146, 10-1341, 10-1369, and 10-1074GM. Additional examples include, but are not limited to, those described in Klein et al., *Nature*, 492(7427): 118-22 (2012), Horwitz et al., *Proc Natl Acad Sci USA*, 110(41): 16538-43 (2013), Scheid et al., *Science*, 333: 1633-1637 (2011), Scheid et al., *Nature*, 458:636-640 (2009), Eroshkin et al, *Nucleic Acids Res.*, 42 (Database issue):Dl 133-9 (2014), Mascola et al., *Immunol Rev.*, 254 (1):225-44 (2013), such as 2F5, 4E10, M66.6, CAP206-CH12, 10E81 (all of which bind the MPER of gp41); PG9, PG16, CHOI-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies that can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include those described in Sajadi, et al., *Cell*. (2018) 173(7): 1783-1795; Sajadi, et al., *J Infect Dis*. (2016) 213(1): 156-64; Klein et al., *Nature*, 492(7427): 118-22 (2012), Horwitz et al., *Proc Natl Acad Sci USA*, 110(41): 16538-43 (2013), Scheid, et al., *Science*, 333: 1633-1637 (2011), Scheid, et al., *Nature*, 458:636-640 (2009), Eroshkin et al, *Nucleic Acids Res.*, 42 (Database issue):Dl 133-9 (2014), Mascola et al., *Immunol Rev.*, 254 (1):225-44 (2013), such as 2F5, 4E10, M66.6, CAP206-CH12, 10E8, 10E8v4, 10E8-5R-100cF, DH511.11P, 7b2, 10-1074, and LN01 (all of which bind the MPER of gp41).

Examples of additional antibodies include, but are not limited to, BF520.1, BiIA-SG, CHOI, CH59, CAP256V2LS, DH270.1, DH270.6, D1D2, C13hmAb, GS-9722 (elipovimab), BG18, GS-9721, GS-9723, PGT145, PGT121, PGT-121.60, PGT-121.66, PGT122, PGT-123, PGT-124, PGT-125, PGT-126, PGT-151, PGT-130, PGT-134, PGT-135, PGT-128, PGT-136, PGT-137, PGT-138, PGT-139, DH511-2, N49P7.1, N60P1.1, N60P25.1, N60P2.1, N60P31.1, N60P22, NIH45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, VRC-07-523, VRC07-523LS, VRC24, VRC41.01, IMC-HIV, iMabm36, eCD4-Ig, IOMA, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01. Examples of those targeting HIV in such a manner include bavituximab, UB-421, C2F5, 2G12, C4E10, C2F5+C2G12+C4E10, 8ANC195, 3BNC117, 3BNC117-LS, 3BNC60, 10-1074, 10-1074-LS, GS-9722, DH411-2, PGT145, PGT121, PGT-151, PGT-133, MDX010 (ipilimumab), DH511, N6, N6LS, N49P6, N49P7, N49P9, N49P11, VRC01 VRC-01-LS, PGDM1400, A32, 7B2, 10E8, 10E8VLS, 3810109, 10E8v4, CAP256-VRC26.25, DRVIA7, SAR-441236, VRC-07-523, VRC07-523LS, VRC-HIVMAB080-00-AB, VRC-HIVMAB060-00-AB, P2G12, and VRC07. Examples of HIV bispecific antibodies include MGD014, and TMB-bispecific. Examples of HIV bispecific and trispecific antibodies include, but are not limited to, MGD014, B12BiTe, BiIA-SG, TMB-bispecific, SAR-441236, VRC-01/PGDM-1400/10E8v4, 10E8.4/iMab, 10E8v4/PGT121-VRC01, and combinations thereof.

Example of in vivo delivered bNAbs such as AAV8-VRC07 and mRNA encoding anti-HIV antibody VRC01. Additional examples of in vivo delivered bNAbs include engineered B-cells encoding 3BNC117 (Hartweger et al., *J. Exp. Med.* 2019, 1301).

Pharmacokinetic Enhancers

In certain embodiments, the compounds or pharmaceutically acceptable salts thereof described herein are combined with at least one pharmacokinetic enhancer. Examples of pharmacokinetic enhancers include cobicistat and ritonavir.

Additional Therapeutic Agents

In certain embodiments, the compounds or pharmaceutically acceptable salts thereof described herein are combined with at least one additional therapeutic agent. Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences), WO 2013/091096 (Boehringer Ingelheim), WO 2018/145021 (Gilead Sciences), and WO2017/106346 (Gilead Sciences), each of which is herein incorporated by reference in its entirety.

HIV Vaccines

In certain embodiments, the compounds or pharmaceutically acceptable salts thereof described herein are combined with at least one HIV vaccine. Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV subtype C vaccine, Remune, ITV-1, Contre Vir, Ad5-ENVA-48, DCVax-001 (CDX-2401), Vacc-4x, Vacc-C5, VAC-3 S, multiclade DNA recombinant adenovirus-5 (rAd5), rAd5 gag-pol env A/B/C vaccine, Pennvax-G, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140[delta] V2.TV1+MF-59, rVSVIN HIV gag vaccine, SeV-Gag vaccine, AT-20, DNK-4, ad35-Grin/ENV, TBC-M4, HIV AX, HIVAX-2, NYVAC-HIV-PT1, NYVAC-HIV-PT4, DNA-HIV-PT123, rAAV1-PG9DP, GOVX-B11, GOVX-B21, TVI-HIV, Ad-4 (Ad4-env Clade C+Ad4-mGag), Paxvax, EN41-UGR7C, EN41-FPA2, PreVaxTat, AE-H, MYM-V101, CombiHIVvac, AD VAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MV A mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV vaccine (GLA-SE adjuvanted), HIV p24gag pri, me-boost plasmid DNA vaccine, arenavirus vector-based immunotherapies (Vaxwave, TheraT), MVA-BN HIV vaccine regimen, UBI HIV gp120, mRNA based prophylactic vaccines, and TBL-1203HI. Additional examples of HIV vaccines include, but are not limited to, HIV MAG DNA vaccine, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, Venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replieating RNA/self-amplifying RNA vaccines, and combinations thereof. Examples of other additional agents that are vaccines include, but are not limited to, AAVLP-EHV vaccine, AE-298p, anti-CD40.Env-gp140 vaccine, Ad4-EnvC150, BG505 SOSIP.664 gp140 adjuvanted vaccine, BG505 SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, MPER-656 liposome subunit vaccine, Pennvax-G/MVA-CMDR, ChAdV63.HIVconsv, SeV-EnvF, N123-VRC-34.01 inducing epitope-based HIV vaccine, GOVX-C55, TVI-HIV-1, ENOB-HV-11, ENOB-HV-12, MagaVax, DNA and Sev vectors vaccine expressing SCaVII, VIR-1111, DermaVir, HIV-1 iglb12 neutralizing VRC-01 antibody-stimulating anti-CD4 vaccine, arenavirus vector-based vaccines, VPI-211, multimeric HIV gp120 vaccine (Fred Hutchinson cancer center), and combinations thereof.

Birth Control (Contraceptive) Combination Therapy

In certain embodiments, the compounds or pharmaceutically acceptable salts thereof described herein are combined with at least one birth control or contraceptive regimen. Therapeutic agents used for birth control (contraceptive) that can be combined with an agent of this disclosure include without limitation cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); BIKTARVY® (bictegravir, tenofovir alafenamide, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfmavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate. Additional therapeutic agents can be selected from, for instance, tenofovir alafenamide and elvitegravir; tenofovir alafenamide+elvitegravir (rectal formulation, HIV infection); PEGylated raltegravir; lamivudine+lopinavir+ritonavir+abacavir; tenofovir+emtricitabine+maraviroc, and combinations thereof.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase. In a specific embodiment, a compound disclosed herein, or a pharmaceutically acceptable salt thereof, is combined with an HIV nucleoside or nucleotide inhibitor of reverse transcriptase and an HIV capsid inhibitor or an HIV capsid polymerization inhibitor. In a specific embodiment, a compound disclosed herein, or a pharmaceutically acceptable salt thereof, is combined with an HIV capsid inhibitor or an HIV capsid polymerization inhibitor. In a specific embodiment, a compound disclosed herein, or a pharmaceutically acceptable salt thereof, is combined with one, two, three or four HIV bNAbs. In a specific embodiment, a compound disclosed herein, or a pharmaceutically acceptable salt thereof, is combined with one, two, three or four HIV bNAbs and a HIV capsid inhibitor or an HIV capsid polymerization inhibitor. In a specific embodiment, a compound disclosed herein, or a pharmaceutically acceptable salt thereof, is combined with one, two, three or four HIV bNAbs, an HIV capsid inhibitor or an HIV capsid polymerization inhibitor, and an HIV nucleoside or nucleotide inhibitor of reverse transcriptase. In another embodiment, a compound disclosed herein, or a pharmaceutical composition thereof, is combined with two HIV nucleoside or nucleotide inhibitor of reverse transcriptase.

Gene Therapy and Cell Therapy

In certain embodiments, the compounds or pharmaceutically acceptable salts thereof described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include without limitation LB-1903, ENOB-HV-01, ENOB-HV-31, GOVX-B01, HSPCs overexpressing ALDH1 (LV-800, HIV infection), AGT103-T, and SupT1 cell-based therapy. Examples of dendritic cell therapy include without limitation AGS-004. CCR5 gene editing agents include without limitation SB-728T, SB-728-HSPC. CCR5 gene inhibitors include without limitation Cal-1, and lentivirus vector CCR5 shRNA/TRIM5alpha/TAR decoy-transduced autologous CD34-positive hematopoietic progenitor cells (HIV infection/HIV-related lymphoma). In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In certain embodiments, the compounds or pharmaceutically acceptable salts thereof described herein are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T Cell Therapy

In some embodiments, the compounds or pharmaceutically acceptable salts thereof described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include A-1801, A-1902, convertible CAR-T, VC-CAR-T, CMV-N6-CART, anti-HIV duoCAR-T, anti-CD4 CART-cell therapy, CD4 CAR+C34-CXCR4+CCR5 ZFN T-cells, anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the C46 peptide.

TCR T-Cell Therapy

In certain embodiments, the compounds or pharmaceutically acceptable salts thereof described herein are combined with a population of TCR-T-cells. TCR-T-cells are engineered to target HIV derived peptides present on the surface of virus-infected cells, for example, ImmTAV.

B-Cell Therapy

In certain embodiments, the compounds or pharmaceutically acceptable salts thereof described herein are combined with at least one B-cell therapy. In certain embodiments, the antibodies or antigen-binding fragments described herein are combined with a population of B cells genetically modified to express broadly neutralizing antibodies, such as 3BNC117 (Hartweger et al., J. Exp. Med. 2019, 1301, Moffett et al., Sci. Immunol. 4, eaax0644 (2019) 17 May 2019.

A compound as disclosed herein (e.g., any compound of formula I) may be combined with one, two, three, or four additional therapeutic agents in any dosage amount of the compound of formula I (e.g., from 1 mg to 500 mg of compound).

In one embodiment, kits comprising a compound disclosed herein, or a pharmaceutically acceptable salt thereof, in combination with one or more (e.g., one, two, three, one or two, or one to three) additional therapeutic agents are provided.

In one embodiment, the additional therapeutic agent or agents of the kit is an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), compounds that target the HIV capsid, latency reversing agents, capsid polymerization inhibitors, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents of the kit are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In a specific embodiment, the kit includes a compound disclosed herein, or a pharmaceutically acceptable salt thereof, and an HIV nucleoside or nucleotide inhibitor of reverse transcriptase. In a specific embodiment, the kit includes a compound disclosed herein, or a pharmaceutically acceptable salt thereof, and an HIV nucleoside or nucleotide inhibitor of reverse transcriptase and an HIV non-nucleoside inhibitor of reverse transcriptase. In another specific embodiment, the kit includes a compound disclosed herein, or a pharmaceutically acceptable salt thereof, and an HIV nucleoside or nucleotide inhibitor of reverse transcriptase, and an HIV protease inhibiting compound. In an additional embodiment, the kit includes a compound disclosed herein, or a pharmaceutically acceptable salt thereof, an HIV nucleoside or nucleotide inhibitor of reverse transcriptase, an HIV non-nucleoside inhibitor of reverse transcriptase, and a pharmacokinetic enhancer. In certain embodiments, the kit includes a compound disclosed herein, or a pharmaceutically acceptable salt thereof, at least one HIV nucleoside inhibitor of reverse transcriptase, an integrase inhibitor, and a pharmacokinetic enhancer. In another embodiment, the kit includes a compound disclosed herein, or a pharmaceutically acceptable salt thereof, and two HIV nucleoside or nucleotide inhibitors of reverse transcriptase. In a specific embodiment, the kit includes a compound disclosed herein, or a pharmaceutically acceptable salt thereof, an HIV nucleoside or nucleotide inhibitor of reverse transcriptase and an HIV capsid inhibitor or an HIV capsid polymerization inhibitor. In a specific embodiment, the kit includes a compound disclosed herein, or a pharmaceutically acceptable salt thereof, and an HIV capsid inhibitor or an HIV capsid polymerization inhibitor. In a specific embodiment, the kit includes a compound disclosed herein, or a pharmaceutically acceptable salt thereof, and one, two, three or four HIV bNAbs. In a specific embodiment, the kit includes a compound disclosed herein, or a pharmaceutically acceptable salt thereof, one, two, three or four HIV bNAbs and an HIV capsid inhibitor or an HIV capsid polymerization inhibitor. In a specific embodiment, the kit includes a compound disclosed herein, or a pharmaceutically acceptable salt thereof, one, two, three or four HIV bNAbs, an HIV capsid inhibitor or an HIV capsid polymerization inhibitor, and an HIV nucleoside or nucleotide inhibitor of reverse transcriptase. In a specific embodiment, the kit includes a compound disclosed herein, or a pharmaceutically acceptable salt thereof, an HIV nucleoside inhibitor of reverse transcriptase and an HIV capsid inhibitor.

Birth Control (Contraceptive) Combination Therapy

In certain embodiments, the compounds or pharmaceutically acceptable salts thereof described herein are combined with at least one birth control combination therapy. Therapeutic agents used for birth control (contraceptive) include cyproterone acetate, desogestrel, dienogest, drospirenone, estradiol valerate, ethinyl estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the compounds or pharmaceutically acceptable salts thereof described herein are combined with at least one gene and/or cell therapy. Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Examples of dendritic cell therapy include AGS-004.

Example of CCR5 gene editing drugs include SB-728T.

Example of CCR5 gene inhibitors include Cal-1.

Gene Editors

In certain embodiments, the compounds or pharmaceutically acceptable salts thereof described herein are combined with at least one gene editor. The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT-101.

CAR-T Cell Therapy

In certain embodiments, the compounds or pharmaceutically acceptable salts thereof described herein are combined with at least one CAR-T cell therapy. A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof. Cells can be autologous or allogeneic.

Examples of HIV CAR-T include VC-CAR-T, anti-CD4 CART cell therapy, autologous hematopoietic stem cells genetically engineered to express a CD4 CAR and the C46 peptide.

TCR-T Cell Therapy

In certain embodiments, the compounds or pharmaceutically acceptable salts thereof described herein are combined with at least one TCR-T cell therapy. TCR-T cells are engineered to target HIV derived peptides present on the surface of virus-infected cells.

HIV Long-Acting Therapy

In certain embodiments, the compounds or pharmaceutically acceptable salts thereof described herein are combined with at least one HIV long-acting therapy. Examples of drugs that are being developed as long-acting regimens include cabotegravir, rilpivirine, any integrase LA, VM-1500 LAI, maraviroc (LAI), tenofovir implant, MK-8591 implant, doravirine, raltegravir, and long-acting dolutegravir.

HBV Combination Therapy

In certain embodiments, a method for treating or preventing an HBV infection in a human having or at risk of having the infection is provided, comprising administering to the human a therapeutically effective amount of a composition described herein, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a composition described herein, in combination with a therapeutically effective amount of one or more (e.g., one, two, three, four, one or two, one to three, or one to four) additional therapeutic agents.

In certain embodiments, pharmaceutical compositions including an compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In certain embodiments, kits including a compound of the present disclosure, or a pharmaceutically acceptable salt thereof, in combination with one or more (e.g., one, two, three, four, one or two, one to three, or one to four) additional therapeutic agents are provided.

In certain embodiments, an agent of the present disclosure, or a pharmaceutically acceptable salt thereof, is combined with one, two, three, four or more additional therapeutic agents. In certain embodiments, an agent of the present disclosure, or a pharmaceutically acceptable salt thereof, is combined with two additional therapeutic agents. In certain embodiments, an agent of the present disclosure, or a pharmaceutically acceptable salt thereof, is combined with three additional therapeutic agents. In certain embodiments, an agent of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when an agent of the present disclosure is combined with one or more additional therapeutic agents as described herein, the components of the composition are administered as a simultaneous or sequential regimen. When administered sequentially, the combination may be administered in two or more administrations.

Co-administration of an agent disclosed herein with one or more additional therapeutic agents generally refers to simultaneous or sequential administration of an agent disclosed herein and one or more additional therapeutic agents, such that therapeutically effective amounts of each agent are present in the body of the patient.

Co-administration includes administration of unit dosages of the agents disclosed herein before or after administration of unit dosages of one or more additional therapeutic agents. The agent disclosed herein may be administered within seconds, minutes, or hours of the administration of one or more additional therapeutic agents. For example, in some embodiments, a unit dose of an agent disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of an agent disclosed herein within seconds or minutes. In some embodiments, a unit dose of an agent disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an agent disclosed herein.

In certain embodiments, the compounds or pharmaceutically acceptable salts thereof described herein are combined with one or more additional therapeutic agents in a unitary dosage form for simultaneous administration to a patient, for example as a solid dosage form for oral administration.

In certain embodiments, the compounds or pharmaceutically acceptable salts thereof described herein are combined with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, hepatitis b core antigen (HBcAg) inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi, endonuclease modulators, ribonucelotide reductase inhibitors, HBV E antigen inhibitors, covalently closed circular DNA (cccDNA) inhibitors, farnesoid X receptor agonists, STING agonists, anti-HBV antibodies, CCR2 chemokine antagonists, Caspase-9 stimulator, CD3 modulator, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, ZCCHC14 inhibitors, inducers of tertiary lymphoid aggregates, nucleic acid polymers (e.g. NAPs and STOPS), PD-1 inhibitors, PD-L1 inhibitors, recombinant thymosin alpha-1, bruton's tyrosine kinase (BTK) inhibitors, KDM inhibitors, HBV replication inhibitors, arginase inhibitors, gene therapy and cell therapy, gene editors, CAR-T cell therapy, TCR-T cell therapy, other HBV drugs, and combinations thereof. In certain embodiments, the present description provides a method for treating an HBV infection, comprising administering to a patient in need thereof a therapeutically effective amount of a composition described herein, in combination with a therapeutically effective amount of one or more (e.g., one, two, three, four, one or two, one to three, or one to four) additional therapeutic agents which are suitable for treating an HBV infection.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof. Additional examples include, but are not limited to, DARPins®, anti-pMHC TCR-like antibodies, homing meganucleases (e.g., ARCUS), and combinations thereof.

In certain embodiments, the compounds or pharmaceutically acceptable salts thereof described herein are combined with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, endonuclease modulators, epigenetic modifiers, Farnesoid X receptor agonists, free fatty acid (Ffa) receptor 2 (Ffar2; PR43) agonists, free fatty acid (Ffa) receptor 3 (Ffar3; GPR441) agonists, HBV DNA polymerase inhibitors, HBV replication inhibitors, HBV RNAse inhibitors, HBV viral entry inhibitors, HBx inhibitors, Hepatitis B large envelope protein inhibitor, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, Non canonical RNA polymerase PAPD5 inhibitors. Non canonical RNA polymerase PAPD7 inhibitors, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NODI, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-7 modulators, TLR-8 modulators, TLR-9 agonists, TLR9 agonists or gene stimulator, toll-like receptor (TLR) modulators, viral ribonucleotide reductase inhibitors, and combinations thereof.

HBV Combination Drugs

In certain embodiments, the compounds described herein are combined with at least one combination drug for the treatment of HBV. Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

In certain embodiments, the compounds or pharmaceutically acceptable salts thereof described herein are combined with at least one other HBV drug. Examples of other drugs for the treatment of HBV include alpha-hydroxytropolones, amdoxovir, beta-hydroxy cytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka ShuNing, alloferon, WS-007, Y-101 (Ti Fen Tai), rSIFN-co, PEG-IIFNm, KW-3, BP-Inter-014, oleanolic acid, HepBnRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds described in US20150210682, (Roche), US 2016/0122344 (Roche), WO2015173164, WO2016023877, US2015252057A (Roche), WO16/28335A1 (Roche), WO16/20186A1 (Roche), US2016237090A (Roche), WO16/07833A1 (Roche), WO16/07832A1 (Roche), US2016176899A (Roche), WO16/02438A1 (Roche), WO16012470A1 (Roche), US2016220586A (Roche), and US2015031687A (Roche). Additional examples of other drugs for treatment of HBV include, but are not limited to, antroquinonol, ARB-199, ccc-R08, HH-003, hepalatide, NCO-48 Fumarate, XTYW-001, SFA-001, ENOB-HB-01, QL-007sofosbuvir, ledipasvir, PA-1010, HPN-BV1, STSG-0002, and combinations thereof.

HBV Vaccines

In certain embodiments, the compounds or pharmaceutically acceptable salts thereof described herein are combined with at least one HBV vaccine. HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, HeberpentaL, DTwP-HepB-Hib, V-419, CVI-HBV-001, Tetrabhay, hepatitis B prophylactic vaccine (Advax Super D), Hepatrol-07, GSK-223192A, ENGERIXB®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine. Additional vaccines include, but are not limited to, CARG-101, YS-HBV-001, IR-101H, TVAX-008, and combinations thereof.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV. Additional examples of HBV therapeutic vaccines include, but are not limited to, HepTcell, hepatitis B therapeutic DNA vaccine, VVX-001, GSK-3528869A (ChAd155-hli-HBV+MVA-HBV+Hbc-HBs/AS01B-4), VBI-2601, VTP-300 (ChAdOxl-SIi-HBV-CPmut-TPA-Ssh prime and MVA-SIi-HBV-CPmut-TPA-Ssh boost), MVA-BN, AVA-2100, HBV-ADV311, YS-HBV-002, HBV Arenavirus vaccines are disclosed, e.g., in WO2017076988 and WO2017198726, and combinations thereof.

HBV DNA Polymerase Inhibitors

In some embodiments, the compounds or pharmaceutically acceptable salts thereof are combined with at least one HBV DNA polymerase inhibitor. Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), fdocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. Additional examples of HBV DNA polymerase inhibitors include, but are not limited to, tenofovir exalidex, ATI-2173, AiB-001, and combinations thereof.

Immunomodulators

In certain embodiments, the compounds or pharmaceutically acceptable salts thereof described herein are combined with at least one immunomodulator. Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, AB-506, RO-6871765, AIC-649, and IR-103.

Toll-Like Receptor (TLR) Modulators

In some embodiments, the compounds or pharmaceutically acceptable salts thereof described herein are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12, and TLR13. TLR modulators include modulators of TLR1, TLR2, TLR3, TLR4, TLR5, TLR6, TLR7, TLR8, TLR9, TLR10, TLR11, TLR12, and TLR13.

Examples of TLR3 modulators include rintatolimod, poly-ICLC, RIBOXXON®, Apoxxim, RIBOXXIM®, IPH-33, MCT-465, MCT-475, and ND-1.1.

Examples of TLR modulators include, but are not limited to, AK-0701.

Examples of TLR4 modulators include, but are not limited to, G-100 and GSK-1795091.

Examples of TLR7 modulators include GS-9620 (vesatolimod), GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, LHC-165, RG-7854, and the compounds described in US20100143301 (Gilead Sciences), US20110098248 (Gilead Sciences), and US20090047249 (Gilead Sciences). Additional examples of TLR7 modulators include, but are not limited to, AL-034, DSP-0509, LHC-165, TMX-101 (imiquimod), and combinations thereof.

Examples of TLR8 modulators include motolimod, resiquimod, 3M-051, 3M-052, MCT-465, IMO-4200, VTX- 763, VTX-1463, GS-9688 and the compounds described in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205, US20160289229, U.S. patent application Ser. No. 15/692,161, and U.S. patent application Ser. No. 15/692,093.

A TLR7/TLR8 modulator includes, but is not limited to, NKTR-262, telratolimod, and BDB-001.

Examples of TLR-8 inhibitors include, but are not limited to, ZG-170607.

Example TLR8 agonists include without limitation E-6887, IMO-4200, IMO-8400, IMO-9200, MCT-465, MEDI-9197, motolimod, resiquimod, selgantolimod (GS-9688), HRS-9950, VTX-1463, VTX-763, 3M-051, 3M-052, and the compounds disclosed in US2016289229 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10. Additional examples of TLR9 modulators include AST-008, cobitolimod, CMP-001, S-540956, litenimod, MGN-1601, BB-001, BB-006, CYT-003, tilsotolimod, PUL-042, and combinations thereof.

Examples of TLR7, TLR8 and TLR9 modulators include the compounds described in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (Bristol Myers Squibb), WO2015057655 (Eisai Co Ltd), WO2017001307 (Roche), WO2018005586 (Bristol Myers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO2018041 63 (Roche), WO2018038877 (3M Co), WO2015057659 (Eisai Co Ltd), WO2017202704 (Roche), WO2018026620 (Bristol Myers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

In some embodiments, the compounds or pharmaceutically acceptable salts thereof as described herein are co-administered with a TLR7, TLR8, TLR9 agonist, or a combination thereof.

Interferon Alpha Receptor Ligands

In certain embodiments, the compounds or pharmaceutically acceptable salts thereof described herein are combined with at least one interferon alpha receptor ligands. Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratories Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa). An additional example of an interferon alpha receptor ligands includes, but is not limited to, PEG-IFN-alpha.

Hyaluronidase Inhibitors

In certain embodiments, the compounds or pharmaceutically acceptable salts thereof described herein are combined with at least one hyaluronidase inhibitor. Examples of hyaluronidase inhibitors include astodrimer.

Hepatitis B Surface Antigen (HBsAg) Inhibitors

In certain embodiments, the compounds or pharmaceutically acceptable salts thereof described herein are combined with at least one Hepatitis B surface antigen inhibitor. Examples of HBsAg inhibitors include HBF-0259, PBHBV-001, PBHBV-2-15, PBHBV-2-1, REP-9 AC, REP-9C, REP-9, REP-2139, REP-2139-Ca, REP-2165, REP-2055, REP- 2163, REP-2165, REP-2053, REP-2031 and REP-006, and REP-9AC'. An additional example of an HBsAg inhibitor includes GP-605.

Examples of HBsAg secretion inhibitors include BM601. Additional examples of HBsAg secretion inhibitors include, but are not limited to, GST-HG-131, AB-452, ALG-010093, and combinations thereof.

Cytotoxic T-Lymphocyte-Associated Protein 4 (Ipi4) Inhibitors

In certain embodiments, the compounds or pharmaceutically acceptable salts thereof described herein are combined with at least one cytotoxic T-lymphocyte-associated protein 4 inhibitor. Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

In certain embodiments, the compounds or pharmaceutically acceptable salts thereof described herein are combined with at least one cyclophilin inhibitors. Examples of cyclophilin inhibitors include CPI-431-32, EDP-494, OCB-030, SCY-635, NVP-015, NVP-018, NVP-019, STG-175, and the compounds described in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

In certain embodiments, the compounds or pharmaceutically acceptable salts thereof described herein are combined with at least one HBV viral entry inhibitor. Examples of HBV viral entry inhibitors include Myrcludex B.

Hepatitis B Large Envelope Protein Inhibitors

In certain embodiments, the compounds or pharmaceutically acceptable salts thereof described herein are combined with at least one hepatitis B large envelope protein inhibitor. Examples of Hepatitis B large envelope protein inhibitors include, but are not limited to, GP-605, GST-HG-121, ALG-010093, and ALG-01013.

Antisense Oligonucleotide Targeting Viral mRNA

In certain embodiments, the compounds or pharmaceutically acceptable salts thereof described herein are combined with at least one antisense oligonucleotide targeting viral mRNA. Examples of antisense oligonucleotide targeting viral mRNA include ISIS-HBVRx, IONIS-HBVRx, IONIS-GSK6-LRx, GSK-3389404, RG-6004. Additional examples of antisense oligonucleotide targeting viral mRNA include, but are not limited to, IONIS-HBV-LRx, BNC-1701, and combinations thereof.

Short Interfering RNAs (siRNA) and ddRNAi

In certain embodiments, the compounds or pharmaceutically acceptable salts thereof described herein are combined with at least one siRNA and/or ddRNAi.

Examples of siRNA include TKM-HBV (TKM-HepB), ALN-HBV, SR-008, HepB-nRNA, and ARC-520, ARC-521, ARB-1740, ARB-1467. Additional examples of siRNA include, but are not limited to, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV DCR-HBVS (DCR-S219), and combinations thereof.

Examples of DNA-directed RNA interference (ddRNAi) include BB-HB-331.

Endonuclease Modulators

In certain embodiments, the compounds or pharmaceutically acceptable salts thereof described herein are combined with at least one endonuclease modulator. Examples of endonuclease modulators include PGN-514.

Ribonucelotide Reductase Inhibitors

In certain embodiments, the compounds or pharmaceutically acceptable salts thereof described herein are combined with at least one ribonucleotide reductase inhibitor. Examples of inhibitors of ribonucleotide reductase include Trimidox.

Nonnucleoside Reverse Transcriptase Inhibitors

In certain embodiments, the compounds or pharmaceutically acceptable salts thereof described herein are combined with at least one nonnucleoside reverse transcriptase inhibitor. Examples of Nonnucleoside Reverse Transcriptase Inhibitors (NNRTIs) include, but are not limited to, the compounds disclosed in WO2018118826 (Merck), WO2018080903 (Merck), WO2018119013 (Merck), WO2017100108 (Idenix), WO2017027434 (Merck), WO2017007701 (Merck), and WO2008005555 (Gilead).

HBV Replication Inhibitors

In certain embodiments, the compounds or pharmaceutically acceptable salts thereof described herein are combined with at least one HBV replication inhibitor. Examples of hepatitis B virus replication inhibitors include, but are not limited to, GP-31502, isothiafludine, IQP-HBV, RM-5038, and Xingantie.

HIV-1 Reverse Transcriptase Inhibitors

In certain embodiments, the compounds or pharmaceutically acceptable salts thereof described herein are combined with at least one HIV-1 reverse transcriptase inhibitor. Examples of HIV-1 reverse transcriptase inhibitors include, but are not limited to, 2,5,6-substituted pyrimidone derivative (HBV).

Non Canonical RNA Polymerase PAPD5 and PAPD7 Inhibitors

In certain embodiments, the compounds or pharmaceutically acceptable salts thereof described herein are combined with at least one non-canonical RNA polymerase PAPD5 and/or PAPD7 inhibitor. Examples of non-canonical RNA polymerase PAPD5 and PAPD7 inhibitors include, but are not limited to, PAPD5 and PAPD7 targeting locked nucleic acid antisense oligonucleotides (HBV infection).

HBV E Antigen Inhibitors

In certain embodiments, the compounds or pharmaceutically acceptable salts thereof described herein are combined with at least one HBV E antigen inhibitor. Examples of HBV E antigen inhibitors include wogonin.

Covalently Closed Circular DNA (cccDNA) Inhibitors

In certain embodiments, the compounds or pharmaceutically acceptable salts thereof described herein are combined with at least one cccDNA inhibitor. Examples of cccDNA inhibitors include BSBI-25, and CHR-101. Another example of a cccDNA inhibitor includes, but is not limited to, ccc-R08.

Farnesoid X Receptor Agonist

In certain embodiments, the compounds or pharmaceutically acceptable salts thereof described herein are combined with at least one farnesoid X receptor (FXR) agonist. Examples of farnesoid x receptor agonist such as EYP-001, GS-9674, EDP-305, MET-409, Tropifexor, AKN-083, RDX-023, BWD-100, LMB-763, INV-3, NTX-023-1, EP-024297 and GS-8670. Another example of a farnesoid x receptor agonist is cilofexor.

Caspase-9 Stimulators

In certain embodiments, the compounds or pharmaceutically acceptable salts thereof described herein are combined with at least one Caspase-9 stimulator. Examples of Caspase-9 stimulators include, but are not limited to, ENOB-HB-01.

CD3 Modulators

In certain embodiments, the compounds or pharmaceutically acceptable salts thereof described herein are combined with at least one CD3 modulator. Examples of CD3 modulators include, but are not limited to, IMC-I109V.

Ffar2 and Ffar3 Agonists

In certain embodiments, the compounds or pharmaceutically acceptable salts thereof described herein are combined with at least one Ffar2 and/or Ffar3 agonist. Examples of Ffar2 and Ffar3 agonists include, but are not limited to, SFA-001.

HBV Antibodies

In certain embodiments, the compounds or pharmaceutically acceptable salts thereof described herein are combined with at least one HBV antibody. Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed). Additional examples of HBV antibodies targeting the surface antigens of the hepatitis B virus include lenvervimab, VIR-3434, and combinations thereof.

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies include HBC-34.

Antibodies against HBV viral peptide/major histocompatibility complex (MHC) class I (pMHC) complexes are described, e.g., in Sastry et al., J Virol. 2011 March; 85(5):1935-42 and in WO2011062562.

CCR2 Chemokine Antagonists

In certain embodiments, the compounds or pharmaceutically acceptable salts thereof described herein are combined with at least one CCR2 chemokine antagonist. Examples of CCR2 chemokine antagonists include propagermanium.

Thymosin Agonists

In certain embodiments, the compounds or pharmaceutically acceptable salts thereof described herein are combined with at least one thymosin agonist. Examples of thymosin agonists include Thymalfasin, recombinant thymosin alpha 1 (GeneScience).

Cytokines

In certain embodiments, the compounds or pharmaceutically acceptable salts thereof described herein are combined with at least one cytokine. Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Interleukin Agonists

In certain embodiments, the compounds or pharmaceutically acceptable salts thereof described herein are combined with an interleukin agonist, including, but not limited to, IL-2, IL-7, IL-15, IL-10, IL-12 agonists; examples of IL-2 agonists such as proleukin (aldesleukin, IL-2); pegylated IL-2 (eg NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include CYT-107.

Nucleoprotein Modulators

In certain embodiments, the compounds or pharmaceutically acceptable salts thereof described herein are combined with at least one nucleoprotein modulator. Nucleoprotein modulators may be either HBV core or capsid protein inhibitors. Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23. Additional examples of nucleoprotein modulators include, but are not limited to, AB-836, AT-130, ALG-001075, ALG-001024, ALG-000184, EDP-514, ARB-1820, GST-HG-141, JNJ-632, GST-HG-141, KL-060332, ABI-H3733, AK-0605, HRS-5091, VNRX-9945, CB-HBV-001, AK-0605, SOC-10, SOC-11, and combinations thereof.

Examples of capsid inhibitors include the compounds described in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira). Additional examples of capsid inhibitors include, but are not limited to, those disclosed in US2018161307 (Gilead Sciences).

Examples of transcript inhibitors include the compounds described in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta), WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

STING Agonists, RJG-I and NOD2 Modulators

In some embodiments, the compounds or pharmaceutically acceptable salts thereof described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

Examples of STING agonists include, but are not limited to, the compounds disclosed in WO 2018065360 (Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), and WO2018060323 (Boehringer).

Retinoic Acid-Inducible Gene I Stimulators

In certain embodiments, the compounds or pharmaceutically acceptable salts thereof described herein are combined with at least one retinoic acid-inducible gene 1 stimulator. Examples of stimulators of retinoic acid-inducible gene 1 include SB-9200, SB-40, SB-44, ORI-7246, ORI-9350, ORI-7537, ORI-9020, ORI-9198, and ORI-7170, RGT-100. An additional example of a stimulator of retinoic acid-inducible gene 1 includes inarigivir soproxil.

NOD2 Stimulators

In certain embodiments, the compounds or pharmaceutically acceptable salts thereof described herein are combined with at least one NOD2 stimulator. Examples of stimulators of NOD2 include SB-9200. An additional example of a stimulator of NOD2 includes inarigivir soproxil.

Phosphatidylinositol 3-Kinase (PI3K) Inhibitors

In certain embodiments, the compounds or pharmaceutically acceptable salts thereof described herein are combined with at least one PI3K inhibitor. Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-dioxygenase (IDO) Pathway Inhibitors

In certain embodiments, the compounds or pharmaceutically acceptable salts thereof described herein are combined with at least one IDO pathway inhibitor. Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds described in US20100015178 (Incyte), US2016137652 (Flexus Biosciences, Inc.), WO2014073738 (Flexus Biosciences, Inc.), and WO2015188085 (Flexus Biosciences, Inc.).

Immune Checkpoint Modulators

In various embodiments, the compounds or pharmaceutically acceptable salts thereof as described herein are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu et al., *J Exp Clin Cancer Res.* (2018) 37:110). In various embodiments, the immune checkpoint proteins or receptors regulate NK cell responses (e, reviewed in Davis et al., *Semin Immunol.* (2017) 31:64-75 and Chiossone et al., *Nat Rev Immunol.* (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In various embodiments, the compounds or pharmaceutically acceptable salts thereof described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors.

Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu et al., *JExp Clin Cancer Res*. (2018) 37:110.

In various embodiments, the compounds as described herein are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis et al., *Semin Immunol*. (2017) 31:64-75; Fang et al., *Semin Immunol*. (2017) 31:37-54; and Chiossone et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. Additional examples of small molecule PD-L1 inhibitors include those disclosed in U.S. Publication No. US2018305315 (Gilead Sciences), US2020017471 (Gilead Sciences) and US2019270727 (Gilead Sciences). In some embodiments, the small molecule inhibitor of CTLA4 comprises BPI-002.

Examples of inhibitors of CTLA4 include, but are not limited to, ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, (MSB0010718C), CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170, (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

PD-1 Inhibitors

In certain embodiments, the compounds or pharmaceutically acceptable salts thereof described herein are combined with at least one PD-1 inhibitor. Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab and mDX-400, JS-001, Camrelizumab, Sintilimab, Sintilimab, tislelizumab, BCD-100, BGB-A333 JNJ-63723283, GLS-010 (WBP-3055), CX-072, AGEN-2034, GNS-1480 (Epidermal growth factor receptor antagonist; Programmed cell death ligand 1 inhibitor), CS-1001, M-7824 (PD-L1/TGF-β bifunctional fusion protein), Genolimzumab, BMS-936559.

PD-L1 Inhibitors

In certain embodiments, the compounds or pharmaceutically acceptable salts thereof described herein are combined with at least one PD-L1 inhibitor. Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, GS-4224, CX-072, and BMS-936559.

Examples of PD-1 inhibitors include the compounds described in WO2017112730 (Incyte Corp), WO2017087777 (Incyte Corp), WO2017017624, WO2014151634 (Bristol Myers Squibb Co), WO201317322 (Bristol Myers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (Bristol Myers Squibb Co), WO20161266460 (Bristol Myers Squibb Co), WO2017087678 (Bristol Myers Squibb Co), WO2016149351 (Bristol Myers Squibb Co), WO2015033299 (Aurigene Discovery Technologies Ltd), WO2015179615 (Eisai Co Ltd; Eisai Research Institute), WO2017066227 (Bristol Myers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (Bristol Myers Squibb Co), WO2015033303 (Aurigene Discovery Technologies Ltd), WO2017205464 (Incyte Corp), WO2016019232 (3M Co; Individual; Texas A&M University System), WO2015160641 (Bristol Myers Squibb Co), WO2017079669 (Incyte Corp), WO2015033301 (Aurigene Discovery Technologies Ltd), WO2015034820 (Bristol Myers Squibb Co), WO2018073754 (Aurigene Discovery Technologies Ltd), WO2016077518 (Bristol Myers Squibb Co), WO2016057624 (Bristol Myers Squibb Co), WO2018044783 (Incyte Corp), WO2016100608 (Bristol Myers Squibb Co), WO2016100285 (Bristol Myers Squibb Co), WO2016039749 (Bristol Myers Squibb Co), WO2015019284 (Cambridge Enterprise Ltd), WO2016142894 (Aurigene Discovery Technologies Ltd), WO2015134605 (Bristol Myers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (Bristol Myers Squibb Co), WO2013144704 (Aurigene Discovery Technologies Ltd), WO2018013789 (Incyte Corp), WO2017176608 (Bristol Myers Squibb Co), WO2018009505 (Bristol Myers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), and WO2018026971 (Arising International), and GS-4224.

In various embodiments, the agents as described herein are combined with anti-TIGIT antibodies, such as BMS-986207, RG-6058, and AGEN-1307. Other examples of PD-1 and/or PDL-1 inhibitors include the compounds described in U.S. Provisional Ser. Nos. 62/630,187, 62/640,534, 62/736,116, and 62/747,029.

TNF Receptor Superfamily (TNFRSF) Member Agonists or Activators

In various embodiments, the compounds or pharmaceutically acceptable salts thereof as described herein are combined with an agonist of one or more TNF receptor superfamily (TNFRSF) members, e.g., an agonist of one or more of TNFRSF1A (NCBI Gene ID: 7132), TNFRSF IB (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-IBB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, IBI-101 and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-pyrrole-2,3-dioxygenase (IDO1) inhibitors

In various embodiments, the compounds or pharmaceutically acceptable salts thereof as described herein, are combined with an inhibitor of indoleamine 2,3-dioxygenase 1 (IDO1; NCBI Gene ID: 3620). Examples of IDO1 inhibitors include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

LAG-3 and TIM-3 Inhibitors In certain embodiments, the agents as described herein are combined with an anti-TIM-3 antibody, such as TSR-022, LY-3321367, MBG-453, and INCAGN-2390.

In certain embodiments, the antibodies or antigen-binding fragments described herein are combined with an anti LAG-3 (Lymphocyte-activation) antibody, such as relatlimab (ONO-4482), LAG-525, MK-4280, REGN-3767, and INCAGN2385.

Examples of additional immune-based therapies that can be combined with a compound or pharmaceutically acceptable salt of this disclosure include interferon alfa, interferon alfa-2b, interferon alfa-n3, pegylated interferon alfa, interferon gamma, Flt3 agonists, gepon, normferon, peginterferon alfa-2a, peginterferon alfa-2b, and RPI-MN.

Inhibitor of Apoptosis Proteins Family Proteins (IAPs)

In certain embodiments, the compounds or pharmaceutically acceptable salts thereof described herein are combined with at least one inhibitor of apoptosis proteins family proteins. Examples of IAP inhibitors include, but are not limited to, APG-1387.

Recombinant Thymosin Alpha-1

In certain embodiments, the compounds or pharmaceutically acceptable salts thereof described herein are combined with at least one recombinant thymosin alpha-1. Examples of recombinant thymosin alpha-1 include NL-004 and PEGylated thymosin alpha-1.

Bruton's Tyrosine Kinase (BTK) Inhibitors

In certain embodiments, the compounds or pharmaceutically acceptable salts thereof described herein are combined with at least one BTK inhibitor. Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds described in US20140330015 (Ono Pharmaceutical), US20130079327 (Ono Pharmaceutical), and US20130217880 (Ono Pharmaceutical).

KDM Inhibitors

In certain embodiments, the compounds or pharmaceutically acceptable salts thereof described herein are combined with at least one KDM inhibitor. Examples of KDM5 inhibitors include the compounds described in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds described in U.S. Pat. No. 9,186,337B2 (Oryzon Genomics), GSK-2879552, and RG-6016. Another example of a KDM1 inhibitor includes, but is not limited to, ORY-2001.

STING Agonists

In certain embodiments, the compounds or pharmaceutically acceptable salts thereof described herein are combined with at least one STING agonist. Examples of STING agonists include SB-11285, AdVCA0848, STINGVAX, and the compounds described in WO 2018065360 (Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

Non-Nucleoside Reverse Transcriptase Inhibitors (NNRTI)

In certain embodiments, the compounds or pharmaceutically acceptable salts thereof described herein are combined with at least one non-nucleoside reverse transcriptase inhibitor (NNRTI). Examples of NNRTI include the compounds described in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

In certain embodiments, the compounds or pharmaceutically acceptable salts thereof described herein are combined with at least one HBV replication inhibitor. Examples of hepatitis B virus replication inhibitors include isothiafludine, IQP-HBV, RM-5038, and Xingantie.

Arginase Inhibitors

In certain embodiments, the compounds or pharmaceutically acceptable salts thereof described herein are combined with at least one arginase inhibitor. Examples of Arginase inhibitors include CB-1158, C-201, and resminostat.

Bi- and Tri-Specific Natural Killer (NK)-Cell Engagers

In certain embodiments, the compounds or pharmaceutically acceptable salts thereof described herein are combined with at least one bispecific and/or trispecific natural killer (NK)-cell engagers. In various embodiments, the compounds as described herein are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices et al., *Methods Mol Biol.* (2016) 1441:333-346; Fang et al., *Semin Immunol.* (2017) 31:37-54.

In certain embodiments, the compounds or pharmaceutically acceptable salts thereof described herein are combined with pMHC antibodies.

Long-Acting Treatments

In certain embodiments, the compounds or pharmaceutically acceptable salts thereof described herein are combined with at least one long-acting treatment. Examples of long-acting treatments include, but are not limited to, long acting entecavir (subcutaneous depot), long acting tenofovir (TFD and TAF) implants (devices) or subcutaneous depot. An example of long acting entecavir is described in Exploration of long-acting implant formulations of hepatitis B drug entecavir., *Eur J Pharm Sci.* 2019 Aug. 1; 136:104958.

Gene Therapy and Cell Therapy

In certain embodiments, the compounds or pharmaceutically acceptable salts thereof described herein are combined with at least one gene or cell therapy regimen. Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

In certain embodiments, the compounds or pharmaceutically acceptable salts thereof described herein are combined with at least one gene editor. Examples of genome editing systems include a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreS1, PreS2, S, P and/or SP gene(s) is performed by targeting the gene(s) within HBV cccDNA and/or integrated HBV DNA. Additional examples genome editing systems include, but are not limited to, those disclosed in US2019284543 (Gilead Sciences), and US2019338263 (Gilead Sciences).

Example of gene therapy, such as liver targeted anti-HBV gene therapy (using ARCUS technology), or using CRISPR/Cas9 gene editing technology, or EBT-106 (LNP-delivered CRISPR/CasX nuclease.

CAR-T Cell Therapy

In certain embodiments, the compounds or pharmaceutically acceptable salts thereof described herein are combined with at least one CAR-T cell therapy. CAR T cell therapy includes a population of immune effector cells engineered to express a chimeric antigen receptor (CAR), wherein the CAR comprises an HBV antigen-binding domain. In certain embodiments, the antigen-binding domain is a domain disclosed herein. In certain embodiments, the antigen-binding domain is other than a domain disclosed herein. In certain embodiments, the antigen is HBsAg (i.e., HbsAg− CART). The immune effector cell is a T cell or an NK cell. In some embodiments, the T cell is a CD4+ T cell, a CD8+ T cell, or a combination thereof. Cells can be autologous or allogeneic. An example of a CART directed to HBV is described in Cytotherapy. 2018 May; 20(5):697-705. doi: 10.1016/j jcyt.2018.02.

TCR-T Cell Therapy

In certain embodiments, the compounds or pharmaceutically acceptable salts thereof described herein are combined with at least one TCR-T cell therapy. TCR T cell therapy includes T cells expressing HBV-specific T cell receptors. TCR-T cells are engineered to target HBV derived peptides presented on the surface of virus-infected cells. In some embodiments, the T-cells express HBV surface antigen (HBsAg)-specific TCR. Examples of TCR-T therapy directed to treatment of HBV include LTCR-H2-1. An example of a TCR directed to HBV is described in Wisskirchen, K. et al. T cell receptor grafting allows virological control of hepatitis B virus infection. *J Clin Invest.* 2019; 129(7):2932-2945.

TCR-T cell therapy includes T-Cells expressing HBV surface antigen (HBsAg)-specific TCR.

TCR-T cell therapy includes TCR-T therapy directed to treatment of HBV, such as LTCR-H2-1.

In another specific embodiment, a compound described herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators). In some embodiments, the compounds or pharmaceutically acceptable salts thereof can be combined with HBV DNA polymerase inhibitor, DARPins®, anti-pMHC TCR-like antibodies, or combinations thereof.

In another specific embodiment, a compound described herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound described herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, a compound described herein, or a pharmaceutically acceptable salt thereof, is combined with compounds such as those described in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, when a compound disclosed herein is combined with one, two, three, or four additional therapeutic agents as described above, the components of the composition are administered as a simultaneous or sequential regimen. When administered sequentially, the combination may be administered in two or more administrations.

V. Routes of Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. In certain embodiments, the compounds disclosed are dosed parenterally. In certain embodiments, the compounds disclosed are dosed intravenously, subcutaneously, or intramuscularly. In some embodiments, the compound of Formula (I), Formula (Ia) or Formula (Ib), or a pharmaceutically acceptable salt thereof, is administered subcutaneously. In some embodiments, the compound of Formula (I), Formula (Ia) or Formula (Ib), or a pharmaceutically acceptable salt thereof, is administered intravenously. In some embodiments, the compound of Formula (I), Formula (Ia) or Formula (Ib), or a pharmaceutically acceptable salt thereof, is administered intramuscularly. In some embodiments, the compound of Formula (I), Formula (Ia) or Formula (Ib), or a pharmaceutically acceptable salt thereof, is administered orally. It will be appreciated that the preferred route may vary with for example the condition of the recipient. An advantage of certain compounds disclosed herein is that they are orally bioavailable and can be dosed orally.

In some embodiments, the compound of the Formula (I), Formula (Ia) or Formula (Ib), or a pharmaceutically acceptable salt thereof, is administered via injection, using an injection device. In some embodiments, the injection device is or includes a syringe, which can be employed manually, or as part of a syringe-containing injection device. A wide variety of injection devices can be used, including, but not limited to, a handheld or wearable autoinjector, a handheld or wearable manual injector, an on-body injector, a syrette, a jet injector, or a pen injector, each of which can be reusable or disposable.

In some embodiments, the compound of Formula (I), Formula (Ia) or Formula (Ib), or a pharmaceutically acceptable salt thereof, can be administered with a syringe suitable for administration of the compound. In some embodiments, the syringe is disposable. In some embodiments, the syringe is reusable. In some embodiments, the syringe is pre-filled with the compound of Formula (I), Formula (Ia) or Formula (Ib), or a pharmaceutically acceptable salt thereof.

In some embodiments, the compound of Formula (I), Formula (Ia) or Formula (Ib), or a pharmaceutically acceptable salt thereof, can be administered with an autoinjector comprising a syringe. In some embodiments, the syringe is disposable. In some embodiments, the syringe is reusable. In some embodiments, the syringe is pre-filled with the compound of Formula (I), Formula (Ia) or Formula (Ib), or a pharmaceutically acceptable salt thereof.

In some embodiments, the compound of Formula (I), Formula (Ia) or Formula (Ib), or a pharmaceutically acceptable salt thereof, is formulated for subcutaneous administration. In some embodiments, the compound of Formula (I), Formula (Ia) or Formula (Ib), or a pharmaceutically acceptable salt thereof, is formulated as a solution or suspension. In some embodiments, the compound of Formula (I), Formula (Ia) or Formula (Ib), or a pharmaceutically acceptable salt thereof, is formulated as a solution for subcutaneous administration. In some embodiments, the compound of Formula (I), Formula (Ia) or Formula (Ib), or a pharmaceutically acceptable salt thereof, is formulated as a suspension for subcutaneous administration. In some embodiments, the compound of Formula (I), Formula (Ia) or Formula (Ib), or a pharmaceutically acceptable salt thereof, is formulated at a concentration of about 50 mg/mL to about 500 mg/mL, such as about 50 mg/mL to about 400 mg/mL, about 50 mg/mL to about 300 mg/mL, about 50 mg/mL to about 200 mg/mL, about 50 mg/mL to about 150 mg/mL, or about 50 mg/mL to about 100 mg/mL.

A compound of the present disclosure may be administered to an individual in accordance with an effective dosing regimen for a desired period of time or duration, such as at least about 1 week, about 2 weeks, about 4 weeks, about 8 weeks, about 12 weeks, about 16 weeks, about 20 weeks, about 24 weeks, or about 48 weeks, or longer. In one variation, the compound is administered on a daily or intermittent schedule for the duration of the individual's life.

In some embodiments, the dosing regimen includes administration of the compound of Formula (I), Formula (Ia) or Formula (Ib), or a pharmaceutically acceptable salt thereof, for at least about 1 year, 2 years, 3 years, 4 years, 5 years, 10 years, or longer. In some embodiments, the dosing regimen includes a permanent administration of the compound of Formula (I), Formula (Ia) or Formula (Ib), or a pharmaceutically acceptable salt thereof.

The dosage or dosing frequency of a compound of the present disclosure may be adjusted over the course of the treatment, based on the judgment of the administering physician.

In some embodiments, the compound of Formula (I), Formula (Ia) or Formula (Ib), or a pharmaceutically acceptable salt thereof, is administered on a daily or intermittent schedule. The compound may be administered to an individual (e.g., a human) in an effective amount. In some embodiments, the compound is administered once daily. In some embodiments, the compound of Formula (I), Formula (Ia) or Formula (Ib), or a pharmaceutically acceptable salt thereof, is administered on a monthly schedule. In some embodiments, the compound of Formula (I), Formula (Ia) or Formula (Ib), or a pharmaceutically acceptable salt thereof, is administered once about every 1 week, about every 2 weeks, about every 4 weeks, about every 8 weeks, about every 12 weeks, about every 16 weeks, about every 20 weeks, about every 24 weeks, or once about every 48 weeks. In some embodiments, the compound of Formula (I), Formula (Ia) or Formula (Ib), or a pharmaceutically acceptable salt thereof, is administered once every 4 weeks (or monthly). In some embodiments, the compound of Formula (I), Formula (Ia) or Formula (Ib), or a pharmaceutically acceptable salt thereof, is administered once every 8 weeks (or 2 months). In some embodiments, the compound of Formula (I), Formula (Ia) or Formula (Ib), or a pharmaceutically acceptable salt thereof, is administered once every 12 weeks (or three months). In some embodiments, the compound of Formula (I), Formula (Ia) or Formula (Ib), or a pharmaceutically acceptable salt thereof, is administered once every 16 weeks (or four months). In some embodiments, the compound of Formula (I), Formula (Ia) or Formula (Ib), or a pharmaceutically acceptable salt thereof, is administered once every 20 weeks (or five months). In some embodiments, the compound of Formula (I), Formula (Ia) or Formula (Ib), or a pharmaceutically acceptable salt thereof, is administered every 24 weeks (or 6 months). In some embodiments, the compound of Formula (I), Formula (Ia) or Formula (Ib), or a pharmaceutically acceptable salt thereof, is administered every 52 weeks (or yearly).

In some embodiments, the compound of Formula (I), Formula (Ia) or Formula (Ib), or a pharmaceutically acceptable salt thereof, is administered in a dosage amount that is effective. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day. In some embodiments, the dosage is from about 1 mg to about 200 mg, or from about 1 mg to about 1000 mg, or from about 1 mg to about 1500 mg. or from about 1 mg to about 2500 mg of the compound of Formula (I), Formula (Ia) or Formula (Ib), or a pharmaceutically acceptable salt thereof. In certain embodiments, the dosage amount is about 1 mg, about 10 mg, about 20 mg, about 30 mg, about 40 mg, about 50 mg, about 60 mg, about 70 mg, about 80 mg, about 90 mg, about 95 mg, about 100 mg, about 105 mg, about 110 mg, about 120 mg, about 130 mg, about 140 mg, or about 150 mg of the compound of Formula (I), Formula (Ia) or Formula (Ib), or a pharmaceutically acceptable salt thereof. In certain embodiments, the dosage amount is about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of the compound of Formula (I), Formula (Ia) or Formula (Ib), or a pharmaceutically acceptable salt thereof.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. A single dose can also be administered once every month, once every 2 months, once every 3 months, once every 4 months, once every 5 months, or once every 6 months. In some embodiments, a single dose can be administered once every week. A single dose can also be administered once every month.

In some embodiments, a compound of the present disclosure is administered via an implant.

Kits that comprise a compound of the present disclosure, or an enantiomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, implant, or intravenous bag.

VI. Synthesis of Compounds

Compounds disclosed herein may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds that are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the specified reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting certain functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The term "solvent" generally refers to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, methanol, and the like). Unless specified to the contrary, the solvents are inert organic solvents, and the reactions may be carried out under an inert gas (for example, argon or nitrogen).

The term "q.s." means adding a quantity sufficient to achieve a stated function, e.g., to bring a solution to the desired volume (i.e., 100%).

Compounds disclosed herein can be prepared, for instance, according to the following general schemes (which are provided for purposes of illustration, not limitation).

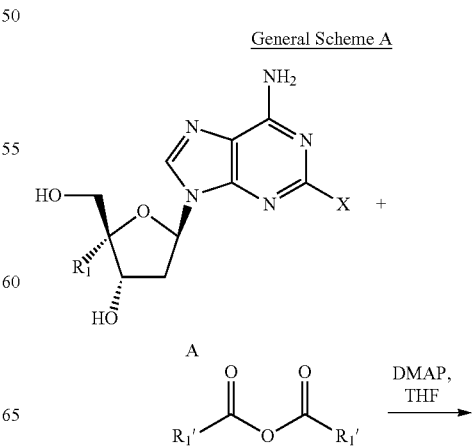

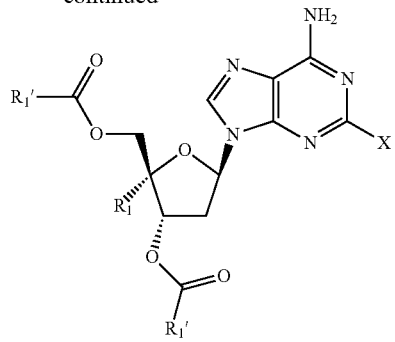

B; R₁' is defined within R² and R⁵

Compounds of formula B can be prepared in one step from compounds of formula A according to General Scheme A. This can be done by combining nucleosides of formula A with an anhydride reagent in the presence of DMAP and THF to yield after isolation compounds of formula B.

Compounds of formulas B, C and D can be prepared in one step from compounds of formula A according to General Scheme B. This can be done by combining nucleosides of formula A with a carboxylic acid reagent (about 0.8 to about 1.5 equivalents) in the presence of DMAP, THF and a reagent to activate the carboxylic acid reagent towards nucleophilic attack (e.g., DIC or EDCI; about 1 to about 2 equivalents) to yield after isolation compounds of formulas B, C and D.

General Scheme C

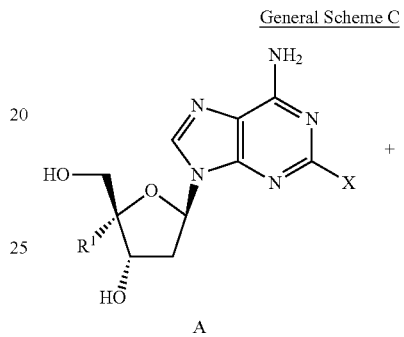

General Scheme B

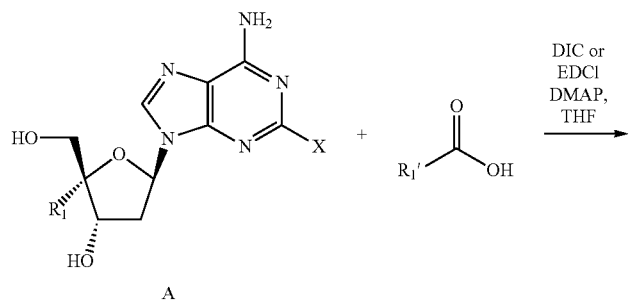

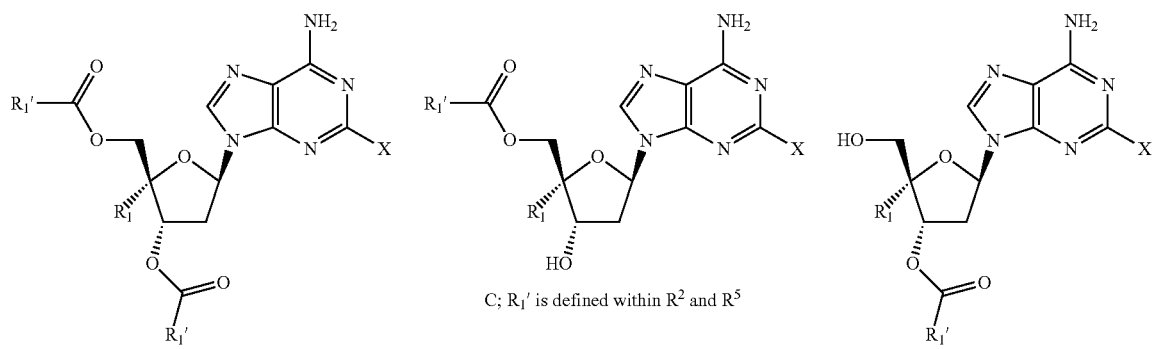

B; R₁' is defined within R² and R⁵

C; R₁' is defined within R² and R⁵

D; R₁' is defined within R² and R⁵

-continued

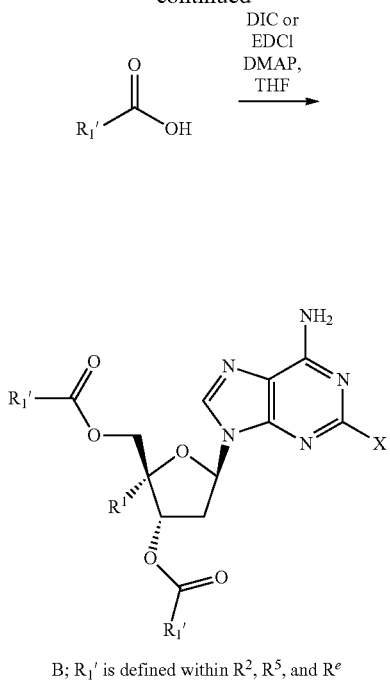

B; R₁' is defined within $R^2$, $R^5$, and $R^e$

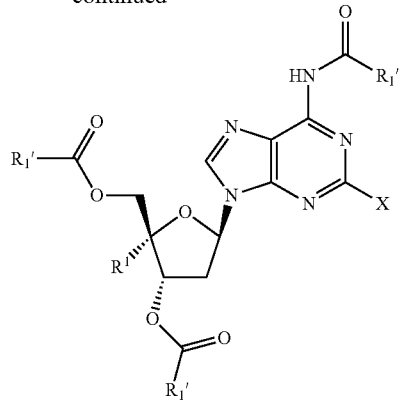

E; R₁' is defined within $R^2$, $R^5$, and $R^e$

Compounds of formulas B and E can be prepared in one step from compounds of formula A according to General Scheme C. This can be done by combining nucleosides of formula A with a carboxylic acid reagent (about 2 to about 3 equivalents) in the presence of DMAP, THF and a reagent to activate the carboxylic acid reagent towards nucleophilic attack (e.g., DIC or EDCI; about 2.5 to about 3.5 equivalents) to yield after isolation compounds of formulas B and E.

General Scheme D

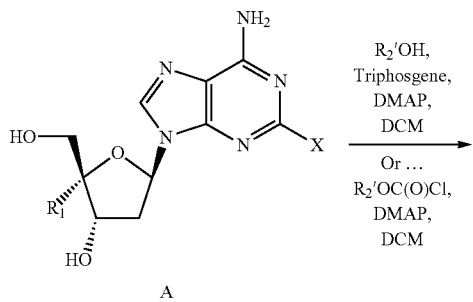

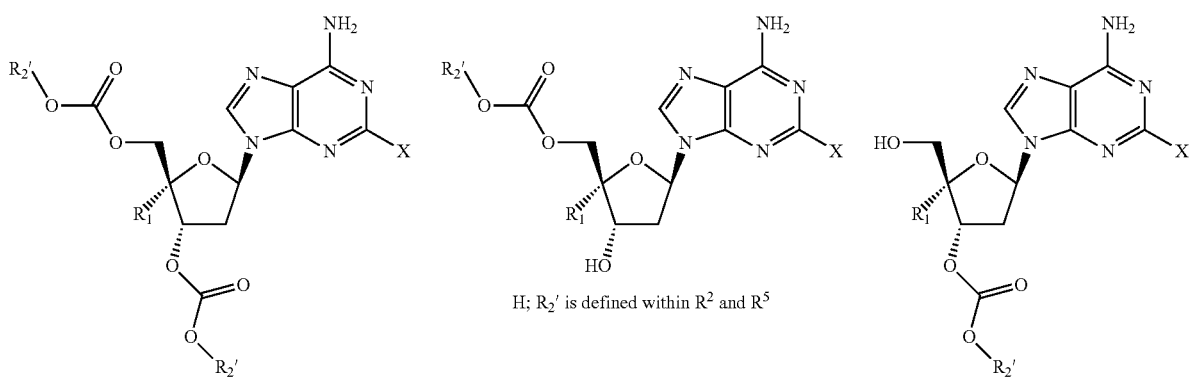

F; R₂' is defined within $R^2$ and $R^5$

H; R₂' is defined within $R^2$ and $R^5$

I; R₂' is defined within $R^2$ and $R^5$

Compounds of formulas F, H and I can be prepared in one step from compounds of formula A according to General Scheme D. This can be done by combining nucleosides of formula A with an alcohol (about 1 to 2 equivalents), triphosgene (about 0.3 to about 0.6 equivalents), DMAP and DCM to yield after isolation compounds of formulas F, H and I. Alternatively this can also be done by combining nucleosides of formula A with a chloroformate (about 1 to 2 equivalents), DMAP and DCM to yield after isolation compounds of formulas F, H and I.

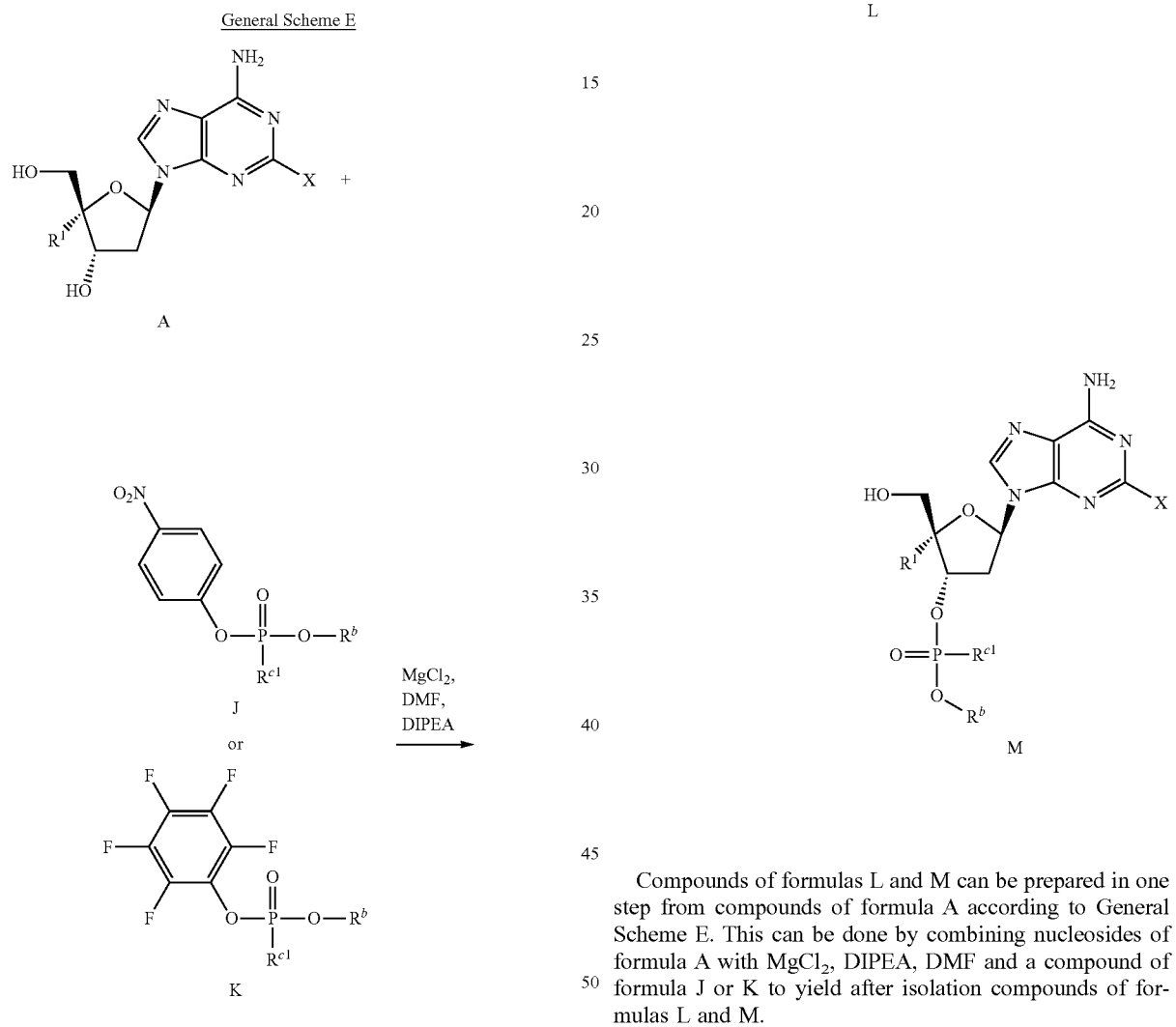

Compounds of formulas L and M can be prepared in one step from compounds of formula A according to General Scheme E. This can be done by combining nucleosides of formula A with MgCl$_2$, DIPEA, DMF and a compound of formula J or K to yield after isolation compounds of formulas L and M.

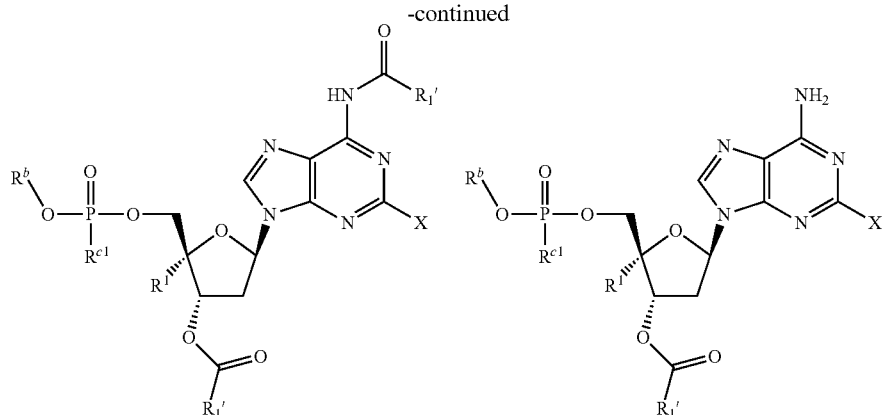

N; R₁' is defined within $R^5$ and $R^e$  
O; R₁' is defined within $R^5$ and $R^e$ Compounds of formula N and O can be prepared in one step from compounds of formula L according to General Scheme F. This can be done by combining compounds of formula L with a carboxylic acid reagent (about 2 equivalents) in the presence of DMAP, THF and a reagent to activate the carboxylic acid reagent towards nucleophilic attack (e.g., DIC or EDCI; about 4 equivalents) to yield after isolation compounds of formulas N and O.

General Scheme G

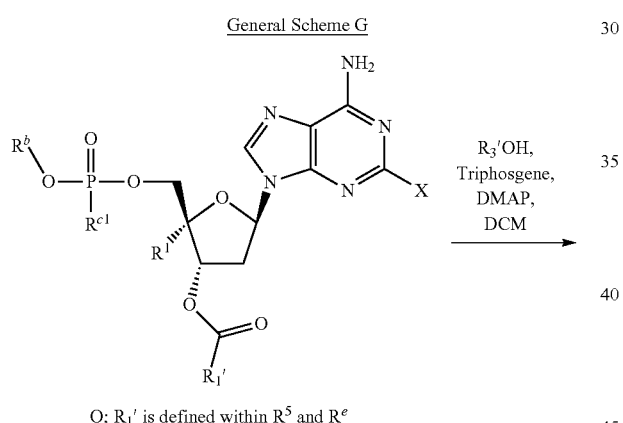

O; R₁' is defined within $R^5$ and $R^e$

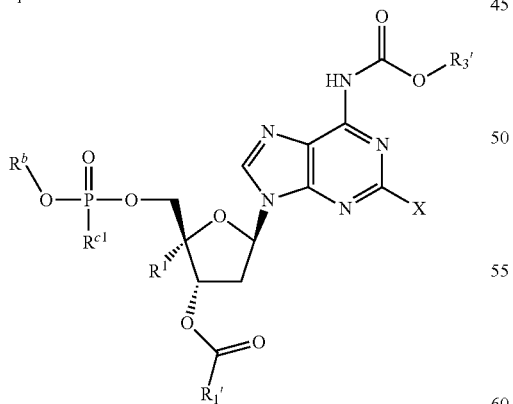

P; R₁' is defined within $R^5$ and $R^e$, R₃' is defined within $R^e$

Compounds of formula P can be prepared in one step from compounds of formula O according to General Scheme G. This can be done by combining compounds of formula O with an alcohol, triphosgene, DMAP and DCM to yield after isolation compounds of formula P.

General Scheme H

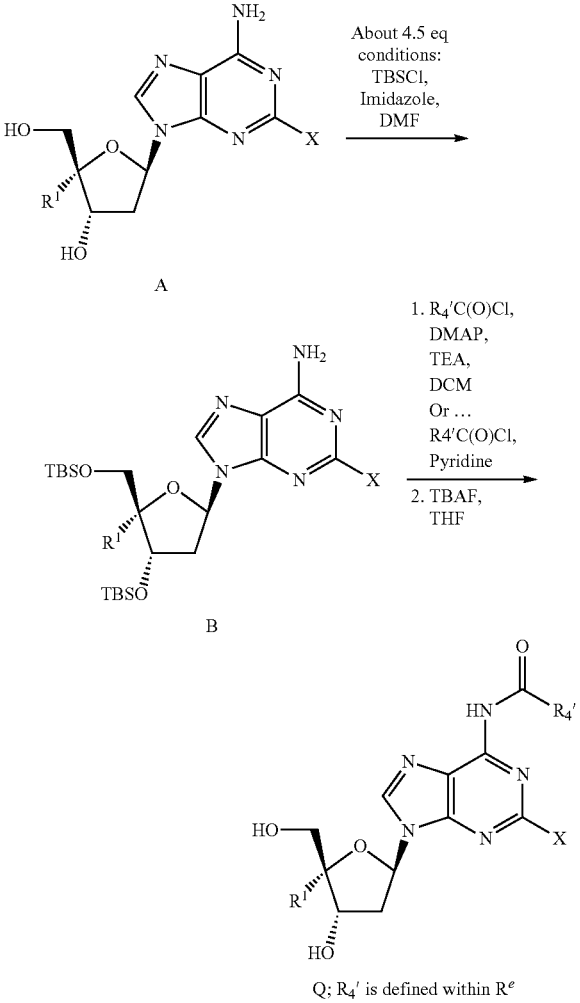

Q; R₄' is defined within $R^e$

Compounds of formula Q can be prepared in three steps from compounds of formula A according to General Scheme H. This can be done by combining nucleosides of formula A with imidazole, DMF and TBSCl (about 4.5 equivalents) to yield after isolation compounds of formula B. Compounds of formula B can then be combined with acid chlorides (which can either be obtained from commercial sources or prepared by combining a carboxylic acid with thionyl chloride and DCM), DMAP, TEA and DCM or combined with acid chlorides and pyridine to yield after isolation compounds containing an amide function group. The resulting compounds containing an amide functional group can then be combined with TBAF and THF to yield after isolation compounds of formula Q.

General Scheme I

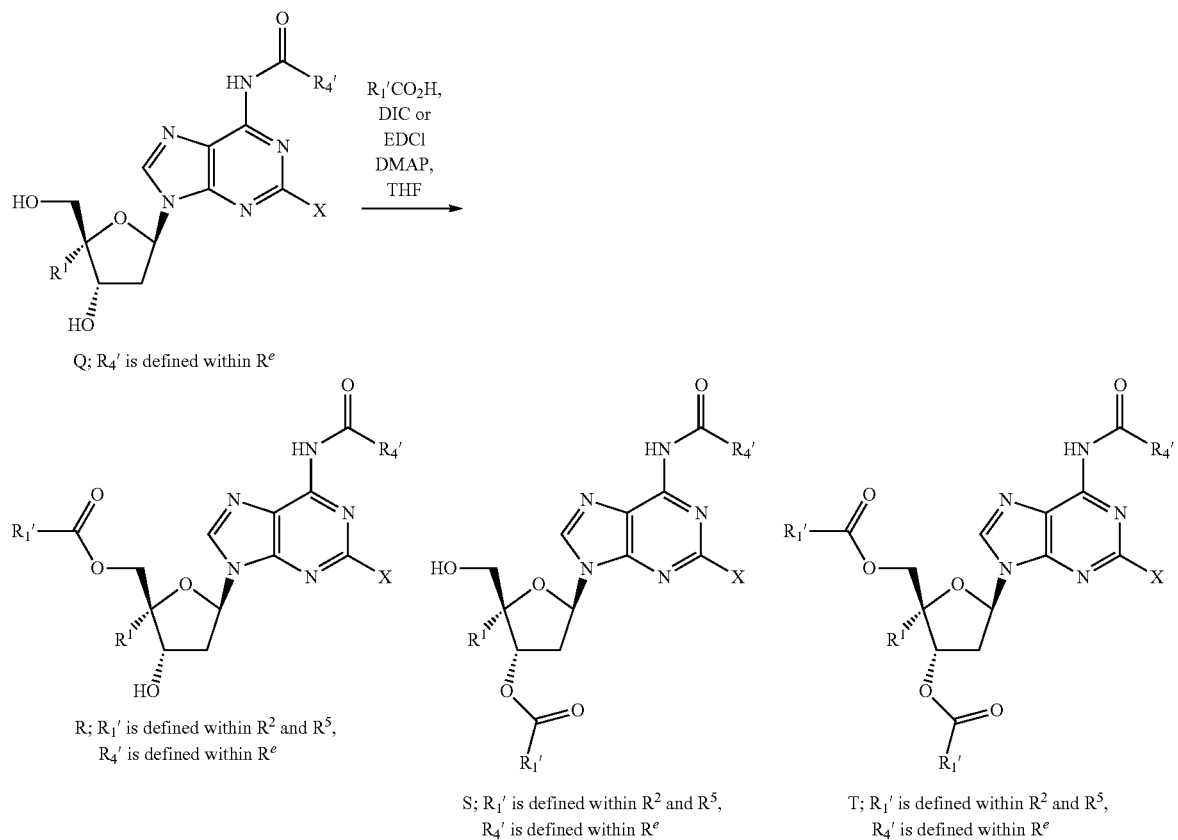

Compounds of formulas R, S and T can be prepared in one step from compounds of formula Q according to General Scheme I. This can be done by combining nucleosides of formula Q with a carboxylic acid reagent (about 0.8 to about 1.5 equivalents) in the presence of DMAP, THF and a reagent to activate the carboxylic acid reagent towards nucleophilic attack (e.g., DIC or EDCI; about 1 to about 2 equivalents) to yield after isolation compounds of formulas R, S and T.

General Scheme J

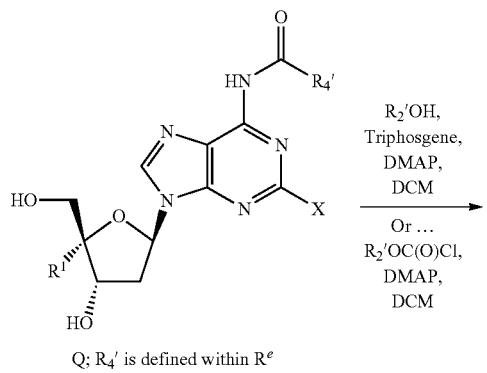

Q; $R_4'$ is defined within $R^e$

-continued

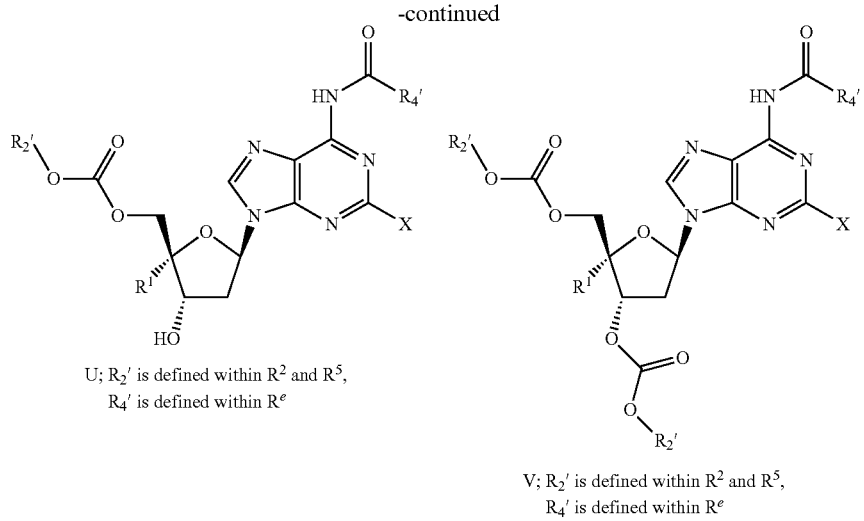

U; R₂' is defined within $R^2$ and $R^5$,
R₄' is defined within $R^e$

V; R₂' is defined within $R^2$ and $R^5$,
R₄' is defined within $R^e$

Compounds of formulas U and V can be prepared in one step from compounds of formula Q according to General Scheme J. This can be done by combining nucleosides of formula Q with an alcohol (about 1 to 2 equivalents), triphosgene (about 0.3 to about 0.6 equivalents), DMAP and DCM to yield after isolation compounds of formulas U and V. Alternatively this can also be done by combining nucleosides of formula Q with a chloroformate (about 1 to 2 equivalents), DMAP and DCM to yield after isolation compounds of formulas U and V.

General Scheme K

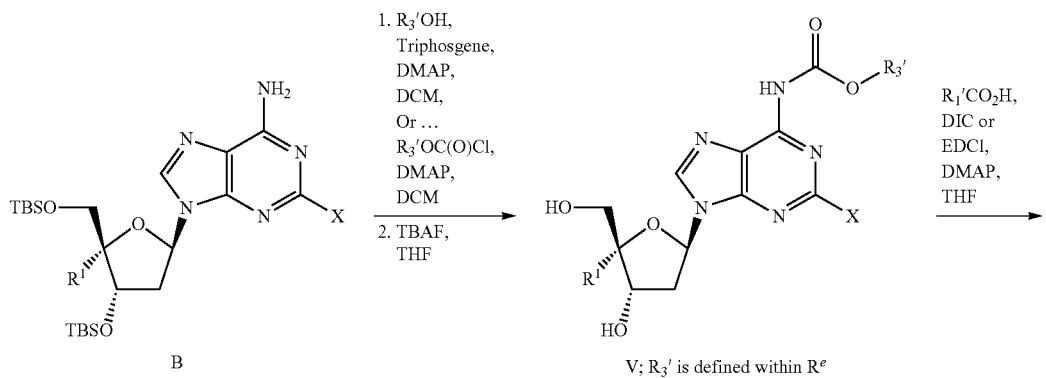

B

V; R₃' is defined within $R^e$

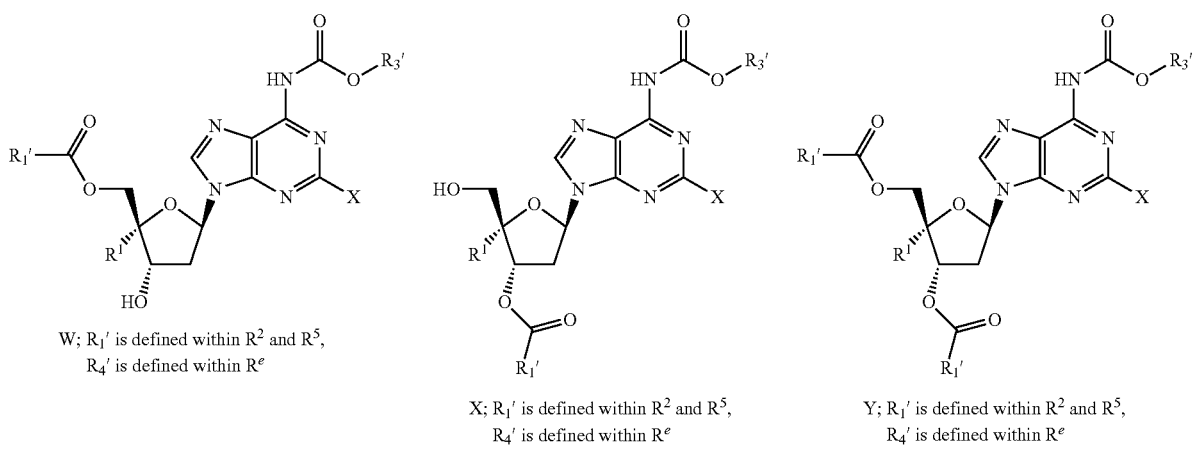

W; R₁' is defined within $R^2$ and $R^5$,
R₄' is defined within $R^e$

X; R₁' is defined within $R^2$ and $R^5$,
R₄' is defined within $R^e$

Y; R₁' is defined within $R^2$ and $R^5$,
R₄' is defined within $R^e$

Compounds of formula V can be prepared in two steps from compounds of formula B according to General Scheme K. This can be done by combining compounds of formula B with an alcohol, triphosgene, DMAP and DCM to yield after isolation compounds containing a carbamate functional group. Alternatively, this can also be done by combining nucleosides of formula B with a chloroformate (about 1 to 2 equivalents), DMAP and DCM to yield after isolation compounds containing a carbamate functional group. These carbamate functional group-containing intermediates can then be combined with TBAF and THF to yield after isolation compounds of formula V. Compounds of formulas W, X and Y can be prepared in one step from compounds of formula V according to General Scheme K. This can be done by combining compounds of formula V with a carboxylic acid reagent (about 0.8 to about 1.5 equivalents) in the presence of DMAP, THF and a reagent to activate the carboxylic acid reagent towards nucleophilic attack (e.g., DIC or EDCI; about 1 to about 2 equivalents) to yield after isolation compounds of formulas W, X and Y.

Compounds of formulas Z and Aa1 can be prepared in one step from compounds of formula V according to General Scheme L. This can be done by combining compounds of formula V with $MgCl_2$, DIPEA, DMF and a compound of formula J or K to yield after isolation compounds of formulas Z and Aa1.

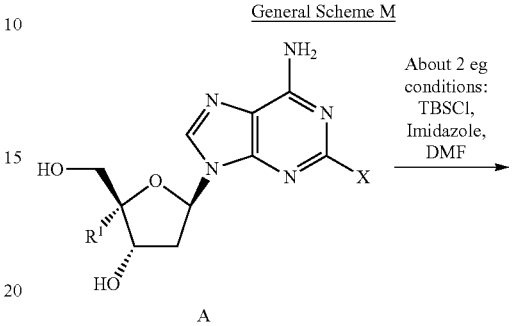

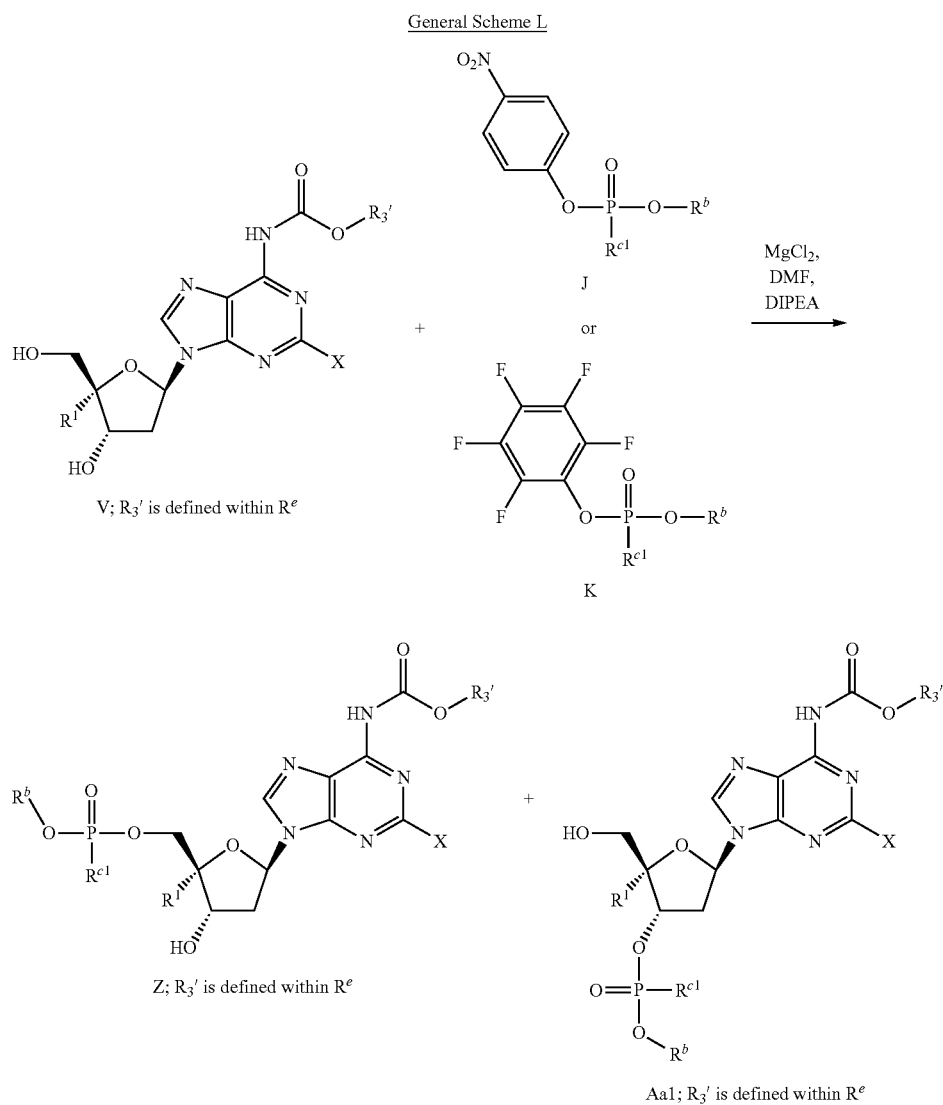

General Scheme N

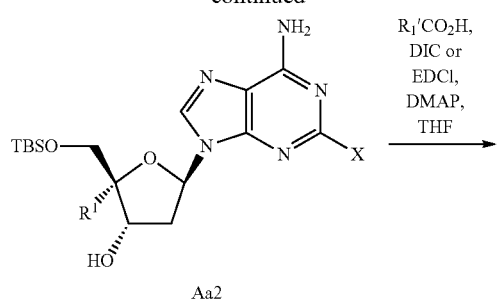

Aa2

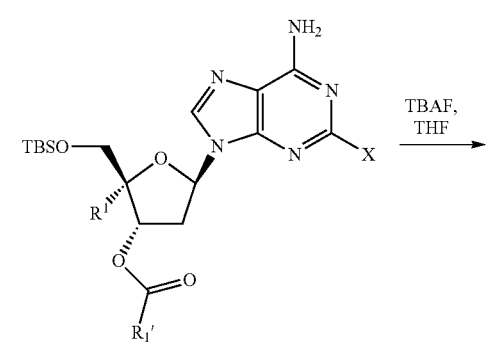

Aa3; R1' is defined within R[5]

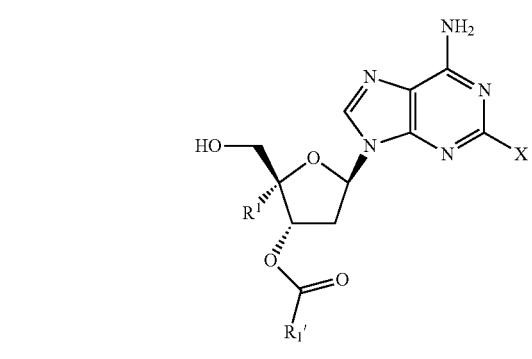

Aa4; R1' is defined within R[5]

Compounds of formula Aa4 can be prepared in three steps from nucleosides of formula A according to General Scheme M. This can be done by combining compounds of formula A with imidazole, DMF and TBSCl (about 2 equivalents) to yield after isolation compounds of formula Aa2. Compounds of formula Aa2 can be combined with a carboxylic acid reagent (about 0.8 to about 1.5 equivalents) in the presence of DMAP, THF and a reagent to activate the carboxylic acid reagent towards nucleophilic attack (e.g., DIC or EDCI; about 1 to about 2 equivalents) to yield after isolation compounds of formula Aa3. Compounds of formula Aa3 can be combined with TBAF and THF to yield after isolation compounds of formula Aa4.

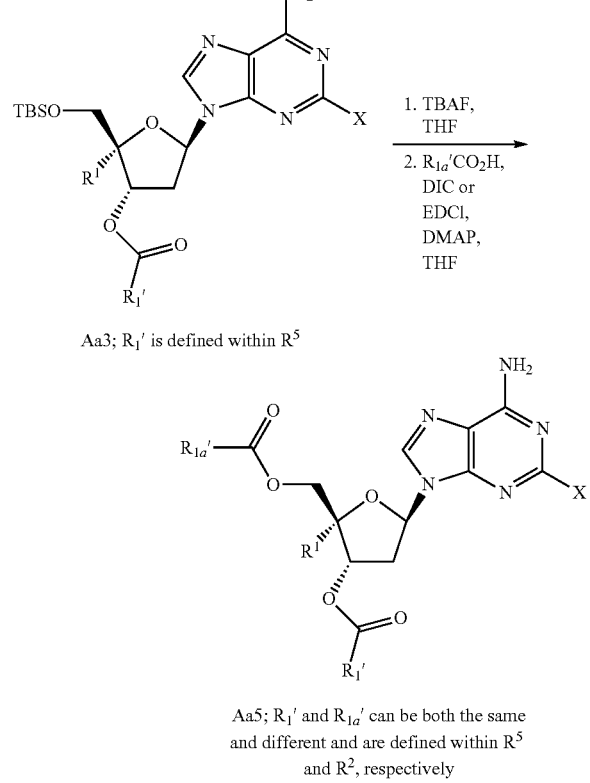

Aa3; R1' is defined within R[5]

Aa5; R1' and R1a' can be both the same and different and are defined within R[5] and R[2], respectively Compounds of formula Aa5 can be prepared from compounds of formula Aa3 in two steps according to General Scheme N. This can be done by combining compounds of formula Aa3 with TBAF and THF to yield after isolation compounds with a hydroxyl functional group. These compounds with a hydroxyl functional group can be combined with a carboxylic acid reagent (about 0.8 to about 1.5 equivalents) in the presence of DMAP, THF and a reagent to activate the carboxylic acid reagent towards nucleophilic attack (e.g., DIC or EDCI; about 1 to about 2 equivalents) to yield after isolation compounds of formula Aa5.

General Scheme O

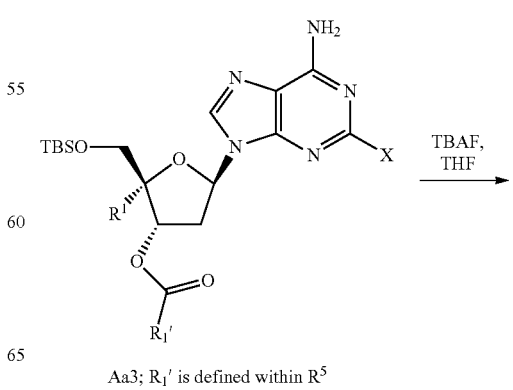

Aa3; R1' is defined within R[5]

-continued

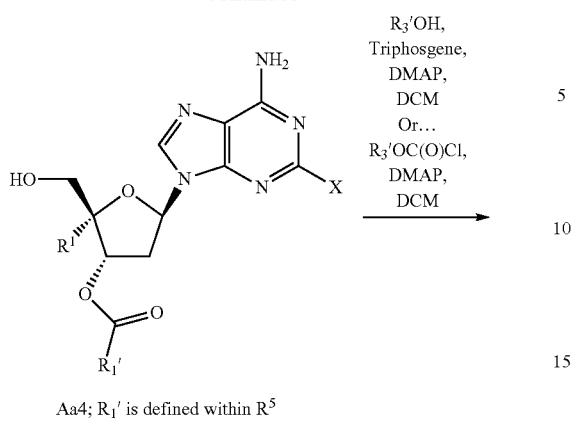

Aa4; R₁' is defined within R⁵

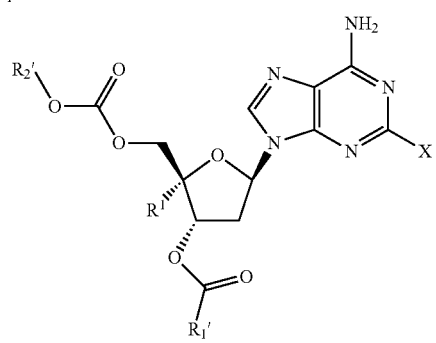

Aa6; R₁' is defined within
R⁵, R₂' is defined within R²

Compounds of formula Aa6 can be prepared from compounds of formula Aa3 in two steps according to General Scheme O. This can be done by combining compounds of formula Aa3 with TBAF and THF to yield after isolation compounds of formula Aa4. Compounds of formula Aa4 can be combined with an alcohol (about 1 equivalent), triphosgene (about 0.3 equivalents), DMAP and DCM to yield after isolation compounds of formula Aa6. Alternatively, this can also be done by combining compounds of formula Aa4 with a chloroformate (about 1 equivalent), DMAP and DCM to yield after isolation compounds of formula Aa6.

General Scheme P

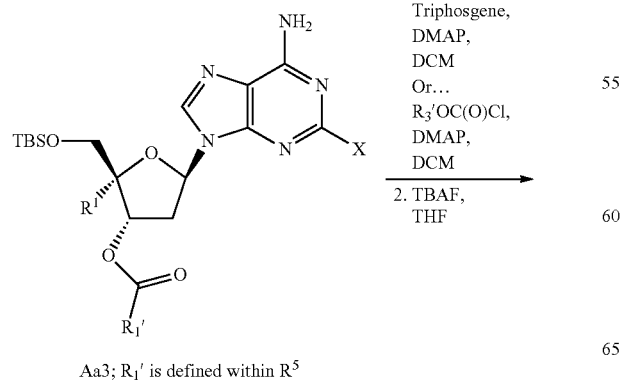

Aa3; R₁' is defined within R⁵

-continued

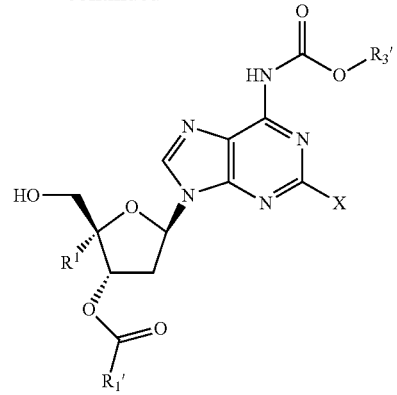

Aa7; R₁' is defined within R⁵,
R₃' is defined within Rᵉ

Compounds of formula Aa7 can be prepared in two steps from compounds of formula Aa3 according to General Scheme P. This can be done by combining compounds of formula Aa3 with an alcohol (about 1 equivalent), triphosgene (about 0.3 equivalents), DMAP and DCM to yield after isolation compounds with a carbamate functional group. Alternatively, this can also be done by combining compounds of formula Aa3 with a chloroformate (about 1 equivalent), DMAP and DCM to yield after isolation compounds containing a carbamate functional group. These carbamate functional group-containing compounds can be combined with TBAF and THF to yield after isolation compounds of formula Aa7.

General Scheme Q

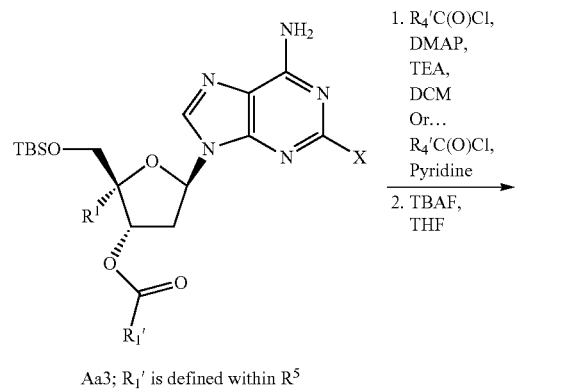

Aa3; R₁' is defined within R⁵

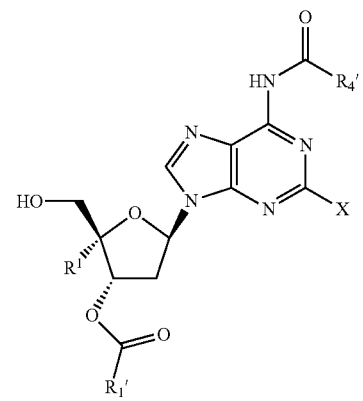

Aa8; R₁' is defined within R⁵,
R₄' is defined within Rᵉ

Compounds of formula Aa8 can be prepared in two steps from compounds of formula Aa3 according to General Scheme Q. This can be done by combining compounds of formula Aa3 with an acid chloride (which can either be obtained from commercial sources or prepared by combining a carboxylic acid with thionyl chloride and DCM), DMAP, TEA and DCM or combined with an acid chloride and pyridine to yield after isolation compounds containing an amide function group. These amide functional group-containing compounds can be combined with TBAF and THF to yield after isolation compounds of formula Aa8.

compounds of formula B with an alkyl halide, $KHCO_3$ and NMP. The resulting products from this reaction can then be treated with TBAF and THF to yield after isolation compounds of the formulas Aa9, Aa10, and Aa11. Compounds of formula Aa9 can be combined with a carboxylic acid reagent (about 0.8 to about 1.5 equivalents) in the presence of DMAP, THF and a reagent to activate the carboxylic acid reagent towards nucleophilic attack (e.g., DIC or EDCI; about 1 to about 2 equivalents) to yield after isolation compounds of formula Aa12. Similar treatment of com-

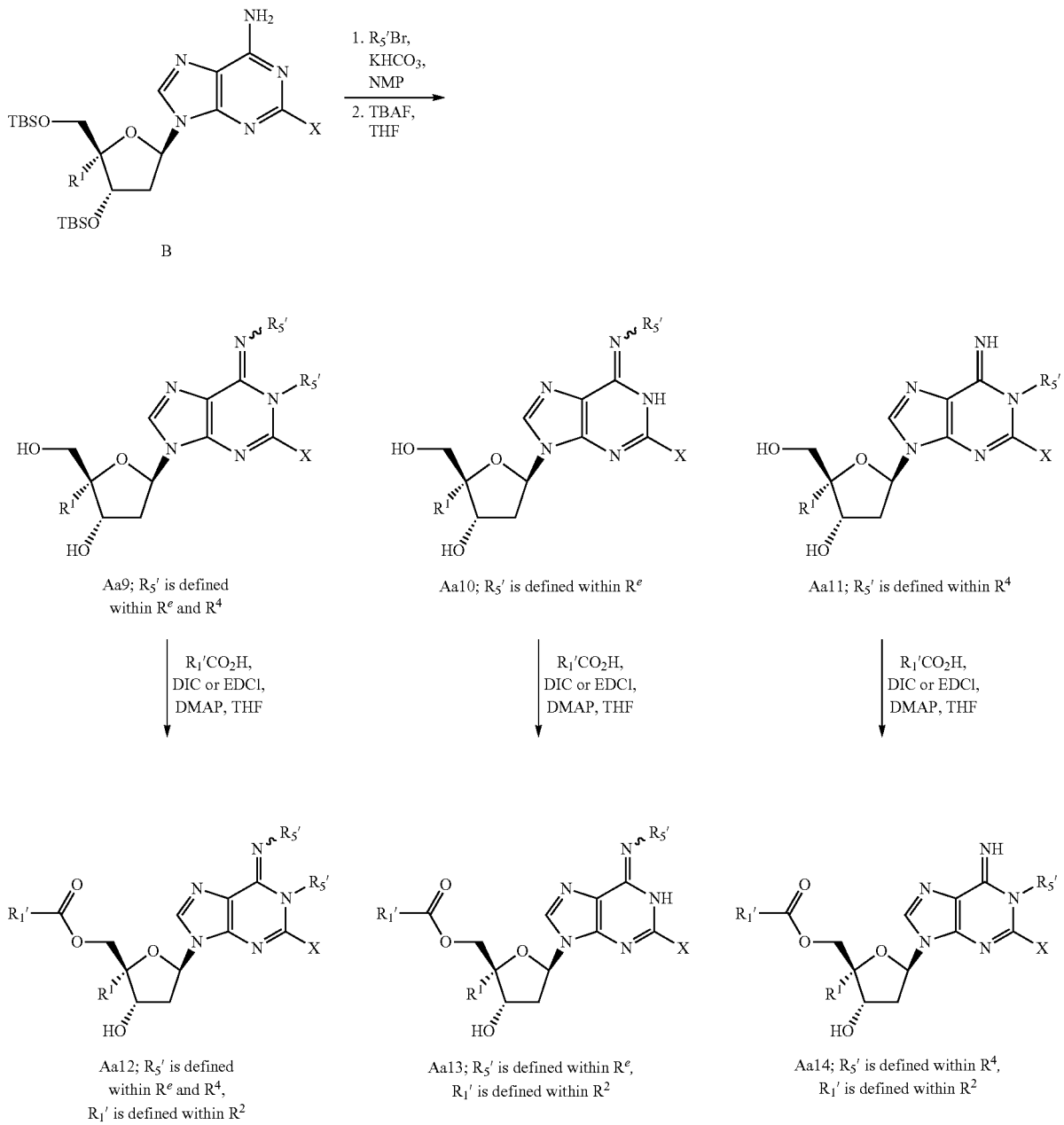

General Scheme R

Compounds of formulas Aa9, Aa10, and Aa11 can be prepared in two steps from compounds of formula B according to General Scheme R. This can be done by combining pounds of formula Aa10 can yield compounds of formula Aa13 and compounds of formula Aa11 can yield compounds of formula Aa14.

General Scheme S

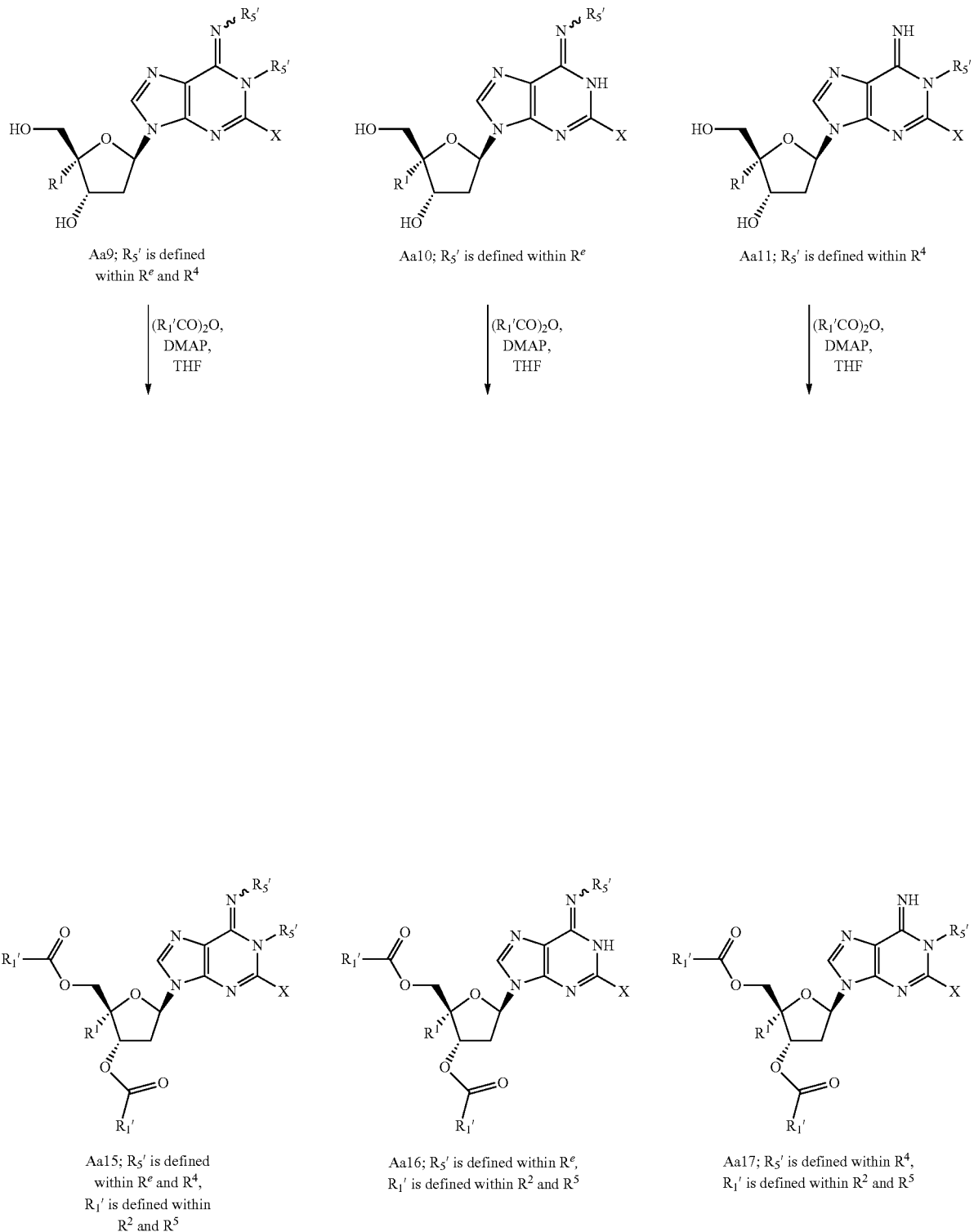

Compounds of formulas Aa15, Aa16, and Aa17 can be prepared in one step from compounds of formulas Aa9, Aa10 and Aa11, respectively, according to General Scheme R. This can be done by, for example, combining compounds of formula Aa9, an anhydride reagent, DMAP and THF to yield after isolation compounds of the formula Aa15. Similarly, compounds of formula Aa16 can be prepared from compounds of formula Aa10 and compounds of formula Aa11 can be prepared from compounds of formula Aa17.

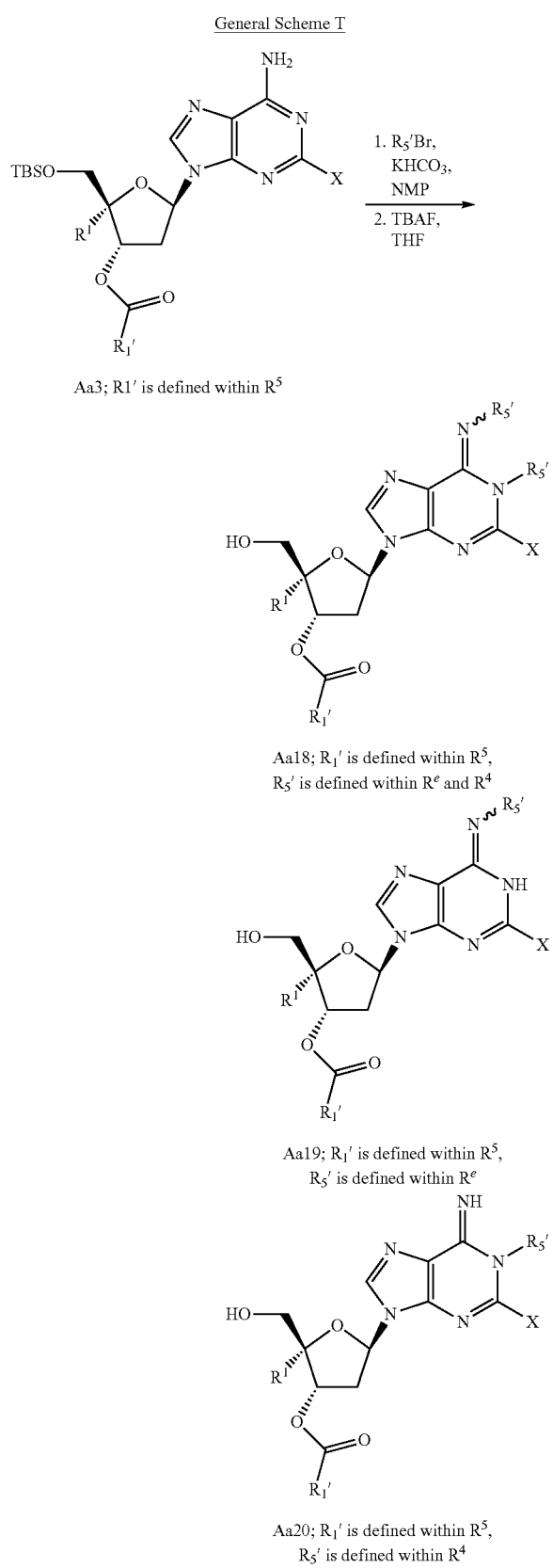

Compounds of formulas Aa18, Aa19, and Aa20 can be prepared in two steps from compounds of formula Aa3 according to General Scheme T. This can be done by combining compounds of formula Aa3 with an alkyl halide, $KHCO_3$ and NMP. The resulting products from this reaction can then be treated with TBAF and THF to yield after isolation compounds of the formulas Aa18, Aa19, and Aa20.

VII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013).

Compounds as described herein can be purified by any means known in the art, including chromatographic means, such as high-performance liquid chromatography (HPLC), preparative thin-layer chromatography, flash-column chromatography and ion-exchange chromatography. Any suitable stationary phase can be used, including normal and reversed phases as well as ionic resins. For example, the disclosed compounds can be purified via silica gel and/or alumina chromatography. See, e.g., Introduction to Modern Liquid Chromatography, 2d ed., L. R. Snyder and J. J. Kirkland, John Wiley and Sons, 1979; and Thin Layer Chromatography, E. Stahl, Springer-Verlag, New York, 1969.

During any of the processes for preparation of the subject compounds, it may be desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known in the art.

Exemplary chemical entities useful in methods of the embodiments will now be described by reference to illustrative synthetic schemes for their general preparation herein and the specific examples provided. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the pendant groups. Each of the reactions depicted in the general schemes can be run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step. The embodiments are also directed to processes and intermediates useful for preparing the subject compounds or pharmaceutically acceptable salts thereof. The following description is, therefore, not intended to limit the scope of the present disclosure.

In some embodiments, the present disclosure generally provides a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in schemes below, and the examples that follow.

The compounds detailed in the Examples were synthesized according to the general synthetic methods described below. Compounds were named using ChemDraw version 18.1.0.535 (PerkinElmer Informatics, Inc.) unless otherwise indicated.

Abbreviations

Certain abbreviations and acronyms are used in describing the experimental details. Although most of these would be understood by one skilled in the art, Table 1 contains a list of many of these abbreviations and acronyms.

TABLE 1

List of abbreviations and acronyms

| Abbreviation | Meaning |
|---|---|
| Å | angstrom |
| ACN | acetonitrile |
| aq | aqueous |
| bs | broad singlet |
| CC50 | 50% cytotoxic concentration |
| d | doublet |
| DCM | dichloromethane |
| dd | doublet of doublets |
| ddd | doublet of doublet of doublets |
| DIC | N-N-diisopropylcarbodiimide |
| DIPEA | N-N-diisopropylethylamine |
| DMAP | dimethylaminopyridine |
| DMF | dimethylformamide |
| DMSO | dimethyl sulfoxide |
| dp | doublet of pentets |
| dt | doublet of triplets |
| EC50 | half maximal effective concentration |
| ECldA | (2R,3S,5R)-5-(6-amino-2-chloro-9H-purin-9-yl)-2-ethynyl-2-(hydroxymethyl)tetrahydrofuran-3-ol |
| EDCI | 1-ethyl-3-(3-dimethylaminopropyl)carbiimide |
| EtOAc | ethyl acetate |
| g | gram(s) |
| h | hour(s) |
| Hex | hexane(s) |
| HPLC | high performance liquid chromatography |
| Hz | hertz |
| J | coupling constant |
| KHCO3 | potassium bicarbonate |
| LC | liquid chromatography |
| LCMS | liquid chromatography-mass spectrometry |
| LiCl | lithium chloride |
| M | molar |
| m | multiplet |
| m/z | mass-to-charge ratio |
| MeOH | methanol |
| mg | milligram(s) |
| MHz | megahertz |
| min | minute(s) |
| mL or ml | milliliter(s) |
| mm | millimeter(s) |
| mmol | millimole(s) |
| MS | mass spectrometry |
| MT-4 or MT4 | metallothionein 4 human T cell line |
| NMP | N-methyl-2-pyrrolidone |
| NMR | nuclear magnetic resonance |
| P | pentet |

TABLE 1-continued

List of abbreviations and acronyms

| Abbreviation | Meaning |
|---|---|
| PMPA | (R)-(((1-(6-amino-9H-purin-9-yl)propan-2-yl)oxy)methyl)phosphonic acid or (R)-9-(2-phosphonomethoxypropyl)adenine or tenofovir |
| q | quartet |
| RT, rt | room temperature |
| s | singlet |
| t | triplet |
| TBAF | tetra-n-butylammonium fluoride |
| TBSCl | tert-butyldimethylsilyl chloride |
| td | triplet of doublets |
| TEA | triethylamine |
| TFA | trifluoroacetic acid |
| THF | tetrahydrofuran |
| tt | triplet of triplets |
| UHPLC | ultra-high performance liquid chromatography |
| µ | micron |
| µl, µL | microliter(s) |
| µM | micromolar |

Example 1

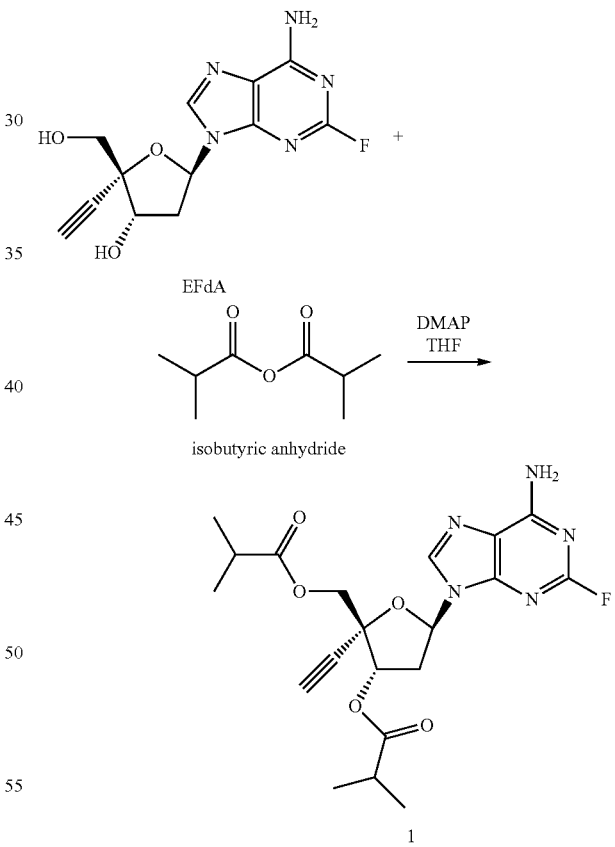

Synthesis of Compound 1: (2R,3S,5R)-5-(6-amino-2-fluoro-9H-purin-9-yl)-2-ethynyl-2-((isobutyryloxy)methyl)tetrahydrofuran-3-yl isobutyrate To a solution of (2R,3S,5R)-5-(6-amino-2-fluoro-9H-purin-9-yl)-2-ethynyl-2-(hydroxymethyl)tetrahydrofuran-3-ol (EFdA, ChemSpace) (300 mg, 1.02 mmol) and DMAP (500 mg, 4.09 mmol) in THF (5 mL) was added isobutyric anhydride (679 μL, 4.09 mmol). The resulting reaction was stirred at room temperature for 1 h. The reaction was quenched by the addition of saturated aqueous sodium bicarbonate and diluted with EtOAc. The organic layer was separated and washed with water then brine. The organics were dried over sodium sulfate, filtered and concentrated. Purification by HPLC chromatography (50% ACN/50% water ramping to 100% ACN) afforded the title compound 1.

¹H NMR (400 MHz, DMSO-d₆) δ 8.36 (s, 1H), 7.93 (d, J=35.4 Hz, 2H), 6.37 (t, J=6.8 Hz, 1H), 5.70 (dd, J=7.0, 5.0 Hz, 1H), 4.41 (d, J=11.6 Hz, 1H), 4.22 (d, J=11.5 Hz, 1H), 3.82 (s, 1H), 3.28-3.10 (m, 1H), 2.73-2.58 (m, 2H), 2.56-2.45 (m, 1H), 1.18 (d, J=7.0 Hz, 3H), 1.15 (d, J=7.0 Hz, 3H), 1.06 (d, J=7.0 Hz, 3H), 1.03 (d, J=7.0 Hz, 3H).

¹⁹F NMR (376 MHz, DMSO-d₆) δ −52.09.

LCMS: MS m/z=434.10 [M+1], $t_R$=0.93 min; LC system: Agilent 1260 Infinity II HPLC; MS system: G6124B Single Quad; Column: Kinetix 2.6u C18 100 A, 50 mm×2.1 mm; Solvents: acetonitrile with 0.1% acetic acid, water with 0.1% acetic acid; Gradient: 0-1.00 min 10%-100% acetonitrile, 1.00-1.35 min 100% acetonitrile, 1.35-1.36 min 100-10% acetonitrile at 2 μL/min.

HPLC: $t_R$=3.23 min; HPLC system: Agilent 1100 series; Column: Gemini 5μ C18 110 A, 50×4.6 mm; Solvents: Acetonitrile with 0.1% TFA, Water with 0.1% TFA; Gradient: 0 min-5.0 min 2-98% acetonitrile, 5.0 min-6.0 min 98% acetonitrile at 2 mL/min.

Example 2

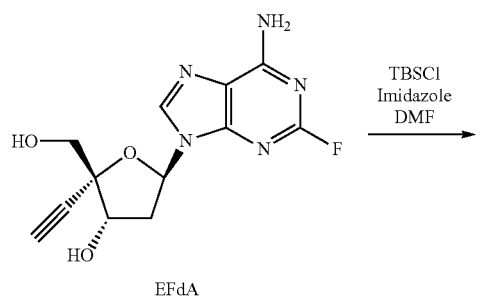

EFdA

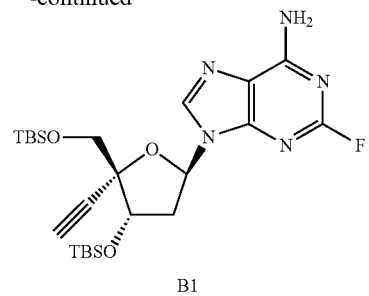

B1

Synthesis of Intermediate B1—9-((2R,4S,5R)-4-((tert-butyldimethylsilyl)oxy)-5-(((tert-butyldimethylsilyl)oxy)methyl)-5-ethynyltetrahydrofuran-2-yl)-2-fluoro-9H-purin-6-amine tert-Butyldimethylsilyl chloride (4.63 g, 30.7 mmol) was added to a solution of EFdA (2.00 g, 6.82 mmol) and imidazole (2.09 g, 30.7 mmol) in dimethylformamide (20 mL). After 18 hours the reaction was diluted with ethyl acetate (100 mL) and washed with water (50 mL), 5% lithium chloride (2×50 mL) and saturated ammonium chloride (2×50 mL). The organic phase was dried over sodium sulfate and the solvent was removed under reduced pressure. The residue was subjected to flash chromatography (30-100% ethyl acetate/hexanes). The fractions containing product were combined and the solvent was removed under reduced pressure, providing the title compound B1.

¹H NMR (400 MHz, Chloroform-d) δ 8.11 (s, 1H), 6.39 (dd, J=7.1, 4.2 Hz, 1H), 5.79 (s, 2H), 4.83 (t, J=7.0 Hz, 1H), 3.98 (d, J=11.2 Hz, 1H), 3.82 (d, J=11.2 Hz, 1H), 2.77-2.60 (m, 2H), 2.57 (s, 1H), 0.95 (s, 9H), 0.91 (s, 9H), 0.15 (s, 3H), 0.14 (s, 3H), 0.11 (s, 3H), 0.07 (s, 3H).

¹⁹F NMR (376 MHz, Chloroform-d) δ −51.10.

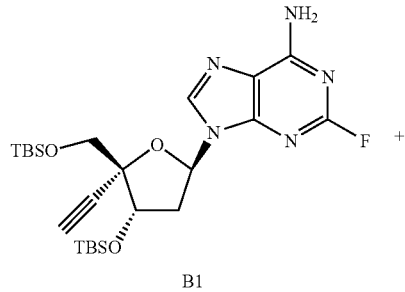

B1

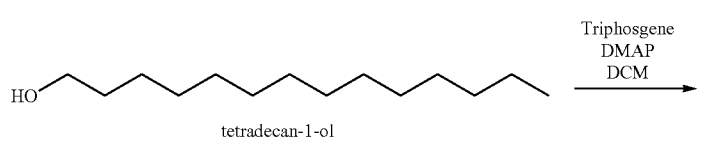

tetradecan-1-ol

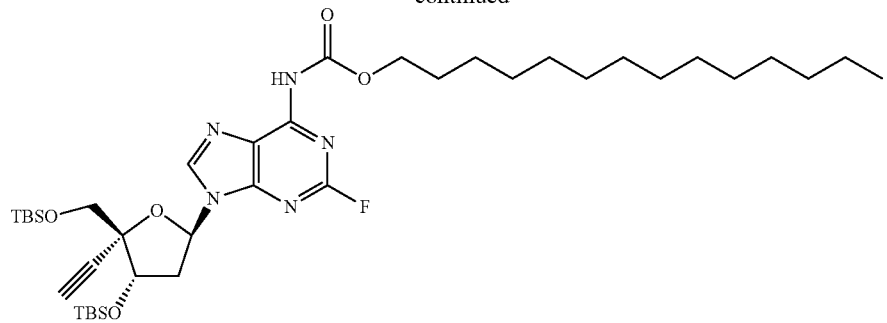

B2

Synthesis of Intermediate B2—Tetradecyl N-[9-[(2R,4S,5R)-4-[tert-butyl(dimethyl)silyl]oxy-5-[[tert-butyl(dimethyl)silyl]oxymethyl]-5-ethynyl-tetrahydrofuran-2-yl]-2-fluoro-purin-6-yl]carbamate 4-Dimethylaminopyridine (140 mg, 1.15 mmol) was added to a solution of triphosgene (34.1 mg, 0.115 mmol) in dichloromethane (4 mL). A solid formed. After 10 minutes intermediate B1 (100 mg, 0.192 mmol) was added. The mixture was stirred at room temperature for 18 h. Tetradecan-1-ol (247 mg, 1.15 mmol) was added. After 90 min the reaction mixture was diluted with dichloromethane (10 mL). The mixture was washed with water (3×10 mL) and saturated ammonium chloride (10 mL). The organic phase was dried over sodium sulfate and the solvent was removed under reduced pressure. The residue was subjected to flash chromatography (0-30% ethyl acetate/hexanes). The fractions containing product were combined and the solvent was removed under reduced pressure, providing the title compound B2.

$^1$H NMR (400 MHz, DMSO-d$_6$) δ 10.90 (s, 1H), 8.54 (s, 1H), 6.34 (dd, J=7.8, 3.8 Hz, 1H), 4.98 (m, 1H), 4.13 (t, J=6.5 Hz, 2H), 3.79 (d, J=11.2 Hz, 1H), 3.65 (d, J=11.3 Hz, 1H), 3.58 (s, 1H), 3.04 (m, 1H), 1.62 (p, J=6.6 Hz, 2H), 1.36 (m, 2H), 1.24 (m, 20H), 0.93 (s, 9H), 0.89-0.83 (m, 3H), 0.72 (s, 9H), 0.16 (m, 6H), −0.04 (s, 3H), −0.19 (s, 3H).

$^{19}$F NMR (376 MHz, DMSO-d$_6$) δ −51.90.

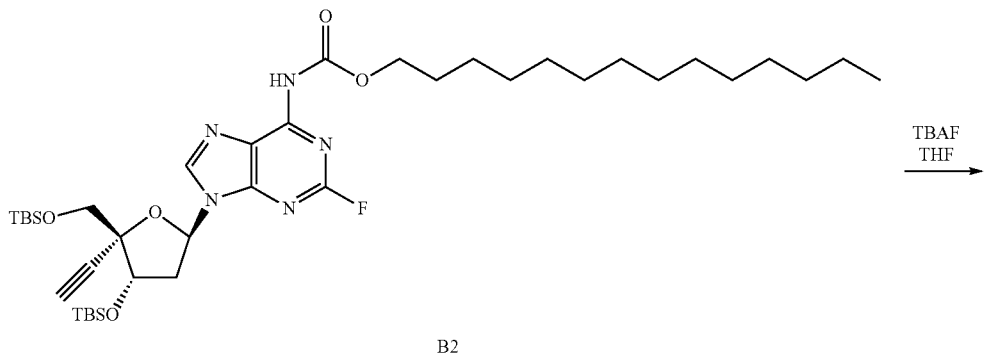

B2

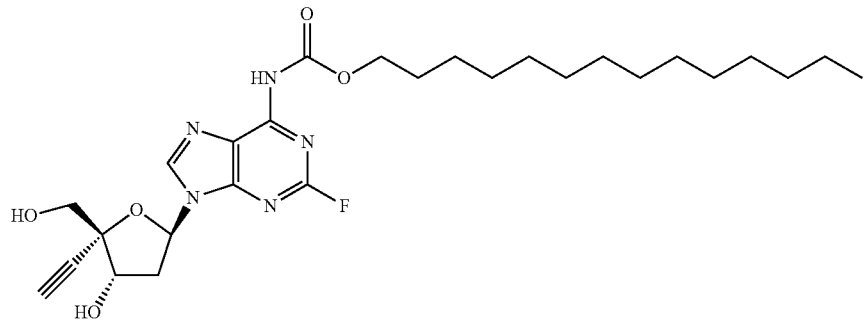

2

Synthesis of Compound 2—Tetradecyl (9-((2R,4S, 5R)-5-ethynyl-4-hydroxy-5-(hydroxymethyl)tetrahydrofuran-2-yl)-2-fluoro-9H-purin-6-yl)carbamate Tetra-n-butylammonium fluoride (1.00 M, 2.09 mL, 2.09 mmol) was added to a solution of intermediate B2 (127 mg,

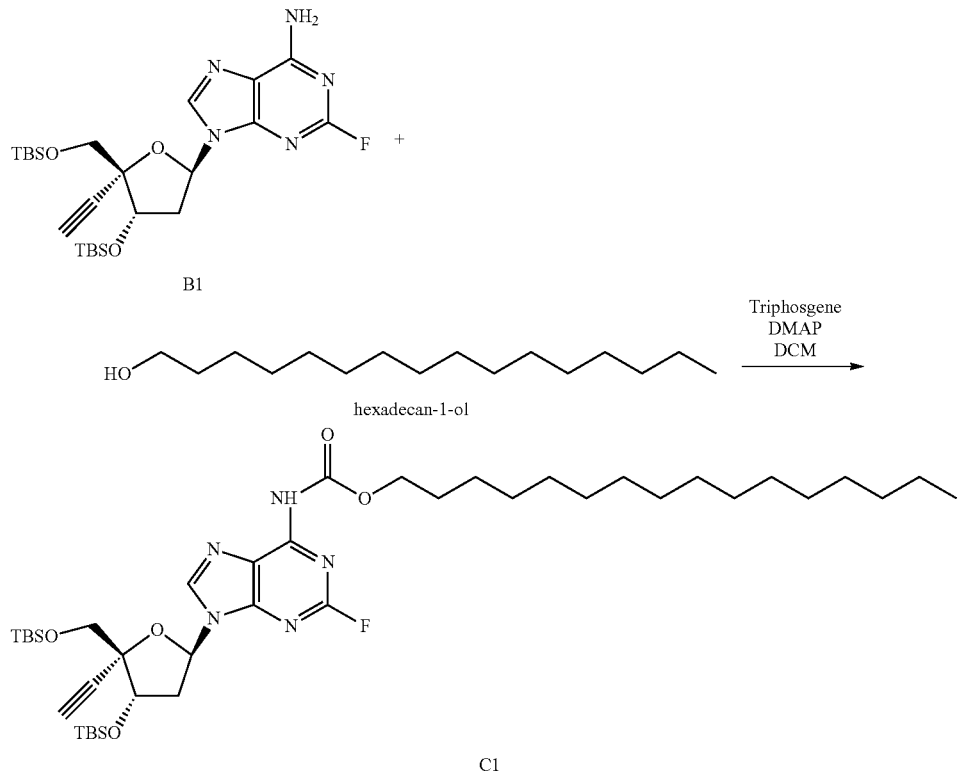

0.161 mmol) in tetrahydrofuran (4.0 mL) at room temperature. After 10 min the reaction was diluted with ethyl acetate (20 mL) and washed with water (3×10 mL), and brine (10 mL). The solvent was removed under reduced pressure. The residue was subjected to preparative HPLC (Gemini, 10 uM, NX-C18, 110 Å 250×30 mm column, 60%-100% acetonitrile/water gradient over 20 minutes). The fractions containing product were combined and subjected to lyophilization providing the title compound 2.

$^1$H NMR (400 MHz, Acetonitrile-d$_3$) δ 9.18 (s, 1H), 8.29 (s, 1H), 6.39 (dd, J=7.1, 5.3 Hz, 1H), 4.74 (q, J=6.3 Hz, 1H), 4.21 (t, J=6.6 Hz, 2H), 4.05 (dd, J=8.3, 4.9 Hz, 1H), 3.84 (dd, J=12.2, 4.6 Hz, 1H), 3.79-3.69 (m, 2H), 2.97 (s, 1H), 2.83 (m, 1H), 2.59 (m, 1H), 1.67 (m, 2H), 1.49-1.36 (m, 2H), 1.36-1.22 (m, 20H), 0.97-0.85 (m, 3H).

$^{19}$F NMR (376 MHz, DMSO-d$_6$) δ −52.16.

LCMS: MS m/z=533.72 [M+1]; t$_R$=1.677 min; LC system: Thermo Dionex Ultimate 3000 UHPLC+focused; MS system: Thermo LCQ Fleet; Column: Phenomenex Kinetex 2.6µ-C18 100 A, 50×2.1 mm; Solvents: Acetonitrile with 0.1% trifluoroacetic acid, water with 0.1% trifluoroacetic acid; Gradient: 0 min-0.2 min 40% acetonitrile, 0.2 min-1.55 min 40%-100% acetonitrile, 1.55 min-2.80 min 100% Acetonitrile, 2.81 min-2.91 min 10% Acetonirile. at 1.0 mL/min.

HPLC: t$_R$=4.303 min; HPLC system: Agilent 1100 series.; Column: Gemini 5µ C18 110 A, 50×6.0 mm; Solvents: A=Acetonitrile with 0.1% TFA, B=Water with 0.1% TFA; Gradient: 0 min-5.0 min 2-98% B, 5.01 min-5.0 min 2% B at 2 mL/min.

Example 3

Synthesis of Intermediate C1—Hexadecyl (9-((2R, 4S,5R)-4-((tert-butyldimethylsilyl)oxy)-5-(((tert-butyldimethylsilyl)oxy)methyl)-5-ethynyltetrahydrofuran-2-yl)-2-fluoro-9H-purin-6-yl)carbamate 4-Dimethylaminopyridine (140 mg, 1.15 mmol) was added to a solution of triphosgene (34.1 mg, 0.115 mmol) in dichloromethane (4 mL). A solid formed. After 10 minutes intermediate B1 (100 mg, 1.92 mmol) was added. The mixture was stirred at room temperature for 20 h. Hexadecan-1-ol (929 mg, 1.92 mmol) was added. After 1 day at 7° C., the reaction mixture was diluted with dichloromethane (10 mL). The mixture was washed with water (3×10 mL) and saturated ammonium chloride (10 mL). The organic phase was dried over sodium sulfate and the solvent was removed under reduced pressure. The residue was subjected to flash chromatography (0-30% ethyl acetate/hexanes). The fractions containing product were combined and the solvent was removed under reduced pressure, providing the title compound C1.

$^1$H NMR (400 MHz, DMSO-d$_6$) δ 10.89 (s, 1H), 8.54 (s, 1H), 6.34 (dd, J=7.8, 3.8 Hz, 1H), 4.98 (t, J=7.2 Hz, 1H), 4.13 (t, J=6.5 Hz, 2H), 3.79 (d, J=11.3 Hz, 1H), 3.65 (d, J=11.3 Hz, 1H), 3.58 (s, 1H), 3.10-2.98 (m, 1H), 2.49-2.43 (m, 1H), 1.69-1.56 (m, 2H), 1.48-1.33 (m, 2H), 1.33-1.22 (m, 24H), 0.93 (s, 9H), 0.91-0.82 (m, 3H), 0.72 (s, 9H), 0.20-0.12 (m, 6H), −0.04 (s, 3H), −0.19 (s, 3H).

$^{19}$F NMR (376 MHz, DMSO-d$_6$) δ −51.90.

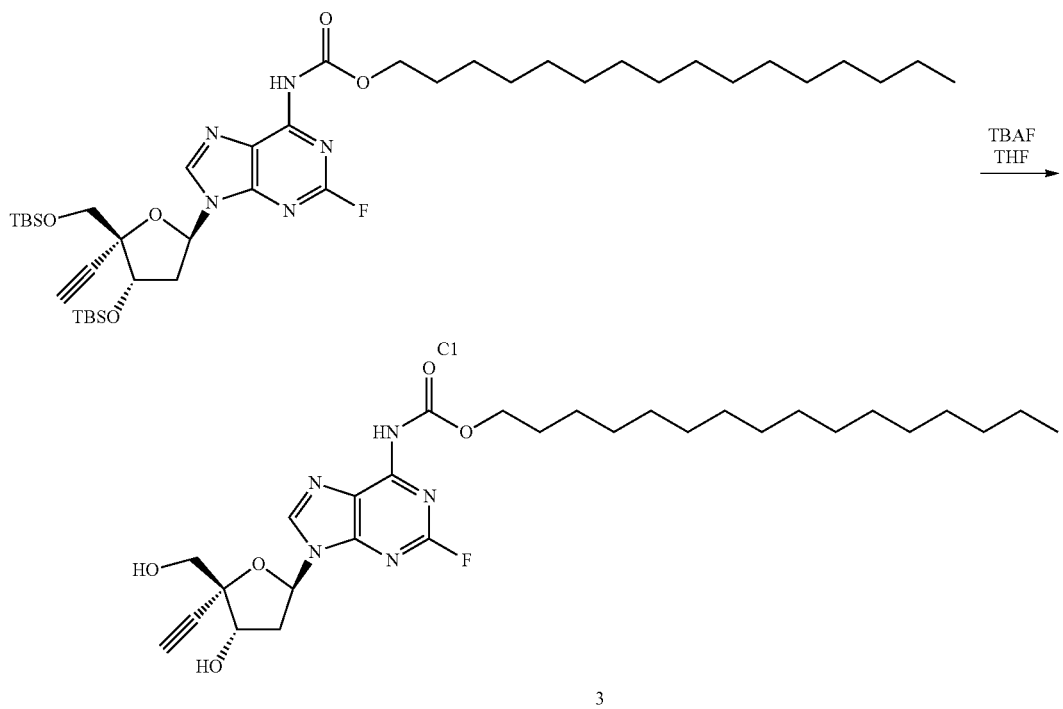

Example 4

Synthesis of Compound 3—Hexadecyl (9-((2R,4S, 5R)-5-ethynyl-4-hydroxy-5-(hydroxymethyl)tetrahydrofuran-2-yl)-2-fluoro-9H-purin-6-yl)carbamate Tetra-n-butylammonium fluoride (1.00 M, 2.11 mL, 2.11 mmol) was added to a solution of intermediate C1 (128 mg, 0.162 mmol) in tetrahydrofuran (4.0 mL) at room temperature. After 20 min the reaction was diluted with ethyl acetate (20 mL) and washed with water (3×10 mL), and brine (10 mL). The solvent was removed under reduced pressure. The residue was subjected to preparative HPLC (Gemini, 10 uM, NX-C18, 110 Å 250×30 mm column, 60%-100% acetonitrile/water gradient over 20 minutes). The fractions containing product were combined and subjected to lyophilization providing the title compound 3.

$^1$H NMR (400 MHz, Acetonitrile-$d_3$) 8.95 (s, 1H), 8.28 (s, 1H), 6.39 (dd, J=7.0, 5.4 Hz, 1H), 4.73 (q, J=6.2 Hz, 1H), 4.22 (t, J=6.6 Hz, 2H), 3.94 (m, 1H), 3.83 (dd, J=12.1, 4.1 Hz, 1H), 3.74 (dd, J=12.2, 8.0 Hz, 1H), 3.63 (d, J=5.6 Hz, 1H), 2.97 (s, 1H), 2.84 (m, 1H), 2.58 (m, 1H), 1.78-1.65 (m, 2H), 1.51-1.37 (m, 2H), 1.37-1.23 (m, 24H), 0.99-0.79 (m, 3H).

$^{19}$F NMR (376 MHz, Acetonitrile-$d_3$) δ −52.37.

LCMS: MS m/z=561.65 [M+1]; $t_R$=1.850 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 40% acetonitrile, 0.2 min-1.55 min 40%-100% acetonitrile, 1.55 min-2.80 min 100% Acetonitrile, 2.81 min-2.91 min 10% Acetonirile. at 1.0 mL/min.

HPLC: $t_R$=4.761 min; HPLC system: Agilent 1100 series.; Column: Gemini 5μ C18 110 A, 50×6.0 mm; Solvents: A=Acetonitrile with 0.1% TFA, B=Water with 0.1% TFA; Gradient: 0 min-5.0 min 2-98% B, 5.01 min-5.0 min 2% B at 2 mL/min.

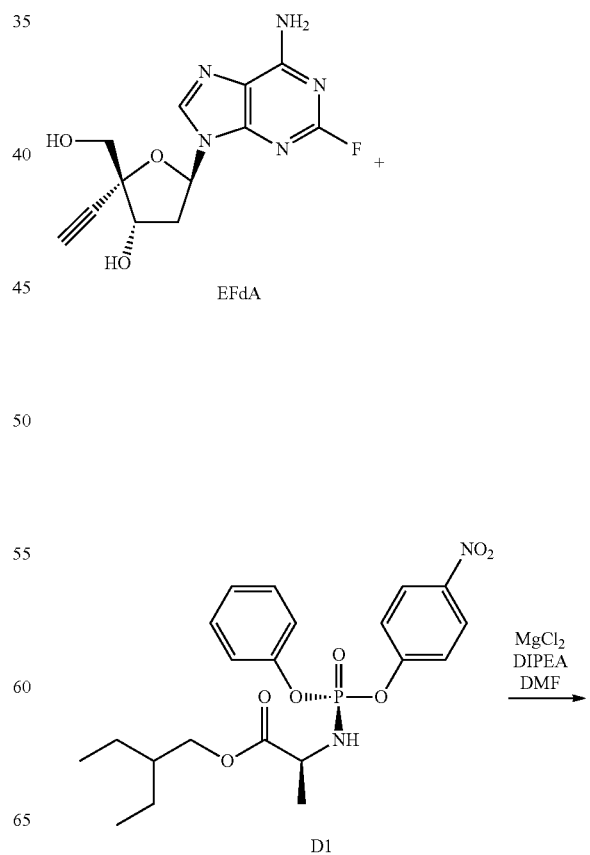

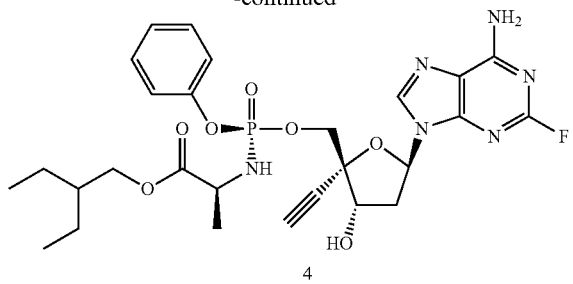

4

Synthesis of Compound 4—2-ethylbutyl ((S)-(((2R, 3S,5R)-5-(6-amino-2-fluoro-9H-purin-9-yl)-2-ethynyl-3-hydroxytetrahydrofuran-2-yl)methoxy)(phenoxy) phosphoryl)-L-alaninate N,N-Diisopropylethylamine (0.297 mL, 0.00171 mmol) was added to a mixture of EFdA (200 mg, 0.682 mmol), intermediate D1 (J. Med. Chem. 2017, 60(5), pp 1648-1661; 307 mg, 0.682 mmol), and magnesium chloride (64.9 mg, 0.682 mmol) in acetonitrile (5 ml). The mixture was heated at 60° C. for 4 days. The reaction was diluted with ethyl acetate (20 ml) and washed with water (20 mL), 0.5N sodium hydroxide (2×20 ml) and then brine (20 ml). The combined organic phases were dried over sodium sulfate and the solvent was removed under reduced pressure. The residue was subjected to flash chromatography (0-30% methanol/dichloromethane). The fractions containing product were combined and the solvent was removed under reduced pressure. The residue was subjected to preparative HPLC (Gemini, 10 uM, NX-C18, 110 Å 250×30 mm column, 60%-100% acetonitrile/water gradient over 20 minutes). The clean fractions containing product were combined and subjected to lyophilization, providing the title compound as a single diastereomer 4.

$^1$H NMR (400 MHz, Acetonitrile-$d_3$) δ 8.03 (s, 1H), 7.40-7.30 (m, 2H), 7.25-7.16 (m, 3H), 6.46-6.25 (m, 3H), 4.83-4.71 (m, 1H), 4.32 (dd, J=11.1, 6.7 Hz, 1H), 4.29-4.18 (m, 2H), 4.02 (dd, J=10.9, 5.7 Hz, 1H), 3.97 (m, 2H), 3.88 (d, J=6.0 Hz, 1H), 3.01 (s, 1H), 2.89-2.79 (m, 1H), 2.60 (dt, J=13.7, 7.7 Hz, 1H), 1.54-1.42 (m, 1H), 1.38-1.27 (m, 7H), 0.87 (t, J=7.4 Hz, 6H).

$^{19}$F NMR (376 MHz, Acetonitrile-$d_3$) δ −53.31.

LCMS: MS m/z=6.04.79 [M+1]; $t_R$=1.430 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: $t_R$=3.358 min; HPLC system: Agilent 1100 series.; Column: Gemini 5μ C18 110 A, 50×6.0 mm; Solvents: A=Acetonitrile with 0.1% TFA, B=Water with 0.1% TFA; Gradient: 0 min-5.0 min 2-98% B, 5.01 min-5.0 min 2% B at 2 mL/min.

Examples 5, 6, and 7

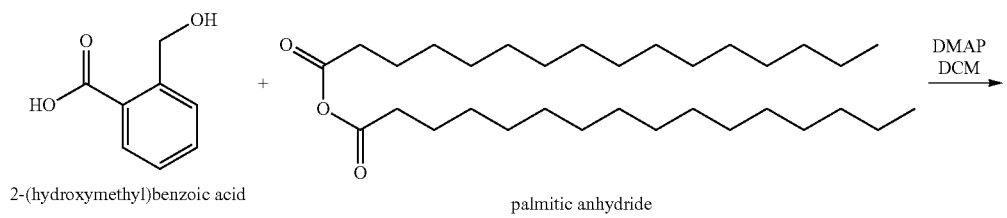

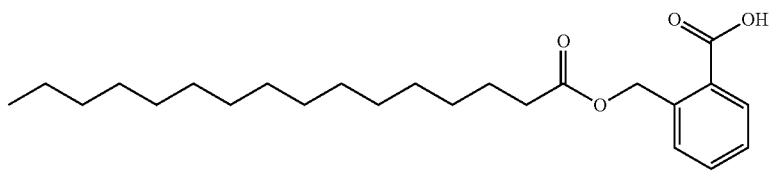

Synthesis of Intermediate E1—2-((palmitoyloxy)methyl)benzoic acid

A mixture of 2-(hydroxymethyl)benzoic acid (720 mg, 4.73 mmol), palmitic anhydride (3000 mg, 6.06 mmol), and DMAP (58 mg, 0.47 mmol) in DCM (30 mL) was refluxed at 50° C. for 2h, cooled with an ice water bath, and 37% aqueous HCl (0.5 mL) added. Upon concentration, the obtained residue was purified by silica gel chromatography (80 g column, eluent: 100% hexane ramping to 50% EtOAc/50% hexane) to give the title compound E1.

$^1$H NMR (400 MHz, DMSO-d6) δ 13.09 (s, 1H), 7.92 (dd, J=7.8, 1.4 Hz, 1H), 7.64-7.56 (m, 1H), 7.53-7.48 (m, 1H), 7.47-7.42 (m, 1H), 5.43 (s, 2H), 2.39 (t, J=7.4 Hz, 2H), 1.56 (m, 2H), 1.32-1.16 (s, 24H), 0.85 (m, 3H).

209 210
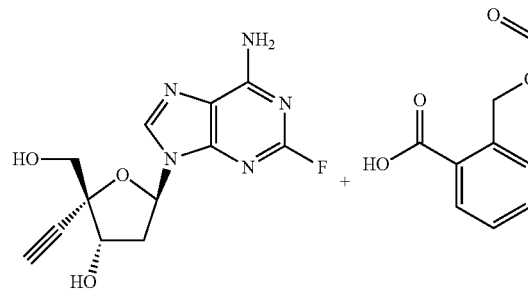
EFdA
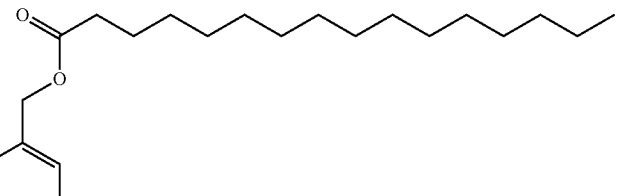
E1
→ DIC
DMAP
DMF
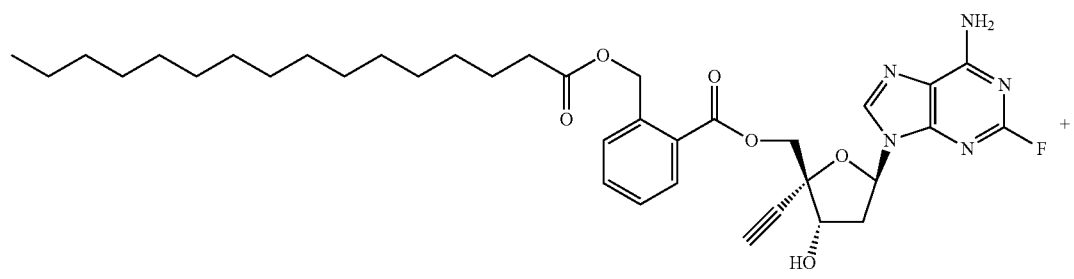
5
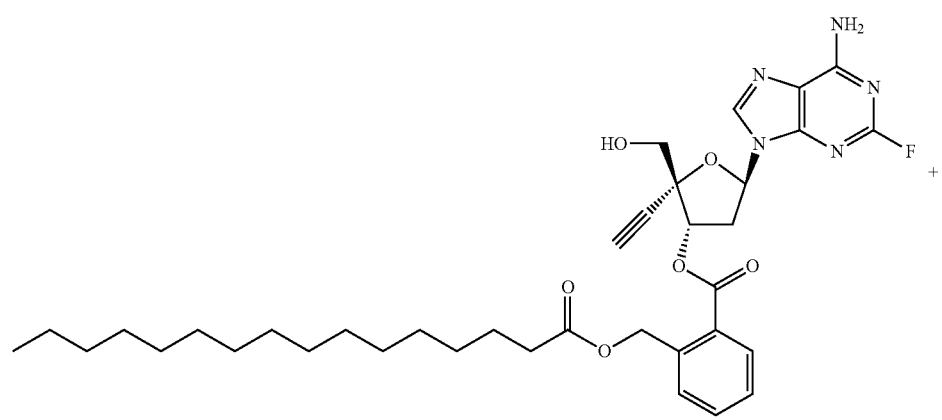
6
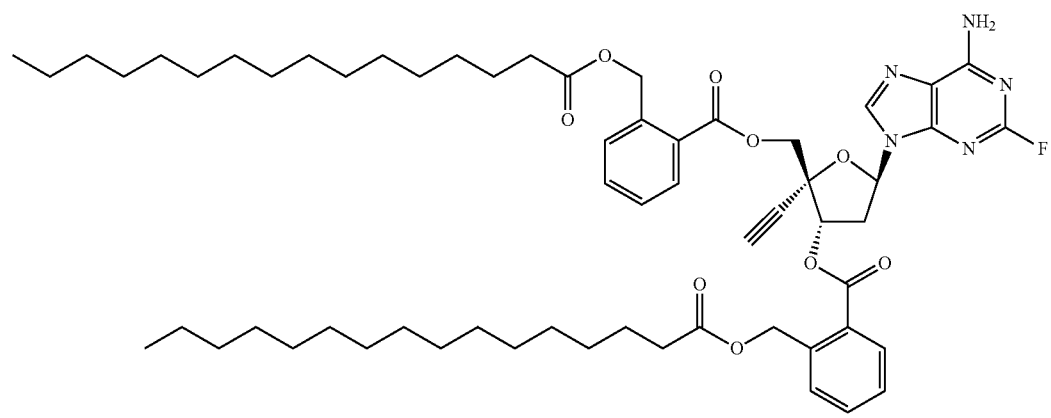
7

Synthesis of Compound 5—((2R,3S,5R)-5-(6-amino-2-fluoro-4,5-dihydro-9H-purin-9-yl)-2-ethynyl-3-hydroxytetrahydrofuran-2-yl)methyl 2-((palmitoyloxy)methyl)benzoate and Synthesis of Compound 6—(2R,3S,5R)-5-(6-amino-2-fluoro-4,5-dihydro-9H-purin-9-yl)-2-ethynyl-2-(hydroxymethyl)tetrahydrofuran-3-yl 2-((palmitoyloxy)methyl)benzoate and Synthesis of Compound 7—(2R,3S,5R)-5-(6-amino-2-fluoro-9H-purin-9-yl)-2-ethynyl-2-(((2-((palmitoyloxy)methyl)benzoyl)oxy)methyl)tetrahydrofuran-3-yl 2-((palmitoyloxy)methyl)benzoate To a mixture of EFdA (100 mg, 0.341 mmol), intermediate E1 (200 mg, 0.512 mmol), and DIC (0.075 mL, 0.512 mmol) in DMF (2 mL) was added DMAP (42 mg, 0.341 mmol). The resulting reaction was stirred at room temperature for 15 h. The reaction was quenched by the addition of MeOH and then products isolated by silica gel chromatography (40 g column, eluent: 100% DCM ramping to 10% MeOH/90% DCM). Example 5 was further purified by reverse phase HPLC (eluent: 10% ACN/90% water ramping to 100% ACN for 8 min, then 100% ACN for 13 min) to yield 33 mg. Example 6 was further purified by reverse phase HPLC (eluent: 10% ACN/90% water ramping to 100% ACN for 8 min, then 100% ACN for 13 min) to yield 8 mg. Example 7 was further purified by silica gel chromatography (12 g column, eluent: 100% DCM ramping to 5% MeOH/95% DCM) to yield the title compound.

Compound 5:
$^1$H NMR (400 MHz, Acetonitrile-$d_3$) δ 7.94 (s, 1H), 7.86 (dd, J=7.8, 1.4 Hz, 1H), 7.61 (td, J=7.6, 1.4 Hz, 1H), 7.53 (d, J=7.7 Hz, 1H), 7.41 (td, J=7.6, 1.3 Hz, 1H), 6.41-6.14 (m, 3H), 5.40 (d, J=14.1 Hz, 1H), 5.34 (d, J=14.1 Hz, 1H), 4.91 (q, J=7.2 Hz, 1H), 4.68 (d, J=11.8 Hz, 1H), 4.48 (d, J=11.8 Hz, 1H), 3.77 (d, J=6.3 Hz, 1H), 3.03 (s, 1H), 2.96 (ddd, J=13.8, 7.1, 4.2 Hz, 1H), 2.62 (dt, J=13.7, 7.9 Hz, 1H), 2.35 (t, J=7.43 Hz, 2H), 1.59 (m, 2H), 1.39-1.19 (m, 24H), 0.90 (m, 3H).
$^{19}$F NMR (376 MHz, Acetonitrile-$d_3$) δ −53.20.
LCMS: MS m/z=666.16 [M+1]; $t_R$=2.28 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.
HPLC: $t_R$=9.18 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 6:
$^1$H NMR (400 MHz, Acetonitrile-$d_3$) δ 8.17 (d, J=7.6 Hz, 1H), 8.03 (s, 1H), 7.72-7.63 (m, 1H), 7.61 (d, J=7.6 Hz, 1H), 7.52 (t, J=7.8 Hz, 1H), 6.50 (dd, J=8.6, 5.9 Hz, 1H), 6.42 (bs, 2H), 5.92 (dd, J=6.5, 2.6 Hz, 1H), 5.53 (d, J=2.7 Hz, 2H), 4.94 (dd, J=9.8, 4.3 Hz, 1H), 3.94 (dd, J=12.3, 4.3 Hz, 1H), 3.88 (dd, J=12.2, 9.8 Hz, 1H), 3.17 (ddd, J=14.6, 8.6, 6.6 Hz, 1H), 2.93 (s, 1H), 2.71 (ddd, J=14.0, 6.0, 2.6 Hz, 1H), 2.42 (t, J=7.5 Hz, 2H), 1.64 (m, 2H), 1.38-1.22 (m, 24H), 0.90 (m, 3H).
$^{19}$F NMR (376 MHz, Acetonitrile-$d_3$) δ −53.79.
LCMS: MS m/z=665.80 [M+1]; $t_R$=2.39 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.
HPLC: $t_R$=9.50 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 7:
$^1$H NMR (400 MHz, Acetonitrile-$d_3$) δ 8.16 (d, J=7.8 Hz, 1H), 7.99 (s, 1H), 7.94 (d, J=7.7 Hz, 1H), 7.70-7.64 (m, 1H), 7.62-7.57 (m, 2H), 7.56-7.48 (m, 2H), 7.38 (t, J=7.38 Hz, 1H), 6.48 (t, J=6.5 Hz, 1H), 6.31 (s, 2H), 6.15 (m, 1H), 5.51 (s, 2H), 5.39 (d, J=4.6 Hz, 2H), 4.80 (d, J=11.7 Hz, 1H), 4.62 (d, J=11.7 Hz, 1H), 3.35 (m, 1H), 3.06 (s, 1H), 2.88 (m, 1H), 2.39 (t, J=7.45 Hz, 2H), 2.34 (t, J=7.45 Hz, 2H), 1.66-1.50 (m, 4H), 1.40-1.22 (m, 48H), 0.95-0.86 (m, 6H).
$^{19}$F NMR (376 MHz, Acetonitrile-$d_3$) δ −52.82.

Examples 8, 9, and 10

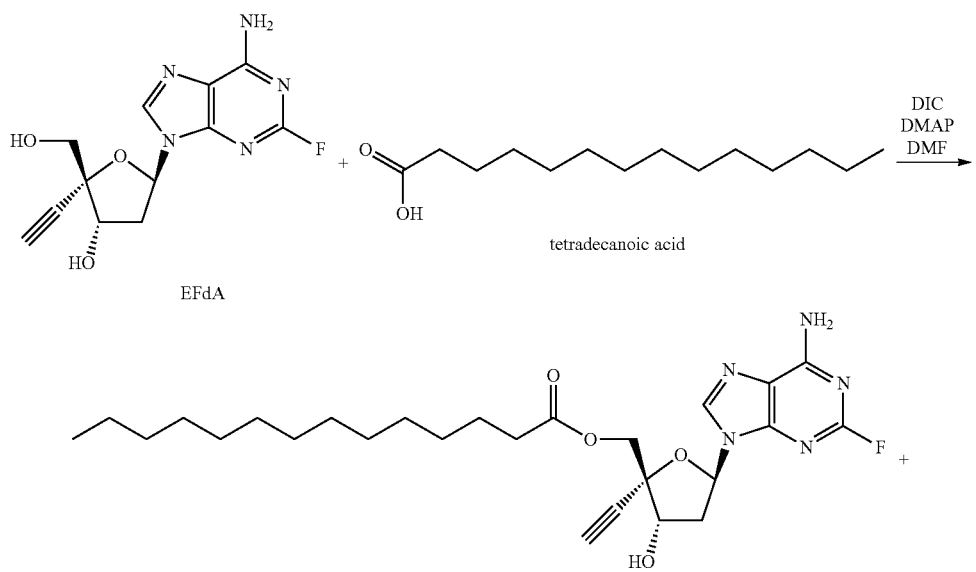

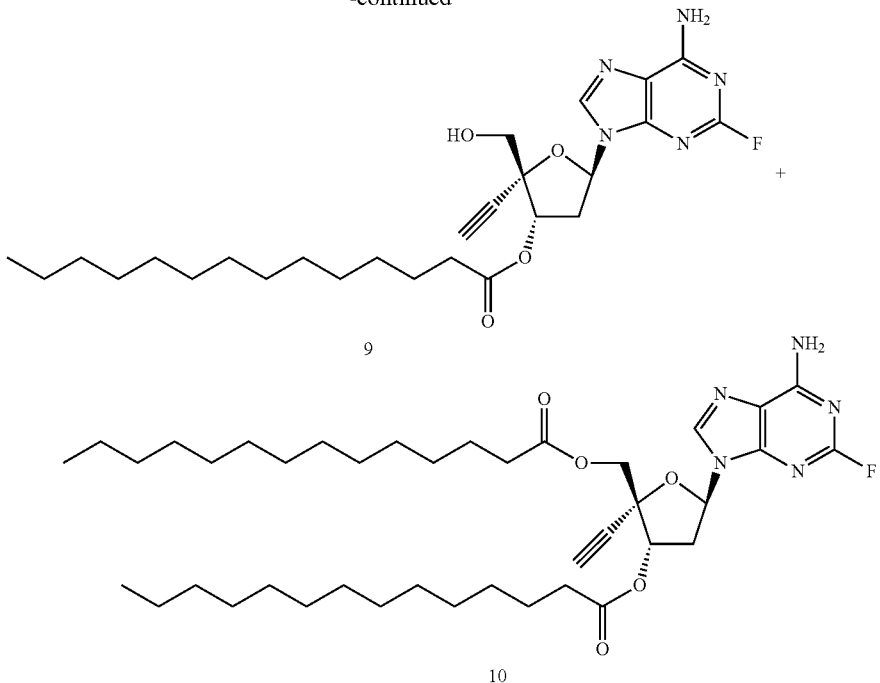

Synthesis of Compound 8—((2R,3S,5R)-5-(6-amino-2-fluoro-9H-purin-9-yl)-2-ethynyl-3-hydroxytetrahydrofuran-2-yl)methyl tetradecanoate and Synthesis of Compound 9—(2R,3S,5R)-5-(6-amino-2-fluoro-9H-purin-9-yl)-2-ethynyl-2-(hydroxymethyl)tetrahydrofuran-3-yl tetradecanoate and Synthesis of Compound 10—(2R,3S,5R)-5-(6-amino-2-fluoro-9H-purin-9-yl)-2-ethynyl-2-((tetradecanoyloxy)methyl)tetrahydrofuran-3-yl tetradecanoate To a mixture of EFdA (3.5 g, 11.9 mmol), tetradecanoic acid (4.09 g, 17.9 mmol), and DIC (2.6 mL, 17.9 mmol) in DMF (10 mL) was added DMAP (1.46 g, 11.9 mmol). The resulting mixture was stirred at rt for 30 min and the reaction quenched by adding methanol (1 mL). The products were isolated by silica gel column chromatography (330 g column, eluent: 100% DCM ramping to 5% MeOH/95% DCM). Example 8 was further purified by silica gel chromatography (80 g column, eluent: 100% DCM ramping to 5% MeOH/95% DCM) to yield 1500 mg. Example 9 was further purified by reverse phase HPLC (eluent: 10% ACN/90% water to 100% ACN for 8 min, then 100% ACN for 10 min) to yield 175 mg. Example 10 was further purified by silica gel chromatography (40 g column, eluent: 100% DCM ramping to 5% MeOH/95% DCM) to yield the title compound.

Compound 8:

$^1$H NMR (400 MHz, Acetonitrile-$d_3$) δ 7.99 (s, 1H), 6.45-6.20 (m, 3H), 4.86-4.68 (m, 1H), 4.45 (d, J=11.9 Hz, 1H), 4.22 (d, J=11.9 Hz, 1H), 3.67 (d, J=6.3 Hz, 1H), 3.00 (s, 1H), 2.88 (ddd, J=13.7, 7.1, 4.1 Hz, 1H), 2.60 (dt, J=13.66, 7.89 Hz, 1H), 2.24 (m, 2H), 1.49 (m, 2H), 1.38-1.18 (m, 20H), 0.91 (m, 3H).

$^{19}$F NMR (376 MHz, Acetonitrile-$d_3$) δ −53.35.

LCMS: MS m/z=503.96 [M+1]; $t_R$=1.90 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.

HPLC: $t_R$=7.89 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 9:

$^1$H NMR (400 MHz, Acetonitrile-$d_3$) δ 8.01 (s, 1H), 6.42 (bs, 2H), 6.36 (dd, J=8.46, 6.02 Hz, 1H), 5.68 (dd, J=6.7, 2.7 Hz, 1H), 4.83 (dd, J=9.9, 4.2 Hz, 1H), 3.86 (dd, J=12.2, 4.2 Hz, 1H), 3.78 (dd, J=12.2, 10.0 Hz, 1H), 3.03 (ddd, J=14.0, 8.5, 6.7 Hz, 1H), 2.94 (s, 1H), 2.53 (ddd, J=14.0, 6.1, 2.7 Hz, 1H), 2.42 (t, J=7.4 Hz, 2H), 1.67 (m, 2H), 1.42-1.26 (m, 20H), 0.91 (m, 3H).

$^{19}$F NMR (376 MHz, Acetonitrile-$d_3$) δ −53.85.

LCMS: MS m/z=503.89 [M+1]; $t_R$=2.06 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.

HPLC: $t_R$=8.45 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 10:

$^1$H NMR (400 MHz, DMSO-$d_6$) δ 8.33 (s, 1H), 7.89 (bs, 2H), 6.35 (t, J=6.7 Hz, 1H), 5.70 (dd, J=7.1, 5.4 Hz, 1H), 4.39 (d, J=11.6 Hz, 1H), 4.23 (d, J=11.6 Hz, 1H), 3.77 (s, 1H), 3.15 (dt, J=13.7, 6.9 Hz, 1H), 2.61 (ddd, J=14.0, 7.0, 5.2 Hz, 1H), 2.39 (m, 2H), 2.26 (m, 2H), 1.58 (m, 2H), 1.46 (m, 2H), 1.35-1.11 (m, 40H), 0.90-0.81 (m, 6H).

$^{19}$F NMR (376 MHz, DMSO-$d_6$) δ −52.10.

Example 11

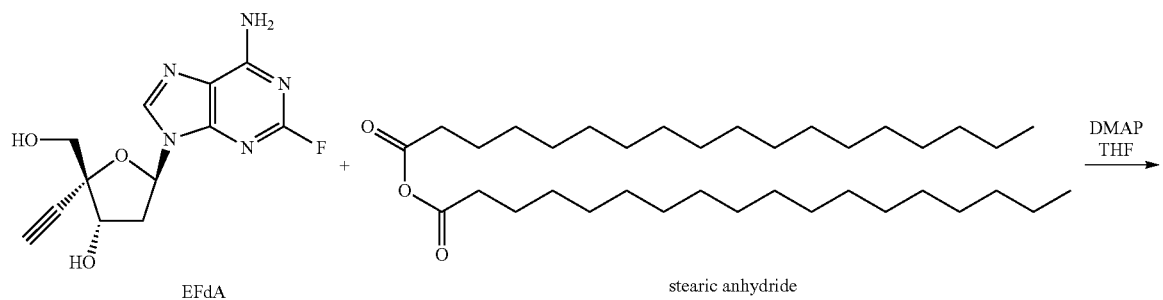

Synthesis of Compound 11—((2R,3S,5R)-5-(6-amino-2-fluoro-9H-purin-9-yl)-2-ethynyl-3-hydroxytetrahydrofuran-2-yl)methyl stearate

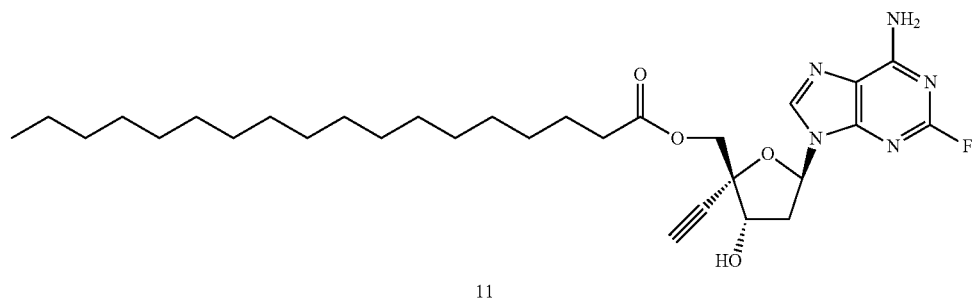

To a mixture of EFdA (100 mg, 0.341 mmol) and stearic anhydride (165 mg, 0.299 mmol) in THF (2 mL) was added DMAP (42 mg, 0.034 mmol) at rt. The resulting mixture was stirred for 2h and the reaction quenched by adding methanol. Upon concentration in vacuo, the residue was purified by reverse phase HPLC (eluent: 10% ACN/90% water to 100% ACN for 5 min, then 100% ACN for 13 min) to afford compound 11, which was further purified by reverse phase HPLC (eluent: 10% ACN/90% water to 100% ACN for 8 min, then 100% ACN for 10 min) to yield the title compound.

$^1$H NMR (400 MHz, Acetonitrile-$d_3$) δ 7.99 (s, 1H), 6.48-6.16 (m, 3H), 4.77 (m, 1H), 4.44 (d, J=11.9 Hz, 1H), 4.22 (d, J=11.9 Hz, 1H), 3.68 (d, J=6.3 Hz, 1H), 2.99 (s, 1H), 2.87 (ddd, J=13.7, 7.2, 4.1 Hz, 1H), 2.60 (m, 1H), 2.22 (m, 2H), 1.50 (m, 2H), 1.41-1.00 (m, 28H), 0.91 (t, J=6.7 Hz, 3H).

$^{19}$F NMR (376 MHz, Acetonitrile-$d_3$) δ −53.34.

LCMS: MS m/z=559.92 [M+1]; $t_R$=2.26 min; LC system: Dionex Ultimate 3000 UHPLC; Column: Phenomenex Kinetex 2.6µ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 µl/min.

HPLC: $t_R$=9.14 min; HPLC system: 1290 Infinity II.; Column: Phenomenex 2.6µ C18 100 A, 100×4.6 mm; Solvents: Acetonitrile with 0.1% TFA, Water with 0.1% TFA; Gradient: 0 min-8.5 min 2-98% ACN at 1.5 mL/min.

Examples 12 and 13

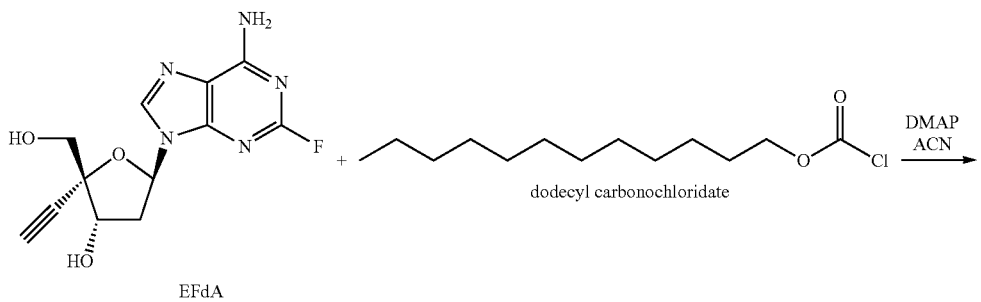

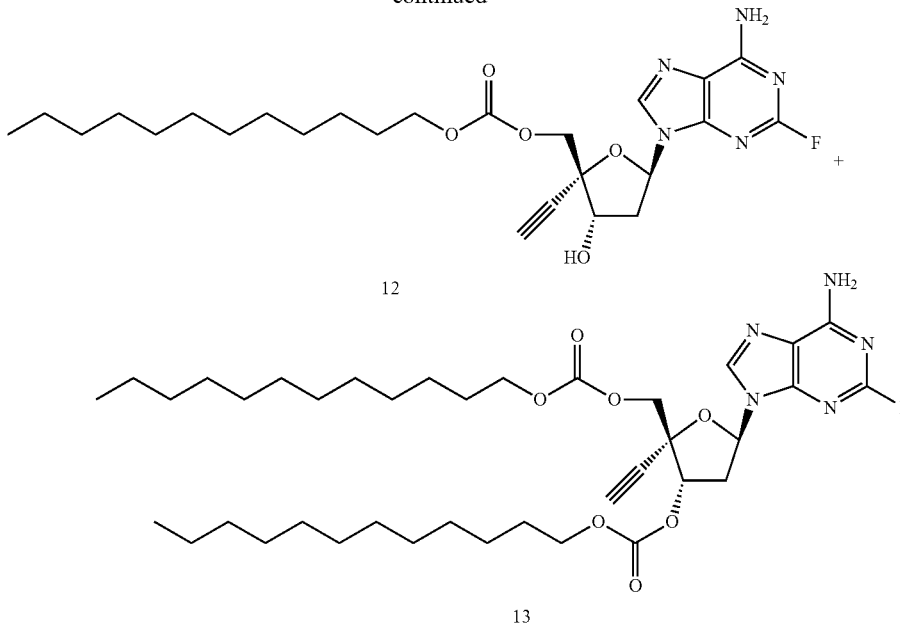

Synthesis of Compound 12—((2R,3S,5R)-5-(6-amino-2-fluoro-9H-purin-9-yl)-2-ethynyl-3-hydroxytetrahydrofuran-2-yl)methyl dodecyl carbonate and Synthesis of Compound 13—((2R,3S,5R)-5-(6-amino-2-fluoro-9H-purin-9-yl)-3-(((dodecyloxy)carbonyl)oxy)-2-ethynyltetrahydrofuran-2-yl)methyl dodecyl carbonate To a mixture of EFdA (100 mg, 0.341 mmol) and DMAP (83 mg, 0.682 mmol) in ACN (2 mL) was added dodecyl carbonochloridate (127 mg, 0.512 mmol). The resulting mixture was stirred at rt for 1 h and the reaction quenched by adding methanol. Upon concentration in vacuo, the residue was purified by silica gel column chromatography (40 g column, 100% DCM ramping to 10% MeOH/90% DCM) to afford compound 12 and compound 13.

Compound 12:

$^1$H NMR (400 MHz, Acetonitrile-$d_3$) δ 7.99 (s, 1H), 6.42 (bs, 2H), 6.29 (dd, J=7.6, 4.4 Hz, 1H), 4.75 (m, 1H), 4.48 (d, J=11.6 Hz, 1H), 4.30 (d, J=11.7 Hz, 1H), 4.05 (m, 2H), 3.81 (d, J=6.1 Hz, 1H), 3.01 (s, 1H), 2.87 (ddd, J=13.7, 7.0, 4.4 Hz, 1H), 2.60 (dt, J=13.7, 7.6 Hz, 1H), 1.59 (m, 2H), 1.36-1.04 (s, 18H), 0.89 (m, 3H).

$^{19}$F NMR (376 MHz, Acetonitrile-$d_3$) δ −53.35.

LCMS: MS m/z=505.95 [M+1]; $t_R$=1.83 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.

HPLC: $t_R$=7.60 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 13:

$^1$H NMR (400 MHz, Acetonitrile-$d_3$) δ 7.98 (s, 1H), 6.49-6.19 (m, 3H), 5.66 (dd, J=7.3, 5.7 Hz, 1H), 4.56 (d, J=11.5 Hz, 1H), 4.36 (d, J=11.6 Hz, 1H), 4.20 (m, 2H), 4.07 (m, 2H), 3.17 (m, 1H), 3.05 (s, 1H), 2.74 (m, 1H), 1.70 (m, 2H), 1.61 (m, 2H), 1.48-1.23 (m, 36H), 0.96-0.86 (m, 6H).

$^{19}$F NMR (376 MHz, Acetonitrile-$d_3$) δ −53.10.

LCMS: MS m/z=717.93 [M+1]; $t_R$=2.73 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.

HPLC: $t_R$=10.70 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Examples 14, 15, and 16

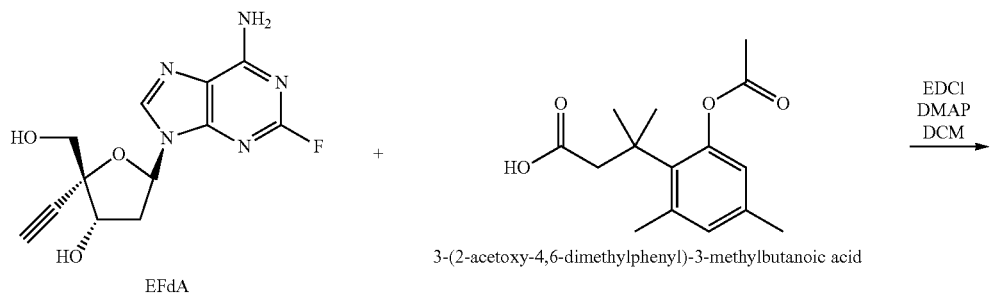

-continued
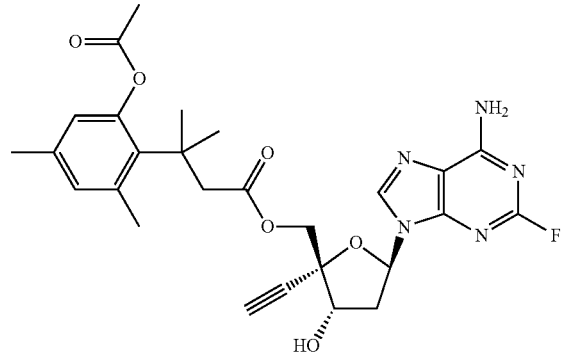
14
+
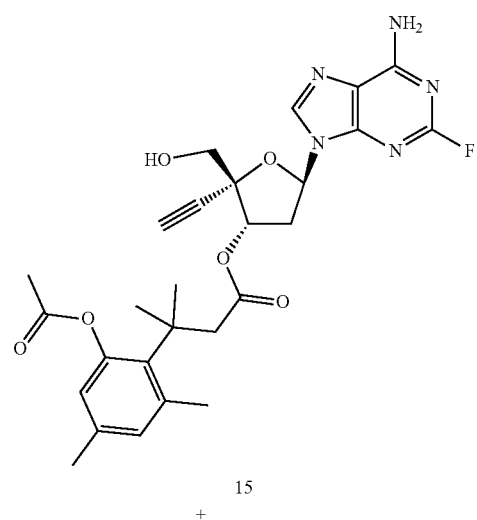
15
+
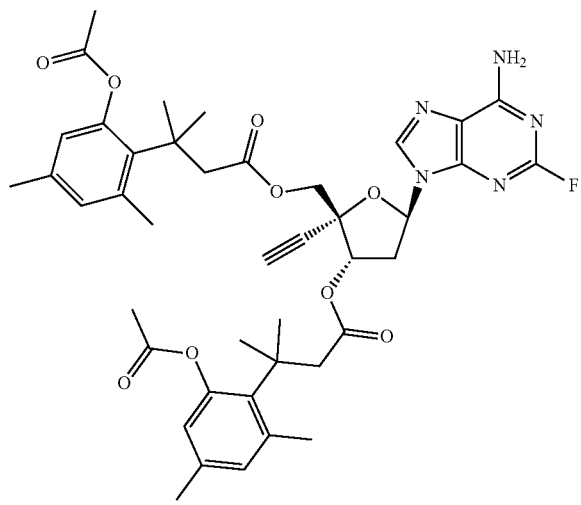
16

Synthesis of Compound 14—((2R,3S,5R)-5-(6-amino-2-fluoro-9H-purin-9-yl)-2-ethynyl-3-hydroxytetrahydrofuran-2-yl)methyl 3-(2-acetoxy-4,6-dimethylphenyl)-3-methylbutanoate and Synthesis of Compound 15—(2R,3S,5R)-5-(6-amino-2-fluoro-9H-purin-9-yl)-2-ethynyl-2-(hydroxymethyl)tetrahydrofuran-3-yl 3-(2-acetoxy-4,6-dimethylphenyl)-3-methylbutanoate and Synthesis of Compound 16—((2R,3S,5R)-3-((3-(2-acetoxy-4,6-dimethylphenyl)-3-methylbutanoyl)oxy)-5-(6-amino-2-fluoro-9H-purin-9-yl)-2-ethynyltetrahydrofuran-2-yl)methyl 3-(2-acetoxy-4,6-dimethylphenyl)-3-methylbutanoate EFdA (240 mg, 0.818 mmol), 3-(2-acetoxy-4,6-dimethylphenyl)-3-methylbutanoic acid (173 mg, 0.655 mmol), EDCI (471 mg, 2.46 mmol), and DMAP (300 mg, 2.46 mmol) were taken up in DCM (6 mL). The resulting reaction mixture was stirred at room temperature for 3 h. The reaction was diluted with DCM (15 ml). The solution was washed with water (2×15 ml), and once with a saturated ammonium chloride solution (15 ml). Combined organic layers were dried over sodium sulfate, filtered and the solvent was removed under reduced pressure. The residue was purified by HPLC chromatography (Gemini, 10 uM, NX-C18, 110 Å 250×30 mm column, 40%-100% acetonitrile/water gradient in 20 min run) to afford the title compounds 14; 15; and 16.

Compound 14:

$^1$H NMR (400 MHz, Acetonitrile-$d_3$) δ 7.98 (s, 1H), 6.82 (d, J=2.3 Hz, 1H), 6.57 (d, J=2.0 Hz, 1H), 6.40 (s, 2H), 6.26 (dd, J=7.6, 4.4 Hz, 1H), 4.55 (t, J=7.3 Hz, 1H), 4.29 (d, J=11.9 Hz, 1H), 4.12 (d, J=11.9 Hz, 1H), 3.01 (s, 1H), 2.97 (s, 1H), 2.91-2.78 (m, 2H), 2.71 (d, J=16.0 Hz, 1H), 2.55 (dt, J=13.7, 7.6 Hz, 1H), 2.49 (s, 3H), 2.23 (s, 3H), 2.20 (s, 3H), 1.48 (s, 3H), 1.46 (s, 3H).

LCMS: MS m/z=540.01 [M+1]; $t_R$=1.38 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: $t_R$=5.42 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 15:

$^1$H NMR (400 MHz, Acetonitrile-$d_3$) δ 7.96 (s, 1H), 6.91 (d, J=2.0 Hz, 1H), 6.66 (d, J=2.0 Hz, 1H), 6.41 (s, 2H), 6.12 (dd, J=8.3, 6.1 Hz, 1H), 5.50 (dd, J=6.6, 2.8 Hz, 1H), 4.69 (s, 1H), 3.78 (d, J=12.2 Hz, 1H), 3.67 (d, J=12.2 Hz, 1H), 3.13 (d, J=15.8 Hz, 1H), 3.01 (s, 1H), 2.92 (s, 1H), 2.89-2.83 (m, 2H), 2.60 (s, 3H), 2.30 (s, 3H), 2.20 (s, 3H), 1.61 (s, 3H), 1.58 (s, 3H).

LCMS: MS m/z=540.05 [M+1]; $t_R$=1.46 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: $t_R$=5.86 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 16:

$^1$H NMR (400 MHz, Acetonitrile-$d_3$) δ 7.94 (s, 1H), 6.93-6.86 (m, 1H), 6.80 (d, J=2.2 Hz, 1H), 6.63 (d, J=2.0 Hz, 1H), 6.55 (d, J=2.0 Hz, 1H), 6.37 (s, 2H), 6.15 (t, J=6.7 Hz, 1H), 5.42 (dd, J=7.1, 5.2 Hz, 1H), 4.22 (d, J=11.8 Hz, 1H), 4.05 (d, J=11.8 Hz, 1H), 3.09 (d, J=15.9 Hz, 1H), 2.96 (s, 1H), 2.91-2.82 (m, 3H), 2.72 (d, J=16.0 Hz, 1H), 2.59 (s, 3H), 2.47 (s, 3H), 2.30 (s, 3H), 2.20 (s, 3H), 2.19 (s, 4H), 2.18 (s, 4H), 1.60 (s, 3H), 1.57 (s, 3H), 1.47 (s, 3H), 1.45 (s, 3H).

LCMS: MS m/z=786.05 [M+1]; $t_R$=1.75 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: $t_R$=7.44 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Examples 17 and 18

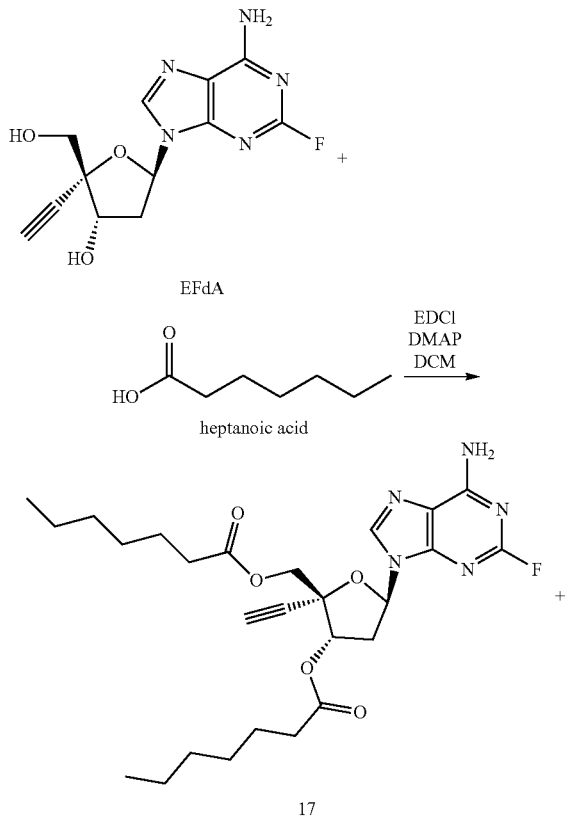

17

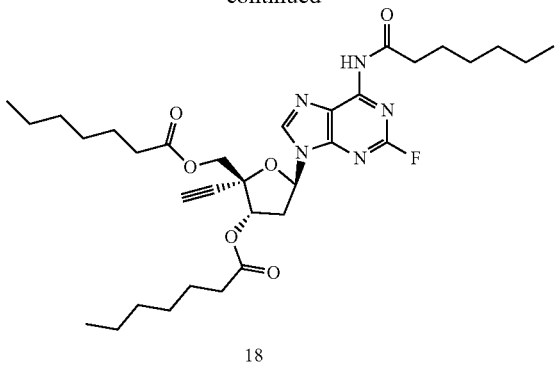

18

Synthesis of Compound 17—(2R,3S,5R)-5-(6-amino-2-fluoro-9H-purin-9-yl)-2-ethynyl-2-((heptanoyloxy)methyl)tetrahydrofuran-3-yl heptanoate and Synthesis of Compound 18—(2R,3S,5R)-2-ethynyl-5-(2-fluoro-6-heptanamido-9H-purin-9-yl)-2-((heptanoyloxy)methyl)tetrahydrofuran-3-yl heptanoate-3-yl 2-((palmitoyloxy)methyl)benzoate EFdA (200 mg, 0.682 mmol), heptanoic acid (266 mg, 2.05 mmol), EDCI (523 mg, 2.73 mmol), and DMAP (333 mg, 2.73 mmol) were taken up in DCM (6 mL). The resulting reaction mixture was stirred at room temperature for 6 h. The reaction was diluted with DCM (15 ml). The solution was washed with water (2×15 ml) and once with saturated ammonium chloride solution (15 ml). Combined organic layers were dried over sodium sulfate, filtered and the solvent was removed under reduced pressure. The residue was purified by HPLC chromatography (Gemini, 10 uM, NX-C18, 110 Å 250×30 mm column, 40%-100% acetonitrile/water gradient in 20 min run) to afford the title compounds 17 and 18.

Compound 17:

$^1$H NMR (400 MHz, Acetonitrile-$d_3$) δ 8.01 (s, 1H), 6.42 (s, 2H), 6.34 (dd, J=7.1, 5.9 Hz, 1H), 5.76 (dd, J=7.3, 5.8 Hz, 1H), 4.47 (d, J=11.8 Hz, 1H), 4.28 (d, J=11.8 Hz, 1H), 3.12 (ddd, J=14.1, 7.4, 5.8 Hz, 1H), 3.02 (s, 1H), 2.67 (ddd, J=14.1, 7.2, 5.8 Hz, 1H), 2.42 (t, J=7.4 Hz, 2H), 2.36-2.21 (m, 2H), 2.20 (s, 2H), 1.74-1.60 (m, 2H), 1.58-1.45 (m, 2H), 1.43-1.19 (m, 10H), 0.97-0.83 (m, 6H).

LCMS: MS m/z=517.99 [M+1]; $t_R$=1.79 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: $t_R$=7.69 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 18:

$^1$H NMR (400 MHz, Acetonitrile-$d_3$) δ 9.07 (s, 1H), 8.24 (s, 1H), 6.42 (dd, J=7.2, 5.7 Hz, 1H), 5.77 (dd, J=7.3, 6.0 Hz, 1H), 4.46 (d, J=11.8 Hz, 1H), 4.30 (d, J=11.8 Hz, 1H), 3.15 (ddd, J=14.2, 7.4, 5.7 Hz, 1H), 3.04 (s, 1H), 2.78-2.66 (m, 3H), 2.43 (t, J=7.4 Hz, 2H), 2.36-2.22 (m, 2H), 1.80-1.59 (m, 4H), 1.51 (dtt, J=11.5, 7.5, 4.4 Hz, 2H), 1.45-1.16 (m, 18H), 0.99-0.81 (m, 9H).

LCMS: MS m/z=629.8 [M+1]; $t_R$=1.98 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: $t_R$=8.73 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Examples 19 and 20

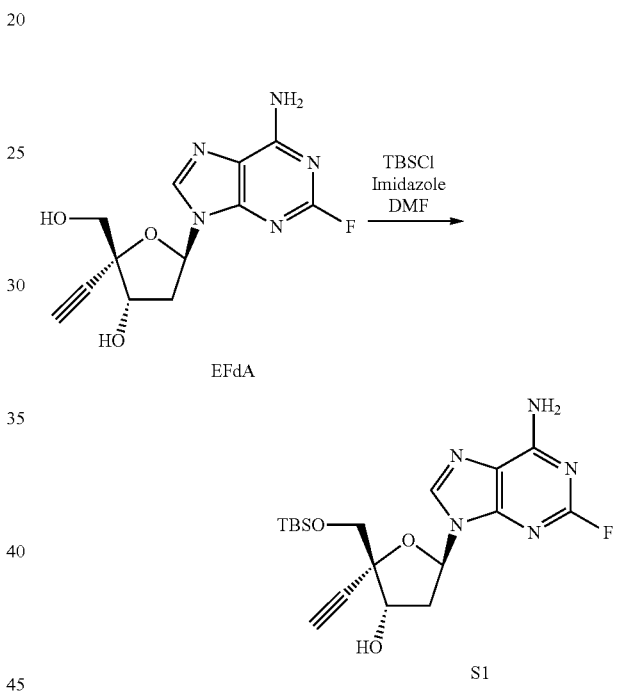

Synthesis of Intermediate S1—(2R,3S,5R)-5-(6-amino-2-fluoro-9H-purin-9-yl)-2-(((tert-butyldimethylsilyl)oxy)methyl)-2-ethynyltetrahydrofuran-3-ol A mixture of EFdA (500 mg, 1.71 mmol), TBSCl (514 mg, 3.41 mmol), and imidazole (464, 6.82 mmol) in DMF (10 mL) was stirred at room temperature overnight. The reaction mixture was diluted with ethyl acetate (30 mL) and washed with saturated aqueous ammonium chloride (20 mL) and brine (20 mL). The organics were dried over sodium sulfate and were concentrated under reduced pressure. The solid residue was purified by silica gel column chromatography using gradient 10-80% ethyl acetate in hexanes to afford the title compound after co-distillation with DCM and drying under high vacuum overnight.

$^1$H NMR (400 MHz, DMSO-$d_6$) δ 8.24 (s, 1H), 7.96-7.71 (m, 2H), 6.22 (dd, J=7.7, 4.2 Hz, 1H), 5.64 (d, J=5.5 Hz, 1H), 4.75-4.53 (m, 1H), 3.89-3.64 (m, 2H), 3.55 (s, 1H), 2.87-2.72 (m, 1H), 2.51-2.37 (m, 1H), 0.80 (s, 9H), −0.02 (s, 3H), −0.07 (s, 3H).

$^{19}$F NMR (376 MHz, DMSO-d$_6$) δ −52.42.

LCMS: MS m/z=408.1 [M+1], $t_R$=0.91 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μl/min.

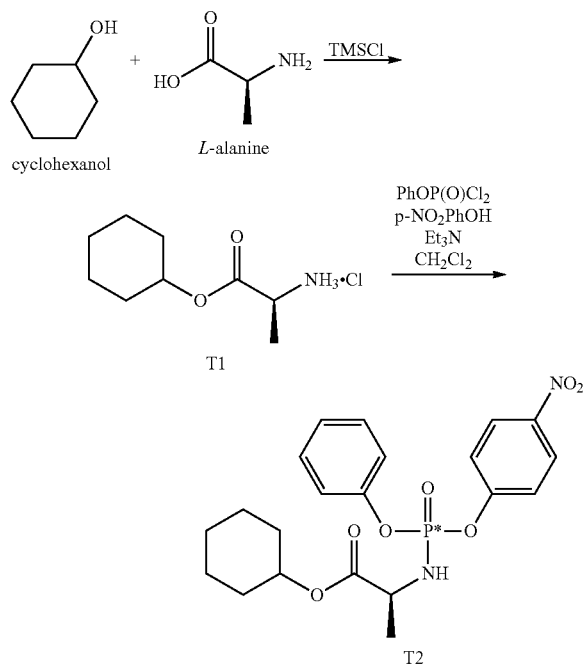

Synthesis of Intermediate T2—cyclohexyl ((4-nitrophenoxy)(phenoxy) phosphoryl)-L-alaninate To a mixture of L-alanine (20.0 g, 224.48 mmol) and cyclohexanol (213.6 g, 2132.6 mmol) was added trimethylsilyl chloride (76.56 mL, 695.9 mmol). The reaction was allowed to stir at 80° C. overnight. The reaction was concentrated, and the residue obtained was co-evaporated with toluene 2×100 mL followed by hexane 500 mL. The residue obtained was dried under high vacuum for 15 min and hexane was slowly added while stirring. The mixture as stirred for 30 min at room temperature and solids were separated by filtration, washed with hexane and dried under high vacuum overnight to afford intermediate T1. $^1$H NMR (400 MHz, DMSO-d6) δ 8.53 (d, J=17.7 Hz, 3H), 4.77 (tt, J=8.4, 3.7 Hz, 1H), 3.99 (t, J=6.9 Hz, 1H), 1.88-1.59 (m, 4H), 1.54-1.12 (m, 8H).

To a solution of intermediate T1 (23.2 g, 111.7 mmol) and phenyl dichlorophosphate (16.2 mL, 108.91 mmol) in anhydrous dichloromethane (400 mL) was added triethylamine (35 mL, 251.33 mmol) at 0° C. under argon atmosphere. The resulting mixture was stirred for 1.5 h at room temperature. 4-Nitrophenol (14.53 g, 104.44 mmol) and triethylamine (18 mL, 125.66 mmol) were then added at 0° C. The reaction mixture was stirred at room temperature for 1 h and was diluted with Et$_2$O and the solids were filtered off. The crude was concentrated under reduced pressure and residue obtained was dissolved in ethyl acetate and was washed with saturated aqueous sodium carbonate solution and brine. The organic layer was separated, dried over sodium sulfate, filtered and concentrated. The crude material was purified by silica gel chromatography (330 g SiO$_2$ Combiflash HP Gold Column, 0-10% methanol/dichloromethane) to afford desired compound as a diastereomeric mixture. The material thus obtained was dried under high vacuum overnight resulting in solidification. Diisopropyl ether (225 mL) was added to the solidified material and extensive sonication resulted in a fine solid in suspension. Isolation of the solids by filtration afforded intermediate T2 as a single isomer by $^1$H NMR and $^{31}$P NMR.

$^1$H NMR (400 MHz, Methanol-d$_4$) δ 8.32-8.23 (m, 2H), 7.52-7.40 (m, 2H), 7.38 (dd, J=8.6, 7.2 Hz, 2H), 7.29-7.17 (m, 3H), 4.68 (dp, J=8.7, 3.8 Hz, 1H), 4.02 (dq, J=9.8, 7.1 Hz, 1H), 1.78-1.64 (m, 3H), 1.57-1.46 (m, 1H), 1.44-1.22 (m, 9H).

$^{31}$P NMR (162 MHz, Methanol-d4) δ −1.32 (s).

LCMS: MS m/z=448.86 [M+1]; $t_R$=1.3 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

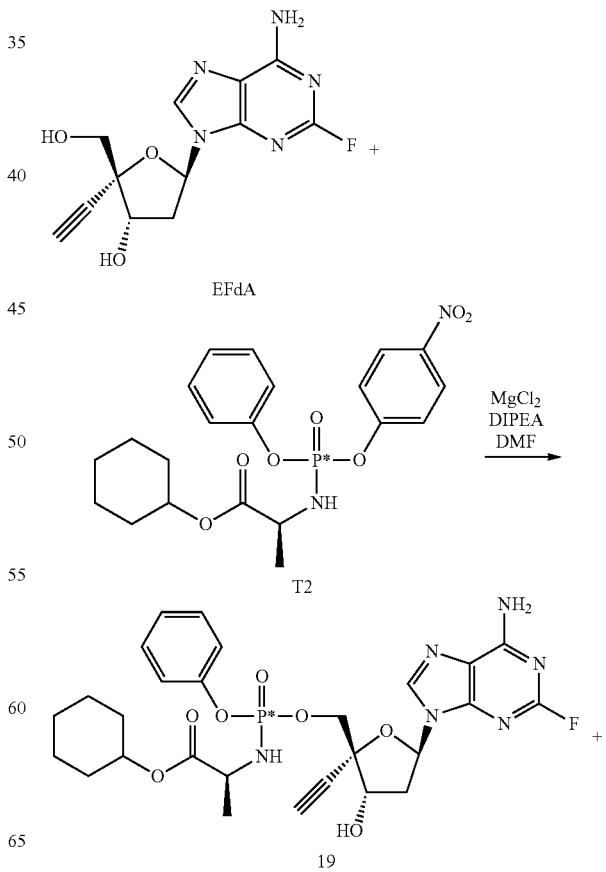

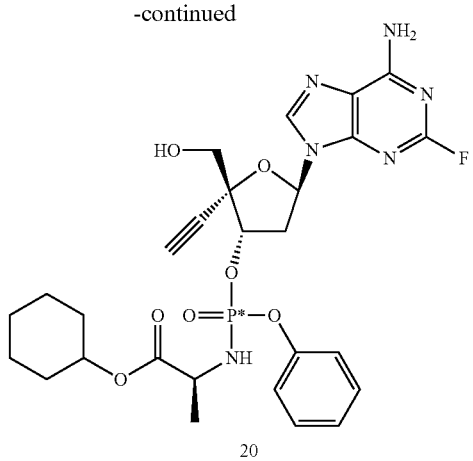

Synthesis of Compound 19—cyclohexyl (((((2R,3S, 5R)-5-(6-amino-2-fluoro-9H-purin-9-yl)-2-ethynyl-3-hydroxytetrahydrofuran-2-yl)methoxy)(phenoxy) phosphoryl)-L-alaninate and Synthesis of Compound 20—cyclohexyl ((S)-(((2R, 3S,5R)-5-(6-amino-2-fluoro-9H-purin-9-yl)-2-ethynyl-2-(hydroxymethyl)tetrahydrofuran-3-yl)oxy) (phenoxy)phosphoryl)-L-alaninate A mixture of EFdA (300 mg, 1.02 mmol), intermediate T2 (688 mg, 1.53 mmol), and MgCl$_2$ (146 mg, 1.53 mmol) was dissolved in DMF (6 mL). To this stirred solution was added N, N-diisopropylethylamine (0.445 mL, 2.56 mmol) dropwise at room temperature. The resulting mixture was stirred at 60° C. overnight. The solvent was removed under reduced pressure (40° C. maintained), and co-evaporated with toluene (10 mL×2). The crude residue was dissolved in DCM, loaded on a silica gel column (40 g) and eluted with a solvent ramp from 0% to 20% MeOH in DCM to afford semi-purified mixture of examples 19 and 20. This material was further purified by HPLC chromatography (Gemini, 10 uM, NX-C18, 110 Å 250×30 mm column, 40%-100% acetonitrile/water gradient in 20 min run) to afford compound 19 as a single diastereomer and compound 20 as a single diastereomer.

Compound 19:

$^1$H NMR (400 MHz, Acetonitrile-d$_3$) δ 8.05 (s, 1H), 7.34 (dd, J=8.6, 7.1 Hz, 2H), 7.20 (d, J=7.7 Hz, 3H), 6.49 (s, 2H), 6.30 (dd, J=7.6, 4.4 Hz, 1H), 4.77 (q, J=7.0 Hz, 1H), 4.70-4.64 (m, 1H, 4.33 (td, J=9.5, 2.3 Hz, 2H), 4.23 (dd, J=11.1, 6.7 Hz, 1H), 3.99 (d, J=5.9 Hz, 1H), 3.94-3.82 (m, 1H), 3.02 (s, 1H), 2.86-2.80 (m, 1H), 2.61 (dt, J=13.6, 7.7 Hz, 1H), 2.24 (s, 2H), 1.84-1.60 (m, 4H), 1.50 (tt, J=9.3, 6.8, 2.9 Hz, 1H), 1.43-1.32 (m, 3H), 1.29 (d, J=7.1 Hz, 4H).

$^{19}$F NMR (377 MHz, Acetonitrile-d$_3$) δ −53.26.

$^{31}$P NMR (162 MHz, Acetonitrile-d$_3$) δ 2.91.

LCMS: MS m/z=602.8 [M+1]; t$_R$=1.35 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

HPLC: t$_R$=5.34 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 20:

$^1$H NMR (400 MHz, Acetonitrile-d$_3$) δ 8.01 (d, J=32.6 Hz, 1H), 7.47-7.36 (m, 2H), 7.34-7.16 (m, 3H), 6.44 (s, 2H), 6.40-6.21 (m, 1H), 5.52-5.31 (m, 1H), 4.83-4.55 (m, 1H), 4.45-4.35 (m, 2H), 4.03 (tt, J=9.7, 7.2 Hz, 1H), 3.91-3.65 (m, 3H), 3.09-2.91 (m, 3H), 2.90-2.68 (m, 1H), 1.90-1.64 (m, 4H), 1.60-1.21 (m, 7H).

$^{31}$P NMR (162 MHz, Acetonitrile-d$_3$) δ 2.51, 2.35.

$^{19}$F NMR (377 MHz, Acetonitrile-d$_3$) δ −53.56, −53.62.

LCMS: MS m/z=602.81 [M+1]; t$_R$=1.45 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.

Examples 21 and 22

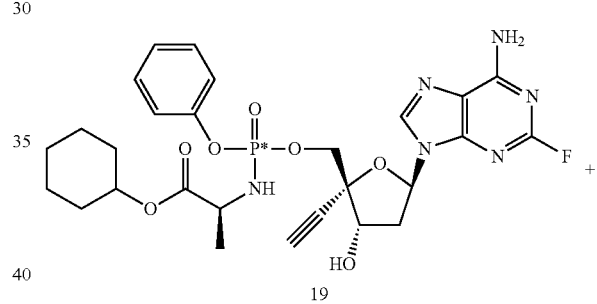

19

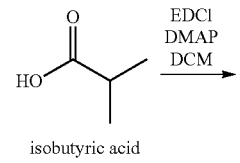

isobutyric acid

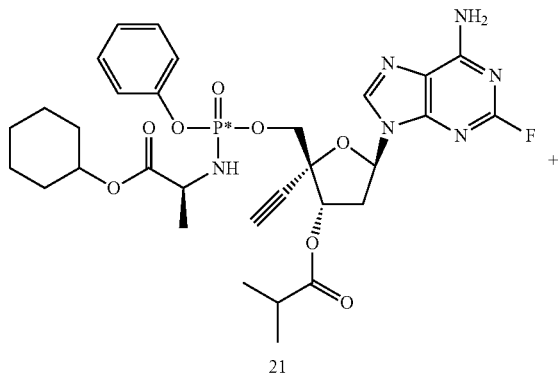

21

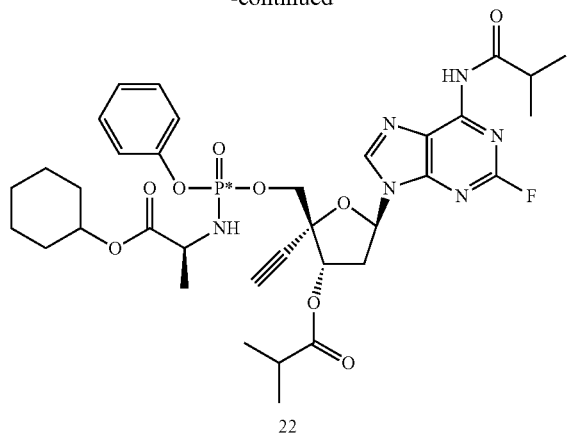

22

Synthesis of Compound 21—(2R,3S,5R)-5-(6-amino-2-fluoro-9H-purin-9-yl)-2-((((((S)-1-(cyclohexyloxy)-1-oxopropan-2-yl)amino)(phenoxy)phosphoryl)oxy)methyl)-2-ethynyltetrahydrofuran-3-yl isobutyrate and Synthesis of Compound 22—cyclohexyl ((((2R,3S,5R)-2-ethynyl-5-(2-fluoro-6-isobutyramido-9H-purin-9-yl)-3-(isobutyryloxy)tetrahydrofuran-2-yl)methoxy)(phenoxy)phosphoryl)-L-alaninate To a mixture of compound 19 (50 mg, 0.083 mmol), isobutyric acid (14.6 mg, 0.166 mmol), EDCI (63.6 mg, 0.33 mmol), and DMAP (40.6 mg, 0.33 mmol) was added DCM (3 mL). The resulting reaction mixture was stirred at room temperature for 3 h. The reaction was diluted with DCM (15 ml). The solution was washed with water (2×15 ml), and once with a saturated ammonium chloride solution (15 ml). The organic layer was dried over sodium sulfate, filtered and solvent was removed under reduced pressure. The residue was purified by HPLC chromatography (Gemini, 10 uM, NX-C18, 110 Å 250×30 mm column, 40%-100% acetonitrile/water gradient in 20 min run) to afford compounds 21 and 22 as single diastereomers.

Compound 21:
$^1$H NMR (400 MHz, Acetonitrile-$d_3$) δ 8.06 (s, 1H), 7.38-7.27 (m, 2H), 7.23-7.14 (m, 3H), 6.41-6.22 (m, 3H), 5.72 (dd, J=7.1, 4.6 Hz, 1H), 4.70 (dt, J=8.7, 4.5 Hz, 1H), 4.37 (dd, J=10.9, 6.3 Hz, 1H), 4.28 (dd, J=10.9, 5.7 Hz, 1H), 4.24-4.12 (m, 1H), 3.95-3.56 (m, 1H), 3.10-2.97 (m, 2H), 2.74-2.57 (m, 2H), 1.83-1.63 (m, 5H), 1.58-1.46 (m, 1H), 1.46-1.34 (m, 4H), 1.30 (dd, J=7.0, 2.6 Hz, 4H), 1.23 (t, J=7.0 Hz, 6H).
$^{19}$F NMR (377 MHz, Acetonitrile-$d_3$) δ -53.20.
$^{31}$P NMR (162 MHz, Acetonitrile-$d_3$) δ 2.58.
LCMS: MS m/z=672.9 [M+1]; $t_R$=1.51 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.
HPLC: $t_R$=6.54 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 22:
$^1$H NMR (400 MHz, Acetonitrile-$d_3$) δ 8.96 (s, 1H), 8.29 (s, 1H), 7.32 (dd, J=8.9, 6.9 Hz, 2H), 7.23-7.10 (m, 3H), 6.45 (t, J=6.6 Hz, 1H), 5.76 (dd, J=7.1, 5.0 Hz, 1H), 4.69 (dt, J=8.7, 4.5 Hz, 1H), 4.42-4.13 (m, 3H), 4.00-3.79 (m, 1H), 3.16-2.93 (m, 3H), 2.83-2.57 (m, 2H), 2.15 (s, 2H), 1.84-1.61 (m, 4H), 1.52 (dt, J=11.8, 4.9 Hz, 1H), 1.45-1.34 (m, 5H), 1.31-1.15 (m, 12H).
$^{19}$F NMR (377 MHz, Acetonitrile-$d_3$) δ -52.14.
$^{31}$P NMR (162 MHz, Acetonitrile-$d_3$) δ 2.60.
LCMS: MS m/z=742.7 [M+1]; $t_R$=1.71 min; LC system: Thermo Dionex Ultimate 3000 UHPLC+focused; MS system: Thermo LCQ Fleet; Column: Phenomenex Kinetex 2.6μ-C18 100 A, 50×2.1 mm; Solvents: Acetonitrile with 0.1% trifluoroacetic acid, water with 0.1% trifluoroacetic acid; Gradient: 0 min-0.2 min 10% acetonitrile, 0.2 min-1.55 min 10%-100% acetonitrile, 1.55 min-2.20 min 100% ACN at 1.0 mL/min.
HPLC: $t_R$=6.91 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Compound 23

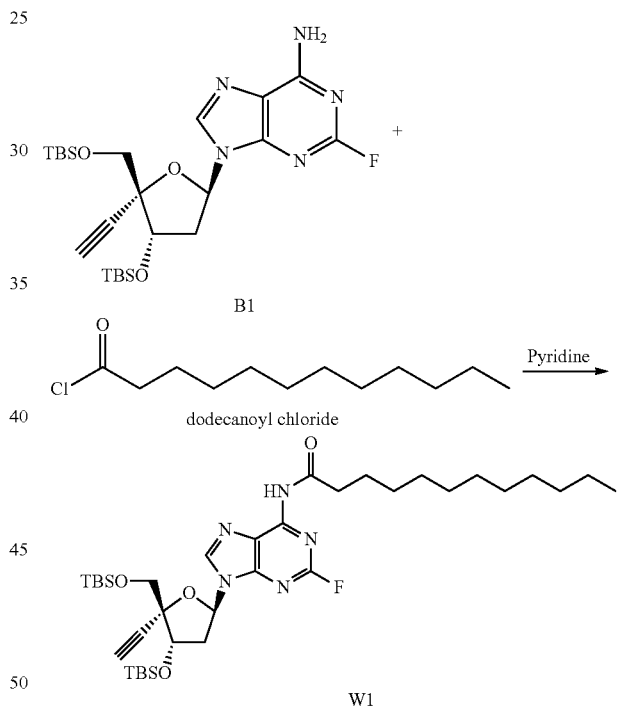

Synthesis of Intermediate W1—N-(9-((2R,4S,5R)-4-((tert-butyldimethylsilyl)oxy)-5-(((tert-butyldimethylsilyl)oxy)methyl)-5-ethynyltetrahydrofuran-2-yl)-2-fluoro-9H-purin-6-yl)dodecanamide To a solution of intermediate B1 (100 mg, 0.192 mmol) in pyridine (2 mL) was added dodecanoyl chloride (72 mg, 0.327 mmol) at rt. The resulting mixture was stirred at rt for 3h. Upon completion the reaction was quenched by adding water, the mixture was concentrated in vacuo and purified by silica gel column chromatography (24 g column, 100% hexane ramping to 50% EtOAc/50% hexane) to give impure intermediate W1 (20 mg), which was used in the next reaction without further purification.

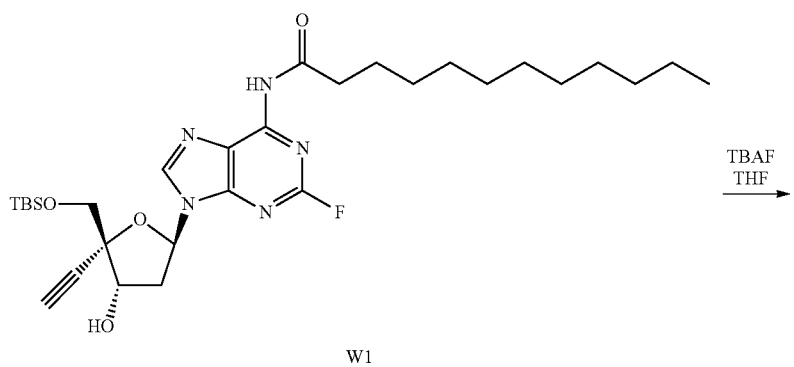

W1

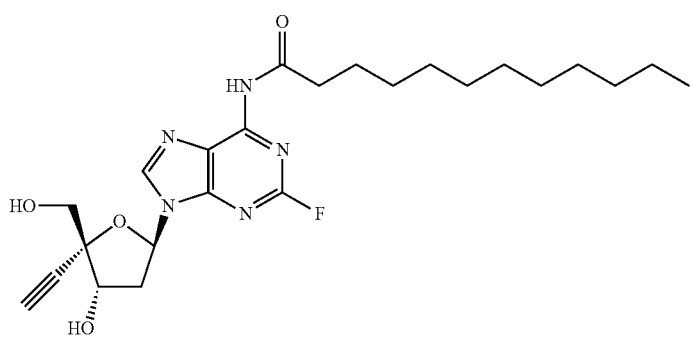

23

Synthesis of Compound 23—N-(9-((2R,4S,5R)-5-ethynyl-4-hydroxy-5-(hydroxymethyl)tetrahydro-furan-2-yl)-2-fluoro-9H-purin-6-yl)dodecanamide Intermediate B1 (20 mg) was dissolved in THE (1 mL) and TBAF (1M in THF, 0.024 mL, 0.0241 mmol) was added. The resulting mixture was stirred at rt for 2h, concentrated in vacuo, and purified by silica gel column chromatography (12 g column, 100% DCM ramping to 5% MeOH/95% DCM) to afford compound 23 as a white solid.

$^1$H NMR (400 MHz, Acetonitrile-$d_3$) δ 9.05 (bs, 1H), 8.28 (s, 1H), 6.38 (dd, J=7.0, 5.3 Hz, 1H), 4.73 (q, J=6.1 Hz, 1H), 3.91 (m, 1H), 3.81 (m, 1H), 3.75 (d, J=6.5 Hz, 1H), 3.66 (d, J=5.5 Hz, 1H), 2.97 (s, 1H), 2.83 (ddd, J=13.5, 6.6, 5.3 Hz, 1H), 2.70 (t, J=7.5 Hz, 2H), 2.57 (dt, J=13.5, 6.8 Hz, 1H), 1.70 (m, 2H), 1.45-1.20 (m, 16H), 0.90 (m, 3H).

$^{19}$F NMR (376 MHz, Acetonitrile-$d_3$) δ -52.59.

LCMS: MS m/z=475.79 [M+1]; $t_R$=1.63 min; LC system: Dionex Ultimate 3000 UHPLC; Column: Phenomenex Kinetex 2.6μ C18 100 A, 50×3.0 mm; Solvents: acetonitrile with 0.1% formic acid, water with 0.1% formic acid; Gradient: 0 min-0.2 min 40% acetonitrile, 0.2 min-1.55 min 40%-100% acetonitrile, 1.55 min-2.80 min 100% acetonitrile, 2.80-2.81 min 100%-40% acetonitrile at 1100 μl/min.

HPLC: $t_R$=6.90 min; HPLC system: 1290 Infinity II.; Column: Phenomenex 2.6μ C18 100 A, 100×4.6 mm; Solvents: Acetonitrile with 0.1% TFA, Water with 0.1% TFA; Gradient: 0 min-8.5 min 2-98% ACN at 1.5 mL/min.

Example 24

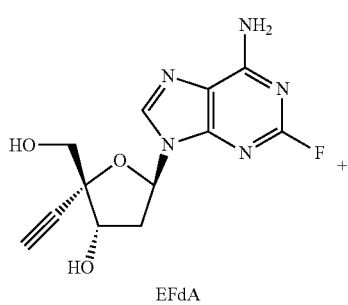

EFdA

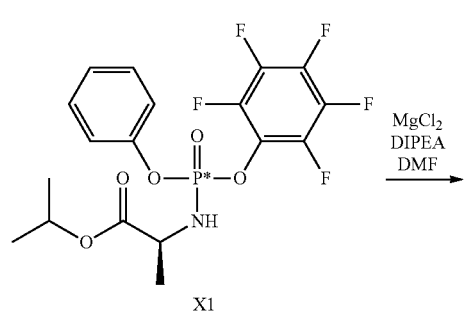

X1

233

-continued

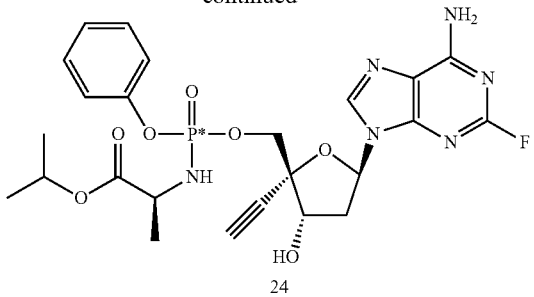

24

Synthesis of Compound 24—isopropyl (((((2R,3S,5R)-5-(6-amino-2-fluoro-9H-purin-9-yl)-2-ethynyl-3-hydroxytetrahydrofuran-2-yl)methoxy)(phenoxy)phosphoryl)-L-alaninate To a mixture of EFdA (200 mg, 0.682 mmol), intermediate X1 (J. Org. Chem. 2011, 76(20), pp 8311-8319; 459 mg, 1.01 mmol), and $MgCl_2$ (97 mg, 1.02 mmol) in DMF (6 mL) was N,N-diisopropyl ethyl amine (0.3 mL, 1.71 mmol) drop-wise at rt. The resulting mixture was stirred at 50° C. for 6h, concentrated in vacuo, purified by silica gel column chromatography (100% DCM ramping up to 10% MeOH/90% DCM), and then by reverse phase HPLC (30% ACN containing 0.1% TFA/70% water containing 0.1% TFA ramping up to 70% ACN containing 0.1% TFA/30% water containing 0.1% TFA) to give compound 24 as a single isomer at phosphorous and a trifluoroacetic acid salt.

$^1$H NMR (400 MHz, Acetonitrile-$d_3$) δ 8.48 (s, 1H), 8.04-7.43 (bs, 1H), 7.40-7.25 (m, 2H), 7.23-6.97 (m, 3H), 6.67 (bs, 1H), 6.34 (dd, J=7.5, 4.0 Hz, 1H), 4.90 (p, J=6.3 Hz, 1H), 4.73 (dd, J=8.0, 7.0 Hz, 1H), 4.60-4.41 (m, 2H), 4.37 (dd, J=11.2, 7.0 Hz, 1H), 4.27 (dd, J=11.2, 6.7 Hz, 1H), 3.88 (m, 1H), 3.06 (s, 1H), 2.81 (ddd, J=13.8, 7.0, 4.0 Hz, 1H), 2.67 (dt, J=13.8, 7.7 Hz, 1H), 1.29 (dd, J=7.1, 0.9 Hz, 3H), 1.19 (d, J=3.8 Hz, 3H), 1.17 (d, J=3.8 Hz, 3H).

$^{19}$F NMR (376 MHz, Acetonitrile-$d_3$) δ −51.86, −77.13.
$^{31}$P NMR (162 MHz, Acetonitrile-$d_3$) δ 3.05.

LCMS: MS m/z=562.87 [M+1]; $t_R$=1.44 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µl/min.
HPLC: $t_R$=4.73 min; HPLC system: 1290 Infinity II.; Column: Phenomenex 2.6µ C18 100 A, 100×4.6 mm; Solvents: Acetonitrile with 0.1% TFA, Water with 0.1% TFA; Gradient: 0 min-8.5 min 2-98% ACN at 1.5 mL/min.

Example 25

Antiviral assay in MT-4 cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (No Drug Control) and 5 µM AZT positive controls. MT-4 cells were pre-infected with 10 µL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature-controlled incubator (37° C.), Cell Titer Glo (Promega) was added to the assay plates and chemiluminescence read using an Envision plate-reader. $EC_{50}$ values were defined as the compound concentration that causes a 50% decrease in luminescence signal, and were calculated using a sigmoidal dose-response model to generate curve fits.

Cytotoxicity Assay in MT-4 Cells

Assays were performed as above except uninfected MT-4 cells were added to each well containing test compound. In addition, 10 µM puromycin was added to the last column of each assay plate to assess a base level of cytotoxicity.

Kinetic Solubility Analysis (CLND)

Buffer Preparation:

0.1N HCl: Hydrochloric acid, 0.1N standardized solution.

1×PBS, 7.4: Phosphate Buffered Saline solution 10×, PBS 50 mL was added to approximately 450 mL HPLC grade $H_2O$. The volume of the solution was then adjusted to 500 mL for a total dilution factor of 1:10 and a final PBS concentration of 1×. The pH of the final solution was measured and found to be 7.4.

Kinetic Solubility from DMSO Stocks: 100-fold dilutions of each DMSO stock solution were prepared in singleton by combining 3 µL of DMSO stock with 297 µL of the appropriate media in a Millipore solubility filter plate with a 0.45 µM polycarbonate filter membrane using Hamilton Starlet liquid handling. The final DMSO concentration is 1.0% and maximum theoretical compound concentration is 100 µM (assuming stock concentration of 10 mM). The filter plate was sealed. Following 24-hour incubation at ambient temperature (24.2-27.5° C.), the samples were vacuum filtered and the filtrates were collected in a 96 well polypropylene plate for analysis. The collection plate was sealed for analysis.

Filtrates were injected into the nitrogen detector for quantification. The results are reported here in µM.

Calculation of Results: The equimolar nitrogen response of the detector was calibrated using standards which spanned the dynamic range of the instrument from 0.08 to 4500 g/mL nitrogen. The filtrates were quantified with respect to this calibration curve. The calculated solubility values were corrected for background nitrogen present in the DMSO and the media used to prepare the samples. All reported values for compounds containing adjacent nitrogen atoms in a ring structure should be increased by ~25%. A comments field contains notes pertinent to the assay of each compound, such as, measured solubility is greater than 75% of the dose concentration, actual solubility may be higher. The solubility results presented assume that the samples were free of nitrogen containing impurities and were stable under the assay conditions.

Compounds of the present disclosure demonstrate antiviral activity in this assay as depicted in Table 2 below. Accordingly, the compounds of the embodiments disclosed herein may be useful for treating the proliferation of the HIV virus, treating AIDS, or delaying the onset of AIDS or ARC symptoms.

TABLE 2

Biologic Data

| Compound No. | Compound Structure | EC50 (nM) | CC50 (nM) | Kinetic Solubility (μg/mL) |
|---|---|---|---|---|
| 1 | 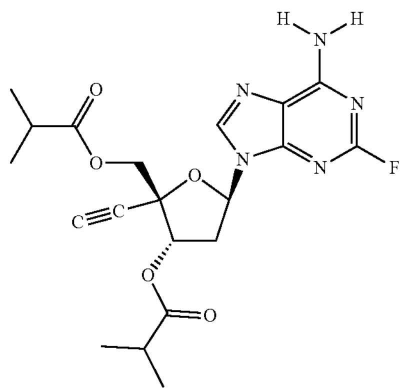 [SMILES: C#C[C@]1(COC(=O)C(C)C)O[C@@H](n2cnc3c(N)nc(F)nc32)C[C@@H]1OC(=O)C(C)C] | 7 | 37303 | 6.6 |
| 2 | 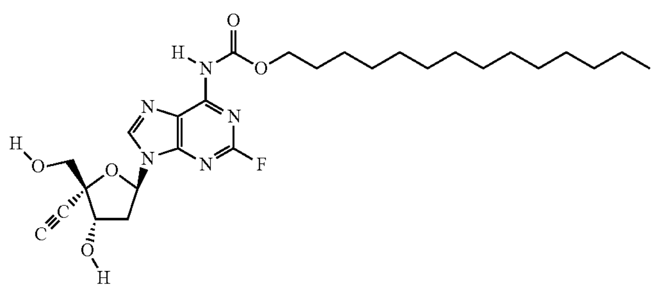 [SMILES: C#C[C@]1(CO)O[C@@H](n2cnc3c(NC(=O)OCCCCCCCCCCCCCC)nc(F)nc32)C[C@@H]1O] | 70 | 13383 | 1.2 |
| 3 | 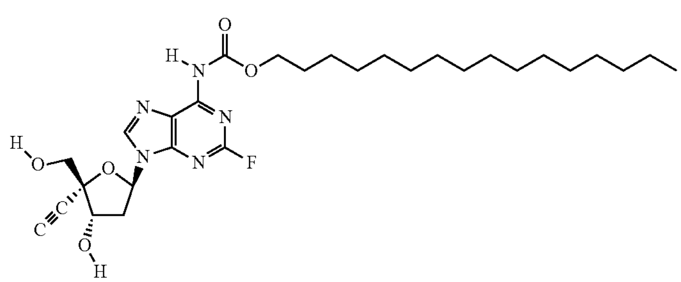 [SMILES: C#C[C@]1(CO)O[C@@H](n2cnc3c(NC(=O)OCCCCCCCCCCCCCCCC)nc(F)nc32)C[C@@H]1O] | 60 | 11792 | |
| 4 | 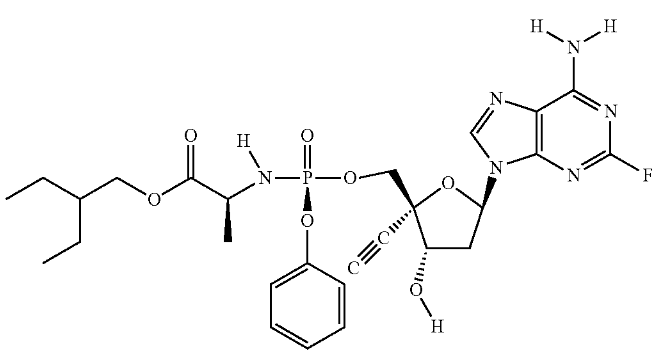 [SMILES: C#C[C@]1(CO[P@@](=O)(N[C@@H](C)C(=O)OCC(CC)CC)Oc2ccccc2)O[C@@H](n2cnc3c(N)nc(F)nc32)C[C@@H]1O] | 8 | | |

TABLE 2-continued

Biologic Data

| Compound No. | Compound Structure | EC50 (nM) | CC50 (nM) | Kinetic Solubility (μg/mL) |
|---|---|---|---|---|
| 5 | 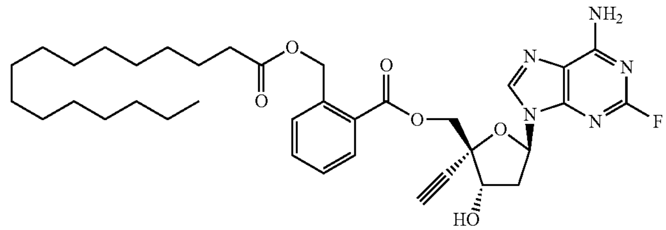 [SMILES: C#C[C@]1(COC(=O)c2ccccc2COC(=O)CCCCCCCCCCCCCCC)O[C@@H](n2cnc3c(N)nc(F)nc32)C[C@@H]1O] | 8 | >50000 | <1 |
| 6 | 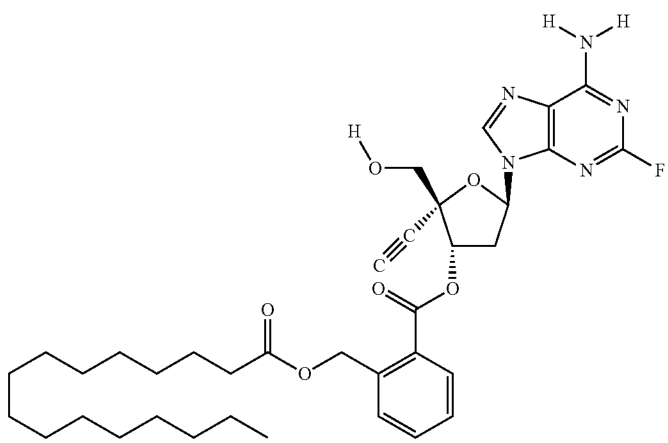 [SMILES: C#C[C@]1(CO)O[C@@H](n2cnc3c(N)nc(F)nc32)C[C@@H]1OC(=O)c1ccccc1COC(=O)CCCCCCCCCCCCCCC] | 29 | >50000 | <1 |
| 7 | 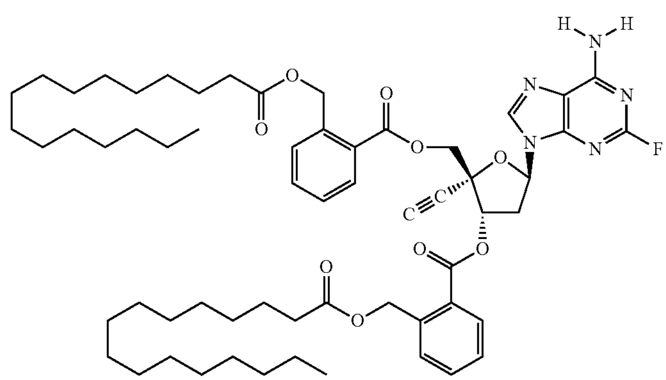 [SMILES: C#C[C@]1(COC(=O)c2ccccc2COC(=O)CCCCCCCCCCCCCCC)O[C@@H](n2cnc3c(N)nc(F)nc32)C[C@@H]1OC(=O)c1ccccc1COC(=O)CCCCCCCCCCCCCCC] | >500 | >50000 | 2 |
| 8 | 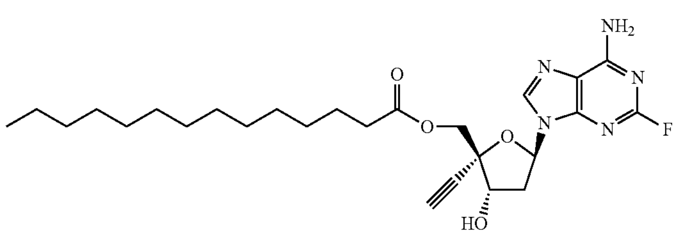 [SMILES: C#C[C@]1(COC(=O)CCCCCCCCCCCCC)O[C@@H](n2cnc3c(N)nc(F)nc32)C[C@@H]1O] | 3 | >20244.6 | <1 |

TABLE 2-continued

Biologic Data

| Compound No. | Compound Structure | EC50 (nM) | CC50 (nM) | Kinetic Solubility (μg/mL) |
| --- | --- | --- | --- | --- |
| 9 | 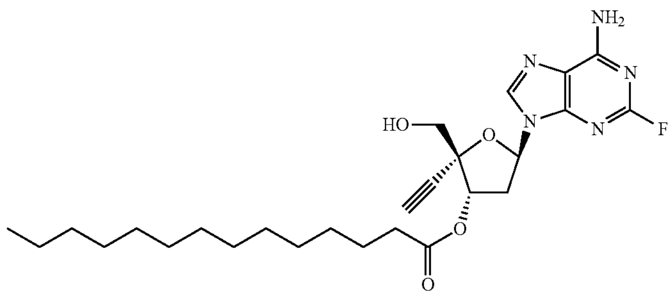 [SMILES: C#C[C@]1(CO)O[C@@H](n2cnc3c(N)nc(F)nc32)C[C@@H]1OC(=O)CCCCCCCCCCCCC] | 4 | >23026.5 | <1 |
| 10 | 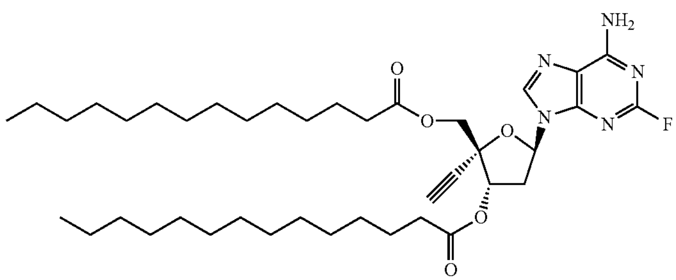 [SMILES: C#C[C@]1(COC(=O)CCCCCCCCCCCCC)O[C@@H](n2cnc3c(N)nc(F)nc32)C[C@@H]1OC(=O)CCCCCCCCCCCCC] | >500 | >50000 | <1 |
| 11 | 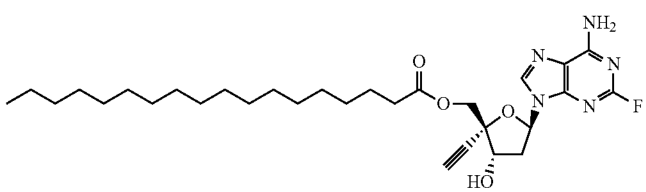 [SMILES: C#C[C@]1(COC(=O)CCCCCCCCCCCCCCCCC)O[C@@H](n2cnc3c(N)nc(F)nc32)C[C@@H]1O] | 7 | >41545.1 | <1 |
| 12 | 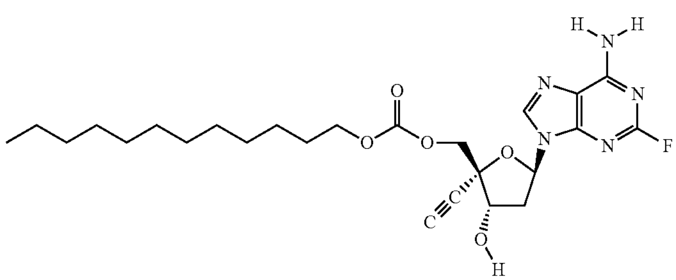 [SMILES: C#C[C@]1(COC(=O)OCCCCCCCCCCCC)O[C@@H](n2cnc3c(N)nc(F)nc32)C[C@@H]1O] | 6 | 16958 | <1 |
| 13 | 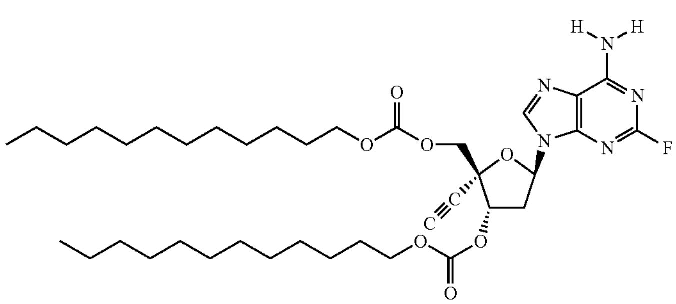 [SMILES: C#C[C@]1(COC(=O)OCCCCCCCCCCCC)O[C@@H](n2cnc3c(N)nc(F)nc32)C[C@@H]1OC(=O)OCCCCCCCCCCCC] | >500 | 5500 | <1 |

TABLE 2-continued

Biologic Data

| Compound No. | Compound Structure | EC50 (nM) | CC50 (nM) | Kinetic Solubility (μg/mL) |
| --- | --- | --- | --- | --- |
| 14 | 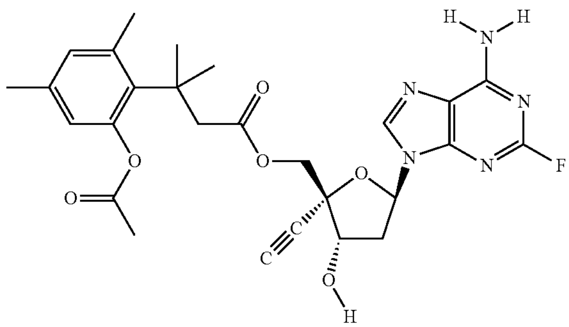 [SMILES: C#C[C@]1(COC(=O)CC(C)(C)c2c(C)cc(C)cc2OC(C)=O)O[C@@H](n2cnc3c(N)nc(F)nc32)C[C@@H]1O] | 4 | >21563 | 37 |
| 15 | 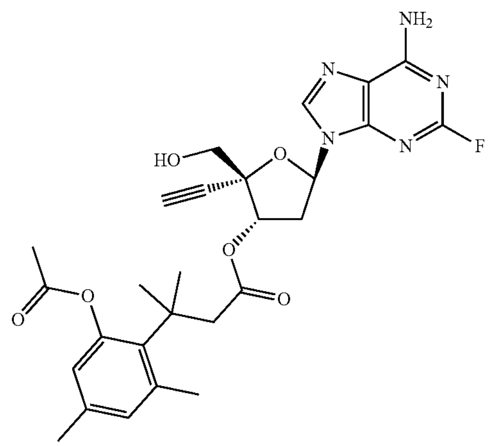 [SMILES: C#C[C@]1(CO)O[C@@H](n2cnc3c(N)nc(F)nc32)C[C@@H]1OC(=O)CC(C)(C)c1c(C)cc(C)cc1OC(C)=O] | 3 | 11752 | 25.1 |
| 16 | 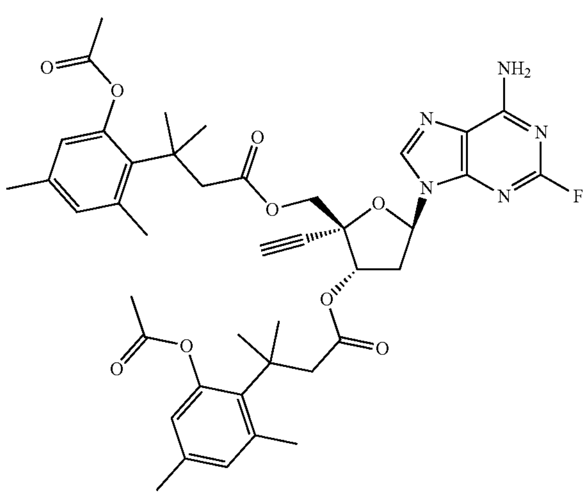 [SMILES: C#C[C@]1(COC(=O)CC(C)(C)c2c(C)cc(C)cc2OC(C)=O)O[C@@H](n2cnc3c(N)nc(F)nc32)C[C@@H]1OC(=O)CC(C)(C)c1c(C)cc(C)cc1OC(C)=O] | 10 | 15657 | <1 |

TABLE 2-continued

Biologic Data

| Compound No. | Compound Structure | EC50 (nM) | CC50 (nM) | Kinetic Solubility (μg/mL) |
|---|---|---|---|---|
| 17 | 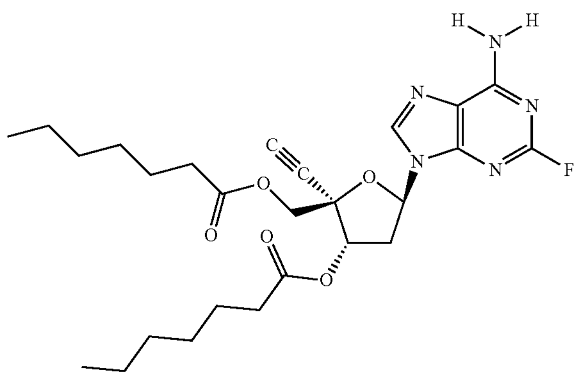 [SMILES: C#C[C@]1(COC(=O)CCCCCC)O[C@@H](n2cnc3c(N)nc(F)nc32)C[C@@H]1OC(=O)CCCCCC] | 7 | >20895.3 | <1 |
| 18 | 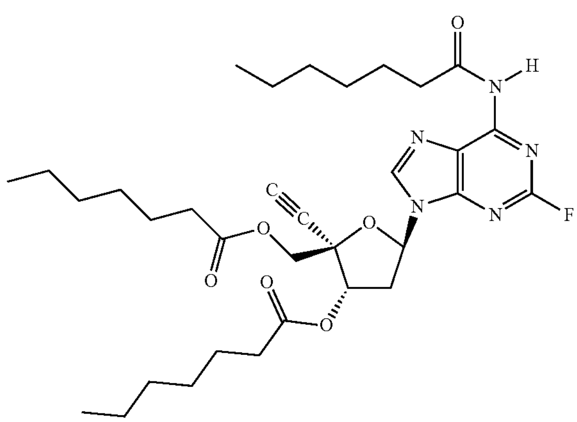 [SMILES: C#C[C@]1(COC(=O)CCCCCC)O[C@@H](n2cnc3c(NC(=O)CCCCCC)nc(F)nc32)C[C@@H]1OC(=O)CCCCCC] | 20 | >10051.4 | 1.5 |
| 19 | 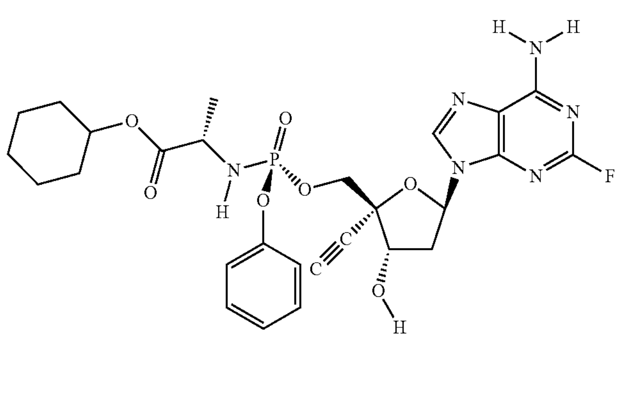 [SMILES: C#C[C@]1(CO[P@@](=O)(N[C@@H](C)C(=O)OC2CCCCC2)Oc2ccccc2)O[C@@H](n2cnc3c(N)nc(F)nc32)C[C@@H]1O] | | | |

TABLE 2-continued

Biologic Data

| Compound No. | Compound Structure | EC50 (nM) | CC50 (nM) | Kinetic Solubility (µg/mL) |
|---|---|---|---|---|
| 20 | 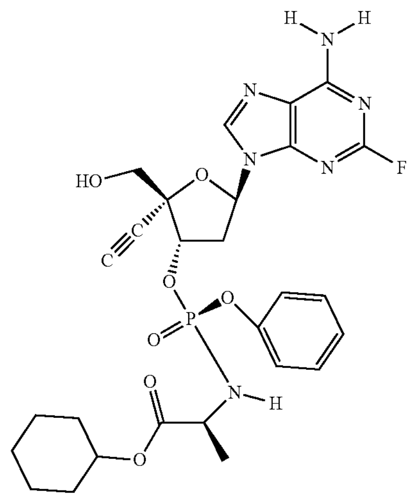 [SMILES: C#C[C@]1(CO)O[C@@H](n2cnc3c(N)nc(F)nc32)C[C@@H]1O[P@@](=O)(N[C@@H](C)C(=O)OC1CCCCC1)Oc1ccccc1] | | | |
| 21 | 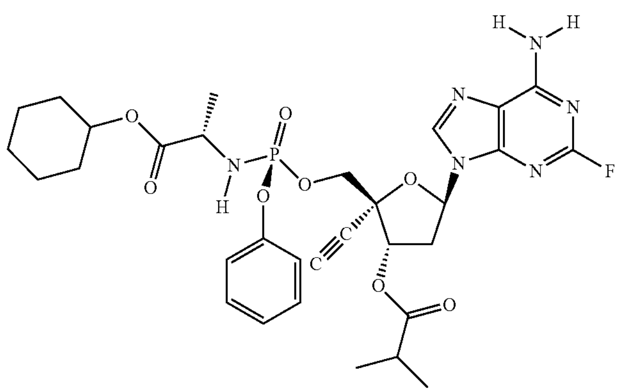 [SMILES: C#C[C@]1(CO[P@@](=O)(N[C@@H](C)C(=O)OC2CCCCC2)Oc2ccccc2)O[C@@H](n2cnc3c(N)nc(F)nc32)C[C@@H]1OC(=O)C(C)C] | | | |
| 22 | 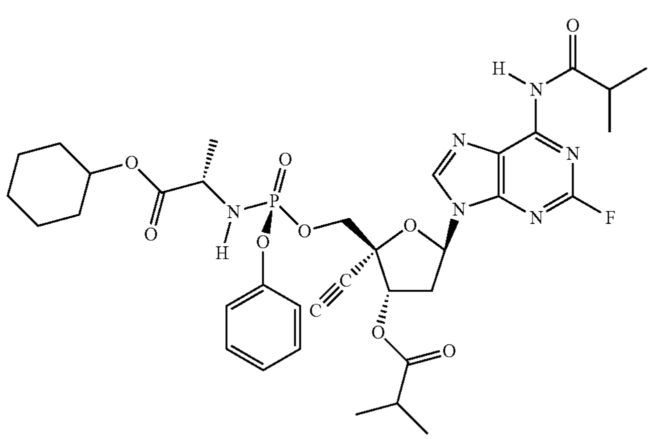 [SMILES: C#C[C@]1(CO[P@@](=O)(N[C@@H](C)C(=O)OC2CCCCC2)Oc2ccccc2)O[C@@H](n2cnc3c(NC(=O)C(C)C)nc(F)nc32)C[C@@H]1OC(=O)C(C)C] | | | |

TABLE 2-continued
Biologic Data
| Compound No. | Compound Structure | EC50 (nM) | CC50 (nM) | Kinetic Solubility (μg/mL) |
|---|---|---|---|---|
| 23 | 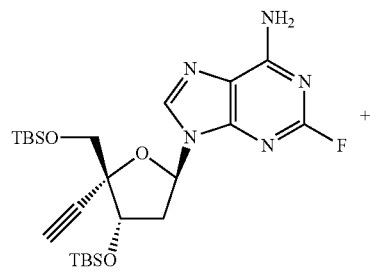 | | | |
| 24 | 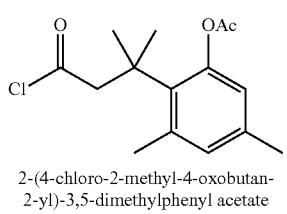 | | | |
PROPHETIC EXAMPLES
Example P-A
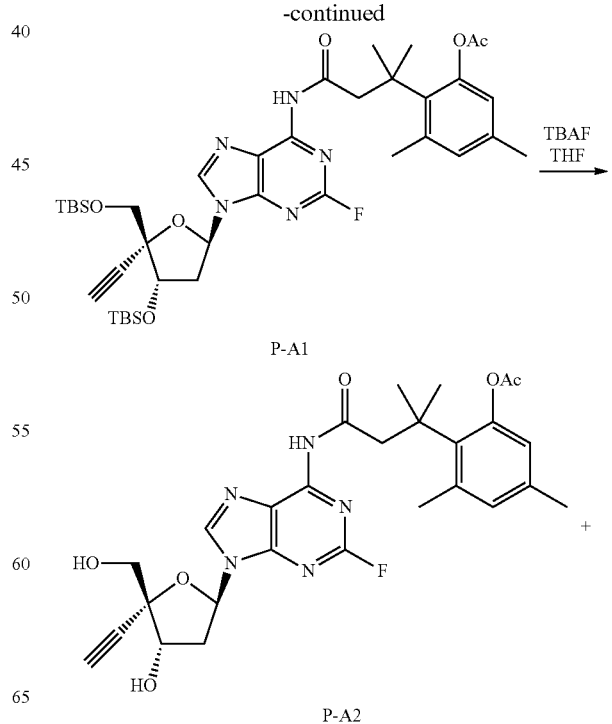

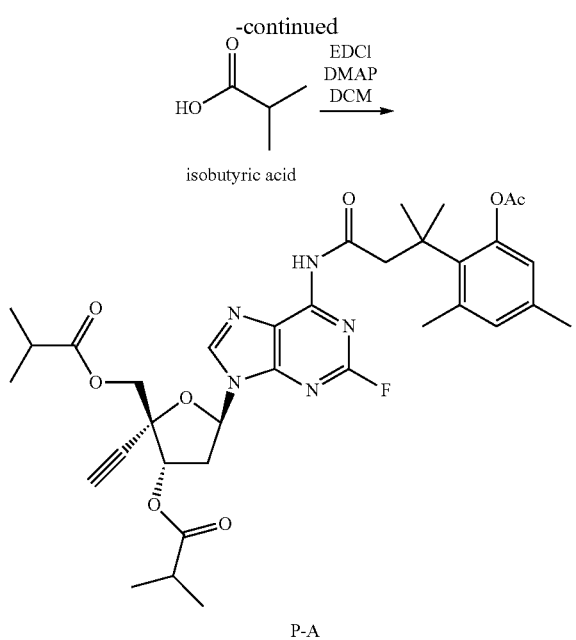

P-A

Synthesis of Compound P-A—(2R,3S,5R)-5-(6-(3-(2-acetoxy-4,6-dimethylphenyl)-3-methylbutana-mido)-2-fluoro-9H-purin-9-yl)-2-ethynyl-2-((isobu-tyryloxy)methyl)tetrahydrofuran-3-yl isobutyrate Intermediate B1 (1 mmol) is dissolved in DCM (10 mL). To this solution is added DMAP (1 eq) and TEA (1 eq). 2-(4-chloro-2-methyl-4-oxobutan-2-yl)-3,5-dimethylphenyl acetate (1 eq; reagent is prepared by stirring a solution of 3-(2-acetoxy-4,6-dimethylphenyl)-3-methylbutanoic acid (Aldrich) and thionyl chloride in DCM which is then concentrated, and the crude reagent is used as is) is then added and the reaction is allowed to proceed. The reaction is quenched by the addition of ice and DCM. The organic layer is separated and dried over sodium sulfate and intermediate P-A1 is isolated by silica gel column chromatography.

Intermediate P-A1 (1 mmol) is dissolved in THF (10 mL) and a solution of TBAF in THF (2 eq) is added. The reaction is allowed to proceed. The reaction is quenched by the addition of ice water and EtOAc, the organic layer is separated and dried over sodium sulfate. The intermediate P-A2 is isolated by silica gel column chromatography.

Intermediate P-A2 (1 mmol) is dissolved in DCM (10 mL). To this solution is added EDCI (2 eq), DMAP (1 eq) and isobutyric acid (2 eq). The reaction is allowed to proceed. The reaction is quenched by the addition of ice and DCM. The organic layer is separated and dried over sodium sulfate and compound P-A is isolated by silica gel column chromatography.

Example P-B

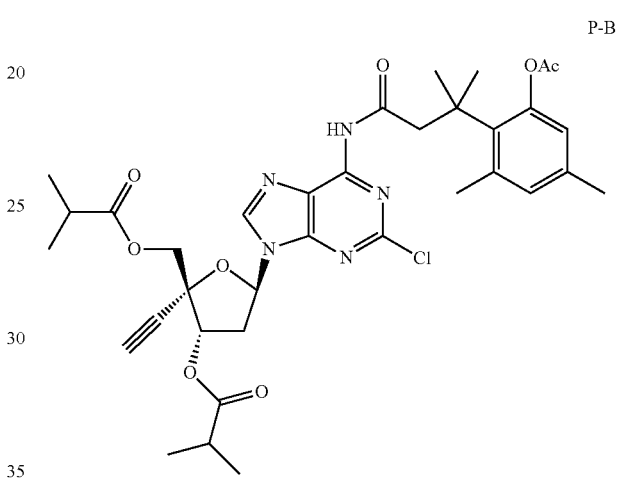

P-B

Synthesis of Compound P-B—(2R,3S,5R)-5-(6-(3-(2-acetoxy-4,6-dimethylphenyl)-3-methylbutana-mido)-2-chloro-9H-purin-9-yl)-2-ethynyl-2-((isobu-tyryloxy)methyl)tetrahydrofuran-3-yl isobutyrate Example P-B is prepared in the same manner as described for example P-A except (2R,3S,5R)-5-(6-amino-2-chloro-9H-purin-9-yl)-2-ethynyl-2-(hydroxymethyl)tetrahydro-furan-3-ol (ECldA, ChemSpace) is used instead of EFdA.

Example P-C

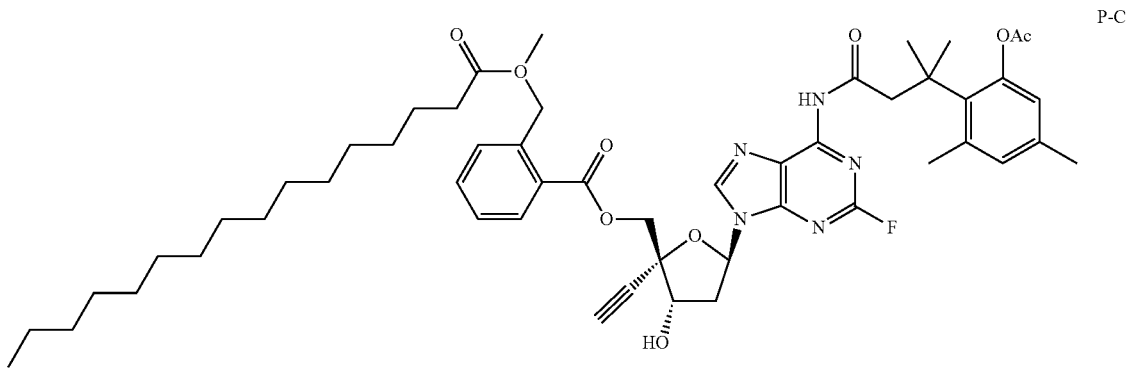

P-C

Synthesis of Compound P-C—((2R,3S,5R)-5-(6-(3-(2-acetoxy-4,6-dimethylphenyl)-3-methylbutanamido)-2-fluoro-9H-purin-9-yl)-2-ethynyl-3-hydroxytetrahydrofuran-2-yl)methyl 2-((palmitoyloxy)methyl)benzoate Example P-C is prepared in the same manner as example P-A except 1 equivalent of intermediate E1 and EDCI are used instead of 2 equivalents of isobutyric acid and EDCI.

Example P-D

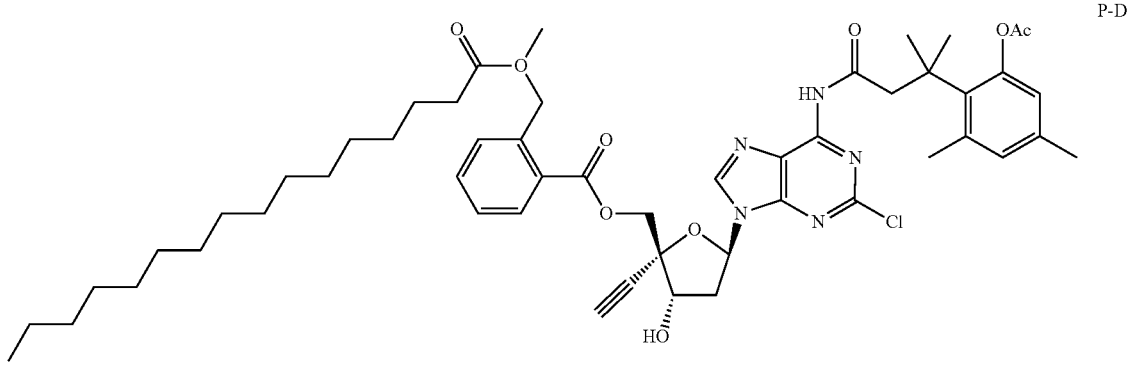

P-D

Synthesis of Compound P-D—((2R,3S,5R)-5-(6-(3-(2-acetoxy-4,6-dimethylphenyl)-3-methylbutanamido)-2-chloro-9H-purin-9-yl)-2-ethynyl-3-hydroxytetrahydrofuran-2-yl)methyl 2-((palmitoyloxy)methyl)benzoate Example P-D is prepared in the same manner as described for example P-C except ECldA is used instead of EFdA.

Example P-E

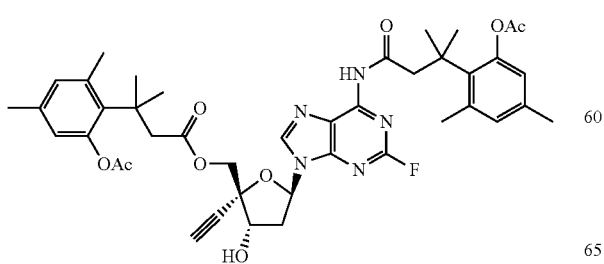

P-E

Synthesis of Compound P-E—((2R,3S,5R)-5-(6-(3-(2-acetoxy-4,6-dimethylphenyl)-3-methylbutanamido)-2-fluoro-9H-purin-9-yl)-2-ethynyl-3-hydroxytetrahydrofuran-2-yl)methyl 3-(2-acetoxy-4,6-dimethylphenyl)-3-methylbutanoate Example P-E is prepared in the same manner as described for example P-A except 1 equivalent of 3-(2-acetoxy-4,6-dimethylphenyl)-3-methylbutanoic acid (Aldrich) and EDCI are used instead of 2 equivalents of isobutyric acid and EDCI.

Example P-F

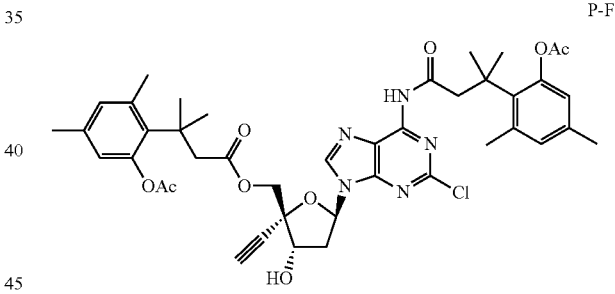

P-F

Synthesis of Compound P-F—((2R,3S,5R)-5-(6-(3-(2-acetoxy-4,6-dimethylphenyl)-3-methylbutanamido)-2-chloro-9H-purin-9-yl)-2-ethynyl-3-hydroxytetrahydrofuran-2-yl)methyl 3-(2-acetoxy-4,6-dimethylphenyl)-3-methylbutanoate Example P-F is prepared in the same manner as described for example P-E except ECldA is used instead of EFdA.

Example P-G

Example P-H

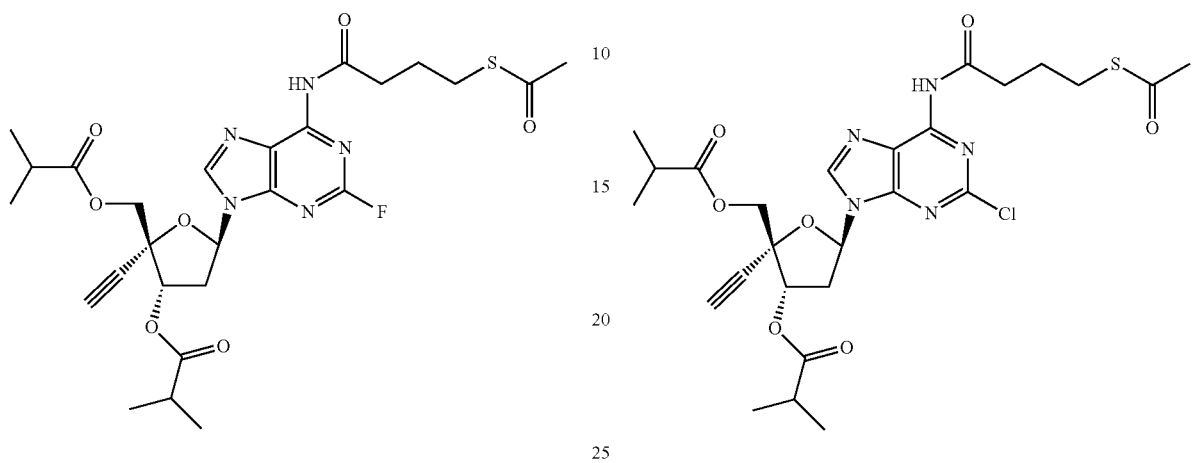

Synthesis of Compound P-G—(2R,3S,5R)-5-(6-(4-(acetylthio)butanamido)-2-fluoro-9H-purin-9-yl)-2-ethynyl-2-((isobutyryloxy)methyl)tetrahydrofuran-3-yl isobutyrate Example P-G is prepared in the same manner as described for example P-A except 4-(acetylthio)butanoic acid (Aldrich) is used instead of 3-(2-acetoxy-4,6-dimethylphenyl)-3-methylbutanoic acid.

Synthesis of Compound P-H—(2R,3S,5R)-5-(6-(4-(acetylthio)butanamido)-2-chloro-9H-purin-9-yl)-2-ethynyl-2-((isobutyryloxy)methyl)tetrahydrofuran-3-yl isobutyrate Example P-H is prepared in the same manner as described for example P-G except ECldA is used instead of EFdA.

Example P-I

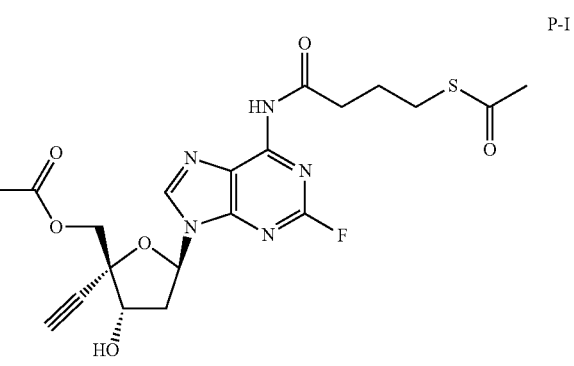

Synthesis of Compound P-I—((2R,3S,5R)-5-(6-(4-(acetylthio)butanamido)-2-fluoro-9H-purin-9-yl)-2-ethynyl-3-hydroxytetrahydrofuran-2-yl)methyl 2-((palmitoyloxy)methyl)benzoate Example P-I is prepared in the same manner as example P-A except 4-(acetylthio)butanoic acid is used instead of 3-(2-acetoxy-4,6-dimethylphenyl)-3-methylbutanoic acid and 1 equivalent of intermediate E1 and EDCI are used instead of 2 equivalents of isobutyric acid and EDCI.

Example P-J

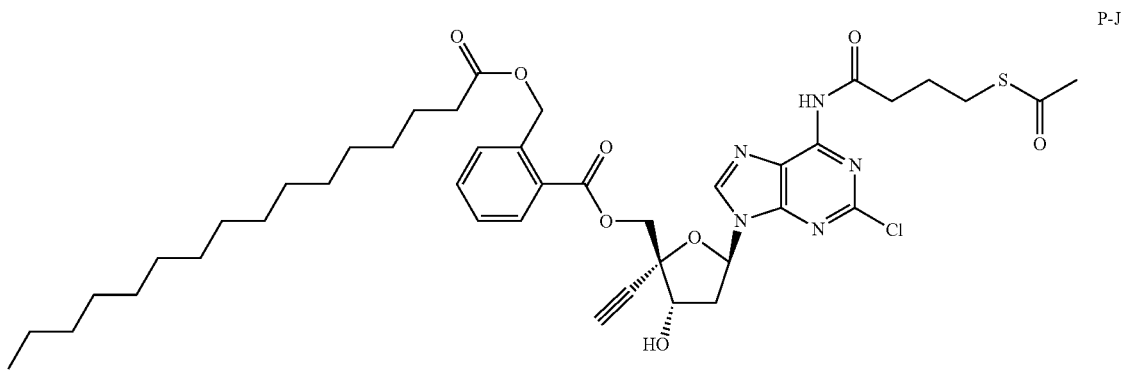 [SMILES: C#C[C@]1(COC(=O)c2ccccc2COC(=O)CCCCCCCCCCCCCCC)O[C@@H](n2cnc3c(NC(=O)CCCSC(C)=O)nc(Cl)nc32)C[C@@H]1O]

Synthesis of Compound P-J—((2R,3S,5R)-5-(6-(4-(acetylthio)butanamido)-2-chloro-9H-purin-9-yl)-2-ethynyl-3-hydroxytetrahydrofuran-2-yl)methyl 2-((palmitoyloxy)methyl)benzoate Example P-J is prepared in the same manner as described for example P-A except ECldA is used instead of EFdA.

Example P-K

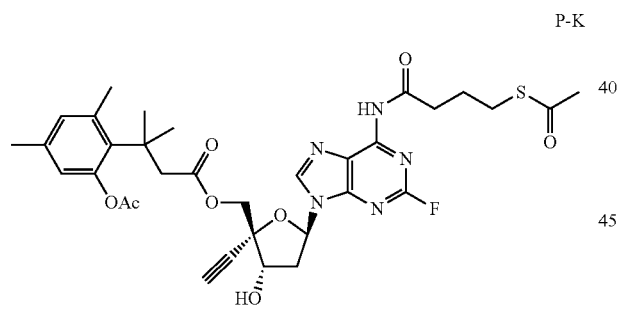

Synthesis of Compound P-K—((2R,3S,5R)-5-(6-(4-(acetylthio)butanamido)-2-fluoro-9H-purin-9-yl)-2-ethynyl-3-hydroxytetrahydrofuran-2-yl)methyl 3-(2-acetoxy-4,6-dimethylphenyl)-3-methylbutanoate Example P-K is prepared in the same manner as described for example P-A except 4-(acetylthio)butanoic acid is used instead of 3-(2-acetoxy-4,6-dimethylphenyl)-3-methylbutanoic acid and 1 equivalent of 3-(2-acetoxy-4,6-dimethylphenyl)-3-methylbutanoic acid (Aldrich) and EDCI are used instead of 2 equivalents of isobutyric acid and EDCI.

Example P-L

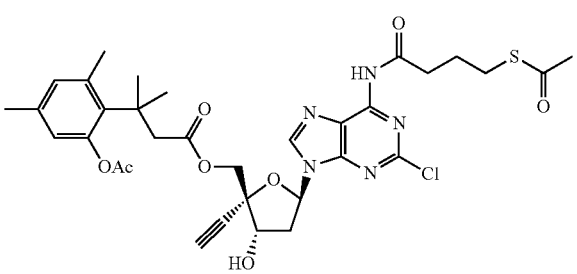

Synthesis of Compound P-L—((2R,3S,5R)-5-(6-(4-(acetylthio)butanamido)-2-chloro-9H-purin-9-yl)-2-ethynyl-3-hydroxytetrahydrofuran-2-yl)methyl 3-(2-acetoxy-4,6-dimethylphenyl)-3-methylbutanoate Example P-L is prepared in the same manner as described for example P-K except ECldA is used instead of EFdA.

Example P-M

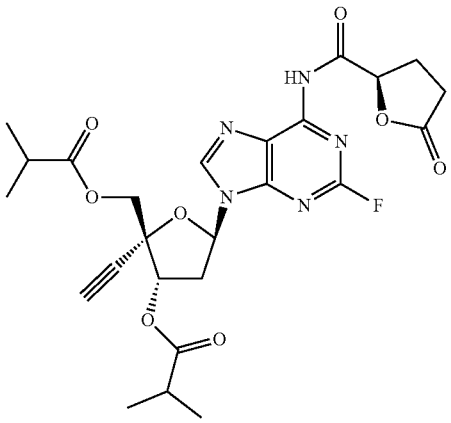

Synthesis of Compound P-M—(2R,3S,5R)-2-ethynyl-5-(2-fluoro-6-((R)-5-oxotetrahydrofuran-2-carboxamido)-9H-purin-9-yl)-2-((isobutyryloxy)methyl)tetrahydrofuran-3-yl isobutyrate Example P-M is prepared in the same manner as described for example P-A except (R)-5-oxotetrahydrofuran-2-carboxylic acid (Aldrich) is used instead of 3-(2-acetoxy-4,6-dimethylphenyl)-3-methylbutanoic acid.

Example P-N

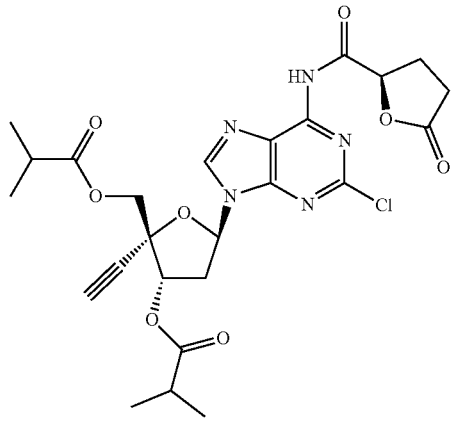

P-N

Synthesis of Compound P-N—(2R,3S,5R)-5-(2-chloro-6-((R)-5-oxotetrahydrofuran-2-carboxamido)-9H-purin-9-yl)-2-ethynyl-2-((isobutyryloxy)methyl)tetrahydrofuran-3-yl isobutyrate Example P-N is prepared in the same manner as described for example P-M except ECldA is used instead of EFdA.

Example P-O

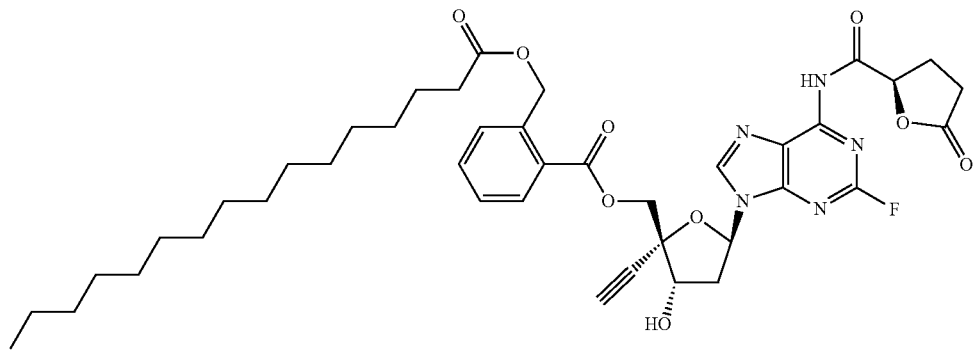

P-O

Synthesis of Compound P-O—((2R,3S,5R)-2-ethynyl-5-(2-fluoro-6-((R)-5-oxotetrahydrofuran-2-carboxamido)-9H-purin-9-yl)-3-hydroxytetrahydrofuran-2-yl)methyl 2-((palmitoyloxy)methyl)benzoate Example P-O is prepared in the same manner as example P-A except (R)-5-oxotetrahydrofuran-2-carboxylic acid is used instead of 3-(2-acetoxy-4,6-dimethylphenyl)-3-methylbutanoic acid and 1 equivalent of intermediate E1 and EDCI are used instead of 2 equivalents of isobutyric acid and EDCI.

Example P-P

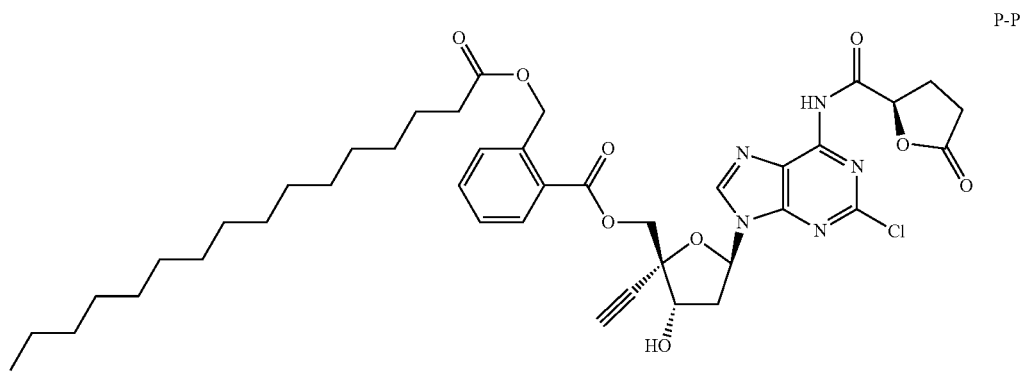 [SMILES: C#C[C@]1(COC(=O)c2ccccc2COC(=O)CCCCCCCCCCCCCCC)O[C@@H](n2cnc3c(NC(=O)[C@H]4CCC(=O)O4)nc(F)nc32)C[C@@H]1O]

Synthesis of Compound P-P—((2R,3S,5R)-5-(2-chloro-6-((R)-5-oxotetrahydrofuran-2-carboxamido)-9H-purin-9-yl)-2-ethynyl-3-hydroxytetrahydrofuran-2-yl)methyl 2-((palmitoyloxy)methyl)benzoate Example P-P is prepared in the same manner as described for example P-O except ECldA is used instead of EFdA.

Example P-Q

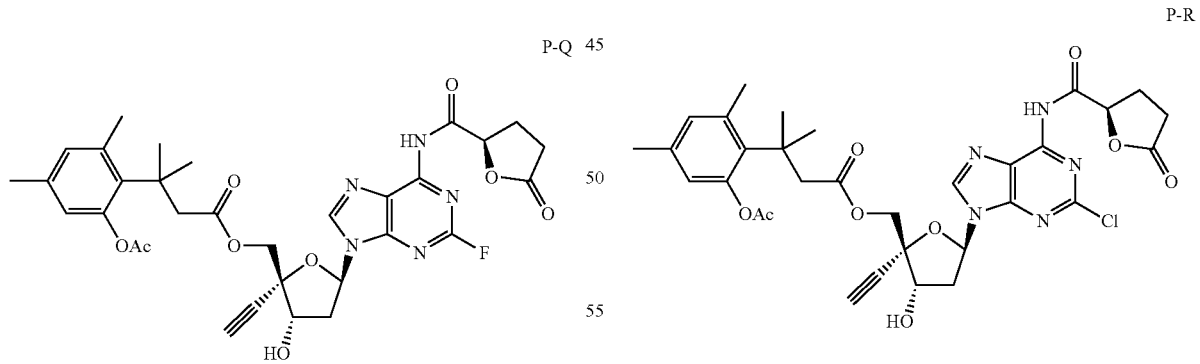

Synthesis of Compound P-Q—((2R,3S,5R)-2-ethynyl-5-(2-fluoro-6-((R)-5-oxotetrahydrofuran-2-carboxamido)-9H-purin-9-yl)-3-hydroxytetrahydrofuran-2-yl)methyl 3-(2-acetoxy-4,6-dimethylphenyl)-3-methylbutanoate Example P-Q is prepared in the same manner as described for example P-A except (R)-5-oxotetrahydrofuran-2-carboxylic acid is used instead of 3-(2-acetoxy-4,6-dimethylphenyl)-3-methylbutanoic acid and 1 equivalent of 3-(2-acetoxy-4,6-dimethylphenyl)-3-methylbutanoic acid (Aldrich) and EDCI are used instead of 2 equivalents of isobutyric acid and EDCI.

Example P-R

Synthesis of Compound P-R—((2R,3S,5R)-5-(2-chloro-6-((R)-5-oxotetrahydrofuran-2-carboxamido)-9H-purin-9-yl)-2-ethynyl-3-hydroxytetrahydrofuran-2-yl)methyl 3-(2-acetoxy-4,6-dimethylphenyl)-3-methylbutanoate Example P-R is prepared in the same manner as described for example P-Q except ECldA is used instead of EFdA.

Example P-S

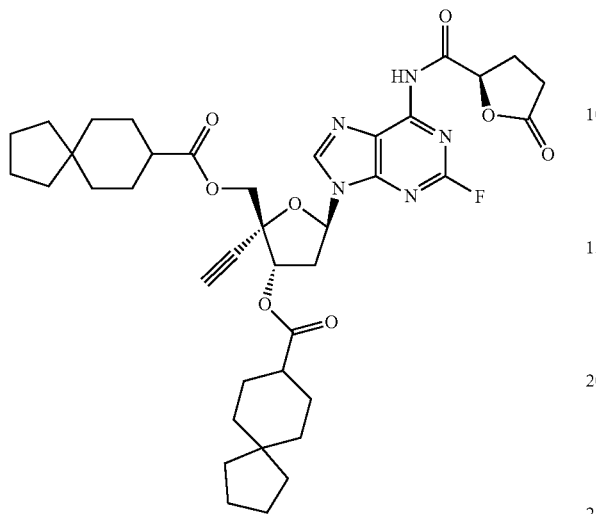

P-S

Synthesis of Compound P-S—((2R,3S,5R)-2-ethynyl-5-(2-fluoro-6-((R)-5-oxotetrahydrofuran-2-carboxamido)-9H-purin-9-yl)-3-((spiro[4.5]decane-8-carbonyl)oxy)tetrahydrofuran-2-yl)methyl spiro[4.5]decane-8-carboxylate Example P-S is prepared in the same manner as example P-A except (R)-5-oxotetrahydrofuran-2-carboxylic acid is used instead of 3-(2-acetoxy-4,6-dimethylphenyl)-3-methylbutanoic acid and spiro[4.5]decane-8-carboxylic acid (Aldrich) is used instead of isobutyric acid.

Example P-T

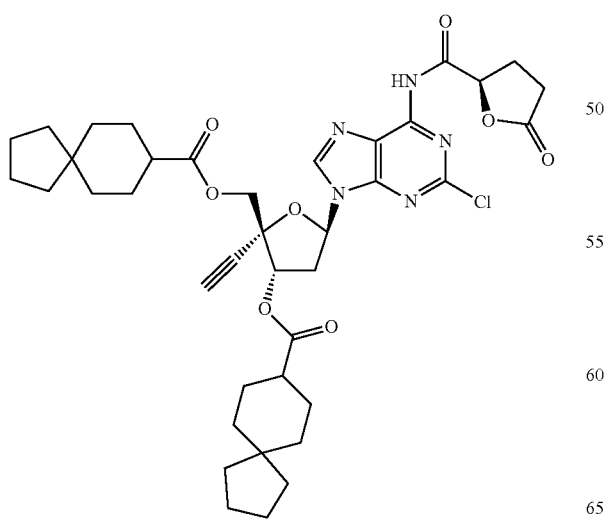

P-T

Synthesis of Compound P-T—((2R,3S,5R)-5-(2-chloro-6-((R)-5-oxotetrahydrofuran-2-carboxamido)-9H-purin-9-yl)-2-ethynyl-3-((spiro[4.5]decane-8-carbonyl)oxy)tetrahydrofuran-2-yl)methyl spiro[4.5]decane-8-carboxylate Example P-T is prepared in the same manner as described for example P-S except ECldA is used instead of EFdA.

Example P-U

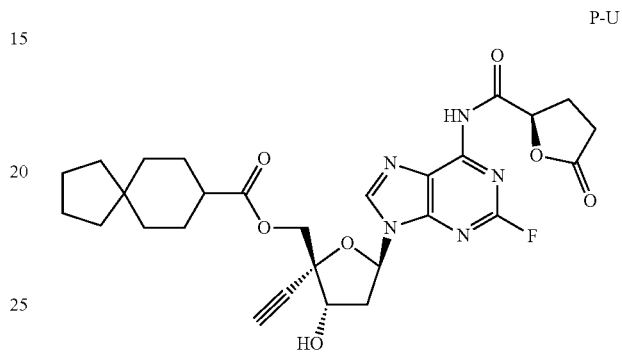

P-U

Synthesis of Compound P-U—((2R,3S,5R)-2-ethynyl-5-(2-fluoro-6-((R)-5-oxotetrahydrofuran-2-carboxamido)-9H-purin-9-yl)-3-hydroxytetrahydrofuran-2-yl)methyl spiro[4.5]decane-8-carboxylate Example P-U is prepared in the same manner as described for example P-A except (R)-5-oxotetrahydrofuran-2-carboxylic acid is used instead of 3-(2-acetoxy-4,6-dimethylphenyl)-3-methylbutanoic acid and 1 equivalent of spiro[4.5]decane-8-carboxylic acid and EDCI are used instead of 2 equivalents of isobutyric acid and EDCI.

Example P-V

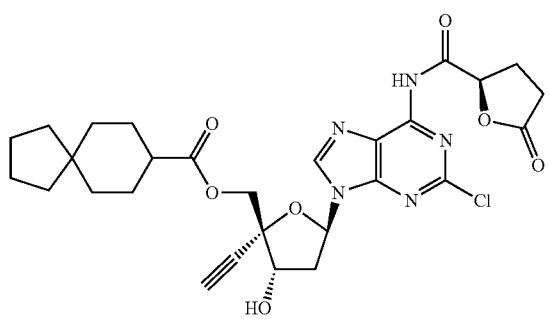

P-V

Synthesis of Compound P-V—((2R,3S,5R)-5-(2-chloro-6-((R)-5-oxotetrahydrofuran-2-carboxamido)-9H-purin-9-yl)-2-ethynyl-3-hydroxytetrahydrofuran-2-yl)methyl spiro[4.5]decane-8-carboxylate Example P-V is prepared in the same manner as described for example P-U except ECldA is used instead of EFdA.

Example P-W

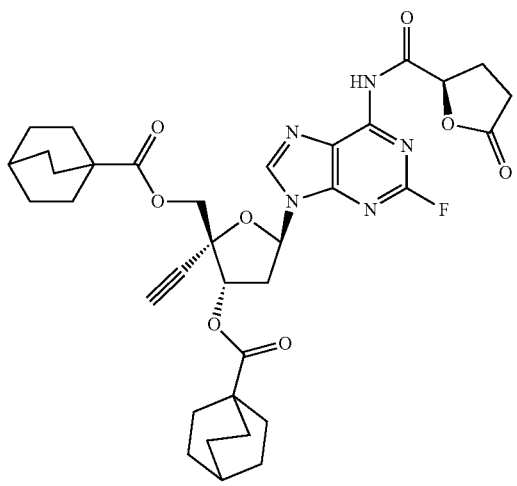

P-W

Synthesis of Compound P-W—((2R,3S,5R)-3-((bicyclo[2.2.2]octane-1-carbonyl)oxy)-2-ethynyl-5-(2-fluoro-6-((R)-5-oxotetrahydrofuran-2-carboxamido)-9H-purin-9-yl)tetrahydrofuran-2-yl)methyl bicyclo[2.2.2]octane-1-carboxylate Example P-W is prepared in the same manner as example P-A except (R)-5-oxotetrahydrofuran-2-carboxylic acid is used instead of 3-(2-acetoxy-4,6-dimethylphenyl)-3-methylbutanoic acid and bicyclo[2.2.2]octane-1-carboxylic acid (Aldrich) is used instead of isobutyric acid.

Example P-X

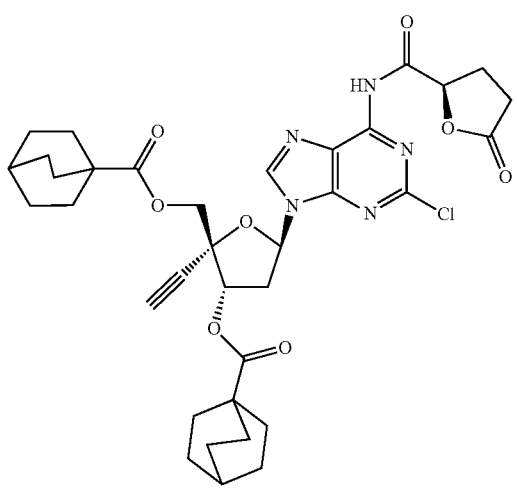

P-X

Synthesis of Compound P-X—((2R,3S,5R)-3-((bicyclo[2.2.2]octane-1-carbonyl)oxy)-5-(2-chloro-6-((R)-5-oxotetrahydrofuran-2-carboxamido)-9H-purin-9-yl)-2-ethynyltetrahydrofuran-2-yl)methyl bicyclo[2.2.2]octane-1-carboxylate Example P-X is prepared in the same manner as described for example P-W except ECldA is used instead of EFdA.

Example P-Y

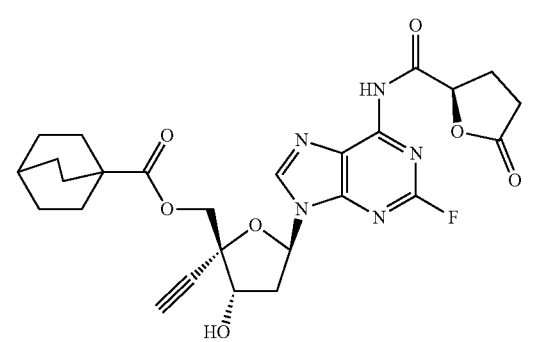

P-Y

Synthesis of Compound P-Y—((2R,3S,5R)-2-ethynyl-5-(2-fluoro-6-((R)-5-oxotetrahydrofuran-2-carboxamido)-9H-purin-9-yl)-3-hydroxytetrahydrofuran-2-yl)methyl bicyclo[2.2.2]octane-1-carboxylate Example P-Y is prepared in the same manner as described for example P-A except (R)-5-oxotetrahydrofuran-2-carboxylic acid is used instead of 3-(2-acetoxy-4,6-dimethylphenyl)-3-methylbutanoic acid and 1 equivalent of bicyclo[2.2.2]octane-1-carboxylic acid and EDCI are used instead of 2 equivalents of isobutyric acid and EDCI.

Example P-Z

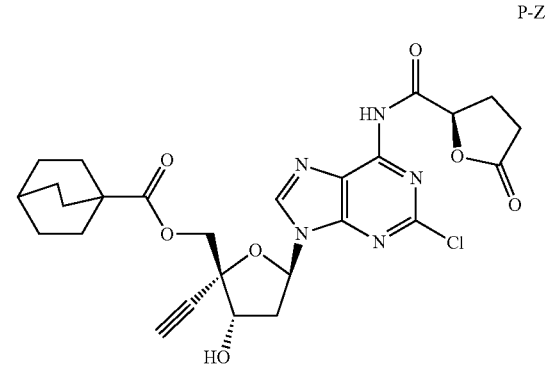 [SMILES: C#C[C@]1(COC(=O)C23CCC(CC2)CC3)O[C@@H](n2cnc3c(NC(=O)[C@H]4CCC(=O)O4)nc(F)nc32)C[C@@H]1O]

P-Z

Synthesis of Compound P-Z—((2R,3S,5R)-5-(2-chloro-6-((R)-5-oxotetrahydrofuran-2-carboxamido)-9H-purin-9-yl)-2-ethynyl-3-hydroxytetrahydrofuran-2-yl)methyl bicyclo[2.2.2]octane-1-carboxylate Example P-Z is prepared in the same manner as described for example P-Y except ECldA is used instead of EFdA.

Example P-AA

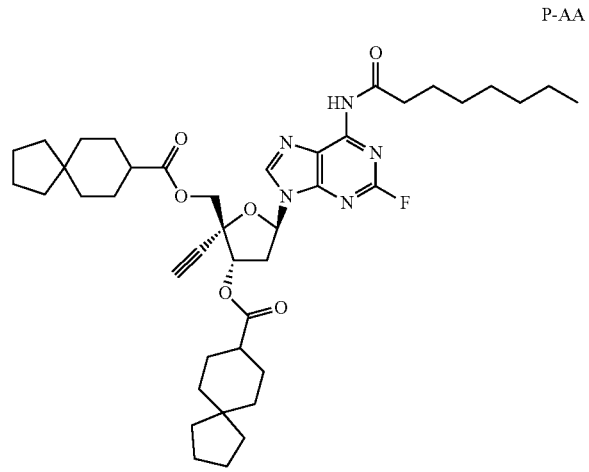 [SMILES: C#C[C@]1(COC(=O)C2CCC3(CCCC3)CC2)O[C@@H](n2cnc3c(NC(=O)CCCCCCC)nc(F)nc32)C[C@@H]1OC(=O)C1CCC2(CCCC2)CC1]

P-AA

Synthesis of Compound P-AA—((2R,3S,5R)-2-ethynyl-5-(2-fluoro-6-octanamido-9H-purin-9-yl)-3-((spiro[4.5]decane-8-carbonyl)oxy)tetrahydrofuran-2-yl)methyl spiro[4.5]decane-8-carboxylate Example P-AA is prepared in the same manner as described for example P-A except n-octanoic acid (Aldrich) is used instead of 3-(2-acetoxy-4,6-dimethylphenyl)-3-methylbutanoic acid and spiro[4.5]decane-8-carboxylic acid is used instead of isobutyric acid.

Example P-BB

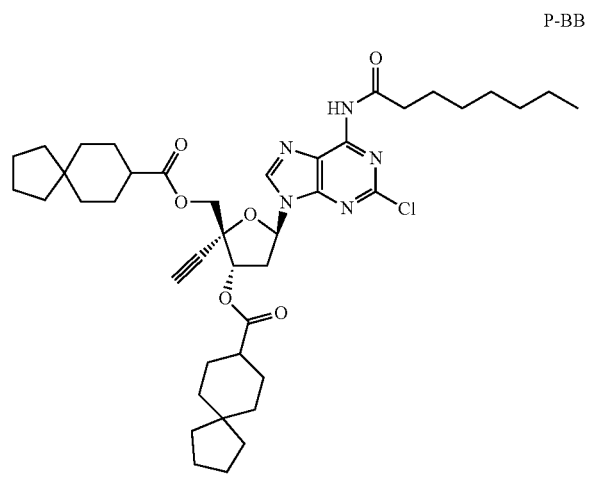 [SMILES: C#C[C@]1(COC(=O)C2CCC3(CCCC3)CC2)O[C@@H](n2cnc3c(NC(=O)CCCCCCC)nc(Cl)nc32)C[C@@H]1OC(=O)C1CCC2(CCCC2)CC1]

P-BB

Synthesis of Compound P-BB—((2R,3S,5R)-5-(2-chloro-6-octanamido-9H-purin-9-yl)-2-ethynyl-3-((spiro[4.5]decane-8-carbonyl)oxy)tetrahydrofuran-2-yl)methyl spiro[4.5]decane-8-carboxylate Example P-BB is prepared in the same manner as described for example P-AA except ECldA is used instead of EFdA.

Example P-CC

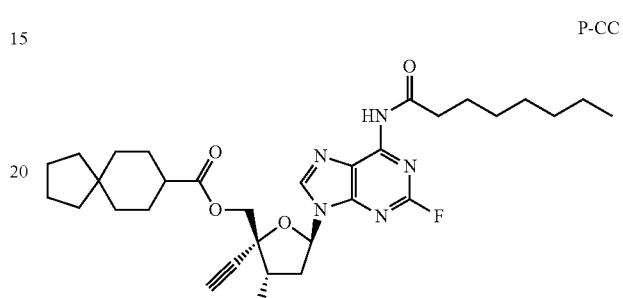

P-CC

Synthesis of Compound P-CC—((2R,3S,5R)-2-ethynyl-5-(2-fluoro-6-octanamido-9H-purin-9-yl)-3-hydroxytetrahydrofuran-2-yl)methyl spiro[4.5]decane-8-carboxylate Example P-CC is prepared in the same manner as described for example P-A except n-octanoic acid (Aldrich) is used instead of 3-(2-acetoxy-4,6-dimethylphenyl)-3-methylbutanoic acid and 1 equivalent of spiro[4.5]decane-8-carboxylic acid and EDCI are used instead of 2 equivalents of isobutyric acid and EDCI.

Example P-DD

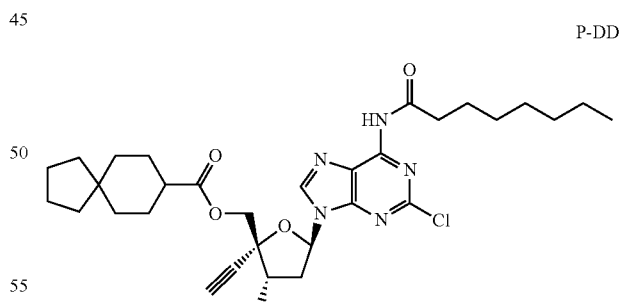

P-DD

Synthesis of Compound P-DD—((2R,3S,5R)-5-(2-chloro-6-octanamido-9H-purin-9-yl)-2-ethynyl-3-hydroxytetrahydrofuran-2-yl)methyl spiro[4.5]decane-8-carboxylate Example P-DD is prepared in the same manner as described for example P-CC except ECldA is used instead of EFdA.

Example P-EE

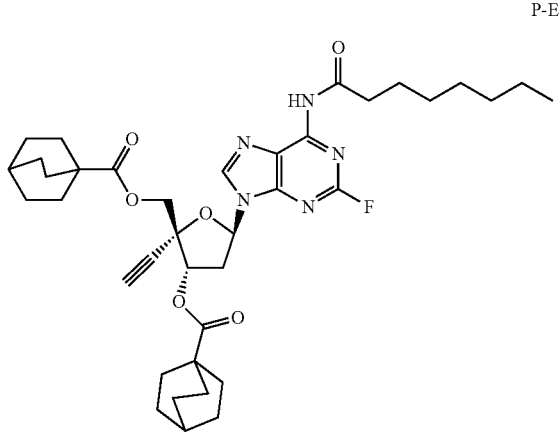

Synthesis of Compound P-EE—((2R,3S,5R)-3-((bi-cyclo[2.2.2]octane-1-carbonyl)oxy)-2-ethynyl-5-(2-fluoro-6-octanamido-9H-purin-9-yl)tetrahydrofuran-2-yl)methyl bicyclo[2.2.2]octane-1-carboxylate Example P-EE is prepared in the same manner as described for example P-A except n-octanoic acid is used instead of 3-(2-acetoxy-4,6-dimethylphenyl)-3-methylbutanoic acid and bicyclo[2.2.2]octane-1-carboxylic acid is used instead of isobutyric acid.

Example P-FF

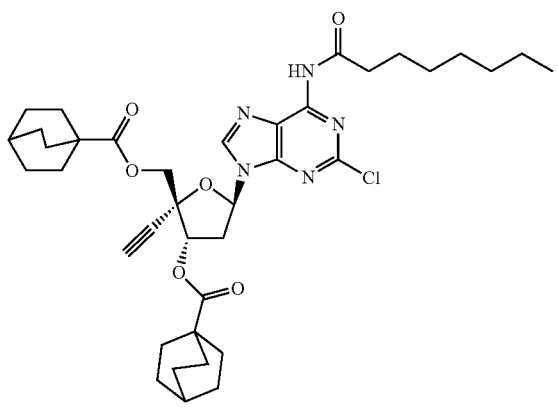

Synthesis of Compound P-FF—((2R,3S,5R)-3-((bi-cyclo[2.2.2]octane-1-carbonyl)oxy)-5-(2-chloro-6-octanamido-9H-purin-9-yl)-2-ethynyltetrahydrofuran-2-yl)methyl bicyclo[2.2.2]octane-1-carboxylate Example P-FF is prepared in the same manner as described for example P-EE except ECldA is used instead of EFdA.

Example P-GG

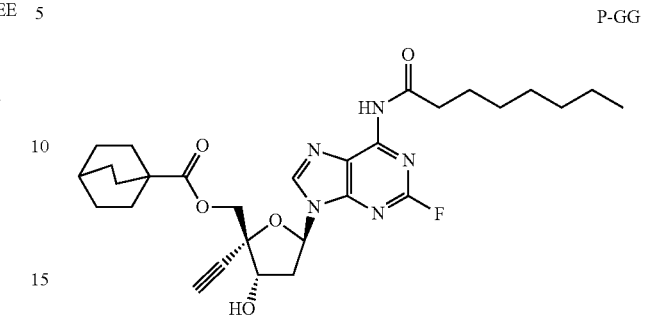

Synthesis of Compound P-GG—((2R,3S,5R)-2-ethynyl-5-(2-fluoro-6-octanamido-9H-purin-9-yl)-3-hydroxytetrahydrofuran-2-yl)methyl bicyclo[2.2.2]octane-1-carboxylate Example P-GG is prepared in the same manner as described for example P-A except n-octanoic acid is used instead of 3-(2-acetoxy-4,6-dimethylphenyl)-3-methylbutanoic acid and 1 equivalent of bicyclo[2.2.2]octane-1-carboxylic acid and EDCI are used instead of 2 equivalents of isobutyric acid and EDCI.

Example P-HH

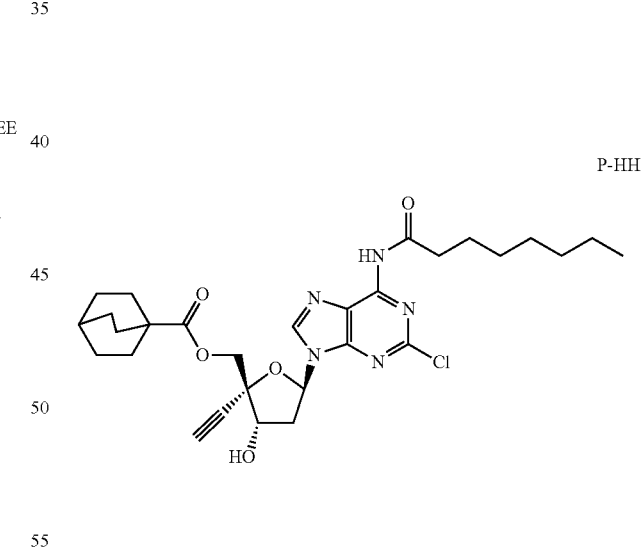

Synthesis of Compound P-HH—((2R,3S,5R)-5-(2-chloro-6-octanamido-9H-purin-9-yl)-2-ethynyl-3-hydroxytetrahydrofuran-2-yl)methyl bicyclo[2.2.2]octane-1-carboxylate Example P-HH is prepared in the same manner as described for example P-GG except ECldA is used instead of EFdA.

Example P-II

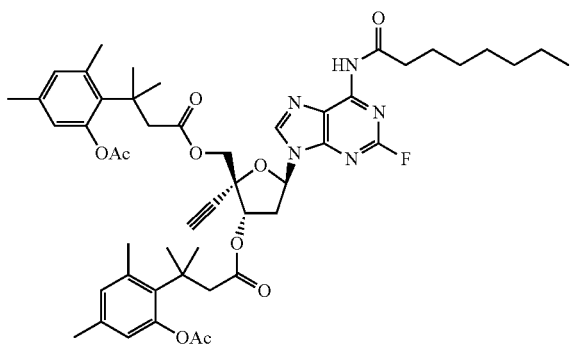

Synthesis of Compound P-II—((2R,3S,5R)-3-((3-(2-acetoxy-4,6-dimethylphenyl)-3-methylbutanoyl)oxy)-2-ethynyl-5-(2-fluoro-6-octanamido-9H-purin-9-yl)tetrahydrofuran-2-yl)methyl 3-(2-acetoxy-4,6-dimethylphenyl)-3-methylbutanoate Example P-II is prepared in the same manner as described for example P-A except n-octanoic acid is used instead of 3-(2-acetoxy-4,6-dimethylphenyl)-3-methylbutanoic acid and 3-(2-acetoxy-4,6-dimethylphenyl)-3-methylbutanoic acid is used instead of isobutyric acid.

Example P-JJ

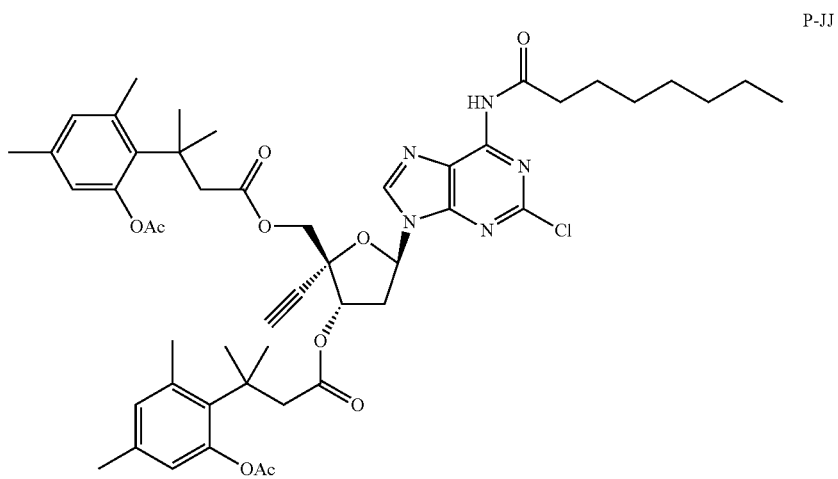 [SMILES: C#C[C@]1(COC(=O)CC(C)(C)c2c(C)cc(C)cc2OC(C)=O)O[C@@H](n2cnc3c(NC(=O)CCCCCCC)nc(Cl)nc32)C[C@@H]1OC(=O)CC(C)(C)c1c(C)cc(C)cc1OC(C)=O]

Synthesis of Compound P-JJ—((2R,3S,5R)-3-((3-(2-acetoxy-4,6-dimethylphenyl)-3-methylbutanoyl)oxy)-5-(2-chloro-6-octanamido-9H-purin-9-yl)-2-ethynyltetrahydrofuran-2-yl)methyl 3-(2-acetoxy-4,6-dimethylphenyl)-3-methylbutanoate Example P-JJ is prepared in the same manner as described for example P-II except ECldA is used instead of EFdA.

Example P-KK

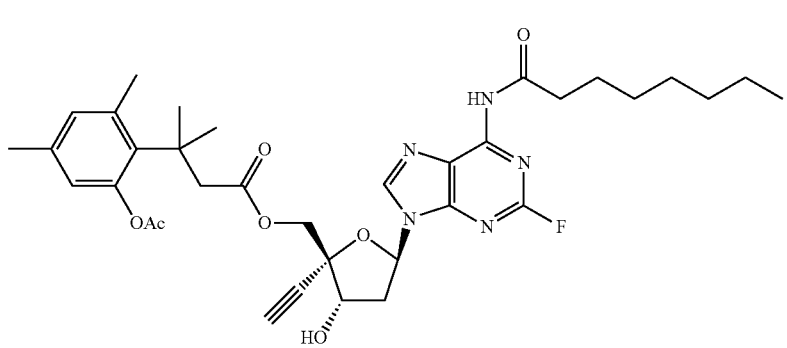

Synthesis of Compound P-KK—((2R,3S,5R)-2-ethynyl-5-(2-fluoro-6-octanamido-9H-purin-9-yl)-3-hydroxytetrahydrofuran-2-yl)methyl 3-(2-acetoxy-4,6-dimethylphenyl)-3-methylbutanoate Example P-KK is prepared in the same manner as described for example P-A except n-octanoic acid is used instead of 3-(2-acetoxy-4,6-dimethylphenyl)-3-methylbutanoic acid and 1 equivalent of 3-(2-acetoxy-4,6-dimethylphenyl)-3-methylbutanoic acid and EDCI are used instead of 2 equivalents of isobutyric acid and EDCI.

Example P-LL

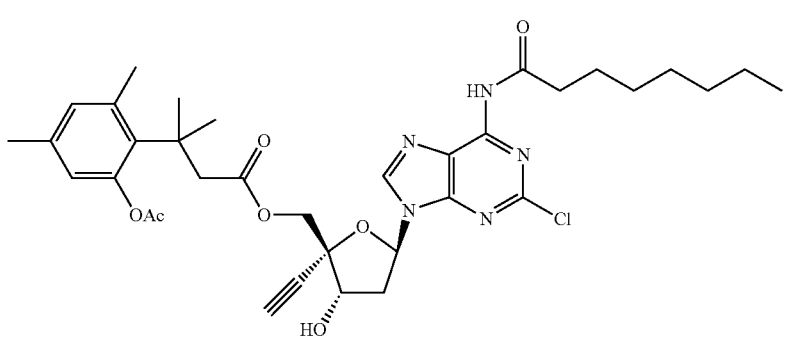

P-LL

Synthesis of Compound P-LL—((2R,3S,5R)-5-(2-chloro-6-octanamido-9H-purin-9-yl)-2-ethynyl-3-hydroxytetrahydrofuran-2-yl)methyl 3-(2-acetoxy-4,6-dimethylphenyl)-3-methylbutanoate Example P-LL is prepared in the same manner as described for example P-MM except ECldA is used instead of EFdA.

Example P-NN

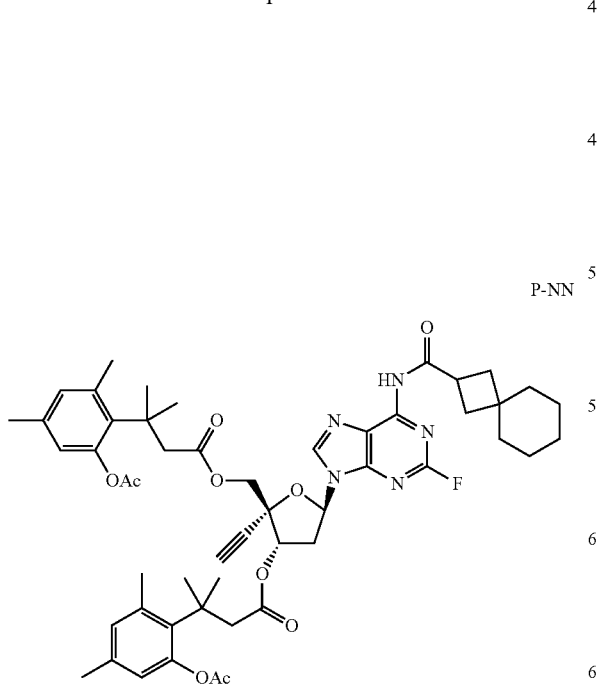

P-NN

Synthesis of Compound P-NN—((2R,3S,5R)-3-((3-(2-acetoxy-4,6-dimethylphenyl)-3-methylbutanoyl)oxy)-2-ethynyl-5-(2-fluoro-6-(spiro[3.5]nonane-2-carboxamido)-9H-purin-9-yl)tetrahydrofuran-2-yl)methyl 3-(2-acetoxy-4,6-dimethylphenyl)-3-methylbutanoate Example P-NN is prepared in the same manner as described for example P-A except spiro[3.5]nonane-2-carboxylic acid (Aldrich) is used instead of 3-(2-acetoxy-4,6-dimethylphenyl)-3-methylbutanoic acid and 3-(2-acetoxy-4,6-dimethylphenyl)-3-methylbutanoic acid is used instead of isobutyric acid.

Example P-OO

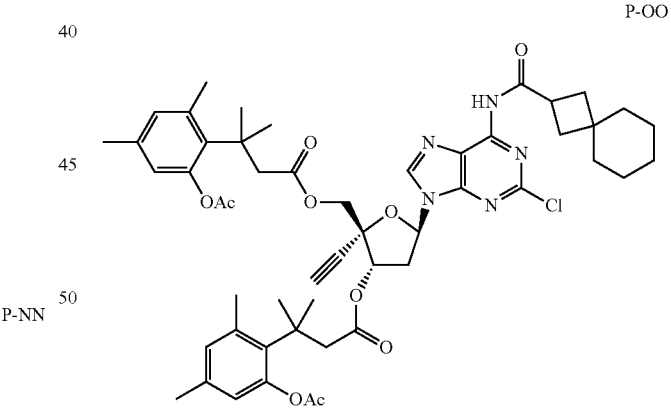

P-OO

Synthesis of Compound P-GO—((2R,3S,5R)-3-((3-(2-acetoxy-4,6-dimethylphenyl)-3-methylbutanoyl)oxy)-5-(2-chloro-6-(spiro[3.5]nonane-2-carboxamido)-9H-purin-9-yl)-2-ethynyltetrahydrofuran-2-yl)methyl 3-(2-acetoxy-4,6-dimethylphenyl)-3-methylbutanoate Example P-OO is prepared in the same manner as described for example P-NN except ECldA is used instead of EFdA.

Example P-PP

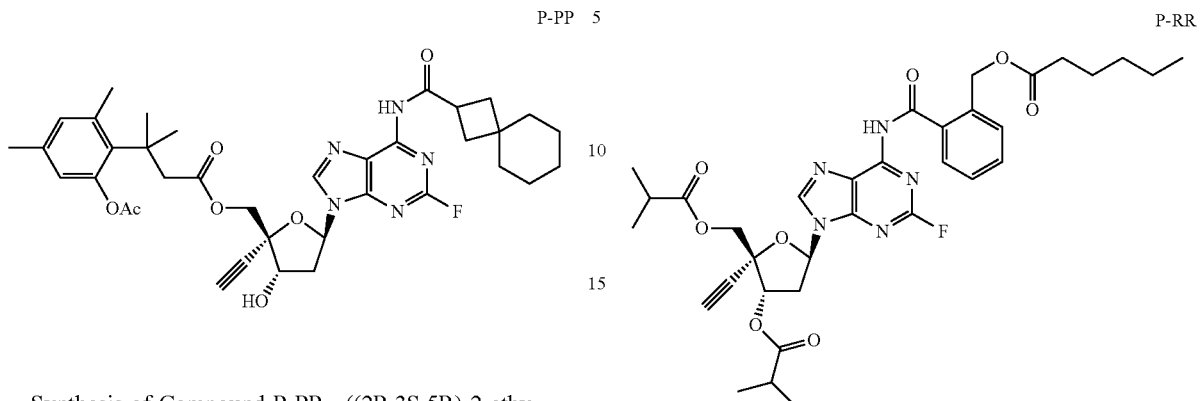

Synthesis of Compound P-PP—((2R,3S,5R)-2-ethynyl-5-(2-fluoro-6-(spiro[3.5]nonane-2-carboxamido)-9H-purin-9-yl)-3-hydroxytetrahydrofuran-2-yl)methyl 3-(2-acetoxy-4,6-dimethylphenyl)-3-methylbutanoate Example P-PP is prepared in the same manner as described for example P-A except spiro[3.5]nonane-2-carboxylic acid is used instead of 3-(2-acetoxy-4,6-dimethylphenyl)-3-methylbutanoic acid and 1 equivalent of 3-(2-acetoxy-4,6-dimethylphenyl)-3-methylbutanoic acid and EDCI are used instead of 2 equivalents of isobutyric acid and EDCI.

Example P-QQ

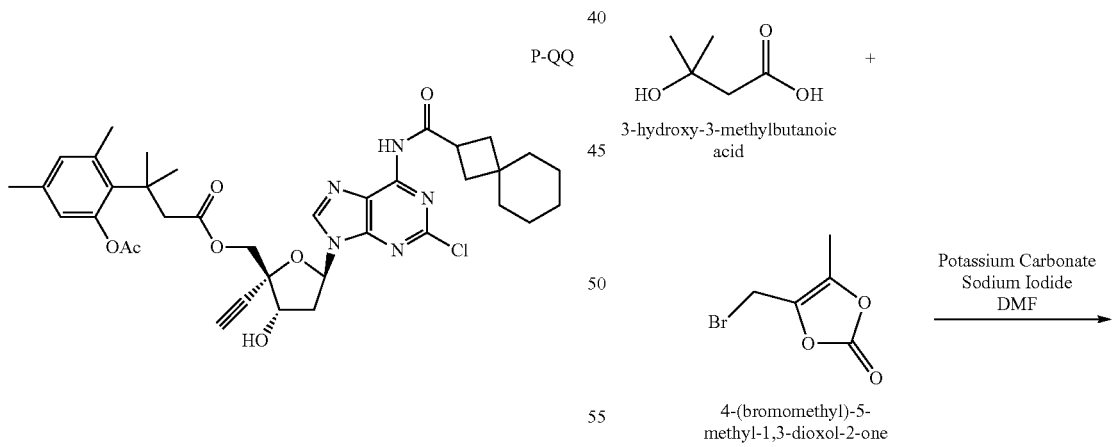

Synthesis of Compound P-QQ—((2R,3S,5R)-5-(2-chloro-6-(spiro[3.5]nonane-2-carboxamido)-9H-purin-9-yl)-2-ethynyl-3-hydroxytetrahydrofuran-2-yl)methyl 3-(2-acetoxy-4,6-dimethylphenyl)-3-methylbutanoate Example P-QQ is prepared in the same manner as described for example P-PP except ECldA is used instead of EFdA.

Example P-RR

Synthesis of Compound P-RR—2-((9-((2R,4S,5R)-5-ethynyl-4-(isobutyryloxy)-5-((isobutyryloxy)methyl)tetrahydrofuran-2-yl)-2-fluoro-9H-purin-6-yl)carbamoyl)benzyl hexanoate Example P-RR is prepared in the same manner as described for example P-A except 2-((hexanoyloxy)methyl)benzoic acid (prepared in a manner similar to that described for intermediate E1 except hexanoic anhydride is used instead of palmitic anhydride) is used instead of 3-(2-acetoxy-4,6-dimethylphenyl)-3-methylbutanoic acid.

Example P-SS

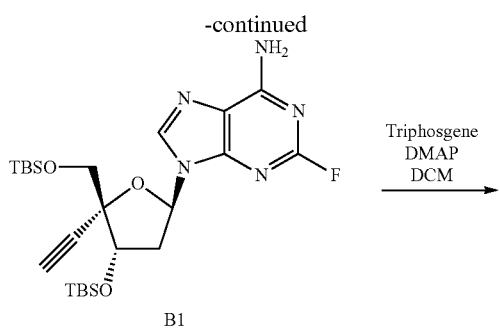
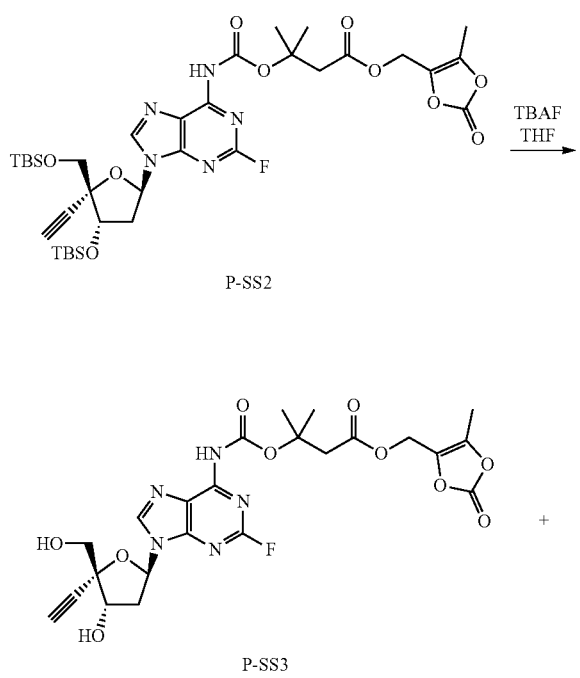
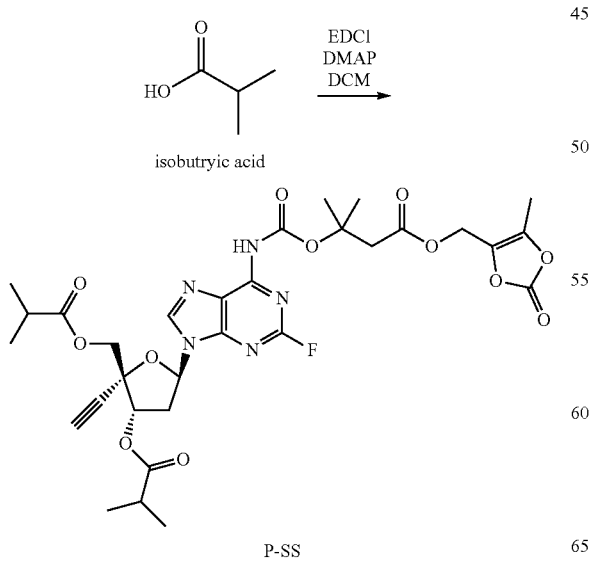

Synthesis of Compound P-SS—(5-methyl-2-oxo-1,3-dioxol-4-yl)methyl 3-(((9-((2R,4S,5R)-5-ethynyl-4-(isobutyryloxy)-5-((isobutyryloxy)methyl)tetrahydrofuran-2-yl)-2-fluoro-9H-purin-6-yl)carbamoyl)oxy)-3-methylbutanoate 3-Hydroxy-3-methyl-butanoic acid (1 mmol), potassium carbonate (1.2 eq), sodium iodide (1 eq) are taken up in DMF (2 mL), the solution is cooled in an ice bath and 4-(bromomethyl)-5-methyl-1,3-dioxol-2-one (1 eq) is added drop wise. The ice bath is then removed, and the reaction is allowed to proceed. The reaction is then diluted with EtOAc and washed with water and then a 5% aqueous solution of LiCl. The organic phase is dried over sodium sulfate and then concentrated. Intermediate P-SS1 is used as is in the next reaction.

Intermediate P-SS2 is made in the same manner as described for intermediate B2 except intermediate P-SS1 is used instead of tetradecan-1-ol.

Intermediate P-SS3 is made from intermediate P-SS2 in the same manner as that described for example B.

Intermediate P-SS3 (1 mmol) is dissolved in DCM (10 mL). To this solution is added EDCI (2 eq), DMAP (1 eq) and isobutyric acid (2 eq). The reaction is allowed to proceed. The reaction is quenched by the addition of ice and DCM. The organic layer is separated and dried over sodium sulfate and example P-SS is isolated by silica gel column chromatography.

Example P-TT

Synthesis of Compound P-TT—(5-methyl-2-oxo-1,3-dioxol-4-yl)methyl 3-(((2-chloro-9-((2R,4S,5R)-5-ethynyl-4-(isobutyryloxy)-5-((isobutyryloxy)methyl)tetrahydrofuran-2-yl)-9H-purin-6-yl)carbamoyl)oxy)-3-methylbutanoate Example P-TT is prepared in the same manner as described for example P-PP except ECldA is used instead of EFdA.

Example P-UU

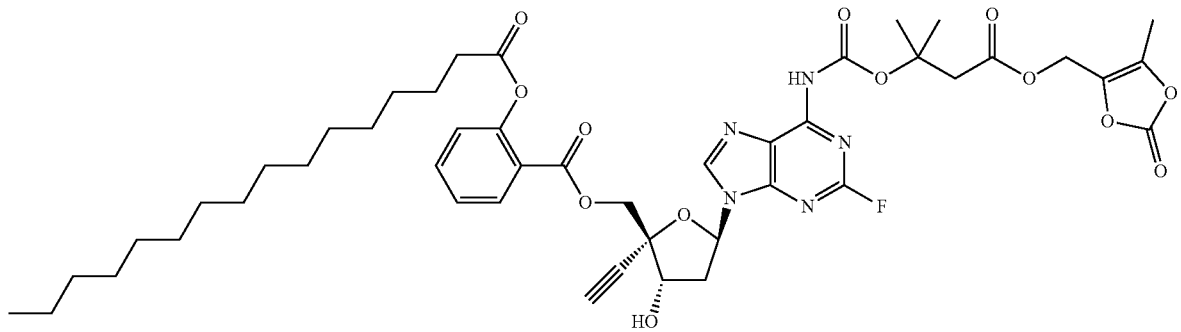

Synthesis of Compound P-UU—((2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-3-hydroxytetrahydrofuran-2-yl)methyl 2-(palmitoyloxy)benzoate Example P-UU is prepared in the same manner as described for example P-SS except that 1 equivalent of intermediate E1 and EDCI are used instead of 2 equivalents of isobutyric acid and EDCI.

Example P-VV

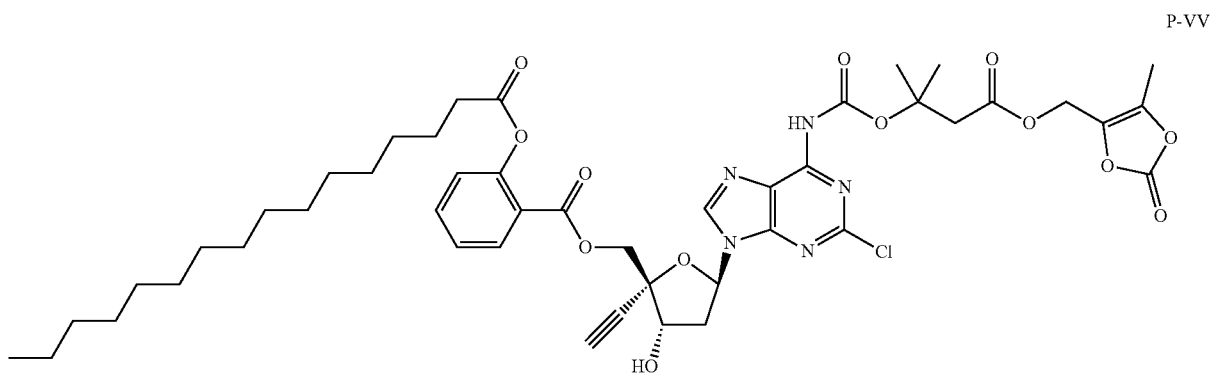 [SMILES: C#C[C@]1(COC(=O)c2ccccc2OC(=O)CCCCCCCCCCCCCCC)O[C@@H](n2cnc3c(NC(=O)OC(C)(C)CC(=O)OCc4oc(=O)oc4C)nc(Cl)nc32)C[C@@H]1O]

Synthesis of Compound P-VV—((2R,3S,5R)-5-(2-chloro-6-((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-3-hydroxytetrahydrofuran-2-yl)methyl 2-(palmitoyloxy)benzoate Example P-VV is prepared in the same manner as described for example P-UU except ECldA is used instead of EFdA.

Example P-WW

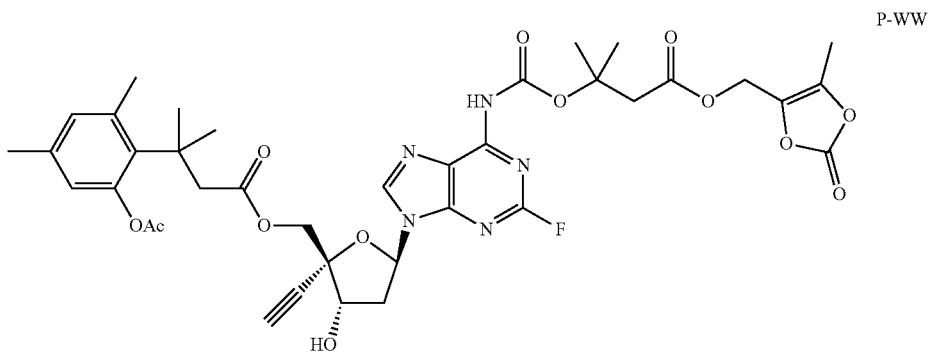 [SMILES: C#C[C@]1(COC(=O)CC(C)(C)c2c(C)cc(C)cc2OC(C)=O)O[C@@H](n2cnc3c(NC(=O)OC(C)(C)CC(=O)OCc4oc(=O)oc4C)nc(F)nc32)C[C@@H]1O]

P-WW

Synthesis of Compound P-WW—((2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-3-hydroxytetrahydrofuran-2-yl)methyl 3-(2-acetoxy-4,6-dimethylphenyl)-3-methylbutanoate Example P-WW is prepared in the same manner as described for P-SS except 1 equivalent of 3-(2-acetoxy-4,6-dimethylphenyl)-3-methylbutanoic acid (Aldrich) and EDCI are used instead of 2 equivalents of isobutyric acid and EDCI.

Example P-XX

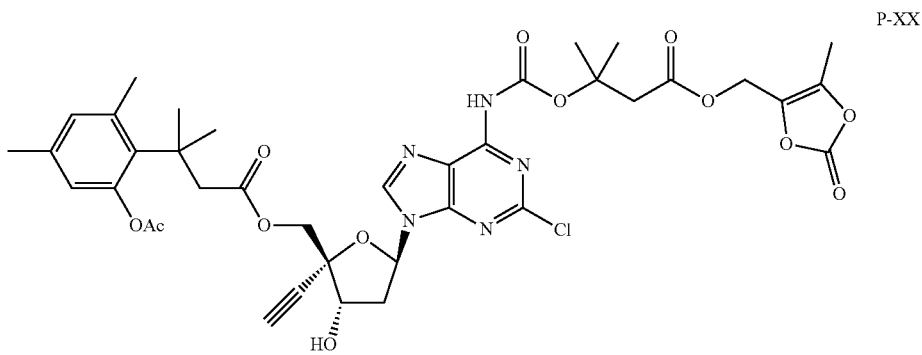 [SMILES: C#C[C@]1(COC(=O)CC(C)(C)c2c(C)cc(C)cc2OC(C)=O)O[C@@H](n2cnc3c(NC(=O)OC(C)(C)CC(=O)OCc4oc(=O)oc4C)nc(Cl)nc32)C[C@@H]1O]

P-XX

Synthesis of Compound P-XX—((2R,3S,5R)-5-(2-chloro-6-((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-3-hydroxytetrahydrofuran-2-yl)methyl 3-(2-acetoxy-4,6-dimethylphenyl)-3-methylbutanoate Example P-XX is prepared in the same manner as described for example P-WW except ECldA is used instead of EFdA.

Example P-YY

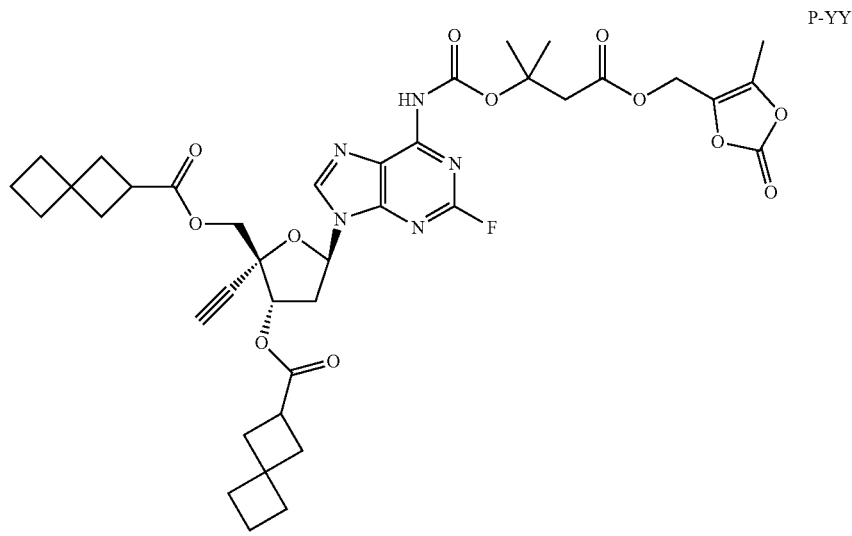 [SMILES: C#C[C@]1(COC(=O)C2CC3(CCC3)C2)O[C@@H](n2cnc3c(NC(=O)OC(C)(C)CC(=O)OCc4oc(=O)oc4C)nc(F)nc32)C[C@@H]1OC(=O)C1CC2(CCC2)C1]

Synthesis of Compound P-YY—((2R,3S,5R)-2-ethynyl-5-(2-fluoro-6-(((((2-methyl-4-((5-methyl-2-oxo-1,3-dioxol-4-yl)methoxy)-4-oxobutan-2-yl)oxy)carbonyl)amino)-9H-purin-9-yl)-3-((spiro[3.3]heptane-2-carbonyl)oxy)tetrahydrofuran-2-yl)methyl spiro[3.3]heptane-2-carboxylate Example P-YY is prepared in the same manner as described for P-SS except spiro[3.3]heptane-2-carboxylic acid (Aldrich) is used instead of isobutyric acid.

Example P-ZZ

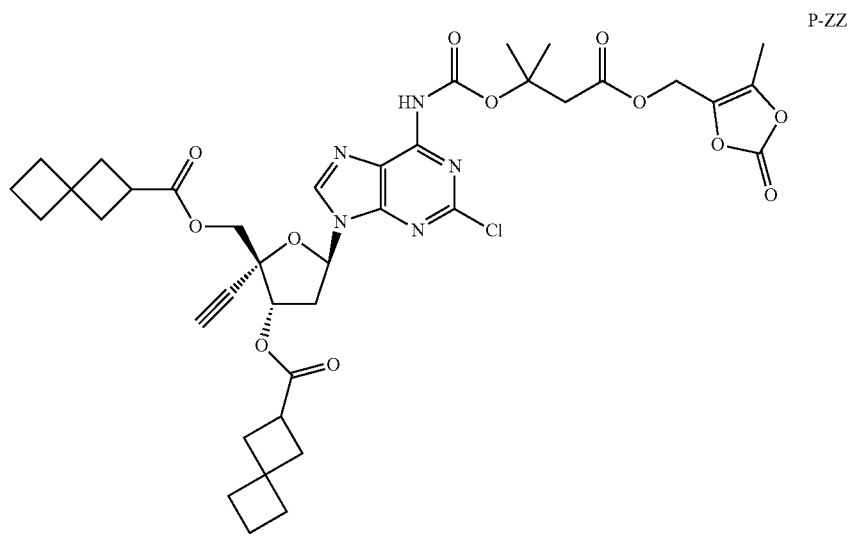 [SMILES: C#C[C@]1(COC(=O)C2CC3(CCC3)C2)O[C@@H](n2cnc3c(NC(=O)OC(C)(C)CC(=O)OCc4oc(=O)oc4C)nc(Cl)nc32)C[C@@H]1OC(=O)C1CC2(CCC2)C1]

Synthesis of Compound P-ZZ—((2R,3S,5R)-5-(2-chloro-6-(((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-3-((spiro[3.3]heptane-2-carbonyl)oxy)tetrahydrofuran-2-yl)methyl spiro[3.3]heptane-2-carboxylate Example P-ZZ is prepared in the same manner as described for example P-YY except ECldA is used instead of EFdA.

Example P-AAA

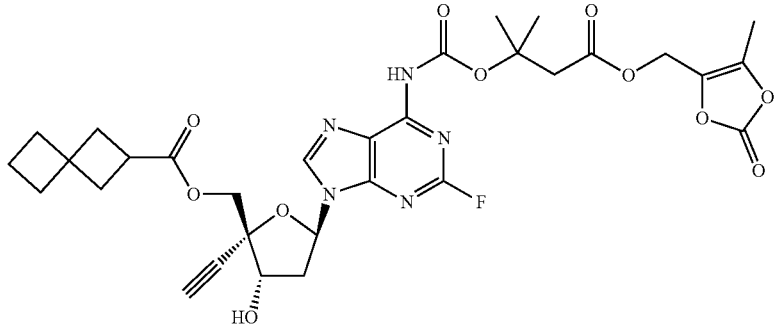

P-AAA

Synthesis of Compound P-AAA—((2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-3-hydroxytetrahydrofuran-2-yl)methyl spiro[3.3]heptane-2-carboxylate Example P-AAA is prepared in the same manner as described for example P-SS except 1 equivalent of spiro[3.3]heptane-2-carboxylic acid and EDCI are used instead of 2 equivalents of isobutyric acid and EDCI.

Example P-BBB

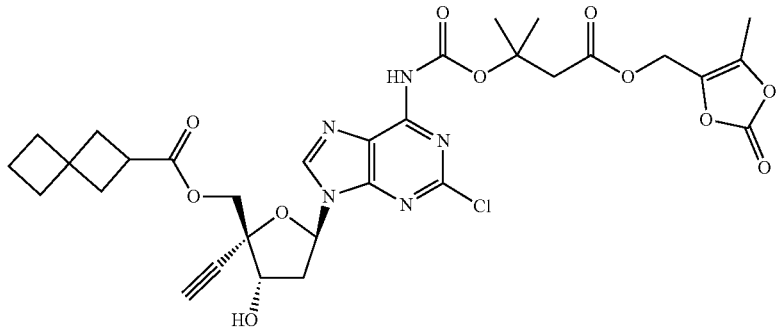

P-BBB

Synthesis of Compound P-BBB—((2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-3-hydroxytetrahydrofuran-2-yl)methyl spiro[3.3]heptane-2-carboxylate Example P-BBB is prepared in the same manner as described for example P-AAA except ECldA is used instead of EFdA.

Example P-CCC

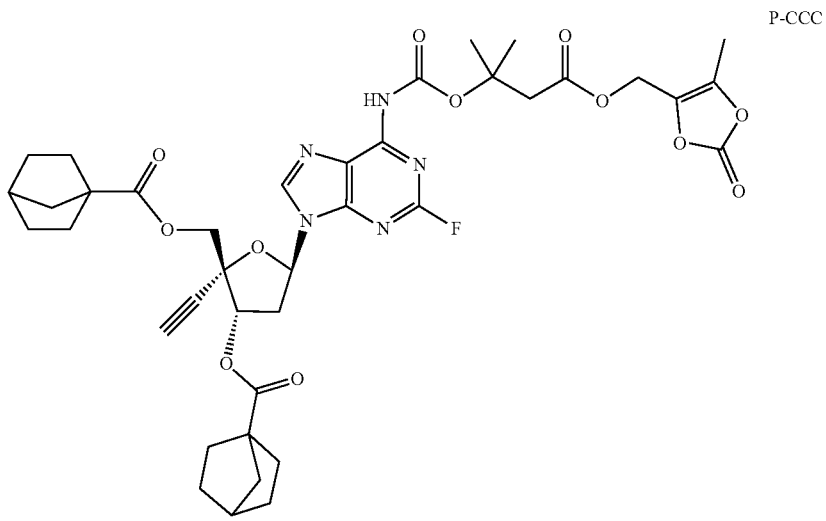 [SMILES: C#C[C@]1(COC(=O)C23CCC(CC2)C3)O[C@@H](n2cnc3c(NC(=O)OC(C)(C)CC(=O)OCc4oc(=O)oc4C)nc(F)nc32)C[C@@H]1OC(=O)C12CCC(CC1)C2]

Synthesis of Compound P-CCC—((2R,3S,5R)-3-((bicyclo[2.2.1]heptane-1-carbonyl)oxy)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)tetrahydrofuran-2-yl)methyl bicyclo[2.2.1]heptane-1-carboxylate Example P-CCC is prepared in the same manner as described for P-SS except bicyclo[2.2.1]heptane-1-carboxylic acid (Aldrich) is used instead of isobutyric acid.

Example P-DDD

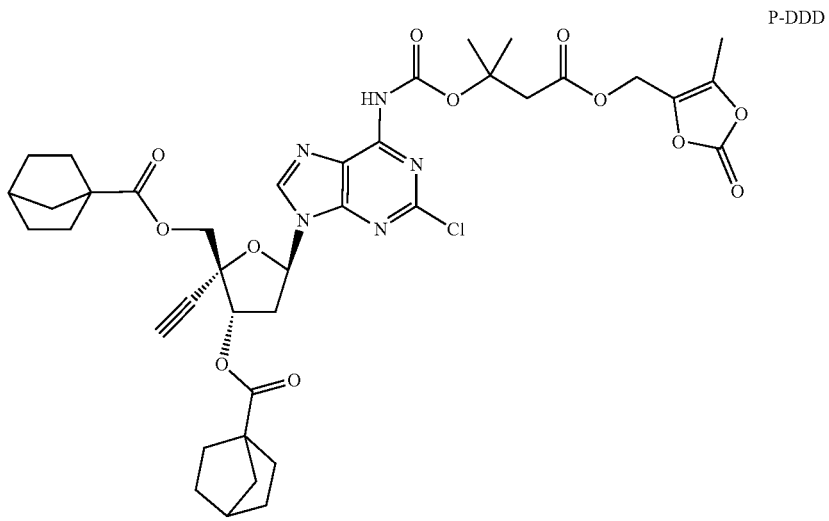 [SMILES: C#C[C@]1(COC(=O)C23CCC(CC2)C3)O[C@@H](n2cnc3c(NC(=O)OC(C)(C)CC(=O)OCc4oc(=O)oc4C)nc(Cl)nc32)C[C@@H]1OC(=O)C12CCC(CC1)C2]

Synthesis of Compound P-DDD—((2R,3S,5R)-3-((bicyclo[2.2.1]heptane-1-carbonyl)oxy)-5-(2-chloro-6-((((2-methyl-4-((5-methyl-2-oxo-1,3-dioxol-4-yl)methoxy)-4-oxobutan-2-yl)oxy)carbonyl)amino)-9H-purin-9-yl)-2-ethynyltetrahydrofuran-2-yl)methyl bicyclo[2.2.1]heptane-1-carboxylate Example P-DDD is prepared in the same manner as described for example P-CCC except ECldA is used instead of EFdA.

Example P-EEE

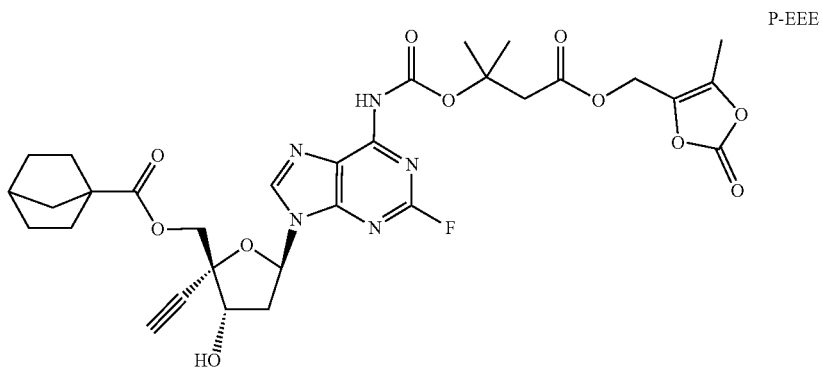 [SMILES: C#C[C@]1(COC(=O)C23CCC(CC2)C3)O[C@@H](n2cnc3c(NC(=O)OC(C)(C)CC(=O)OCc4oc(=O)oc4C)nc(F)nc32)C[C@@H]1O]

P-EEE

Synthesis of Compound P-EEE—((2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-3-hydroxytetrahydrofuran-2-yl)methyl bicyclo[2.2.1]heptane-1-carboxylate Example P-EEE is prepared in the same manner as described for example P-SS except 1 equivalent of bicyclo[2.2.1]heptane-1-carboxylic acid and EDCI are used instead of 2 equivalents of isobutyric acid and EDCI.

Example P-FFF

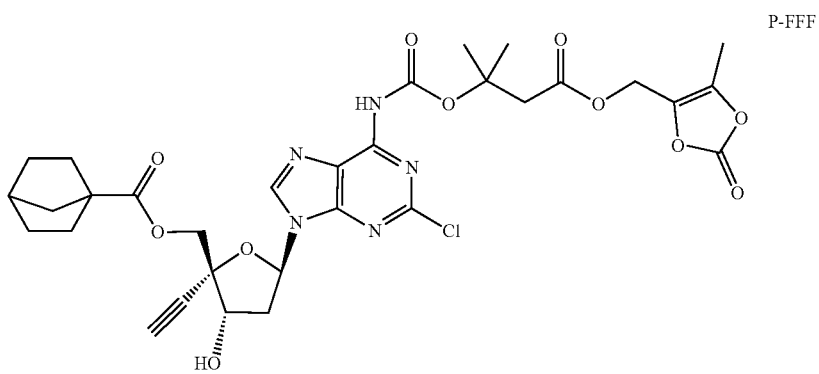 [SMILES: C#C[C@]1(COC(=O)C23CCC(CC2)C3)O[C@@H](n2cnc3c(NC(=O)OC(C)(C)CC(=O)OCc4oc(=O)oc4C)nc(Cl)nc32)C[C@@H]1O]

P-FFF

Synthesis of Compound P-FFF—((2R,3S,5R)-5-(2-chloro-6-((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-3-hydroxytetrahydrofuran-2-yl)methyl bicyclo[2.2.1]heptane-1-carboxylate Example P-FFF is prepared in the same manner as described for example P-EEE except ECldA is used instead of EFdA.

Example P-GGG

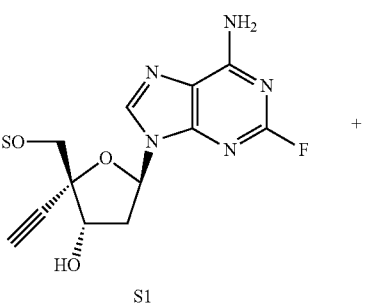

S1

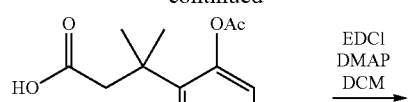

3-(2-acetoxy-4,6-dimethylphenyl)-
3-methylbutanoic acid

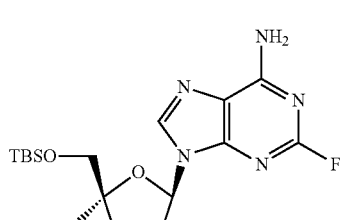

P-GGG1

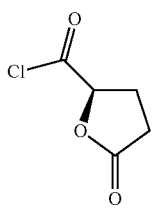

(R)-5-oxotetrahydrofuran-
2-carbonyl chloride

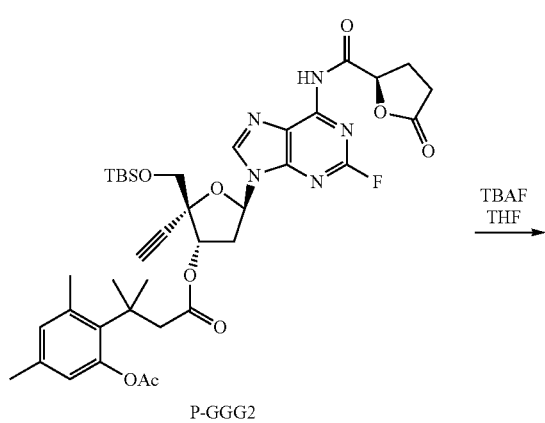

P-GGG2

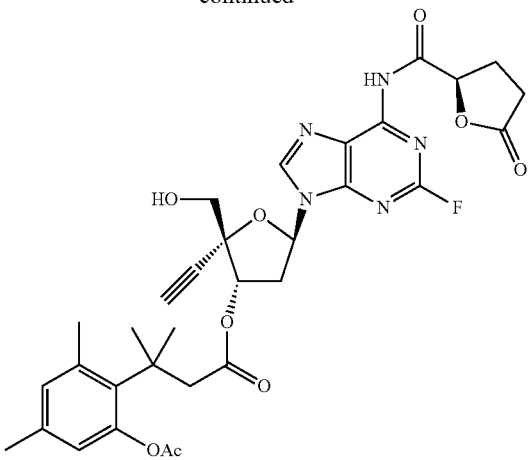

P-GGG

Synthesis of Compound P-GGG—(2R,3S,5R)-2-ethynyl-5-(2-fluoro-6-((R)-5-oxotetrahydrofuran-2-carboxamido)-9H-purin-9-yl)-2-(hydroxymethyl)tetrahydrofuran-3-yl 3-(2-acetoxy-4,6-dimethylphenyl)-3-methylbutanoate Intermediate S1 (1 mmol) is dissolved in DCM (10 mL). To this solution is added EDCI (1 eq), DMAP (1 eq) and 3-(2-acetoxy-4,6-dimethylphenyl)-3-methylbutanoic acid (1 eq). The reaction is allowed to proceed. The reaction is quenched by the addition of ice and DCM. The organic layer is separated and dried over sodium sulfate and intermediate P-GGG1 is isolated by silica gel column chromatography.

Intermediate P-GGG1 (1 mmol) is dissolved in DCM (10 mL). To this solution is added DMAP (1 eq) and TEA (1 eq). (R)-5-oxotetrahydrofuran-2-carbonyl chloride (1 eq; reagent is prepared by stirring a solution of (R)-5-oxotetrahydrofuran-2-carboxylic acid and thionyl chloride in DCM which is then concentrated, and the crude reagent is used as is) is then added and the reaction is allowed to proceed. The reaction is quenched by the addition of ice and diluted with additional DCM. The organic layer is separated and dried over sodium sulfate and intermediate P-GGG2 is isolated by silica gel column chromatography.

Intermediate P-GGG2 (1 mmol) is dissolved in THE (10 mL) and a solution of TBAF in THE (1 eq) is added. The reaction is allowed to proceed. The reaction is quenched by the addition of ice water and diluted with EtOAc. The organic layer is separated and dried over sodium sulfate. Example P-GGG is isolated by silica gel column chromatography.

Example P-HHH

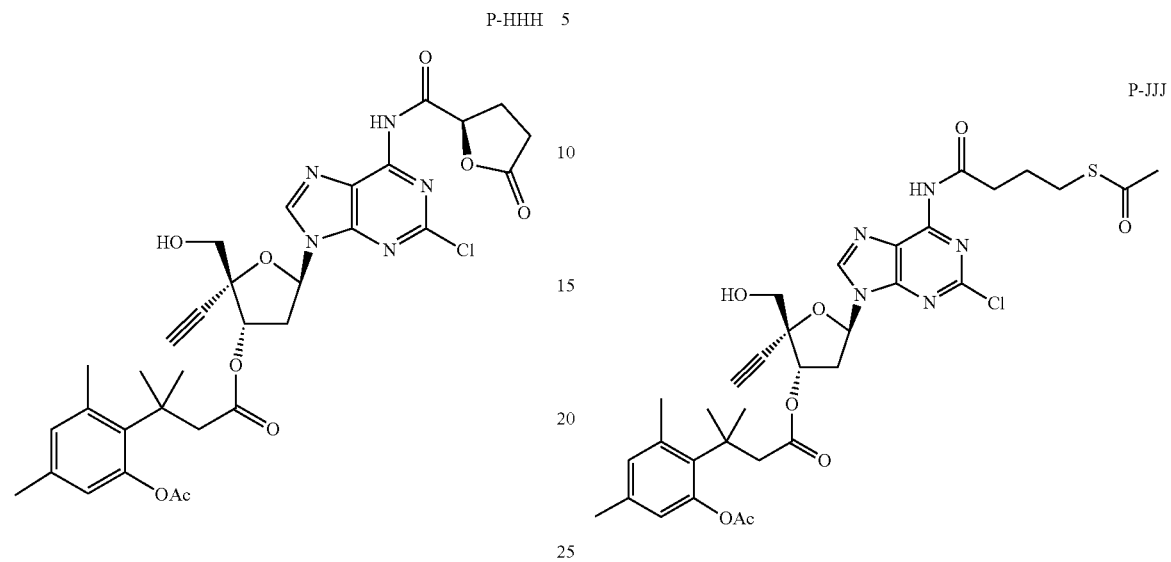

P-HHH

Synthesis of Compound P-HHH—(2R,3S,5R)-5-(2-chloro-6-((R)-5-oxotetrahydrofuran-2-carboxamido)-9H-purin-9-yl)-2-ethynyl-2-(hydroxymethyl)tetrahydrofuran-3-yl 3-(2-acetoxy-4,6-dimethylphenyl)-3-methylbutanoate Example P-HHH is prepared in the same manner as described for example P-GGG except ECldA is used instead of EFdA.

Example P-III

Example P-JJJ

P-JJJ

Synthesis of Compound P-JJJ—(2R,3S,5R)-5-(6-(4-(acetylthio)butanamido)-2-chloro-9H-purin-9-yl)-2-ethynyl-2-(hydroxymethyl)tetrahydrofuran-3-yl 3-(2-acetoxy-4,6-dimethylphenyl)-3-methylbutanoate Example P-JJJ is prepared in the same manner as described for example P-III except ECldA is used instead of EFdA.

Example P-KKK

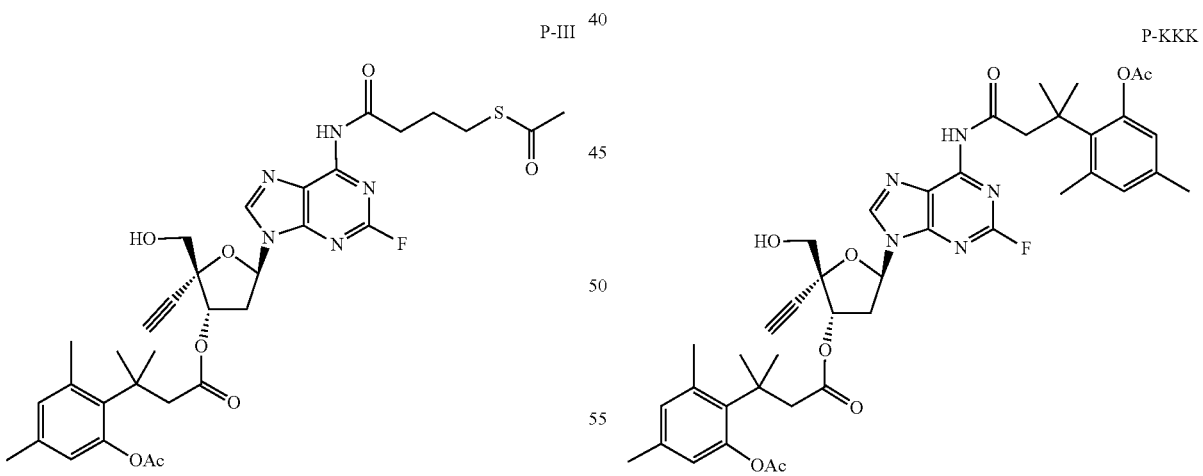

P-III

Synthesis of Compound P-III—(2R,3S,5R)-5-(6-(4-(acetylthio)butanamido)-2-fluoro-9H-purin-9-yl)-2-ethynyl-2-(hydroxymethyl)tetrahydrofuran-3-yl 3-(2-acetoxy-4,6-dimethylphenyl)-3-methylbutanoate Example P-III is prepared in the same manner as described for example P-GGG except S-(4-chloro-4-oxobutyl) ethanethioate is used instead of (R)-5-oxotetrahydrofuran-2-carbonyl chloride.

P-KKK

Synthesis of Compound P-KKK—(2R,3S,5R)-5-(6-(3-(2-acetoxy-4,6-dimethylphenyl)-3-methylbutanamido)-2-fluoro-9H-purin-9-yl)-2-ethynyl-2-(hydroxymethyl)tetrahydrofuran-3-yl 3-(2-acetoxy-4,6-dimethylphenyl)-3-methylbutanoate Example P-KKK is prepared in the same manner as described for example P-GGG except 2-(4-chloro-2-methyl- 4-oxobutan-2-yl)-3,5-dimethylphenyl acetate is used instead of (R)-5-oxotetrahydrofuran-2-carbonyl chloride.

Example P-LLL

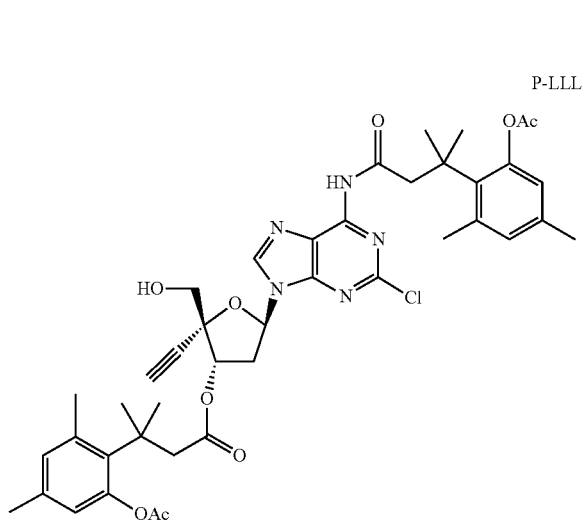

Synthesis of Compound P-LLL—(2R,3S,5R)-5-(6-(3-(2-acetoxy-4,6-dimethylphenyl)-3-methylbutanamido)-2-chloro-9H-purin-9-yl)-2-ethynyl-2-(hydroxymethyl)tetrahydrofuran-3-yl 3-(2-acetoxy-4,6-dimethylphenyl)-3-methylbutanoate Example P-LLL is prepared in the same manner as described for example P-KKK except ECldA is used instead of EFdA.

Example P-MMM

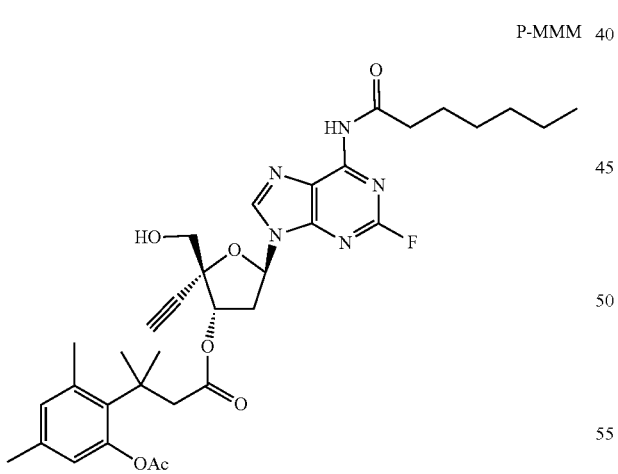

Synthesis of Compound P-MMM—(2R,3S,5R)-2-ethynyl-5-(2-fluoro-6-heptanamido-9H-purin-9-yl)-2-(hydroxymethyl)tetrahydrofuran-3-yl 3-(2-acetoxy-4,6-dimethylphenyl)-3-methylbutanoate Example P-MMM is prepared in the same manner as described for example P-GGG except heptanoyl chloride is used instead of (R)-5-oxotetrahydrofuran-2-carbonyl chloride.

Example P-NNN

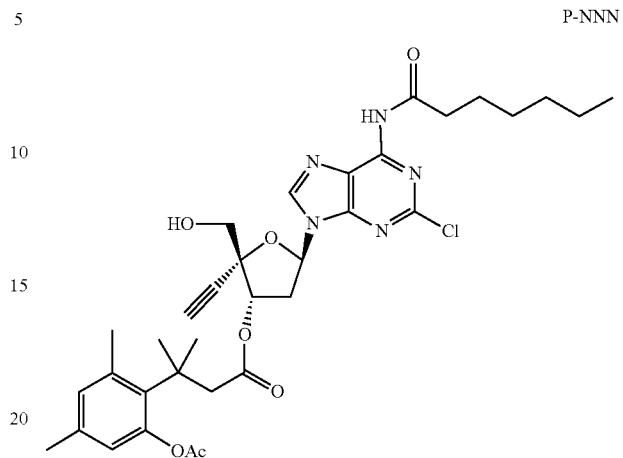

Synthesis of Compound P-NNN—(2R,3S,5R)-5-(2-chloro-6-heptanamido-9H-purin-9-yl)-2-ethynyl-2-(hydroxymethyl)tetrahydrofuran-3-yl 3-(2-acetoxy-4,6-dimethylphenyl)-3-methylbutanoate Example P-NNN is prepared in the same manner as described for example P-MMM except ECldA is used instead of EFdA.

Example P-OOO

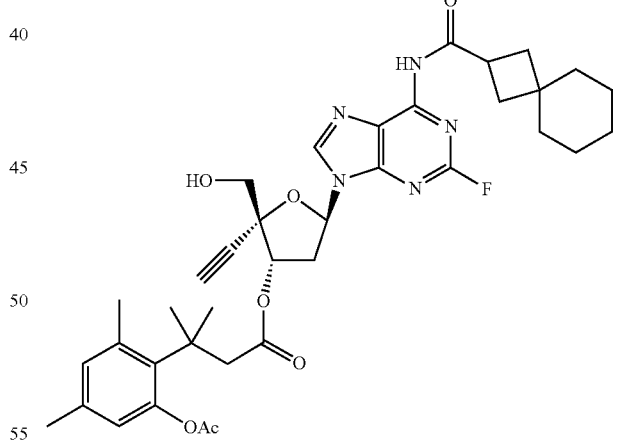

Synthesis of Compound P-OOO—(2R,3S,5R)-2-ethynyl-5-(2-fluoro-6-(spiro[3.5]nonane-2-carboxamido)-9H-purin-9-yl)-2-(hydroxymethyl)tetrahydrofuran-3-yl 3-(2-acetoxy-4,6-dimethylphenyl)-3-methylbutanoate Example P-OOO is prepared in the same manner as described for example P-GGG except spiro[3.5]nonane-2-carbonyl chloride is used instead of (R)-5-oxotetrahydrofuran-2-carbonyl chloride.

Example P-PPP

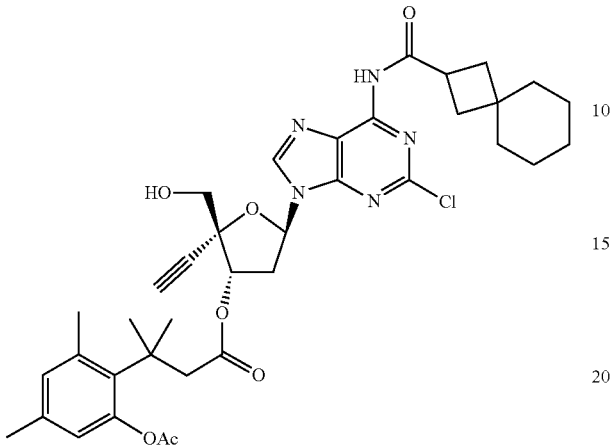

P-PPP

Synthesis of Compound P-PPP—(2R,3S,5R)-5-(2-chloro-6-(spiro[3.5]nonane-2-carboxamido)-9H-purin-9-yl)-2-ethynyl-2-(hydroxymethyl)tetrahydrofuran-3-yl 3-(2-acetoxy-4,6-dimethylphenyl)-3-methylbutanoate Example P-PPP is prepared in the same manner as described for example P-OOO except ECldA is used instead of EFdA.

Example P-QQQ

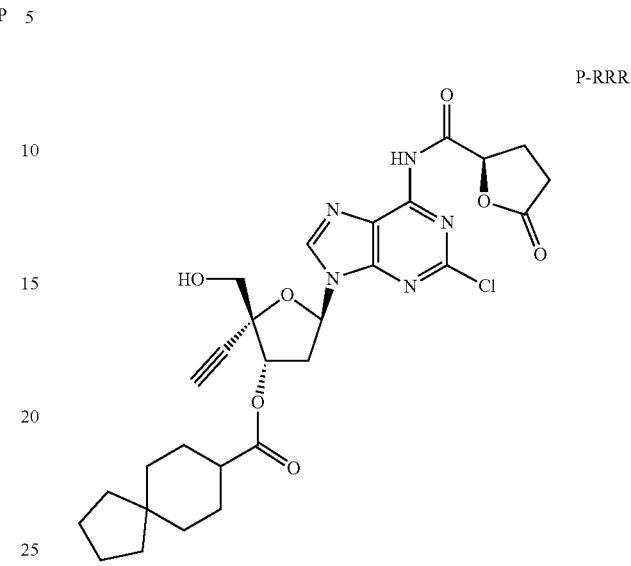

P-QQQ

Synthesis of Compound P-QQQ—(2R,3S,5R)-2-ethynyl-5-(2-fluoro-6-((R)-5-oxotetrahydrofuran-2-carboxamido)-9H-purin-9-yl)-2-(hydroxymethyl)tetrahydrofuran-3-yl spiro[4.5]decane-8-carboxylate Example P-QQQ is prepared in the same manner as described for example P-GGG except spiro[4.5]decane-8-carboxylic acid (Aldrich) is used instead of 3-(2-acetoxy-4,6-dimethylphenyl)-3-methylbutanoic acid.

Example P-RRR

P-RRR

Synthesis of Compound P-RRR—(2R,3S,5R)-5-(2-chloro-6-((R)-5-oxotetrahydrofuran-2-carboxamido)-9H-purin-9-yl)-2-ethynyl-2-(hydroxymethyl)tetrahydrofuran-3-yl spiro[4.5]decane-8-carboxylate Example P-RRR is prepared in the same manner as described for example P-QQQ except ECldA is used instead of EFdA.

Example P-SSS

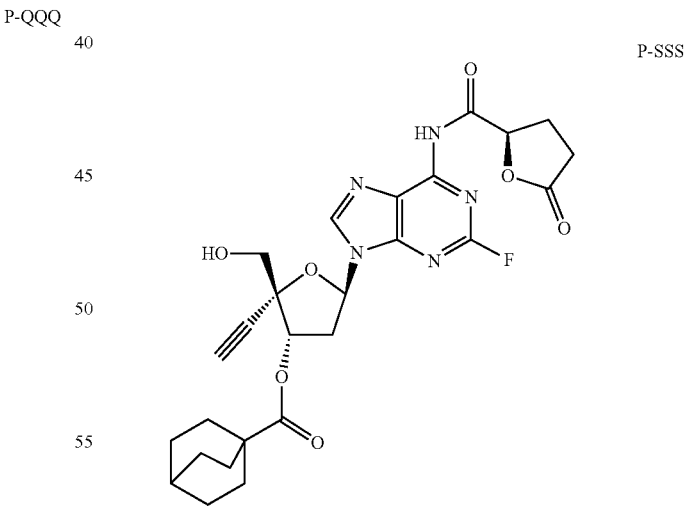

P-SSS

Synthesis of Compound P-SSS—(2R,3S,5R)-2-ethynyl-5-(2-fluoro-6-((R)-5-oxotetrahydrofuran-2-carboxamido)-9H-purin-9-yl)-2-(hydroxymethyl)tetrahydrofuran-3-yl bicyclo[2.2.2]octane-1-carboxylate Example P-SSS is prepared in the same manner as described for example P-GGG except bicyclo[2.2.2]octane- 1-carboxylic acid is used instead of 3-(2-acetoxy-4,6-dimethylphenyl)-3-methylbutanoic acid.

Example P-TTT

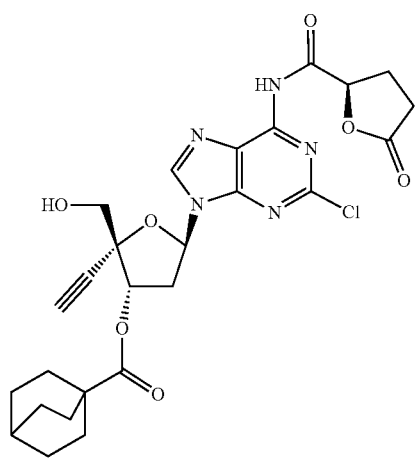

P-TTT

Synthesis of Compound P-TTT—(2R,3S,5R)-5-(2-chloro-6-((R)-5-oxotetrahydrofuran-2-carboxamido)-9H-purin-9-yl)-2-ethynyl-2-(hydroxymethyl)tetrahydrofuran-3-yl bicyclo[2.2.2]octane-1-carboxylate Example P-TTT is prepared in the same manner as described for example P-SSS except ECldA is used instead of EFdA.

Example P-UUU

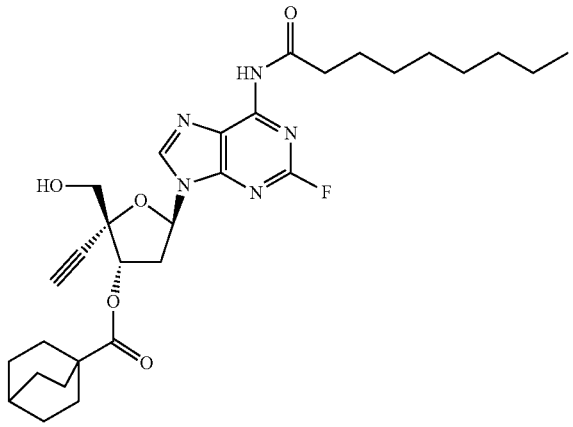

P-UUU

Synthesis of Compound P-UUU—(2R,3S,5R)-2-ethynyl-5-(2-fluoro-6-nonanamido-9H-purin-9-yl)-2-(hydroxymethyl)tetrahydrofuran-3-yl bicyclo[2.2.2]octane-1-carboxylate Example P-UUU is prepared in the same manner as described for example P-GGG except bicyclo[2.2.2]octane- 1-carboxylic acid is used instead of 3-(2-acetoxy-4,6-dimethylphenyl)-3-methylbutanoic acid and nonanoyl chloride is used instead of (R)-5-oxotetrahydrofuran-2-carbonyl chloride.

Example P-VVV

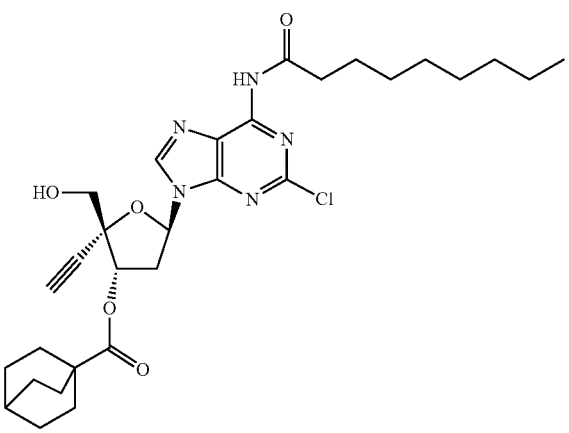

P-VVV

Synthesis of Compound P-VVV—(2R,3S,5R)-5-(2-chloro-6-nonanamido-9H-purin-9-yl)-2-ethynyl-2-(hydroxymethyl)tetrahydrofuran-3-yl bicyclo[2.2.2]octane-1-carboxylate Example P-VVV is prepared in the same manner as described for example P-UUU except ECldA is used instead of EFdA.

Example P-WWW

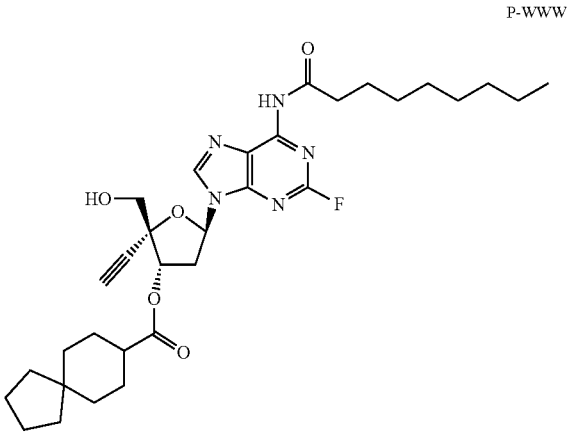 [SMILES: C#C[C@]1(CO)O[C@@H](n2cnc3c(NC(=O)CCCCCCCC)nc(F)nc32)C[C@@H]1OC(=O)C1CCC2(CCCC2)CC1]

P-WWW

Synthesis of Compound P-WWW—(2R,3S,5R)-2-ethynyl-5-(2-fluoro-6-nonanamido-9H-purin-9-yl)-2-(hydroxymethyl)tetrahydrofuran-3-yl spiro[4.5]decane-8-carboxylate Example P-UUU is prepared in the same manner as described for example P-GGG except spiro[4.5]decane-8- carboxylic acid is used instead of 3-(2-acetoxy-4,6-dimethylphenyl)-3-methylbutanoic acid and nonanoyl chloride is used instead of (R)-5-oxotetrahydrofuran-2-carbonyl chloride.

Example P-XXX

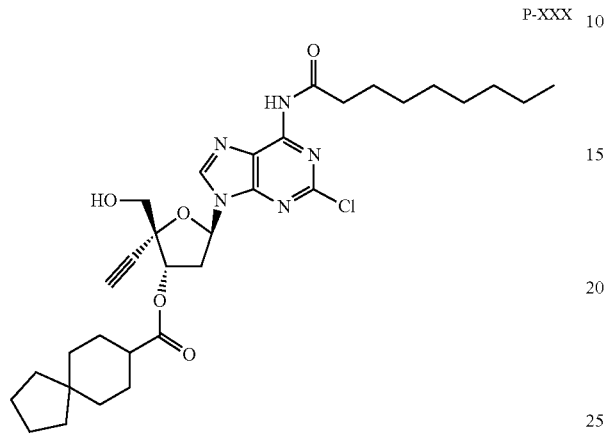

P-XXX

Synthesis of Compound P-XXX—(2R,3S,5R)-5-(2-chloro-6-nonanamido-9H-purin-9-yl)-2-ethynyl-2-(hydroxymethyl)tetrahydrofuran-3-yl spiro[4.5]decane-8-carboxylate Example P-XXX is prepared in the same manner as described for example P-WWW except ECldA is used instead of EFdA.

Example P-YYY

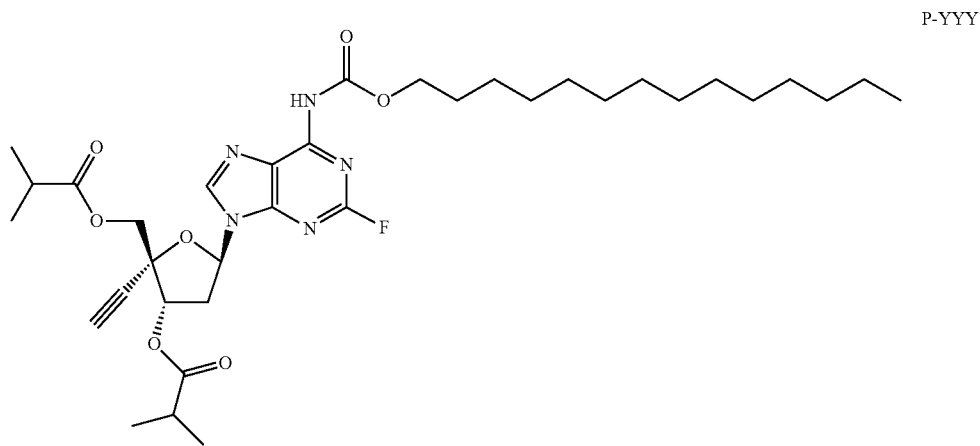 [SMILES: C#C[C@]1(COC(=O)C(C)C)O[C@@H](n2cnc3c(NC(=O)OCCCCCCCCCCCCCC)nc(F)nc32)C[C@@H]1OC(=O)C(C)C]

P-YYY

Synthesis of Compound P-YYY—(2R,3S,5R)-2-ethynyl-5-(2-fluoro-6-(((tetradecyloxy)carbonyl)amino)-9H-purin-9-yl)-2-((isobutyryloxy)methyl)tetrahydrofuran-3-yl isobutyrate Example P-YYY is prepared is prepared in the same manner as described for example P-SS except tetradecan-1-ol is used instead of intermediate P-SS1.

Example P-ZZZ
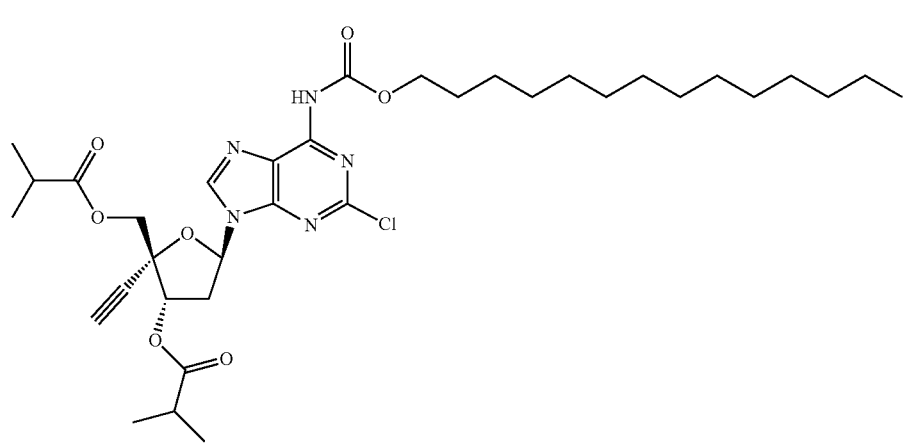
Synthesis of Compound P-ZZZ—(2R,3S,5R)-5-(2-chloro-6-(((tetradecyloxy)carbonyl)amino)-9H-purin-9-yl)-2-ethynyl-2-((isobutyryloxy)methyl)tetrahydrofuran-3-yl isobutyrate
Example P-ZZZ is prepared in the same manner as described for example P-YYY except ECldA is used instead of EFdA.
Example P-AAAA
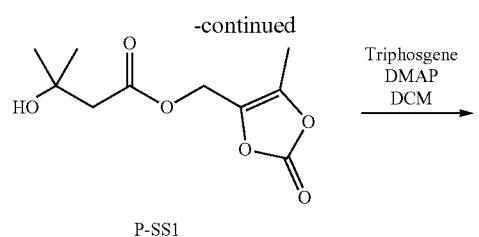
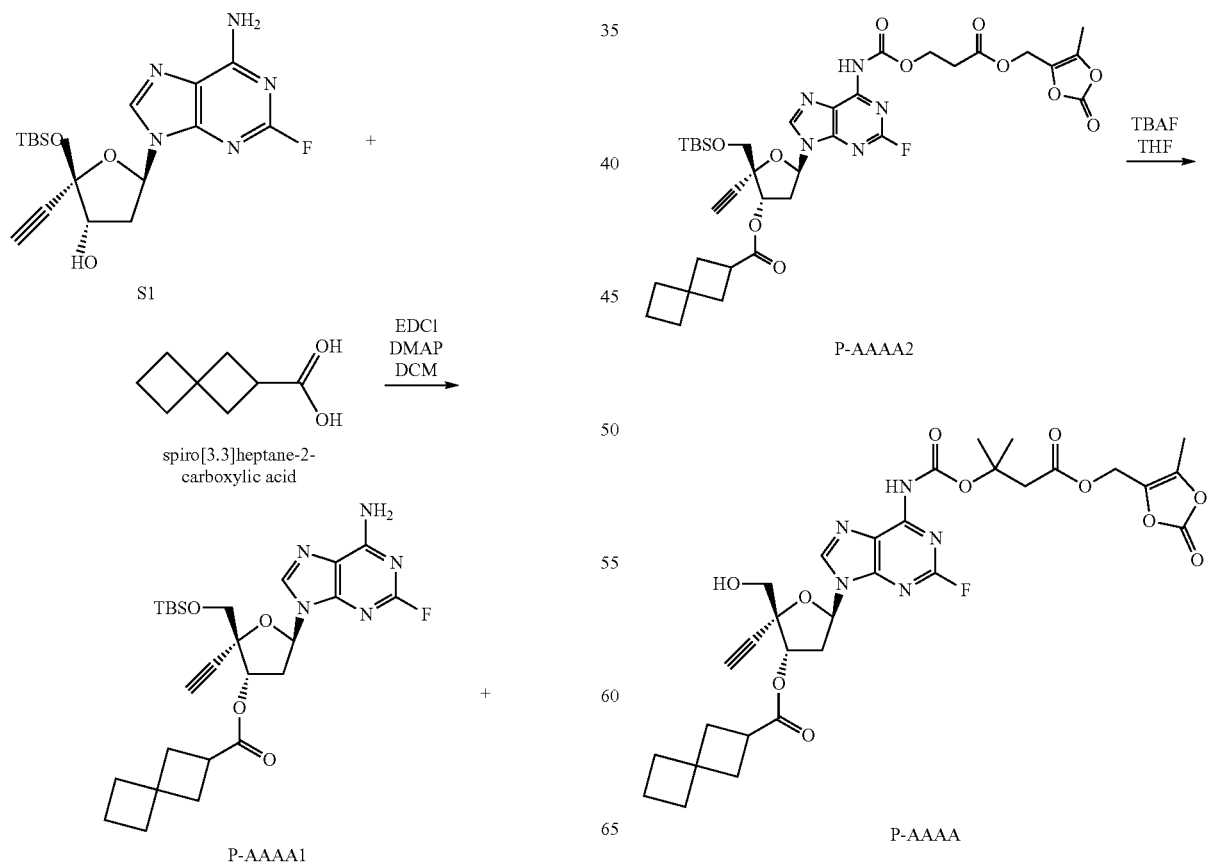

Synthesis of Compound P-AAAA—(2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-2-(hydroxymethyl)tetrahydrofuran-3-yl spiro[3.3]heptane-2-carboxylate Intermediate P-AAAA1 is prepared in the same manner as described for intermediate P-GGG1 except spiro[3.3]heptane-2-carboxylic acid is used instead of 3-(2-acetoxy-4,6-dimethylphenyl)-3-methylbutanoic acid.

Intermediate P-AAAA2 is prepared in the same manner as described for intermediate B2 except intermediate P-AAAA1 is used instead of intermediate B1 and intermediate P-SS1 is used instead of tetradecan-1-ol.

Example P-AAAA is prepared in the same manner as described for example P-GGG except intermediate P-AAAA2 is used instead of intermediate P-GGG2.

Example P-BBBB

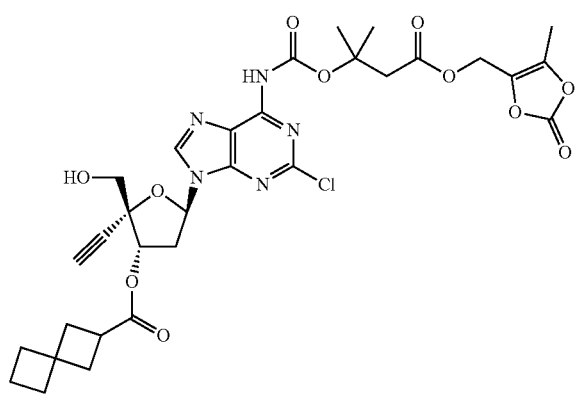

P-BBBB

Synthesis of Compound P-BBBB—(2R,3S,5R)-5-(2-chloro-6-((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-2-(hydroxymethyl)tetrahydrofuran-3-yl spiro[3.3]heptane-2-carboxylate Example P-BBBB is prepared in the same manner as described for example P-AAAA except ECldA is used instead of EFdA.

Example P-CCCC

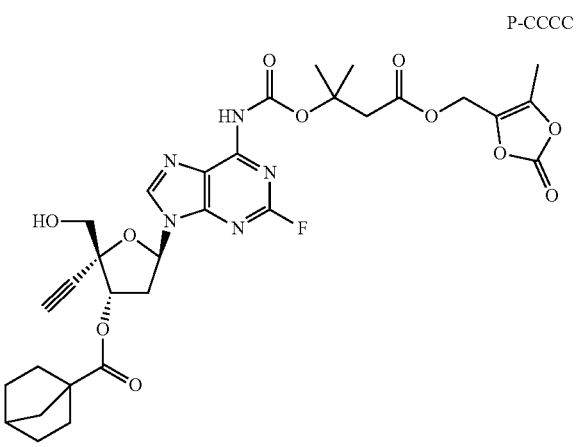 [SMILES: C#C[C@]1(CO)O[C@@H](n2cnc3c(NC(=O)OC(C)(C)CC(=O)OCc4oc(=O)oc4C)nc(F)nc32)C[C@@H]1OC(=O)C12CCC(CC1)C2]

P-CCCC

Synthesis of Compound P-CCCC—(2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-2-(hydroxymethyl)tetrahydrofuran-3-yl bicyclo[2.2.1]heptane-1-carboxylate Example P-CCCC is prepared in the same manner as described for example P-AAAA except bicyclo[2.2.1]heptane-1-carboxylic acid is used instead of spiro[3.3]heptane-2-carboxylic acid.

Example P-DDDD

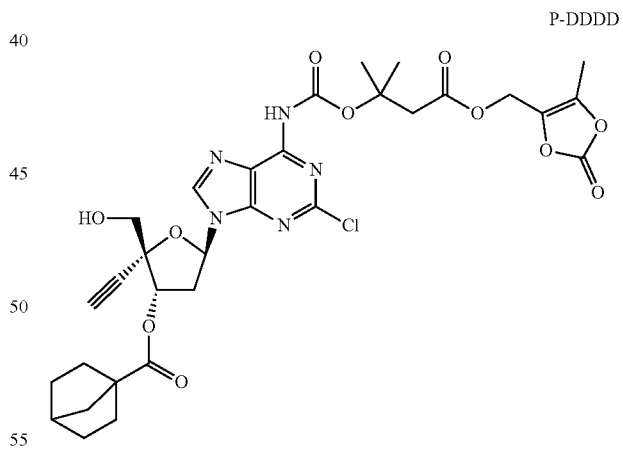

P-DDDD

Synthesis of Compound P-DDDD—(2R,3S,5R)-5-(2-chloro-6-((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-2-(hydroxymethyl)tetrahydrofuran-3-yl bicyclo[2.2.1]heptane-1-carboxylate Example P-DDDD is prepared in the same manner as described for example P-CCCC except ECldA is used instead of EFdA.

Example P-EEEE

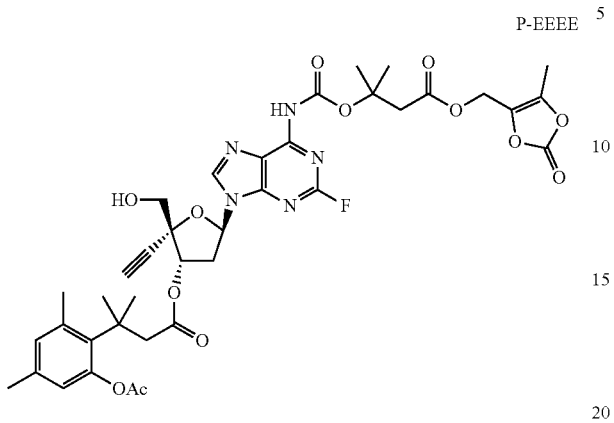

P-EEEE

Synthesis of Compound P-EEEE—(2R,3S,5R)-2-ethynyl-5-(2-fluoro-6-((((2-methyl-4-((5-methyl-2-oxo-1,3-dioxol-4-yl)methoxy)-4-oxobutan-2-yl)oxy)carbonyl)amino)-9H-purin-9-yl)-2-(hydroxymethyl)tetrahydrofuran-3-yl 3-(2-acetoxy-4,6-dimethylphenyl)-3-methylbutanoate Example P-EEEE is prepared in the same manner as described for example P-AAAA except intermediate P-GGG1 is used instead of intermediate P-AAAA1.

Example P-FFFF

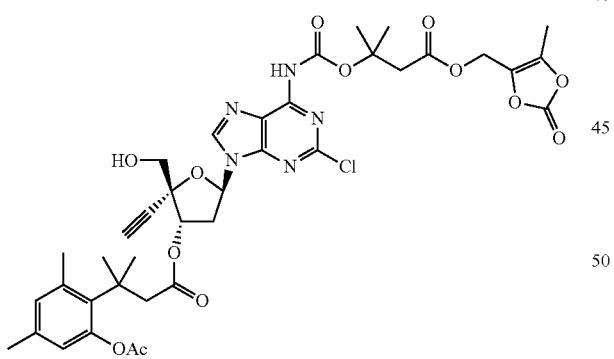

P-FFFF

Synthesis of Compound P-FFFF—(2R,3S,5R)-5-(2-chloro-6-(((((2-methyl-4-((5-methyl-2-oxo-1,3-dioxol-4-yl)methoxy)-4-oxobutan-2-yl)oxy)carbonyl)amino)-9H-purin-9-yl)-2-ethynyl-2-(hydroxymethyl)tetrahydrofuran-3-yl 3-(2-acetoxy-4,6-dimethylphenyl)-3-methylbutanoate Example P-FFFF is prepared in the same manner as described for example P-EEEE except ECldA is used instead of EFdA.

Example P-GGGG

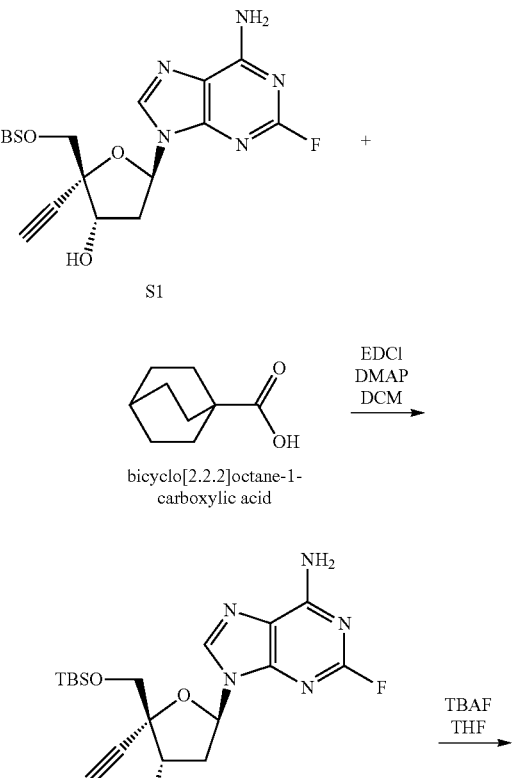

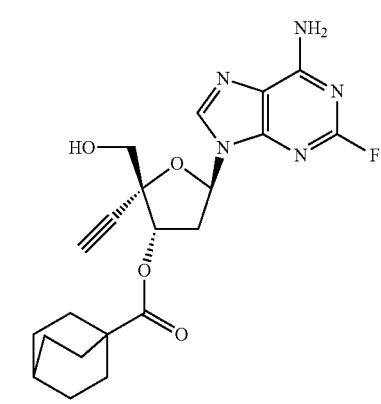

P-GGGG2

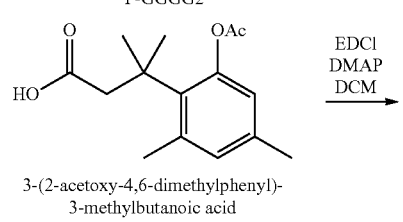

3-(2-acetoxy-4,6-dimethylphenyl)-3-methylbutanoic acid

-continued

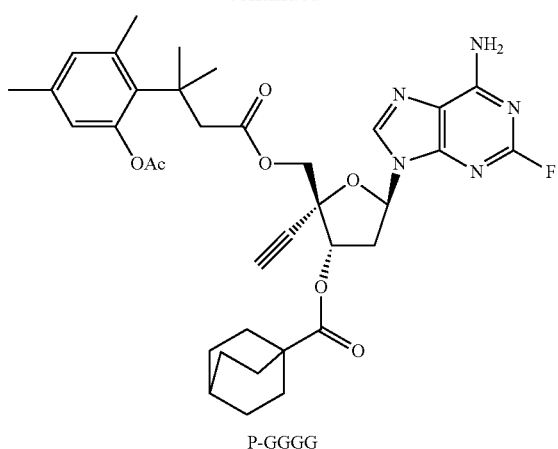 [SMILES: C#C[C@]1(COC(=O)CC(C)(C)c2c(C)cc(C)cc2OC(C)=O)O[C@@H](n2cnc3c(N)nc(F)nc32)C[C@@H]1OC(=O)C12CCC(CC1)CC2]

P-GGGG

Synthesis of Compound P-GGGG—(2R,3S,5R)-2-(((3-(2-acetoxy-4,6-dimethylphenyl)-3-methylbutanoyl)oxy)methyl)-5-(6-amino-2-fluoro-9H-purin-9-yl)-2-ethynyltetrahydrofuran-3-yl bicyclo[2.2.2]octane-1-carboxylate Intermediate P-GGGG1 is prepared in the same manner as described for P-GGG1 except bicyclo[2.2.2]octane-1-carboxylic acid is used instead of 3-(2-acetoxy-4,6-dimethylphenyl)-3-methylbutanoic acid.

Intermediate P-GGGG2 is prepared in the same manner as described for example P-GGG except intermediate P-GGGG1 is used instead of intermediate P-GGG2.

Example P-GGGG is prepared in the same manner as described for example P-A except 1 equivalent of 3-(2-acetoxy-4,6-dimethylphenyl)-3-methylbutanoic acid and EDCI are used instead of 2 equivalents of isobutyric acid and EDCI.

Example P-HHHH

P-HHHH

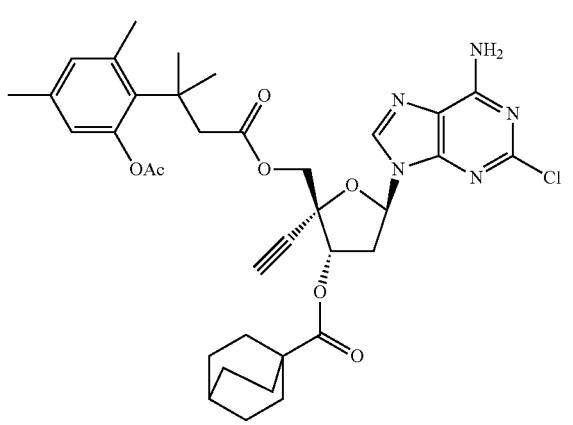

Synthesis of Compound P-HHHH—(2R,3S,5R)-2-(((3-(2-acetoxy-4,6-dimethylphenyl)-3-methylbutanoyl)oxy)methyl)-5-(6-amino-2-chloro-9H-purin-9-yl)-2-ethynyltetrahydrofuran-3-yl bicyclo[2.2.2]octane-1-carboxylate Example P-HHHH is prepared in the same manner as described for example P-GGGG except ECldA is used instead of EFdA.

Example P-IIII

P-IIII

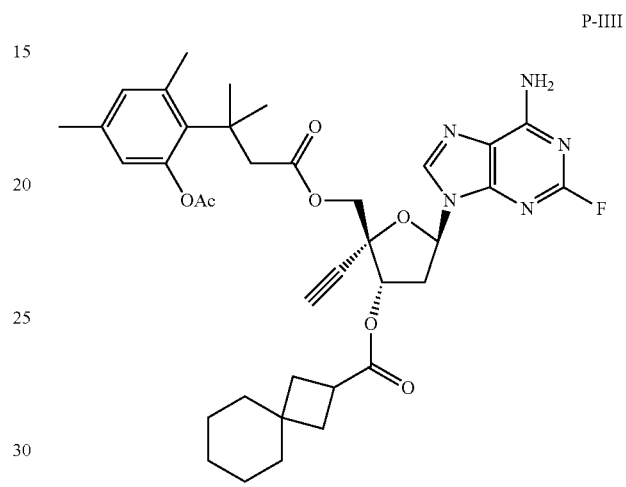

Synthesis of Compound P-IIII—(2R,3S,5R)-2-(((3-(2-acetoxy-4,6-dimethylphenyl)-3-methylbutanoyl)oxy)methyl)-5-(6-amino-2-fluoro-9H-purin-9-yl)-2-ethynyltetrahydrofuran-3-yl spiro[3.5]nonane-2-carboxylate Example P-IIII is prepared in the same manner as described for example P-GGGG except spiro[3.5]nonane-2-carboxylic acid is used instead of bicyclo[2.2.2]octane-1-carboxylic acid.

Example P-JJJJ

P-JJJJ

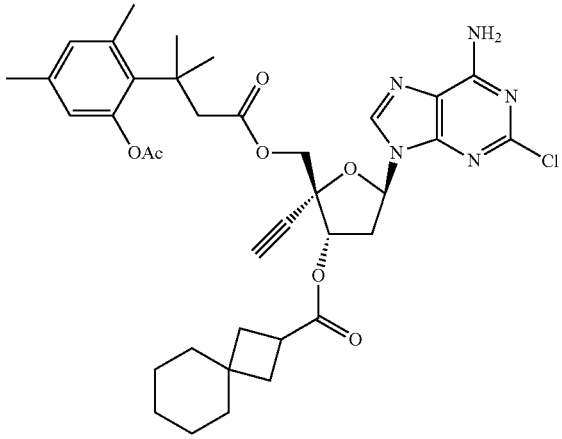

Synthesis of Compound P-JJJJ—(2R,3S,5R)-2-(((3-(2-acetoxy-4,6-dimethylphenyl)-3-methylbutanoyl)oxy)methyl)-5-(6-amino-2-chloro-9H-purin-9-yl)-2-ethynyltetrahydrofuran-3-vi spiro[3.5]nonane-2-carboxylate Example P-JJJJ is prepared in the same manner as described for example P-IIII except ECldA is used instead of EFdA.

Example P-KKKK

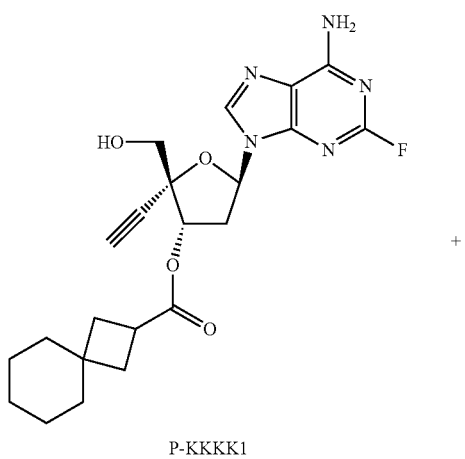

P-KKKK1

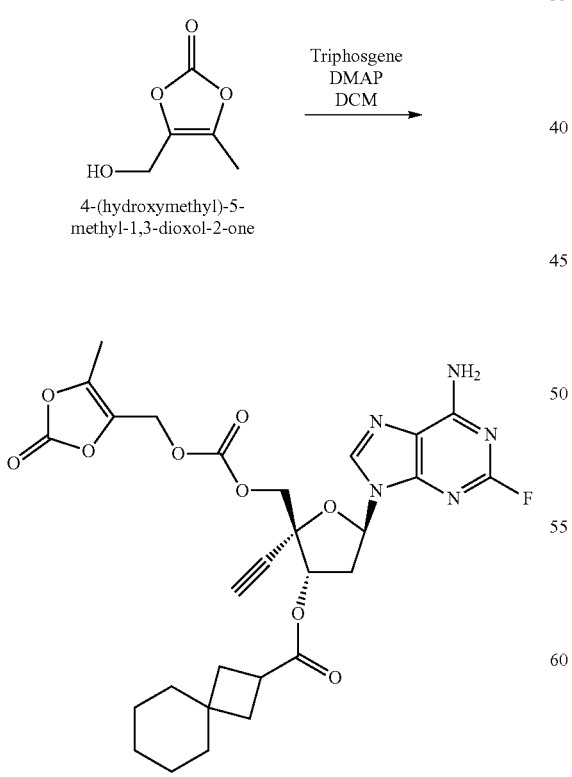

P-KKKK

Synthesis of Compound P-KKKK—(2R,3S,5R)-5-(6-amino-2-fluoro-9H-purin-9-yl)-2-ethynyl-2-(((((5-methyl-2-oxo-1,3-dioxol-4-yl)methoxy)carbonyl)oxy) methyl)tetrahydrofuran-3-yl spiro[3.5]nonane-2-carboxylate Intermediate P-KKKK1 is prepared in the same manner as described for P-GGGG2 except spiro[3.5]nonane-2-carboxylic acid is used instead of bicyclo[2.2.2]octane-1-carboxylic acid.

DMAP (1 mmol) is added to a solution of triphosgene (1 eq) in DCM (10 mL). Intermediate P-KKKK1 (1 mmol) is then added and the reaction is allowed to proceed. 4-(hydroxymethyl)-5-methyl-1,3-dioxol-2-one (1 eq) is then added and the reaction is allowed to proceed. The reaction is quenched by the addition of ice water and diluted with DCM. The organic layer is separated and dried over sodium sulfate. Example P-KKKK is isolated by silica gel column chromatography.

Example P-LLLL

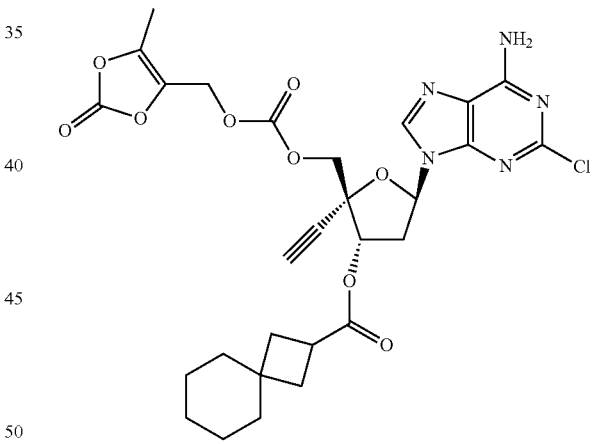

P-LLLL

Synthesis of Compound P-LLLL—(2R,3S,5R)-5-(6-amino-2-chloro-9H-purin-9-yl)-2-ethynyl-2-(((((5-methyl-2-oxo-1,3-dioxol-4-yl)methoxy)carbonyl)oxy) methyl)tetrahydrofuran-3-yl spiro[3.5]nonane-2-carboxylate Example P-LLLL is prepared in the same manner as described for example P-KKKK except ECldA is used instead of EFdA.

311

Example P-MMMM

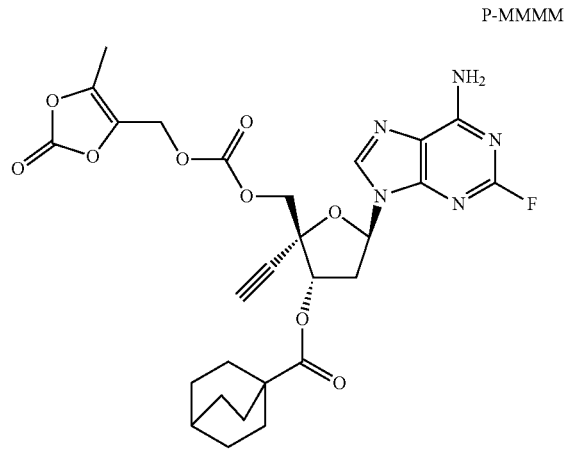 [SMILES: C#C[C@]1(COC(=O)OCc2oc(=O)oc2C)O[C@@H](n2cnc3c(N)nc(F)nc32)C[C@@H]1OC(=O)C12CCC(CC1)CC2]

P-MMMM

Synthesis of Compound P-MMMM—(2R,3S,5R)-5-(6-amino-2-fluoro-9H-purin-9-yl)-2-ethynyl-2-(((((5-methyl-2-oxo-1,3-dioxol-4-yl)methoxy)carbonyl)oxy) methyl)tetrahydrofuran-3-yl bicyclo[2.2.2]octane-1-carboxylate Example P-MMMM is prepared in the same manner example P-KKKK except intermediate P-GGGG2 is used instead of intermediate P-KKKK1.

Example P-NNNN

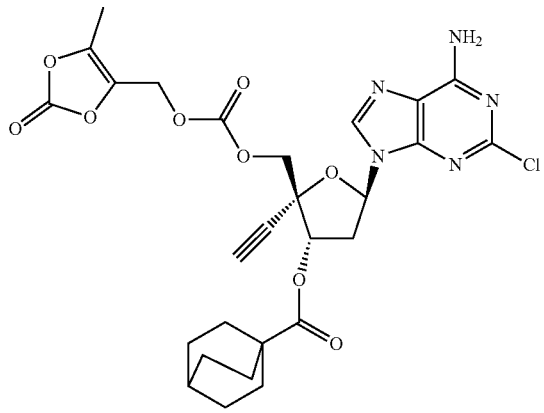

P-NNNN

Synthesis of Compound P-NNNN—(2R,3S,5R)-5-(6-amino-2-chloro-9H-purin-9-yl)-2-ethynyl-2-(((((5-methyl-2-oxo-1,3-dioxol-4-yl)methoxy)carbonyl)oxy) methyl)tetrahydrofuran-3-yl bicyclo[2.2.2]octane-1-carboxylate Example P-NNNN is prepared in the same manner as described for example P-MMMM except ECldA is used instead of EFdA.

312

Example P-OOOO

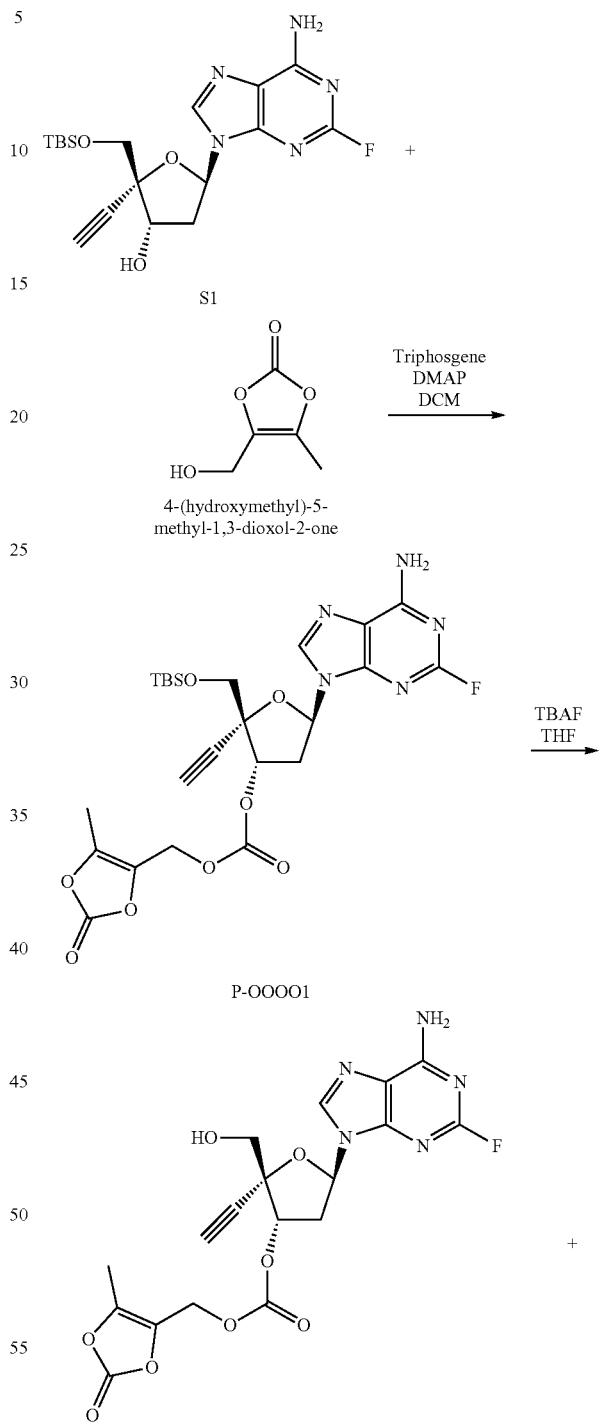

-continued

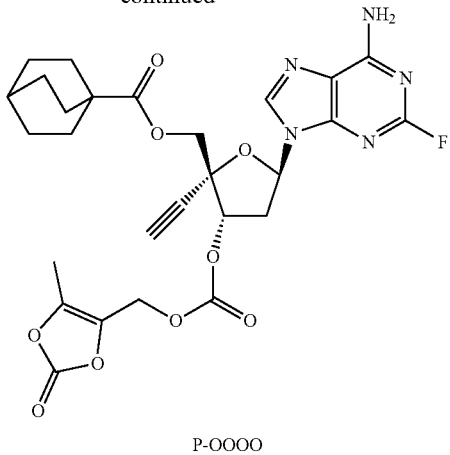

P-OOOO

Synthesis of Compound P-OOOO—((2R,3S,5R)-5-(6-amino-2-fluoro-9H-purin-9-yl)-2-ethynyl-3-((((5-methyl-2-oxo-1,3-dioxol-4-yl)methoxy)carbonyl)oxy)tetrahydrofuran-2-yl)methyl bicyclo[2.2.2]octane-1-carboxylate Intermediate P-OOOO1 is prepared in the same manner described for example P-KKKK except intermediate S1 is used instead of intermediate P-KKKK1.

Intermediate P-OOOO2 is prepared in the same manner described for example P-GGG except intermediate P-OOOO1 is used instead of intermediate P-GGG2.

Example P-OOOO is prepared in the same manner as described for example P-A except 1 equivalent of bicyclo[2.2.2]octane-1-carboxylic acid and EDCI are used instead of 2 equivalents of isobutyric acid and EDCI.

Example P-PPPP

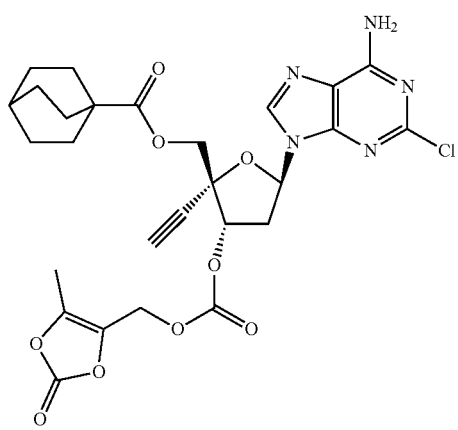

P-PPPP

Synthesis of Compound P-PPPP—((2R,3S,5R)-5-(6-amino-2-chloro-9H-purin-9-yl)-2-ethynyl-3-((((5-methyl-2-oxo-1,3-dioxol-4-yl)methoxy) carbonyl)oxy)tetrahydrofuran-2-yl)methyl bicyclo[2.2.2]octane-1-carboxylate Example P-PPPP is prepared in the same manner as described for example P-OOOO except ECldA is used instead of EFdA.

Example P-QQQQ

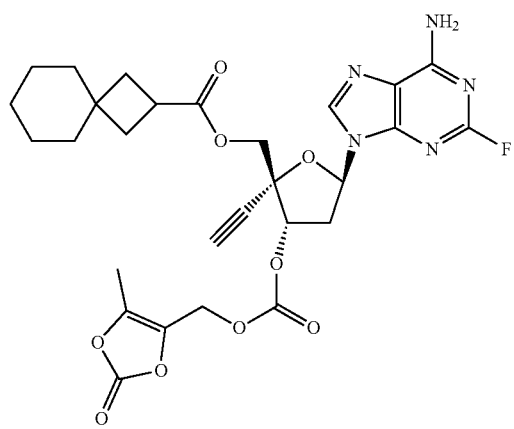

P-QQQQ

Synthesis of Compound P-QQQQ—((2R,3S,5R)-5-(6-amino-2-fluoro-9H-purin-9-yl)-2-ethynyl-3-(((((5-methyl-2-oxo-1,3-dioxol-4-yl)methoxy)carbonyl)oxy) tetrahydrofuran-2-yl)methyl spiro[3.5]nonane-2-carboxylate Example P-QQQQ is prepared in the same manner described for example P-OOOO except spiro[3.5]nonane-2-carboxylic acid is used instead of bicyclo[2.2.2]octane-1-carboxylic acid.

Example P-RRRR

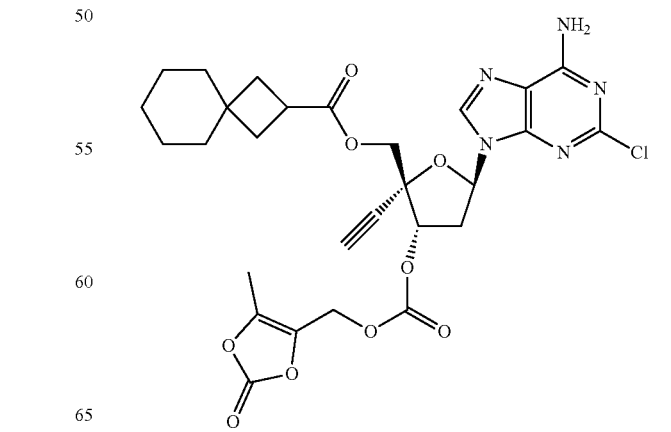

P-RRRR

Synthesis of Compound P-RRRR—((2R,3S,5R)-5-(6-amino-2-chloro-9H-purin-9-yl)-2-ethynyl-3-((((5-methyl-2-oxo-1,3-dioxol-4-yl)methoxy)carbonyl)oxy)tetrahydrofuran-2-yl)methyl spiro[3.5]nonane-2-carboxylate Example P-RRRR is prepared in the same manner as described for example P-QQQQ except ECldA is used instead of EFdA.

Examples P-SSSS, P-TTTT, and P-UUUU

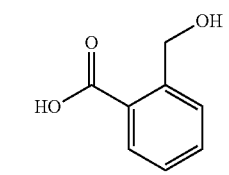

2-(hydroxymethyl)benzoic acid

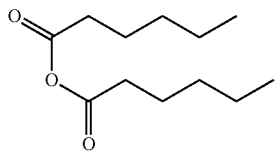

hexanoic anhydride

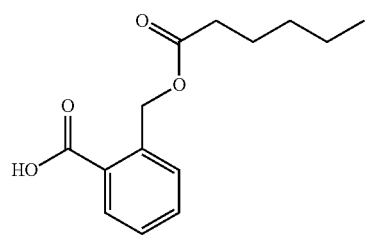

P-SSSS1

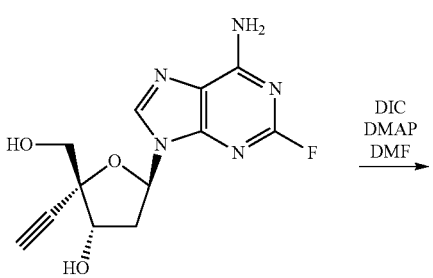

EFdA

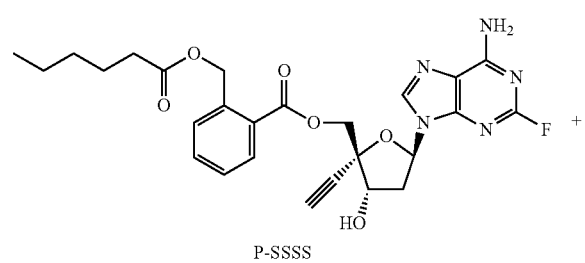

P-SSSS

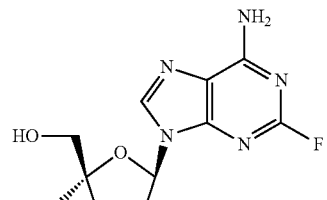

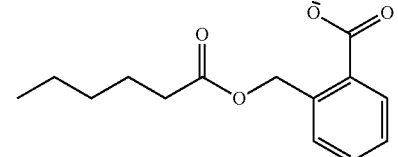

P-TTTT

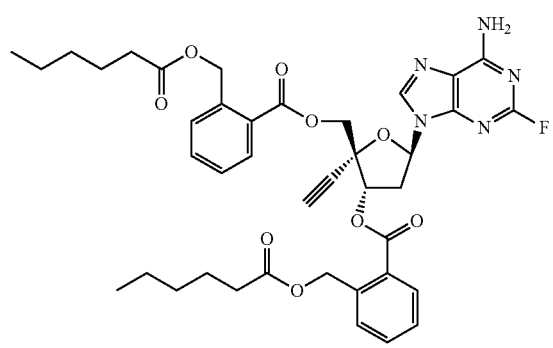

P-UUUU

Synthesis of Compound P-SSSS—((2R,3S,5R)-5-(6-amino-2-fluoro-9H-purin-9-yl)-2-ethynyl-3-hydroxytetrahydrofuran-2-yl)methyl 2-((hexanoyloxy)methyl)benzoate and Synthesis of Compound P-TTTT—(2R,3S,5R)-5-(6-amino-2-fluoro-9H-purin-9-yl)-2-ethynyl-2-(hydroxymethyl)tetrahydrofuran-3-yl 2-((hexanoyloxy)methyl)benzoate and Synthesis of Compound P-UUUU—(2R,3S,5R)-5-(6-amino-2-fluoro-9H-purin-9-yl)-2-ethynyl-2-(((2-((hexanoyloxy)methyl)benzoyl)oxy)methyl) tetrahydrofuran-3-yl 2-((hexanoyloxy)methyl)benzoate Intermediate P-SSSS1 is prepared in the same manner described for intermediate E1 except hexanoic anhydride (Aldrich) is used instead of palmitic anhydride.

Examples P-SSSS, P-TTTT and P-UUUU are prepared in the same manner described for examples E, F, and G except intermediate P-SSSS1 is used instead of intermediate E1.

Examples P-VVVV, P-WWWW, and P-XXXX

Examples P-YYYY, P-ZZZZ, and P-Ax5

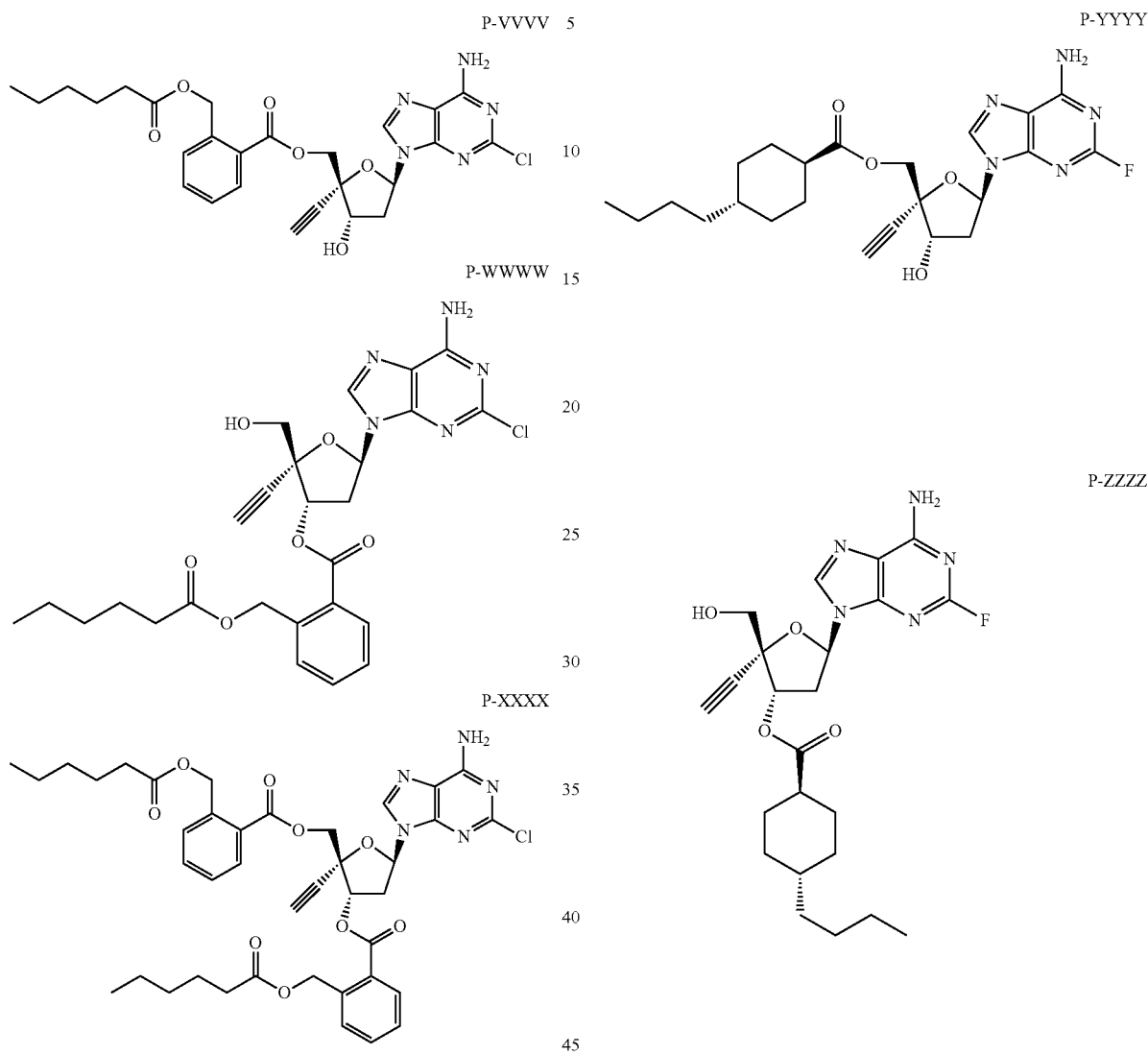

Synthesis of Compound P-VVVV—((2R,3S,5R)-5-(6-amino-2-chloro-9H-purin-9-yl)-2-ethynyl-3-hydroxytetrahydrofuran-2-yl)methyl 2-((hexanoyloxy)methyl)benzoate and Synthesis of Compound P-WWWW—(2R,3S,5R)-5-(6-amino-2-chloro-9H-purin-9-yl)-2-ethynyl-2-(hydroxymethyl)tetrahydrofuran-3-yl 2-((hexanoyloxy)methyl)benzoate and Synthesis of Compound P-XXXX—(2R,3S,5R)-5-(6-amino-2-chloro-9H-purin-9-yl)-2-ethynyl-2-(((2-((hexanoyloxy)methyl)benzoyl)oxy)methyl) tetrahydrofuran-3-yl 2-((hexanoyloxy)methyl)benzoate Examples P-VVVV, P-WWWW, and P-XXXX are prepared in the same manner as described for examples P-SSSS, P-TTTT and P-UUUU except ECldA is used instead of EFdA.

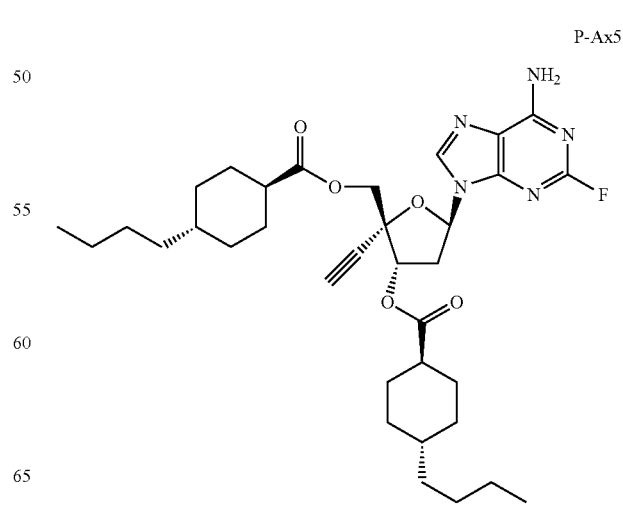

Synthesis of Compound P-YYYY—((2R,3S,5R)-5-(6-amino-2-fluoro-9H-purin-9-yl)-2-ethynyl-3-hydroxytetrahydrofuran-2-yl)methyl (1s,4R)-4-butylcyclohexane-1-carboxylate and Synthesis of Compound P-ZZZZ—(2R,3S,5R)-5-(6-amino-2-fluoro-9H-purin-9-yl)-2-ethynyl-2-(hydroxymethyl)tetrahydrofuran-3-yl (1s,4S)-4-butylcyclohexane-1-carboxylate and Synthesis of Compound P-Ax5—(2R,3S,5R)-5-(6-amino-2-fluoro-9H-purin-9-yl)-2-((((1s,4R)-4-butylcyclohexane-1-carbonyl)oxy)methyl)-2-ethynyltetrahydrofuran-3-yl (1s,4S)-4-butylcyclohexane-1-carboxylate Examples P-YYYY, P-ZZZZ, and P-XXXX are prepared in the same manner as described for examples P-SSSS, P-TTTT and P-UUUU except (1s,4r)-4-butylcyclohexane-1-carboxylic acid (Aldrich) is used instead of intermediate P-SSSS1.

Examples P-Bx5, P-Cx5, and P-Dx5

P-Bx5

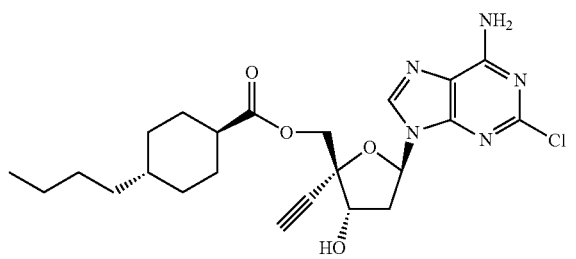

P-Cx5

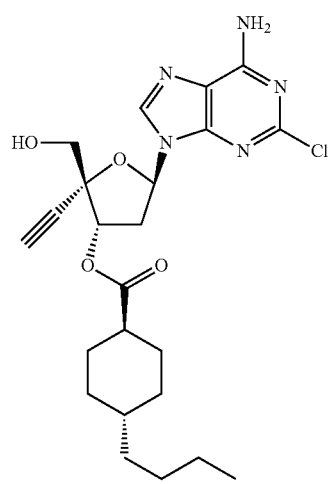

P-Dx5

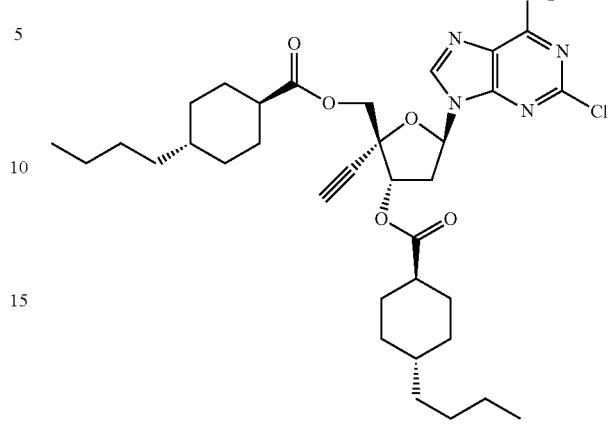

Synthesis of Compound P-Bx5—((2R,3S,5R)-5-(6-amino-2-chloro-9H-purin-9-yl)-2-ethynyl-3-hydroxytetrahydrofuran-2-yl)methyl (1s,4R)-4-butylcyclohexane-1-carboxylate and Synthesis of Compound P-Cx5—(2R,3S,5R)-5-(6-amino-2-chloro-9H-purin-9-yl)-2-ethynyl-2-(hydroxymethyl)tetrahydrofuran-3-yl (1s,4S)-4-butylcyclohexane-1-carboxylate and Synthesis of Compound P-Dx5—(2R,3S,5R)-5-(6-amino-2-chloro-9H-purin-9-yl)-2-((((1s,4R)-4-butylcyclohexane-1-carbonyl)oxy)methyl)-2-ethynyltetrahydrofuran-3-yl (1s,4S)-4-butylcyclohexane-1-carboxylate Examples P-Bx5, P-Cx5, and P-Dx5 are prepared in the same manner as described for examples P-YYYY, P-ZZZZ and P-Ax5 except ECldA is used instead of EFdA.

Example P-Ex5 and P-Fx5

P-Ex5

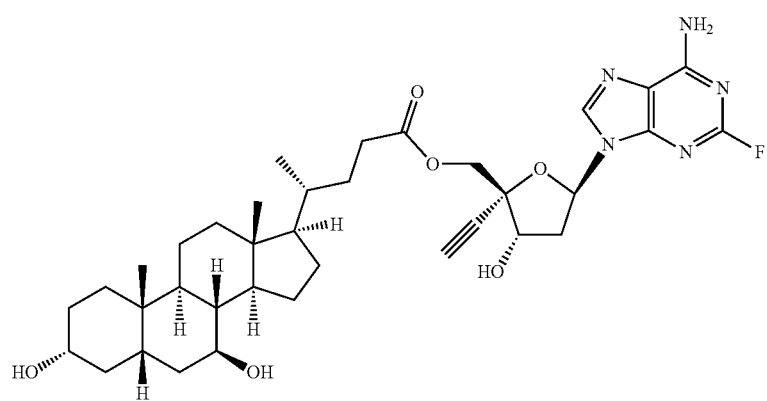

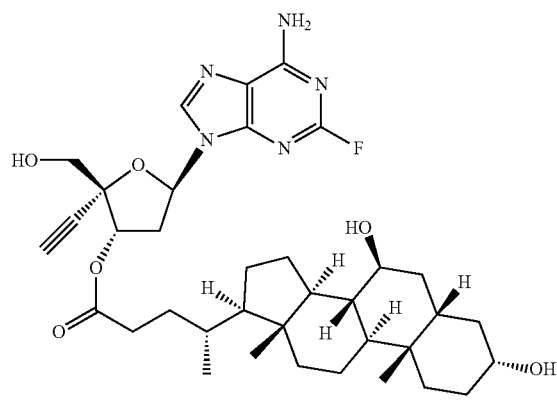

P-Fx5

Synthesis of Compound P-Ex5—((2R,3S,5R)-5-(6-amino-2-fluoro-9H-purin-9-yl)-2-ethynyl-3-hydroxytetrahydrofuran-2-yl)methyl (R)-4-((3R,5S,7S,8R,9S,10S,13R,14S,17R)-3,7-dihydroxy-10,13-dimethylhexadecahydro-1H-cyclopenta[a]phenanthren-17-yl)pentanoate and Synthesis of Compound P-Fx5—(2R,3S,5R)-5-(6-amino-2-fluoro-9H-purin-9-yl)-2-ethynyl-2-(hydroxymethyl)tetrahydrofuran-3-yl (R)-4-((3R,5S,7S,8R,9S,10S,13R,14S,17R)-3,7-dihydroxy-10,13-dimethylhexadecahydro-1H-cyclopenta[a]phenanthren-17-yl)pentanoate Examples P-Ex5 and P-Fx5 are prepared in the same manner as described for examples P-SSSS and P-TTTT except (R)-4-((3R,5S,7S,8R,9S,10S,13R,14S,17R)-3,7-dihydroxy-10,13-dimethylhexadecahydro-1H-cyclopenta[a]phenanthren-17-yl)pentanoic acid (Alfa Aesar) is used instead of intermediate P-SSSS1.

Example P-Gx5 and P-Hx5

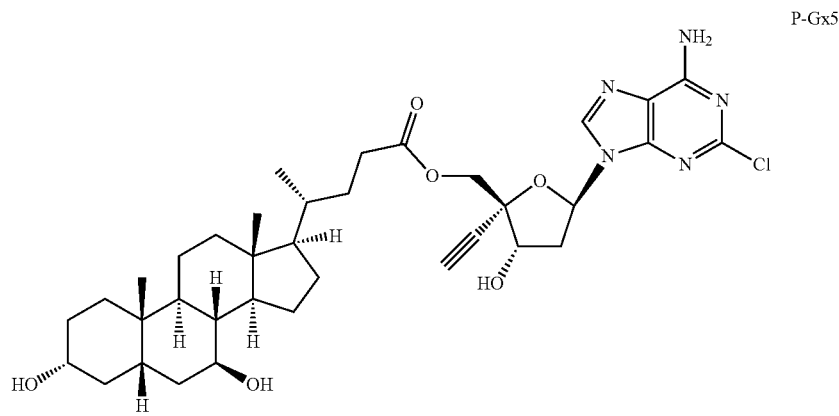

P-Gx5

P-Hx5

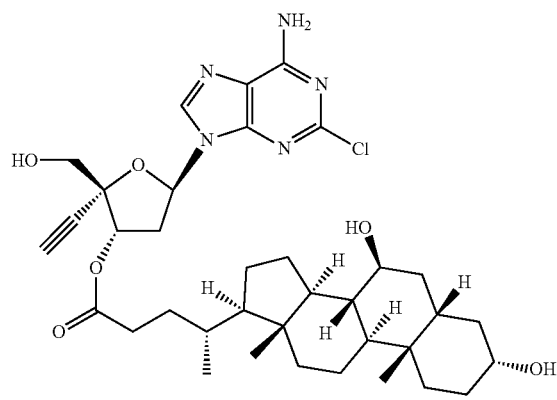

Synthesis of Compound P-Gx5—((2R,3S,5R)-5-(6-amino-2-chloro-9H-purin-9-yl)-2-ethynyl-3-hydroxytetrahydrofuran-2-yl)methyl (R)-4-((3R,5S,7S,8R,9S,10S,13R,14S,17R)-3,7-dihydroxy-10,13-dimethylhexadecahydro-1H-cyclopenta[a]phenanthren-17-yl)pentanoate and Synthesis of Compound P-Hx5—(2R,3S,5R)-5-(6-amino-2-chloro-9H-purin-9-yl)-2-ethynyl-2-(hydroxymethyl)tetrahydrofuran-3-yl (R)-4-((3R,5S,7S,8R,9S,10S,13R,14S,17R)-3,7-dihydroxy-10,13-dimethylhexadecahydro-1H-cyclopenta[a]phenanthren-17-yl)pentanoate Examples P-Gx5 and P-Hx5 are prepared in the same manner as described for examples P-Ex5 and P-Fx5 except ECldA is used instead of EFdA.

Example P-Ix5 & Example P-Jx5

P-Ix5

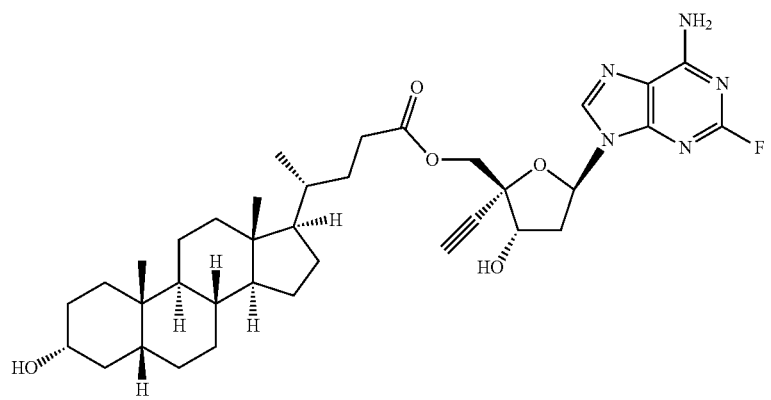

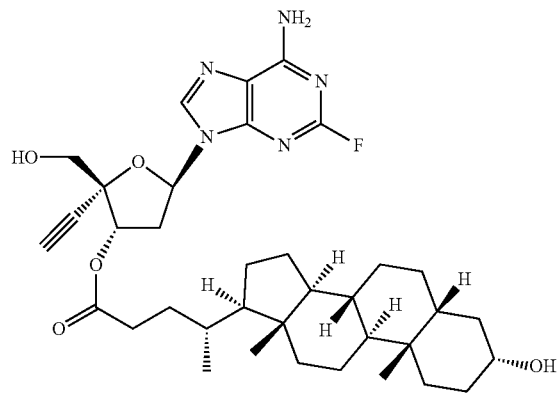

P-Jx5

Synthesis of Compound P-Ix5—((2R,3S,5R)-5-(6-amino-2-fluoro-9H-purin-9-yl)-2-ethynyl-3-hydroxytetrahydrofuran-2-yl)methyl (R)-4-((3R,5R,8R,9S,10S,13R,14S,17R)-3-hydroxy-10,13-dimethylhexadecahydro-1H-cyclopenta[a]phenanthren-17-yl)pentanoate and Synthesis of Compound P-Jx5—(2R,3S,5R)-5-(6-amino-2-fluoro-9H-purin-9-yl)-2-ethynyl-2-(hydroxymethyl)tetrahydrofuran-3-yl (R)-4-((3R,5R,8R,9S,10S,13R,14S,17R)-3-hydroxy-10,13-dimethylhexadecahydro-1H-cyclopenta[a]phenanthren-17-yl)pentanoate Examples P-Ix5 and P-Jx5 are prepared in the same manner as described for examples P-SSSS and P-TTTT except (R)-4-((3R,5R,8R,9S,10S,13R,14S,17R)-3-hydroxy-10,13-dimethylhexadecahydro-1H-cyclopenta[a]phenanthren-17-yl)pentanoic acid (Enamine) is used instead of intermediate P-SSSS1.

Example P-Gx5 & Example P-Hx5

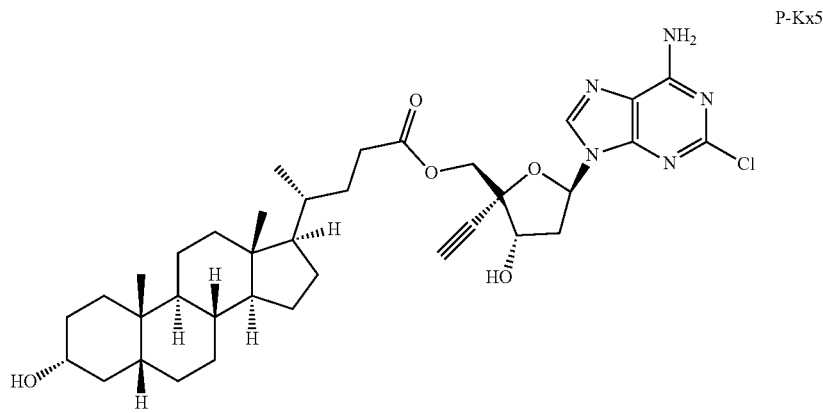

P-Kx5

P-Lx5

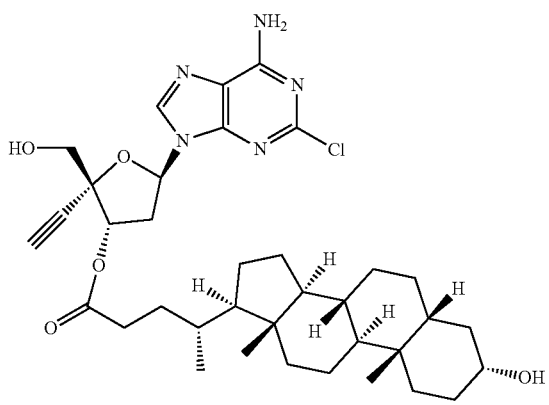

Synthesis of Compound P-Gx5 ((2R,3S,5R)-5-(6-amino-2-chloro-9H-purin-9-yl)-2-ethynyl-3-hydroxytetrahydrofuran-2-yl)methyl (R)-4-((3R,5R,8R,9S,10S,13R,14S,17R)-3-hydroxy-10,13-dimethylhexadecahydro-1H-cyclopenta[a]phenanthren-17-yl)pentanoate and Synthesis of Compound P-Hx5—(2R,3S,5R)-5-(6-amino-2-chloro-9H-purin-9-yl)-2-ethynyl-2-(hydroxymethyl)tetrahydrofuran-3-yl (R)-4-((3R,5R,8R,9S,10S,13R,14S,17R)-3-hydroxy-10,13-dimethylhexadecahydro-1H-cyclopenta[a]phenanthren-17-yl)pentanoate Examples P-Kx5 and P-Lx5 are prepared in the same manner as described for examples P-Ix5 and P-Jx5 except ECldA is used instead of EFdA.

Example P-Mx5

P-Mx5

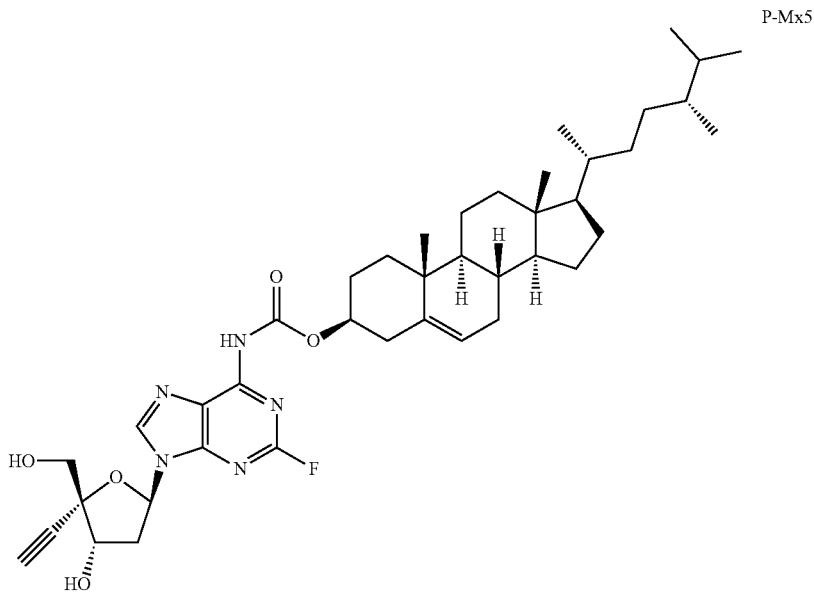

Synthesis of Compound P-Mx5—(3S,8S,9S,10R, 13R,14S,17R)-17-((2R,5R)-5,6-dimethylheptan-2-yl)-10,13-dimethyl-2,3,4,7,8,9,10,11,12,13,14,15,16,17-tetradecahydro-1H-cyclopenta[a]phenanthren-3-yl (9-((2R,4S,5R)-5-ethynyl-4-hydroxy-5-(hydroxymethyl)tetrahydrofuran-2-yl)-2-fluoro-9H-purin-6-yl)carbamate Example P-Mx5 is prepared in the same manner as described for intermediate P-SS3 except (3S,8S,9S,10R, 13R,14S,17R)-17-((2R,5R)-5,6-dimethylheptan-2-yl)-10,13-dimethyl-2,3,4,7,8,9,10,11,12,13,14,15,16,17-tetradecahydro-1H-cyclopenta[a]phenanthren-3-ol is used instead of intermediate P-SS1.

Example P-Nx5

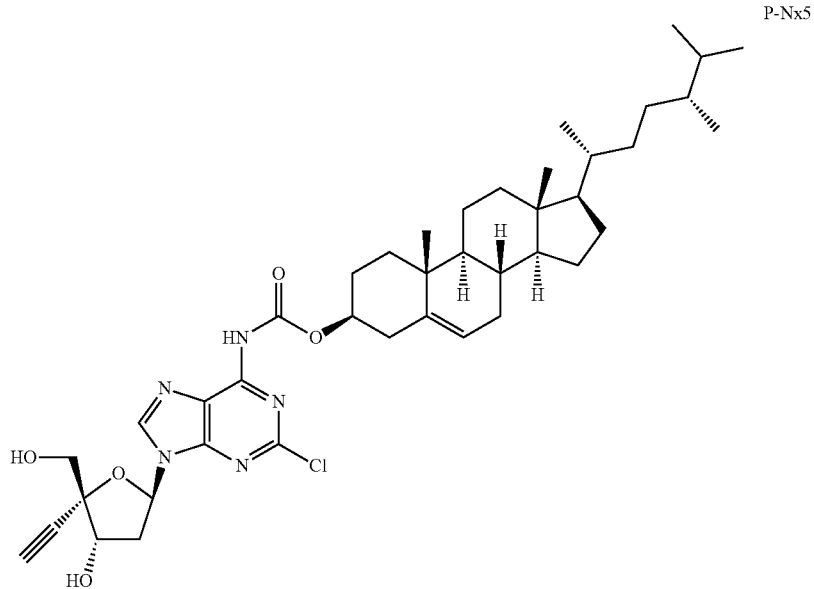

Synthesis of Compound P-Nx5—(3S,8S,9S,10R, 13R,14S,17R)-17-((2R,5R)-5,6-dimethylheptan-2-yl)-10,13-dimethyl-2,3,4,7,8,9,10,11,12,13,14,15,16,17-tetradecahydro-1H-cyclopenta[a]phenanthren-3-yl (2-chloro-9-((2R,4S,5R)-5-ethynyl-4-hydroxy-5-(hydroxymethyl)tetrahydrofuran-2-yl)-9H-purin-6-yl)carbamate Examples P-Nx5 is prepared in the same manner as described for examples P-Mx5 except ECldA is used instead of EFdA.

Example P-Ox5 & Example P-Px5

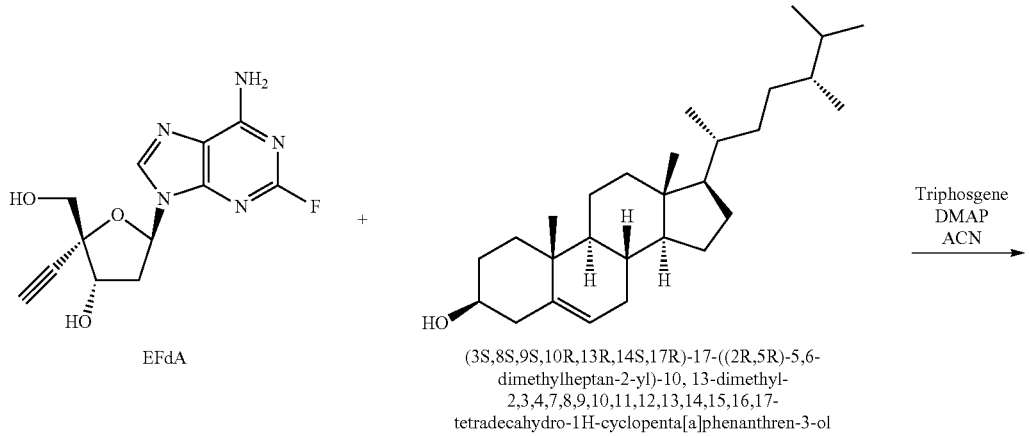

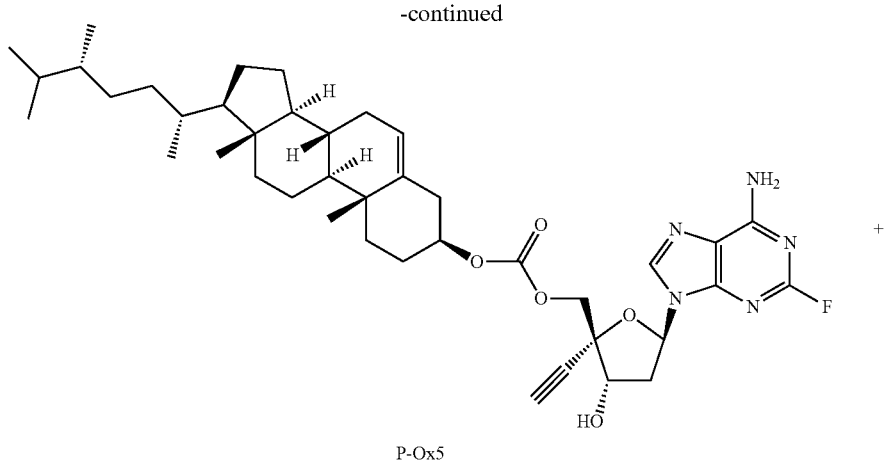

P-Ox5

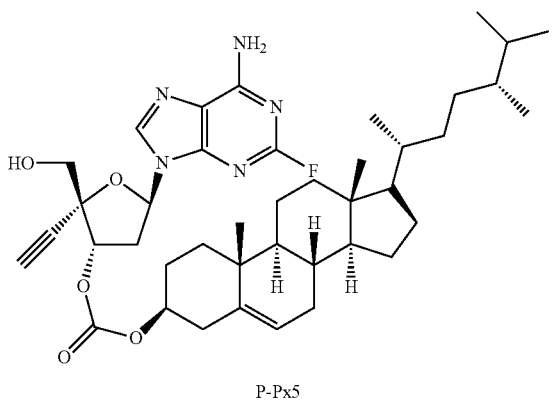

P-Px5

Synthesis of Compound P-Ox5—((2R,3S,5R)-5-(6-amino-2-fluoro-9H-purin-9-yl)-2-ethynyl-3-hydroxytetrahydrofuran-2-yl)methyl ((3S,8S,9S,10R,13R,14S,17R)-17-((2R,5R)-5,6-dimethylheptan-2-yl)-10,13-dimethyl-2,3,4,7,8,9,10,11,12,13, 14,15, 16,17-tetradecahydro-1H-cyclopenta[a]phenanthren-3-yl) carbonate and Synthesis of Compound P-Px5—(2R,3S,5R)-5-(6-amino-2-fluoro-9H-purin-9-yl)-2-ethynyl-2-(hydroxymethyl)tetrahydrofuran-3-yl ((3S,8S,9S,10R,13R,14S,17R)-17-((2R,5R)-5,6-dimethylheptan-2-yl)-10,13-dimethyl-2,3,4,7,8,9,10,11,12,13, 14,15, 16,17-tetradecahydro-1H-cyclopenta[a]phenanthren-3-yl) carbonate DMAP (2 mmol) is added to a solution of triphosgene (2 eq relative to EFdA) in DCM (10 mL). EFdA (1 mmol) is then added and the reaction is allowed to proceed. (3S,8S,9S,10R,13R,14S,17R)-17-((2R,5R)-5,6-dimethylheptan-2-yl)-10,13-dimethyl-2,3,4,7,8,9,10,11,12,13,14,15,16,17-tetradecahydro-1H-cyclopenta[a]phenanthren-3-ol (2 eq) is then added and the reaction is allowed to proceed. The reaction is quenched by the addition of ice water and diluted with DCM. The organic layer is separated and dried over sodium sulfate. Examples P-Ox5 and P-Px5 are isolated by silica gel column chromatography.

Example P-Qx5 & Example P-Rx5

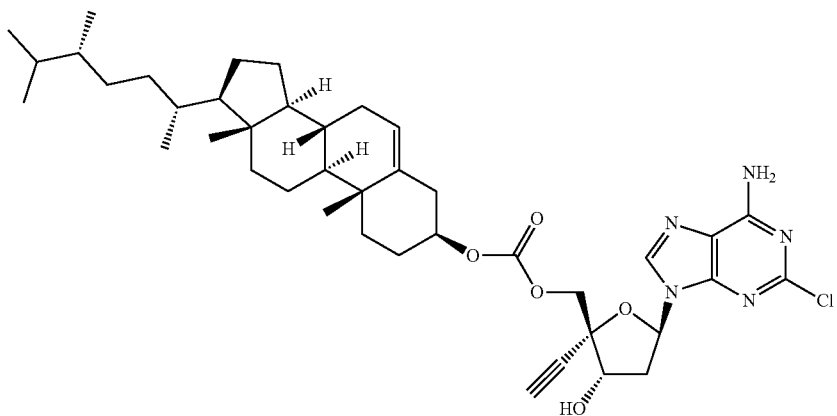

P-Qx5

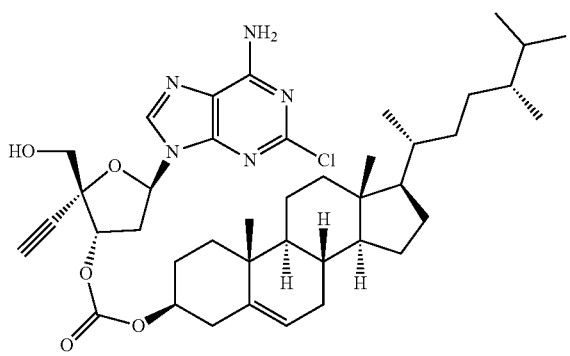

P-Rx5

Synthesis of Compound P-Qx5—((2R,3S,5R)-5-(6-amino-2-chloro-9H-purin-9-yl)-2-ethynyl-3-hydroxytetrahydrofuran-2-yl)methyl ((3S,8S,9S,10R,13R,14S,17R)-17-((2R,5R)-5,6-dimethylheptan-2-yl)-10,13-dimethyl-2,3,4,7,8,9,10,11,12,13,14,15,16,17-tetradecahydro-1H-cyclopenta[a]phenanthren-3-yl) carbonate and Synthesis of Compound P-Rx5—(2R,3S,5R)-5-(6-amino-2-chloro-9H-purin-9-yl)-2-ethynyl-2-(hydroxymethyl)tetrahydrofuran-3-yl ((3S,8S,9S,10R,13R,14S,17R)-17-((2R,5R)-5,6-dimethylheptan-2-yl)-10,13-dimethyl-2,3,4,7,8,9,10,11,12,13, 14,15,16,17-tetradecahydro-1H-cyclopenta[a]phenanthren-3-yl) carbonate Examples P-Qx5 and P-Rx5 are prepared in the same manner as described for examples P-Ox5 and P-Px5 except ECldA is used instead of EFdA.

Example P-Sx5 & Example P-Tx5

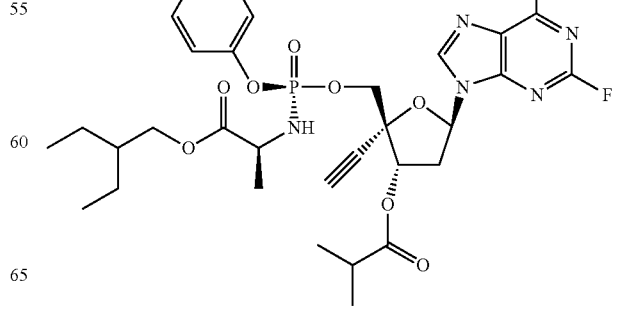

P-Sx5

335
-continued

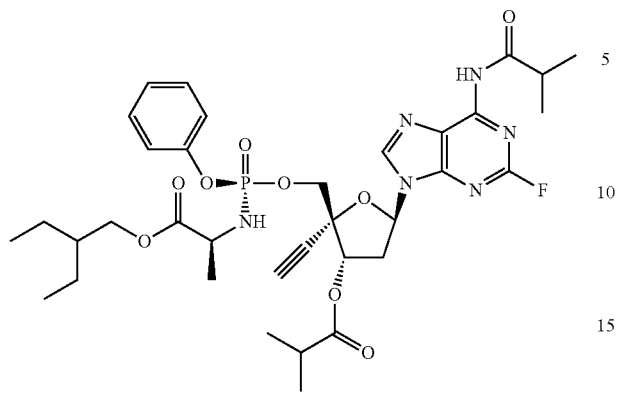
P-Tx5

Synthesis of Compound P-Sx5—(2R,3S,5R)-5-(6-amino-2-fluoro-9H-purin-9-yl)-2-((((S)—(((S)-1-(2-ethylbutoxy)-1-oxopropan-2-yl)amino)(phenoxy)phosphoryl)oxy)methyl)-2-ethynyltetrahydrofuran-3-yl isobutyrate and Synthesis of Compound P-Tx5—(2R,3S,5R)-2-((((S)—(((S)-1-(2-ethylbutoxy)-1-oxopropan-2-yl)amino)(phenoxy)phosphoryl)oxy)methyl)-2-ethynyl-5-(2-fluoro-6-isobutyramido-9H-purin-9-yl)tetrahydrofuran-3-yl isobutyrate Examples P-Sx5 and P-Tx5 are prepared in the same manner described for examples U and V except compound D is used instead of compound T.

Example P-Ux5 & Example P-Vx5

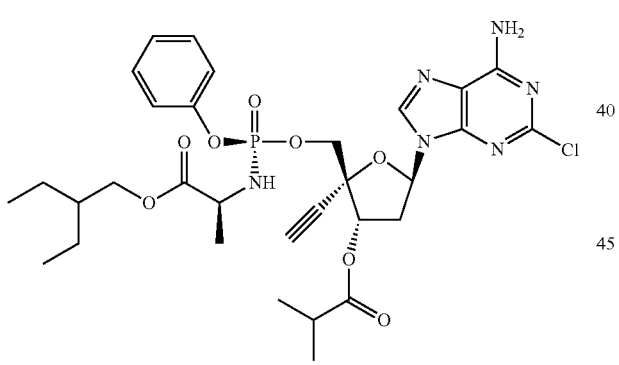
P-Ux5

336
-continued

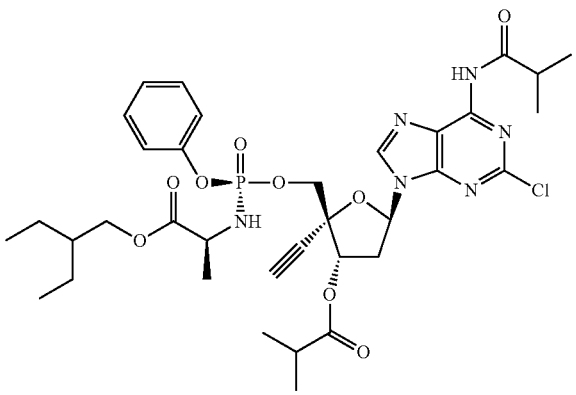
P-Vx5

Synthesis of Compound P-Ux5—(2R,3S,5R)-5-(6-amino-2-chloro-9H-purin-9-yl)-2-((((S)—(((S)-1-(2-ethylbutoxy)-1-oxopropan-2-yl)amino)(phenoxy)phosphoryl) oxy)methyl)-2-ethynyltetrahydrofuran-3-yl isobutyrate and Synthesis of Compound P-Vx5—(2R,3S,5R)-5-(2-chloro-6-isobutyramido-9H-purin-9-yl)-2-((((S)—(((S)-1-(2-ethylbutoxy)-1-oxopropan-2-yl)amino)(phenoxy) phosphoryl)oxy)methyl)-2-ethynyltetrahydrofuran-3-yl isobutyrate Examples P-Ux5 and P-Vx5 are prepared in the same manner as described for examples P-Sx5 and P-Tx5 except ECldA is used instead of EFdA.

Example P-Wx5

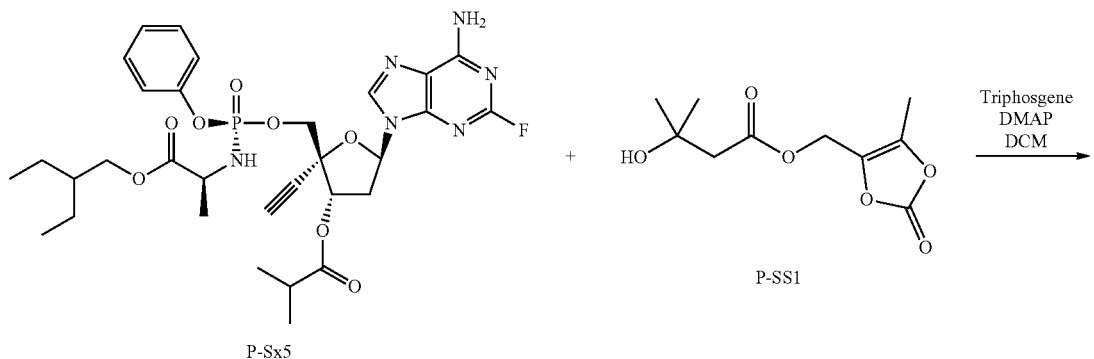
P-Sx5 + P-SS1 — Triphosgene DMAP DCM →

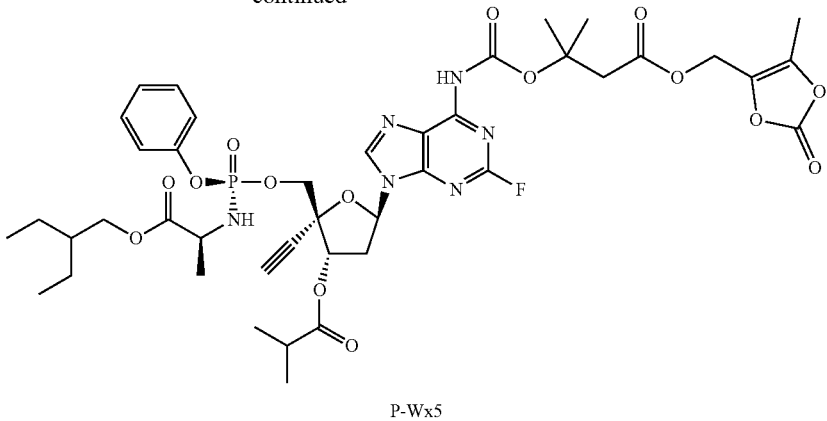

P-Wx5

Synthesis of Compound P-Wx5—(5-methyl-2-oxo-1,3-dioxol-4-yl)methyl 3-(((9-((2R,4S,5R)-5-(((((S)—(((S)-1-(2-ethylbutoxy)-1-oxopropan-2-yl)amino) (phenoxy)phosphoryl)oxy)methyl)-5-ethynyl-4-(isobutyryloxy)tetrahydrofuran-2-yl)-2-fluoro-9H-purin-6-yl)carbamoyl)oxy)-3-methylbutanoate Example P-Wx5 is prepared in the same manner as described for intermediate B2 except compound P-Sx5 is used instead of intermediate B1 and intermediate P-SS1 is used instead of tetradecan-1-ol.

Example P-Xx5

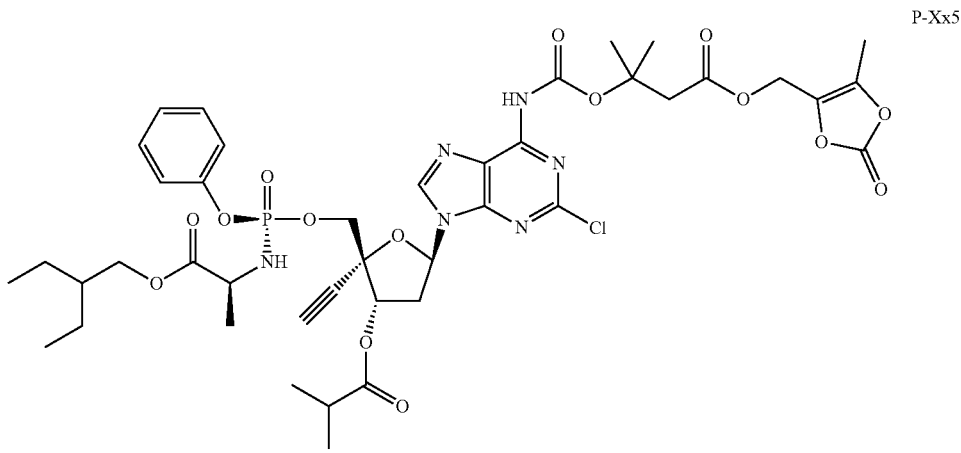 [SMILES: C#C[C@]1(CO[P@@](=O)(N[C@@H](C)C(=O)OCC(CC)CC)Oc2ccccc2)O[C@@H](n2cnc3c(NC(=O)OC(C)(C)CC(=O)OCc4oc(=O)oc4C)nc(Cl)nc32)C[C@@H]1OC(=O)C(C)C]

P-Xx5

Synthesis of Compound P-Xx5—(5-methyl-2-oxo-1,3-dioxol-4-yl)methyl 3-(((2-chloro-9-((2R,4S,5R)-5-(((((S)—(((S)-1-(2-ethylbutoxy)-1-oxopropan-2-yl)amino)(phenoxy)phosphoryl)oxy)methyl)-5-ethynyl-4-(isobutyryloxy)tetrahydrofuran-2-yl)-9H-purin-6-yl)carbamoyl)oxy)-3-methylbutanoate Compound P-Xx5 is prepared in the same manner as described for examples P-Wx5 except ECldA is used instead of EFdA.

Example P-Yx5

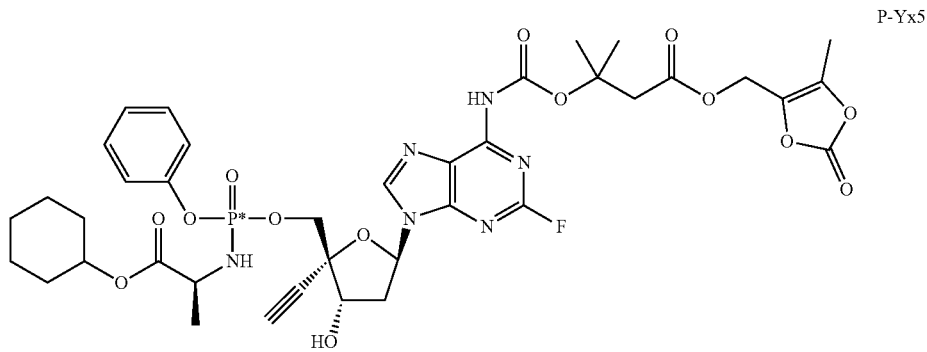

P-Yx5

Synthesis of Compound P-Yx5—(5-methyl-2-oxo-1,3-dioxol-4-yl)methyl 3-(((9-((2R,4S,5R)-5-((((((S)-1-(cyclohexyloxy)-1-oxopropan-2-yl)amino)(phenoxy)phosphoryl)oxy)methyl)-5-ethynyl-4-hydroxytetrahydrofuran-2-yl)-2-fluoro-9H-purin-6-yl)carbamoyl)oxy)-3-methylbutanoate Compound P-Yx5 is prepared in the same manner as described for example T except intermediate PSS3 is used instead of EFdA.

Example P-Zx5

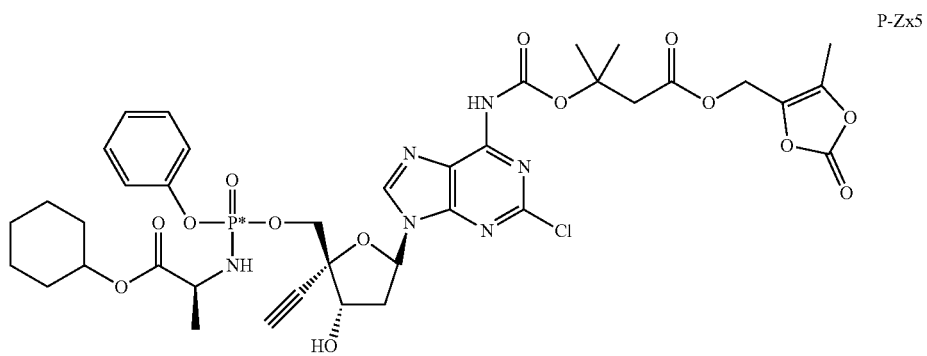

P-Zx5

Synthesis of Compound P-Zx5—(5-methyl-2-oxo-1,3-dioxol-4-yl)methyl 3-(((2-chloro-9-((2R,4S,5R)-5-((((((S)-1-(cyclohexyloxy)-1-oxopropan-2-yl)amino)(phenoxy)phosphoryl)oxy)methyl)-5-ethynyl-4-hydroxytetrahydrofuran-2-yl)-9H-purin-6-yl)carbamoyl)oxy)-3-methylbutanoate Compound P-Zx5 is prepared in the same manner as described for example P-Yx5 except ECldA is used instead of EFdA.

Example P-Ax6

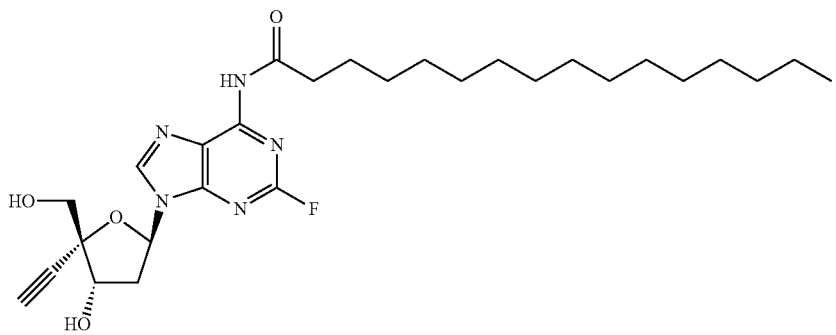

P-Ax6

Synthesis of Compound P-Ax6—N-(9-((2R,4S,5R)-5-ethynyl-4-hydroxy-5-(hydroxymethyl)tetrahydrofuran-2-yl)-2-fluoro-9H-purin-6-yl)palmitamide Compound P-Ax6 is prepared in the same manner as described for intermediate P-A2 except palmitoyl chloride is used instead of 2-(4-chloro-2-methyl-4-oxobutan-2-yl)-3,5-dimethylphenyl acetate.

Example P-Bx6

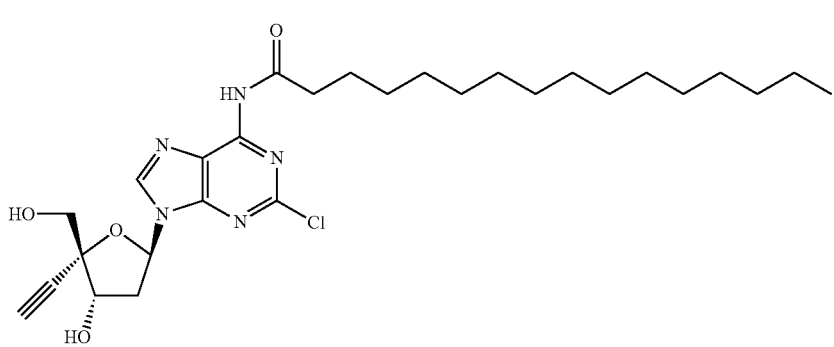

P-Bx6

Synthesis of Compound P-Bx6—N-(2-chloro-9-((2R,4S,5R)-5-ethynyl-4-hydroxy-5-(hydroxymethyl)tetrahydrofuran-2-yl)-9H-purin-6-yl)palmitamide Compound P-Bx6 is prepared in the same manner as described for example P-Ax6 except ECldA is used instead of EFdA.

Example P-Cx6

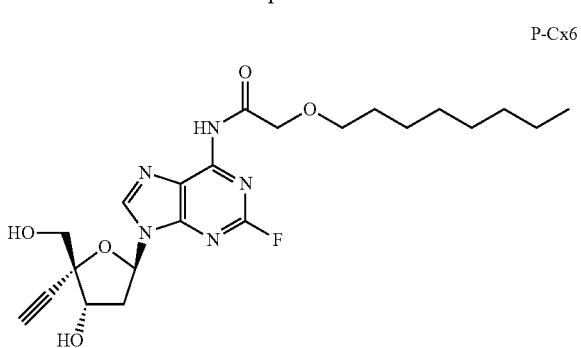

P-Cx6

Synthesis of Compound P-Cx6—N-(9-((2R,4S,5R)-5-ethynyl-4-hydroxy-5-(hydroxymethyl)tetrahydrofuran-2-yl)-2-fluoro-9H-purin-6-yl)-2-(octyloxy)acetamide Compound P-Cx6 is prepared in the same manner as described for intermediate P-A2 except 2-(octyloxy)acetic acid (Chem. Comm., 2018, 54, pp 9969-9972) is used instead of 3-(2-acetoxy-4,6-dimethylphenyl)-3-methylbutanoic acid.

Example P-Dx6

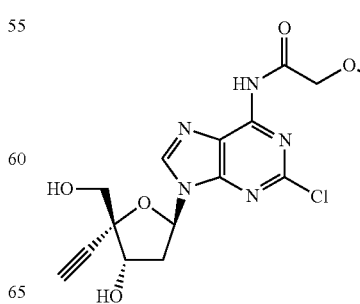

P-Dx6

Synthesis of Compound P-Dx6—N-(2-chloro-9-((2R,4S,5R)-5-ethynyl-4-hydroxy-5-(hydroxymethyl)tetrahydrofuran-2-yl)-9H-purin-6-yl)-2-(octyloxy)acetamide Compound P-Dx6 is prepared in the same manner as described for example P-Cx6 except ECldA is used instead of EFdA.

Example PEx6

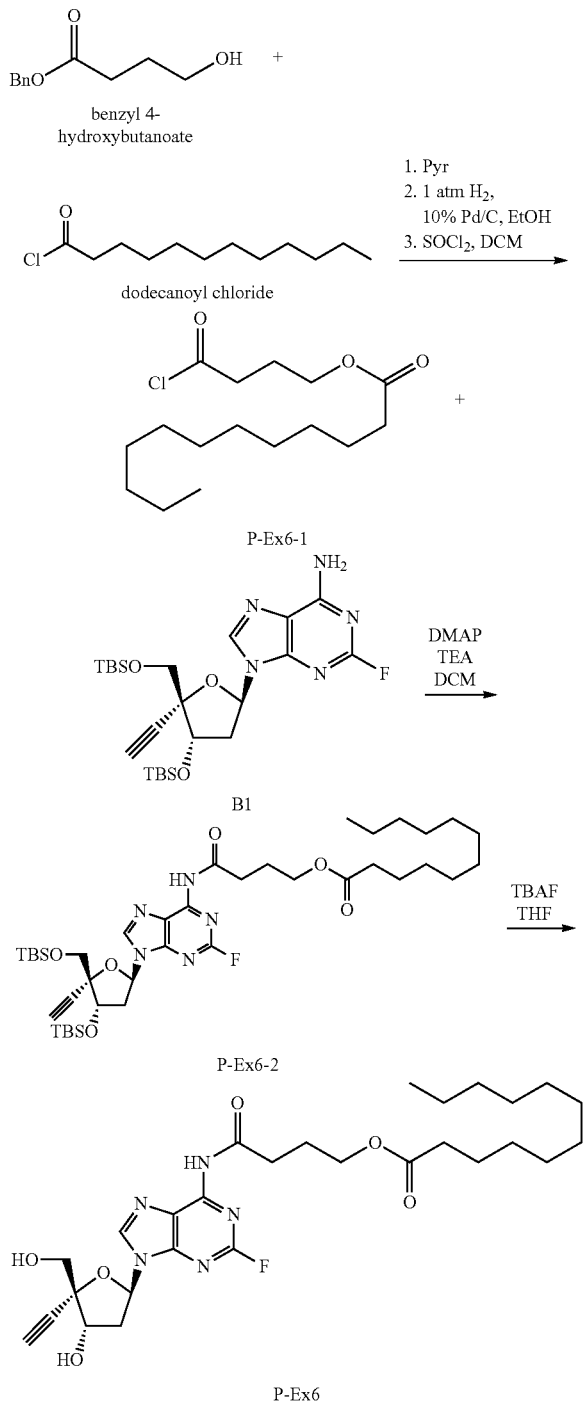

Synthesis of Compound PEx6—4-((9-((2R,4S,5R)-5-ethynyl-4-hydroxy-5-(hydroxymethyl)tetrahydrofuran-2-yl)-2-fluoro-9H-purin-6-yl)amino)-4-oxobutyl dodecanoate To a solution of benzyl 4-hydroxybutanoate (Aldrich; 1 mmol) in pyridine (5 mL) is added dodecanoyl chloride (Aldrich; 1.5 eq) at room temperature. The reaction is allowed to proceed and then concentrated in vacuo. The obtained residue is purified by silica gel column chromatography to yield 4-(benzyloxy)-4-oxobutyl dodecanoate. 4-(benzyloxy)-4-oxobutyl dodecanoate (1 mmol) is dissolved in EtOH (5 mL) and 10% Pd/C (0.2 eq) is added. The resulting mixture is stirred at room temperature under an atmosphere of $H_2$. Upon completion of the reaction the mixture is filtered, and the filtrate is concentrated in vacuo to give 4-(dodecanoyloxy)butanoic acid. 4-(dodecanoyloxy)butanoic acid (1 mmol) is dissolved in DCM (10 mL) and $SOCl_2$ (4 eq is added). The reaction is allowed to proceed and then concentrated to yield intermediate P-Ex6-1.

Intermediate P-Ex6-2 is prepared in the same manner as described for intermediate P-A1 except intermediate P-Ex6-1 is used instead of 2-(4-chloro-2-methyl-4-oxobutan-2-yl)-3,5-dimethylphenyl acetate.

Compound P-Ex6 is prepared in the same manner as described for intermediate P-A2 except intermediate P-Ex6-2 is used instead of intermediate P-A1.

Example P-Fx6

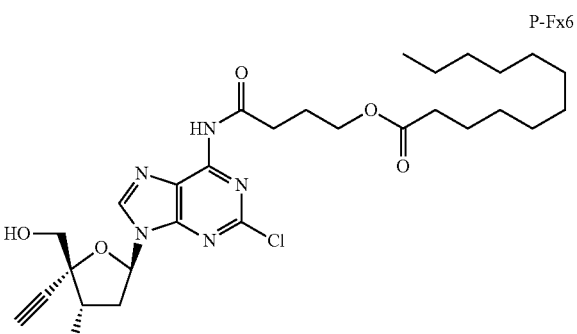

Synthesis of Compound P-Fx6—4-((2-chloro-9-((2R,4S,5R)-5-ethynyl-4-hydroxy-5-(hydroxymethyl)tetrahydrofuran-2-yl)-9H-purin-6-yl)amino)-4-oxobutyl dodecanoate Compound P-Fx6 is prepared in the same manner as described for example P-Ex6 except ECldA is used instead of EFdA.

Example P-Gx6

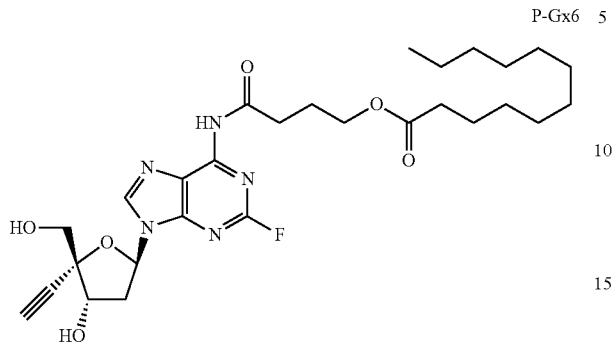

Synthesis of Compound P-Gx6—2-(((9-((2R,4S, 5R)-5-ethynyl-4-hydroxy-5-(hydroxymethyl)tetrahydrofuran-2-yl)-2-fluoro-9H-purin-6-yl)carbamoyl)oxy)ethyl dodecanoate Compound P-Gx6 is prepared in the same manner as described for example B except 2-hydroxyethyl dodecanoate (Chem. Pharm. Bull., 2016, 64(2), pp. 161-170) is used instead of tetradecan-1-ol.

Example P-Hx6

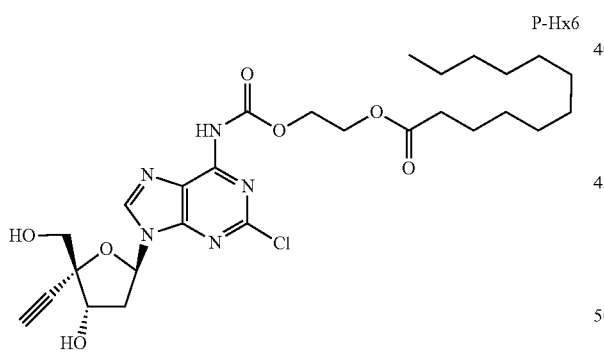

Synthesis of Compound P-Hx6—2-(((2-chloro-9-((2R,4S,5R)-5-ethynyl-4-hydroxy-5-(hydroxymethyl)tetrahydrofuran-2-yl)-9H-purin-6-yl)carbamoyl)oxy)ethyl dodecanoate Compound P-Hx6 is prepared in the same manner as described for example P-Gx6 except ECldA is used instead of EFdA.

Example P-Ix6

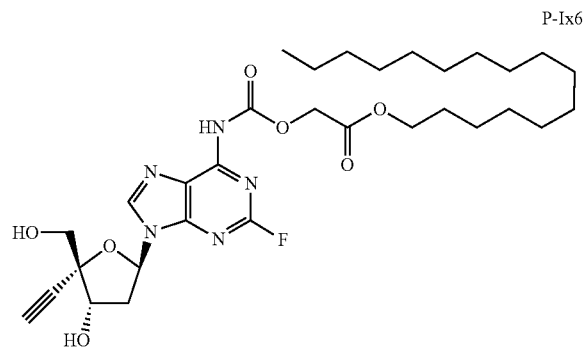 [SMILES: C#C[C@]1(CO)O[C@@H](n2cnc3c(NC(=O)OCC(=O)OCCCCCCCCCCCCCCCC)nc(F)nc32)C[C@@H]1O]

Synthesis of Compound P-Ix6—hexadecyl 2-(((9-((2R,4S,5R)-5-ethynyl-4-hydroxy-5-(hydroxymethyl)tetrahydrofuran-2-yl)-2-fluoro-9H-purin-6-yl)carbamoyl)oxy)acetate Compound P-Ix6 is prepared in the same manner as described for intermediate P-SS3 except that glycolic acid (Aldrich) is used instead of 3-hydroxy-3-methoxybutanoic acid and 1-bromohexadecane (Aldrich) is used instead of 4-(bromomethyl)-5-methyl-1,3-dioxol-2-one.

Example P-Jx6

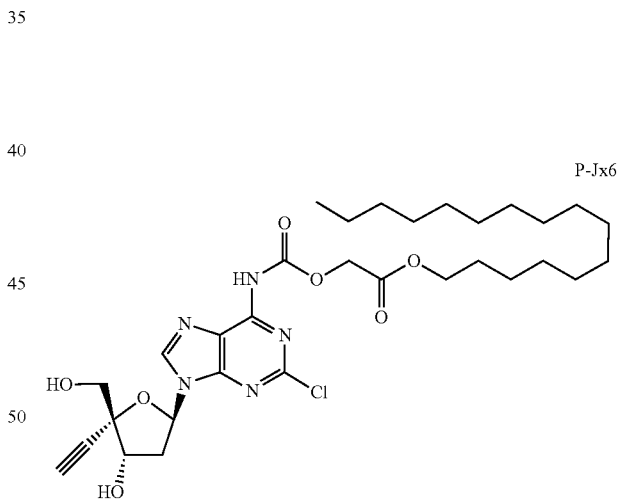

Synthesis of Compound P-Jx6—hexadecyl 2-(((2-chloro-9-((2R,4S,5R)-5-ethynyl-4-hydroxy-5-(hydroxymethyl)tetrahydrofuran-2-yl)-9H-purin-6-yl)carbamoyl)oxy)acetate Compound P-Jx6 is prepared in the same manner as described for example P-Ix6

Example P-Kx6 & Example P-Lx6

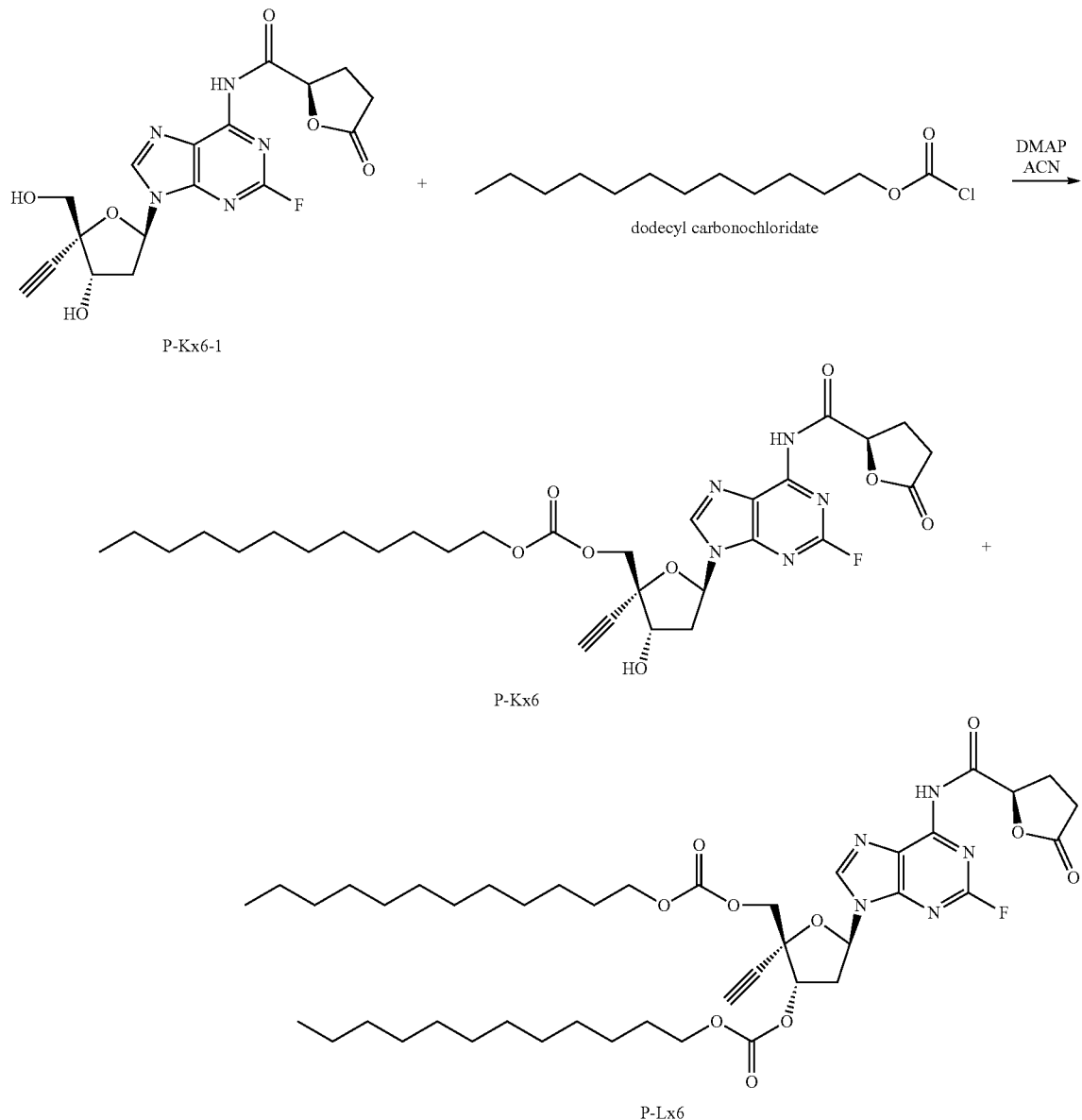

Synthesis of Compound P-Kx6—dodecyl (((2R,3S, 5R)-2-ethynyl-5-(2-fluoro-6-((R)-5-oxotetrahydrofuran-2-carboxamido)-9H-purin-9-yl)-3-hydroxytetrahydrofuran-2-yl)methyl) carbonate and Synthesis of Compound P-Lx6—dodecyl (((2R,3S, 5R)-3-(((dodecyloxy)carbonyl)oxy)-2-ethynyl-5-(2-fluoro-6-((R)-5-oxotetrahydrofuran-2-carboxamido)-9H-purin-9-yl)tetrahydrofuran-2-yl)methyl) carbonate Compounds P-Kx6 and P-Lx6 are prepared in the same manner as described for examples L and M except intermediate P-Kx6-1 (prepared in the same manner as described for intermediate P-A2 except (R)-5-oxotetrahydrofuran-2-carboxylic acid is used instead of 3-(2-acetoxy-4,6-dimethylphenyl)-3-methylbutanoic acid) is used instead of EFdA.

Example P-Mx6 & Example P-Nx6

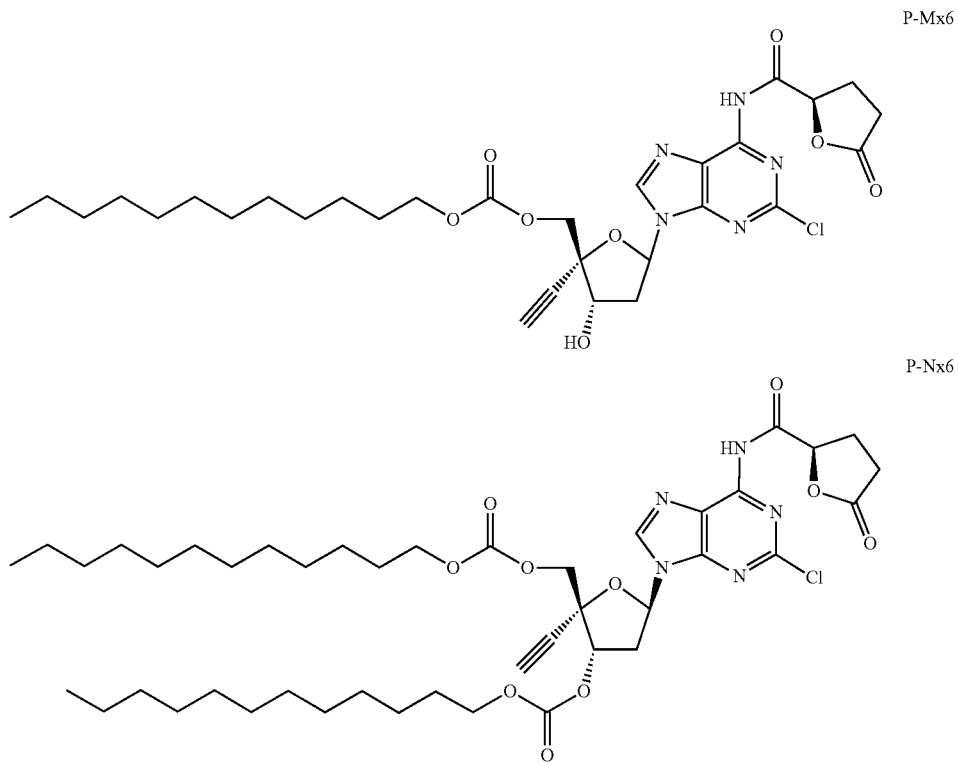

Synthesis of Compound P-Mx6—((2R,3S,5R)-5-(2-chloro-6-((R)-5-oxotetrahydrofuran-2-carboxamido)-9H-purin-9-yl)-2-ethynyl-3-hydroxytetrahydrofuran-2-yl)methyl dodecyl carbonate and Synthesis of Compound P-Nx6—((2R,3S,5R)-5-(2-chloro-6-((R)-5-oxotetrahydrofuran-2-carboxamido)-9H-purin-9-yl)-3-(((dodecyloxy)carbonyl)oxy)-2-ethynyltetrahydrofuran-2-yl)methyl dodecyl carbonate Compounds P-Mx6 and P-Nx6 are prepared in the same manner as described for examples P-Kx6 and P-Lx6 except ECldA is used instead of EFdA.

Example P-Ox6 & Example P-Px6

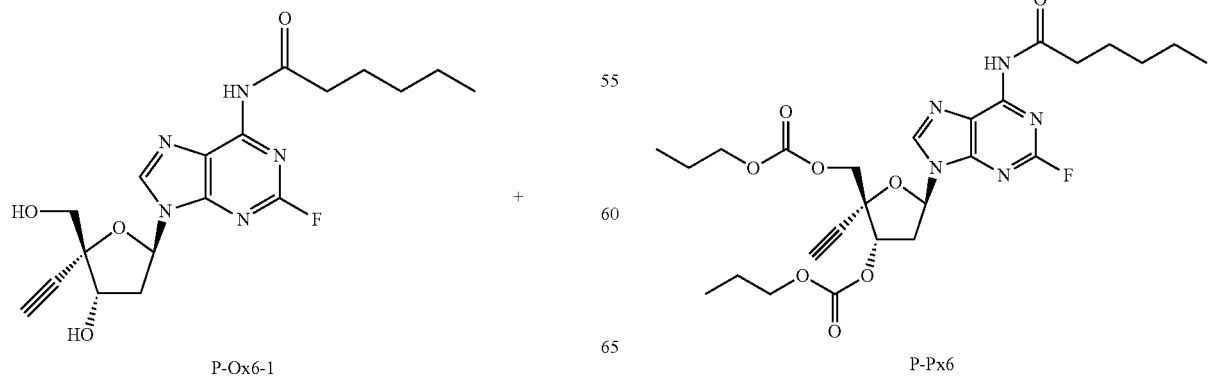

Synthesis of Compound P-Ox6—((2R,3S,5R)-2-ethynyl-5-(2-fluoro-6-hexanamido-9H-purin-9-yl)-3-hydroxytetrahydrofuran-2-yl)methyl propyl carbonate and

Synthesis of Compound P-Px6—((2R,3S,5R)-2-ethynyl-5-(2-fluoro-6-hexanamido-9H-purin-9-yl)-3-((propoxycarbonyl)oxy)tetrahydrofuran-2-yl)methyl propyl carbonate Compounds P-Ox6 and P-Px6 are prepared in the same manner as described for examples L and M except intermediate P-Ox6-1 (prepared in the same manner as described for intermediate P-A2 except hexanoic acid (Aldrich) is used instead of 3-(2-acetoxy-4,6-dimethylphenyl)-3-methylbutanoic acid) is used instead of EFdA and propyl carbonochloridate is used instead of dodecyl cabonochloridate.

Example P-Qx6 & Example P-Rx6

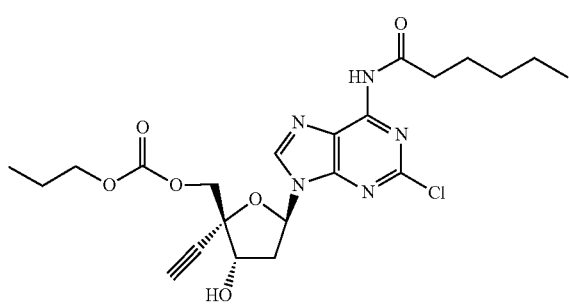

P-Qx6

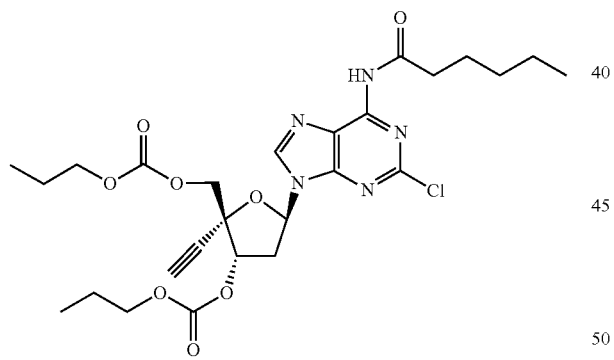

P-Rx6

Synthesis of Compound P-Qx6—((2R,3S,5R)-5-(2-chloro-6-hexanamido-9H-purin-9-yl)-2-ethynyl-3-hydroxytetrahydrofuran-2-yl)methyl propyl carbonate and

Synthesis of Compound P-Rx6—((2R,3S,5R)-5-(2-chloro-6-hexanamido-9H-purin-9-yl)-2-ethynyl-3-((propoxycarbonyl)oxy)tetrahydrofuran-2-yl)methyl propyl carbonate Compounds P-Qx6 and P-Rx6 are prepared in the same manner as described for examples P-Ox6 and P-Px6 except ECldA is used instead of EFdA.

Example P-Sx6

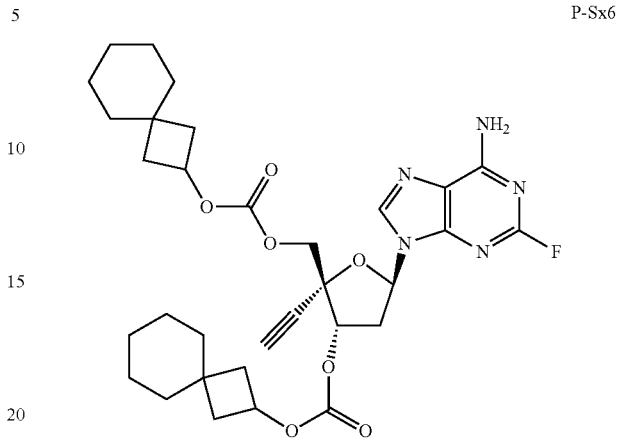

P-Sx6

Synthesis of Compound P-Sx6—(2R,3S,5R)-5-(6-amino-2-fluoro-9H-purin-9-yl)-2-ethynyl-2-((((spiro[3.5]nonan-2-yloxy)carbonyl)oxy)methyl)tetrahydrofuran-3-yl spiro[3.5]nonan-2-yl carbonate Compound P-Sx6 is prepared in the same manner as described for example P-Px5 except spiro[3.5]nonan-2-ol (Aldrich) is used instead of (3S,8S,9S,10R,13R,14S,17R)-17-((2R,5R)-5,6-dimethylheptan-2-yl)-10,13-dimethyl-2,3,4,7,8,9,10,11,12,13,14,15,16,17-tetradecahydro-1H-cyclopenta[a]phenanthren-3-ol.

Example P-Tx6

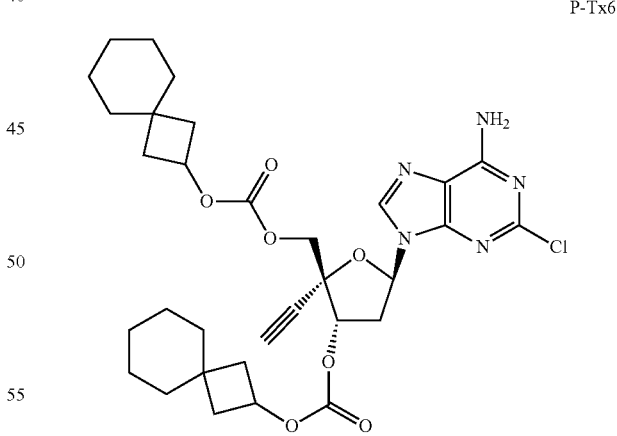

P-Tx6

Synthesis of Compound P-Tx6—(2R,3S,5R)-5-(6-amino-2-chloro-9H-purin-9-yl)-2-ethynyl-2-((((spiro[3.5]nonan-2-yloxy)carbonyl)oxy)methyl)tetrahydrofuran-3-yl spiro[3.5]nonan-2-yl carbonate Example P-Tx6 is prepared in the same manner as described for example P-Sx6 except ECldA is used instead of EFdA.

353
Example P-Ux6

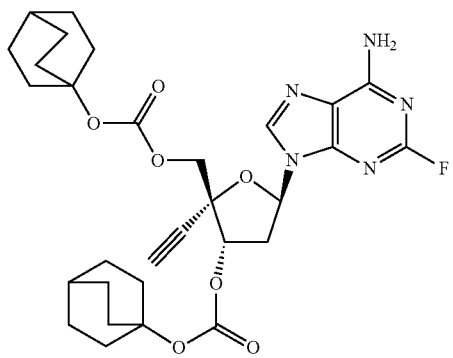

P-Ux6

Synthesis of Compound P-Ux6—(2R,3S,5R)-5-(6-amino-2-fluoro-9H-purin-9-yl)-2-((((bicyclo[2.2.2]octan-1-yloxy)carbonyl)oxy)methyl)-2-ethynyltetrahydrofuran-3-yl bicyclo[2.2.2]octan-1-yl carbonate Compound P-Ux6 is prepared in the same manner as described for example P-Px5 except bicyclo[2.2.2]octan-1-ol (Aldrich) is used instead of (3S,8S,9S,10R,13R,14S,17R)-17-((2R,5R)-5,6-dimethylheptan-2-yl)-10,13-dim-

354 ethyl-2,3,4,7,8,9,10,11,12,13,14,15,16,17-tetradecahydro-1H-cyclopenta[a]phenanthren-3-ol.

Example P-Vx6

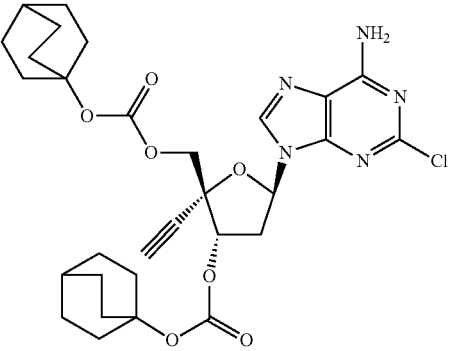

P-Vx6

Synthesis of Compound P-Vx6—(2R,3S,5R)-5-(6-amino-2-chloro-9H-purin-9-yl)-2-((((bicyclo[2.2.2]octan-1-yloxy)carbonyl)oxy)methyl)-2-ethynyltetrahydrofuran-3-yl bicyclo[2.2.2]octan-1-yl carbonate Compound P-Vx6 is prepared in the same manner as described for example P-Ux6 Intermediate P-Wx6-4, P-Wx6-5, and P-Wx6-6

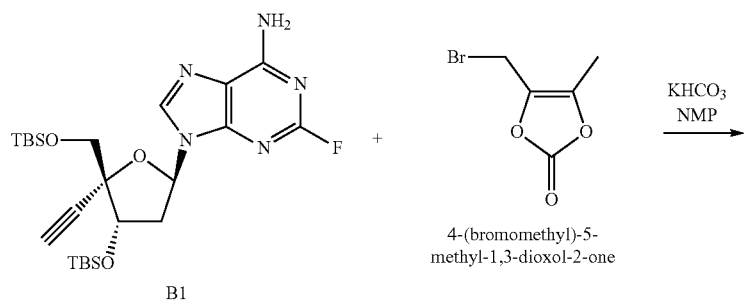

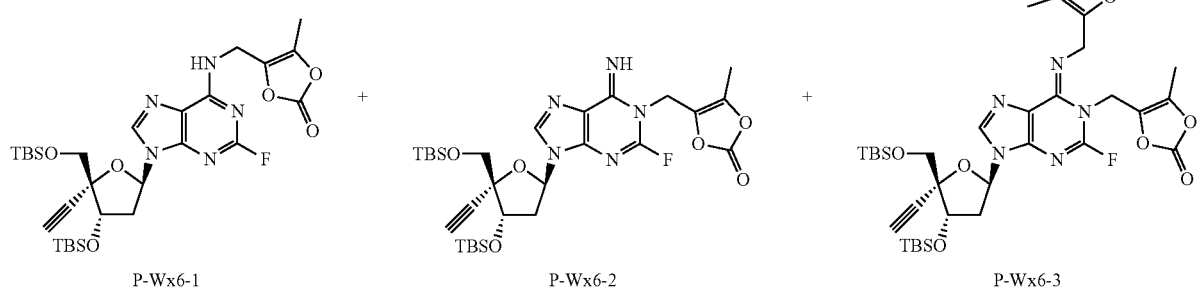

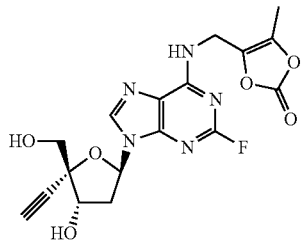
P-Wx6-4

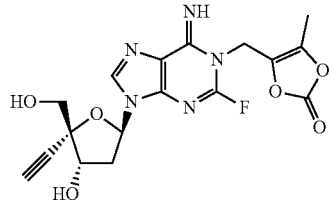
P-Wx6-5

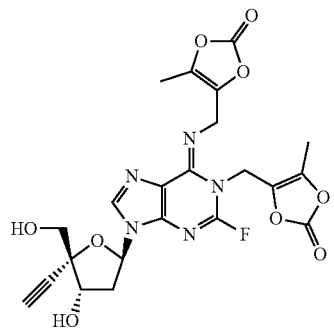
P-Wx6-6

Synthesis of Intermediate P-Wx6-4—4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one and Synthesis of Intermediate P-Wx6-5—4-((9-((2R,4S,5R)-5-ethynyl-4-hydroxy-5-(hydroxymethyl)tetrahydrofuran-2-yl)-2-fluoro-6-imino-6,9-dihydro-1H-purin-1-yl)methyl)-5-methyl-1,3-dioxol-2-one and Synthesis of Intermediate P-Wx6-6—4-((((Z)-9-((2R,4S,5R)-5-ethynyl-4-hydroxy-5-(hydroxymethyl)tetrahydrofuran-2-yl)-2-fluoro-1-((5-methyl-2-oxo-1,3-dioxol-4-yl)methyl)-1,9-dihydro-6H-purin-6-ylidene)amino)methyl)-5-methyl-1,3-dioxol-2-one Intermediate B1 (1 mmol) is dissolved in NMP (10 mL). To this solution is added 4-(bromomethyl)-5-methyl-1,3-dioxol-2-one (4 eq) and KHCO₃ (4 eq). The reaction is heated to 70° C. and allowed to proceed. The reaction is cooled to room temperature, quenched by the addition of ice and diluted with EtOAc. The layers are separated, and the organic phase is extracted with a 5% (w/v) solution of LiCl in water. The organic phase is dried over sodium sulfate, filtered and the filtrate in concentrated. The intermediates P-Wx6-1, P-Wx6-2 and P-Wx6-3 are isolated from the concentrate by silica gel column chromatography.

Intermediate P-Wx6-1 is converted to P-Wx6-4 in the same manner as that described for the conversion of intermediate B2 to example B. Intermediate P-Wx6-2 is similarly converted to P-Wx6-5 and intermediate P-Wx6-3 is similarly converted to P-Wx6-6.

Example P-Wx6

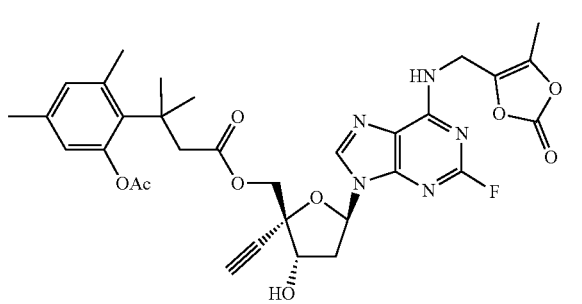
P-Wx6

Synthesis of Compound P-Wx6—((2R,3S,5R)-2-ethynyl-5-(2-fluoro-6-(((5-methyl-2-oxo-1,3-dioxol-4-yl)methyl)amino)-9H-purin-9-yl)-3-hydroxytetrahydrofuran-2-yl)methyl 3-(2-acetoxy-4,6-dimethylphenyl)-3-methylbutanoate Compound P-Wx6 is prepared in the same manner as described for example P-A except intermediate P-Wx6-4 is used instead of EFdA, and 1 equivalent of 3-(2-acetoxy-4,6-dimethylphenyl)-3-methylbutanoic acid and EDCI are used instead of 2 equivalents of isobutyric acid and EDCI.

Example P-Xx6

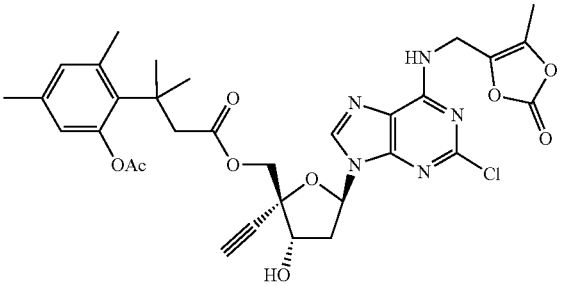
P-Xx6

Synthesis of Compound P-Xx6—((2R,3S,5R)-5-(2-chloro-6-(((5-methyl-2-oxo-1,3-dioxol-4-yl)methyl)amino)-9H-purin-9-yl)-2-ethynyl-3-hydroxytetrahydrofuran-2-yl)methyl 3-(2-acetoxy-4,6-dimethylphenyl)-3-methylbutanoate Compound P-Xx6 is prepared in the same manner as described for example P-Wx6 except ECldA is used instead of EFdA.

Example P-Yx6

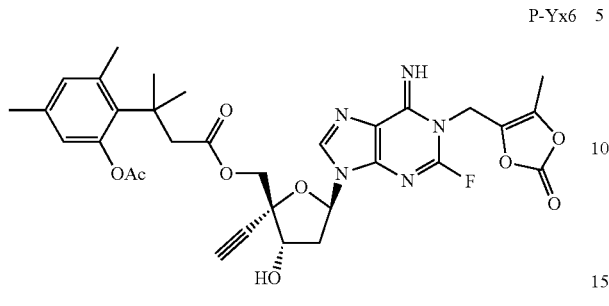

Synthesis of Compound P-Yx6—((2R,3S,5R)-2-ethynyl-5-(2-fluoro-6-imino-1-((5-methyl-2-oxo-1,3-dioxol-4-yl)methyl)-1,6-dihydro-9H-purin-9-yl)-3-hydroxytetrahydrofuran-2-yl)methyl 3-(2-acetoxy-4,6-dimethylphenyl)-3-methylbutanoate Compound P-Yx6 is prepared in the same manner as described for example P-A except intermediate P-Wx6-5 is used instead of EFdA and 1 equivalent of 3-(2-acetoxy-4,6-dimethylphenyl)-3-methylbutanoic acid and EDCI are used instead of 2 equivalents of isobutyric acid and EDCI.

Example P-Zx6

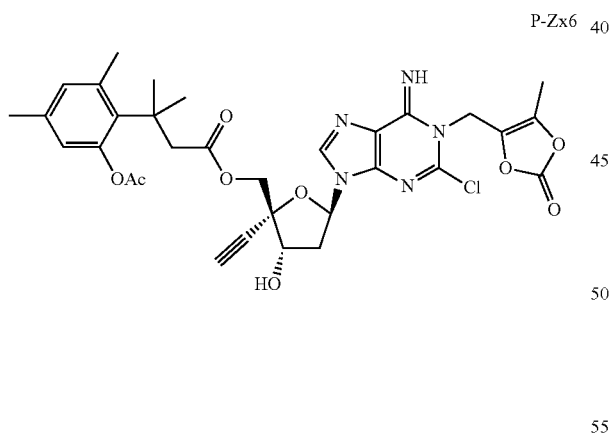

Synthesis of Compound P-Zx6—((2R,3S,5R)-5-(2-chloro-6-imino-1-((5-methyl-2-oxo-1,3-dioxol-4-yl)methyl)-1,6-dihydro-9H-purin-9-yl)-2-ethynyl-3-hydroxytetrahydrofuran-2-yl)methyl 3-(2-acetoxy-4,6-dimethylphenyl)-3-methylbutanoate Compound P-Zx6 is prepared in the same manner as described for example P-Yx6 except ECldA is used instead of EFdA.

Example P-Ax7

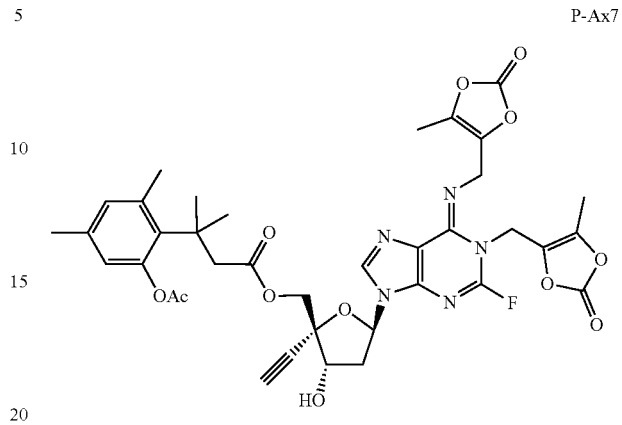

Synthesis of Compound P-Ax7—((2R,3S,5R)-2-ethynyl-5-((Z)-2-fluoro-1-((5-methyl-2-oxo-1,3-dioxol-4-yl)methyl)-6-(((5-methyl-2-oxo-1,3-dioxol-4-yl)methyl)imino)-1,6-dihydro-9H-purin-9-yl)-3-hydroxytetrahydrofuran-2-yl)methyl 3-(2-acetoxy-4,6-dimethylphenyl)-3-methylbutanoate Compound P-Ax7 is prepared in the same manner as described for example P-A except intermediate P-Wx6-6 is used instead of EFdA and 1 equivalent of 3-(2-acetoxy-4,6-dimethylphenyl)-3-methylbutanoic acid and EDCI are used instead of 2 equivalents of isobutyric acid and EDCI.

Example P-Bx7

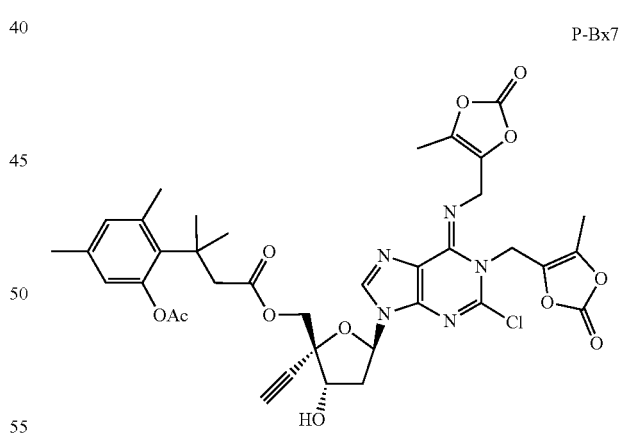

Synthesis of Compound P-Bx7—((2R,3S,5R)-5-((Z)-2-chloro-1-((5-methyl-2-oxo-1,3-dioxol-4-yl)methyl)-6-(((5-methyl-2-oxo-1,3-dioxol-4-yl)methyl)imino)-1,6-dihydro-9H-purin-9-yl)-2-ethynyl-3-hydroxytetrahydrofuran-2-yl)methyl 3-(2-acetoxy-4,6-dimethylphenyl)-3-methylbutanoate Compound P-Bx7 is prepared in the same manner as described for example P-Ax7 except ECldA is used instead of EFdA.

Example P-Cx7

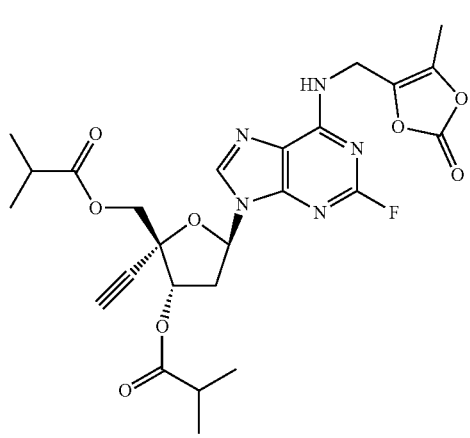

Synthesis of Compound P-Cx7—(2R,3S,5R)-2-ethynyl-5-(2-fluoro-6-(((5-methyl-2-oxo-1,3-dioxol-4-yl)methyl)amino)-9H-purin-9-yl)-2-((isobutyryloxy)methyl)tetrahydrofuran-3-yl isobutyrate Compound P-Cx7 is prepared in the same manner as that described for example A except intermediate P-Wx6-4 is used instead of EFdA.

Example P-Dx7

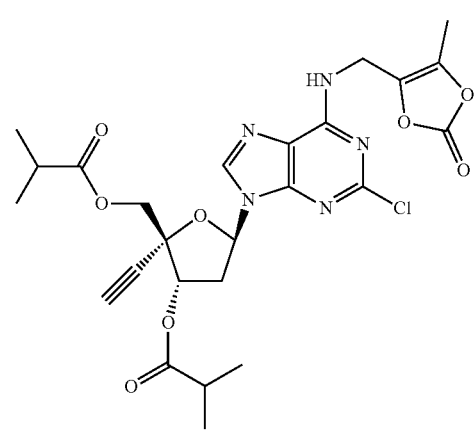

Synthesis of Compound P-Dx7—(2R,3S,5R)-5-(2-chloro-6-(((5-methyl-2-oxo-1,3-dioxol-4-yl)methyl)amino)-9H-purin-9-yl)-2-ethynyl-2-((isobutyryloxy)methyl)tetrahydrofuran-3-yl isobutyrate Compound P-Dx7 is prepared in the same manner as described for example P-Cx7 except ECldA is used instead of EFdA.

Example P-Ex7

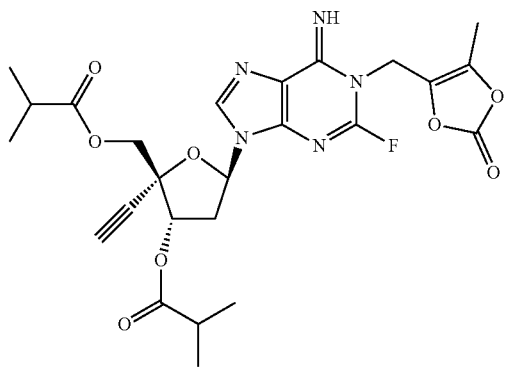

Synthesis of Compound P-Ex7—(2R,3S,5R)-2-ethynyl-5-(2-fluoro-6-imino-1-((5-methyl-2-oxo-1,3-dioxol-4-yl)methyl)-1,6-dihydro-9H-purin-9-yl)-2-((isobutyryloxy)methyl)tetrahydrofuran-3-yl isobutyrate Compound P-Ex7 is prepared in the same manner as that described for example A except intermediate P-Wx6-5 is used instead of EFdA.

Example P-Fx7

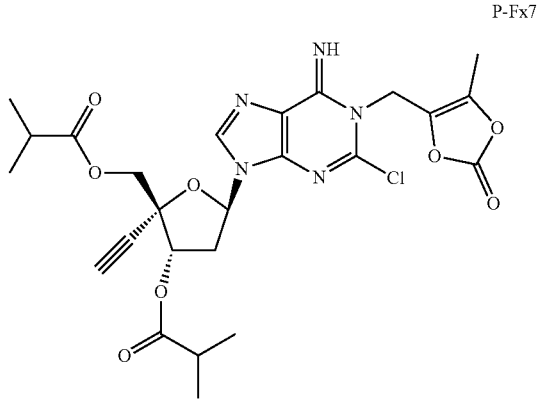 [SMILES: C#C[C@]1(COC(=O)C(C)C)O[C@@H](n2cnc3c(=N)n(Cc4oc(=O)oc4C)c(F)nc32)C[C@@H]1OC(=O)C(C)C]

Synthesis of Compound P-Fx7—(2R,3S,5R)-5-(2-chloro-6-imino-1-((5-methyl-2-oxo-1,3-dioxol-4-yl)methyl)-1,6-dihydro-9H-purin-9-yl)-2-ethynyl-2-((isobutyryloxy)methyl)tetrahydrofuran-3-yl isobutyrate Compound P-Fx7 is prepared in the same manner as described for example P-Ex7 except ECldA is used instead of EFdA.

361
Example P-Gx7

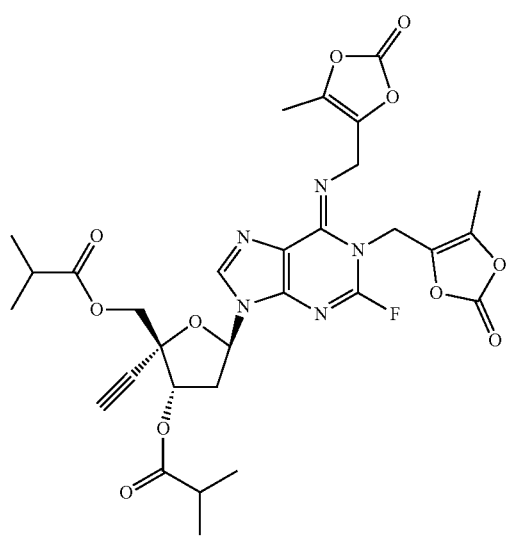

P-Gx7

362
Example P-Hx7

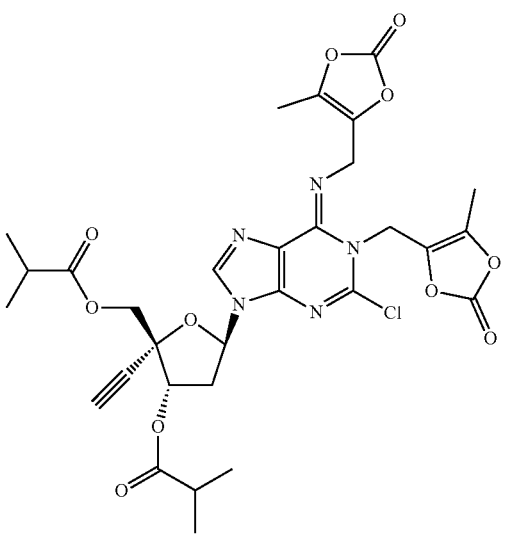

P-Hx7

Synthesis of Compound P-Gx7—(2R,3S,5R)-2-ethynyl-5-((Z)-2-fluoro-1-((5-methyl-2-oxo-1,3-dioxol-4-yl)methyl)-6-(((5-methyl-2-oxo-1,3-dioxol-4-yl)methyl)imino)-1,6-dihydro-9H-purin-9-yl)-2-((isobutyryloxy)methyl) tetrahydrofuran-3-yl isobutyrate Compound P-Ex7 is prepared in the same manner as that described for example A except intermediate P-Wx6-6 is used instead of EFdA.

Synthesis of Compound P-Hx7—(2R,3S,5R)-5-((Z)-2-chloro-1-((5-methyl-2-oxo-1,3-dioxol-4-yl)methyl)-6-(((5-methyl-2-oxo-1,3-dioxol-4-yl)methyl)imino)-1,6-dihydro-9H-purin-9-yl)-2-ethynyl-2-((isobutyryloxy)methyl)tetrahydrofuran-3-yl isobutyrate Compound P-Gx7 is prepared in the same manner as described for example P-Hx7 Examples P-Ix7, P-Jx7, and P-Kx7

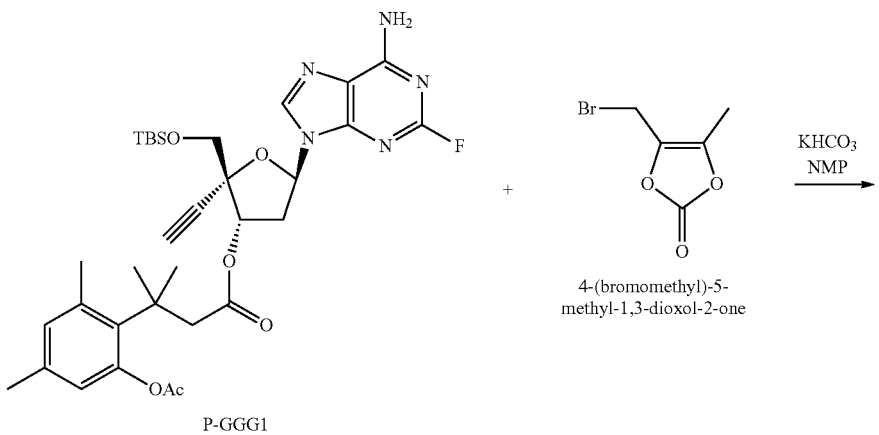

P-GGG1

4-(bromomethyl)-5-methyl-1,3-dioxol-2-one

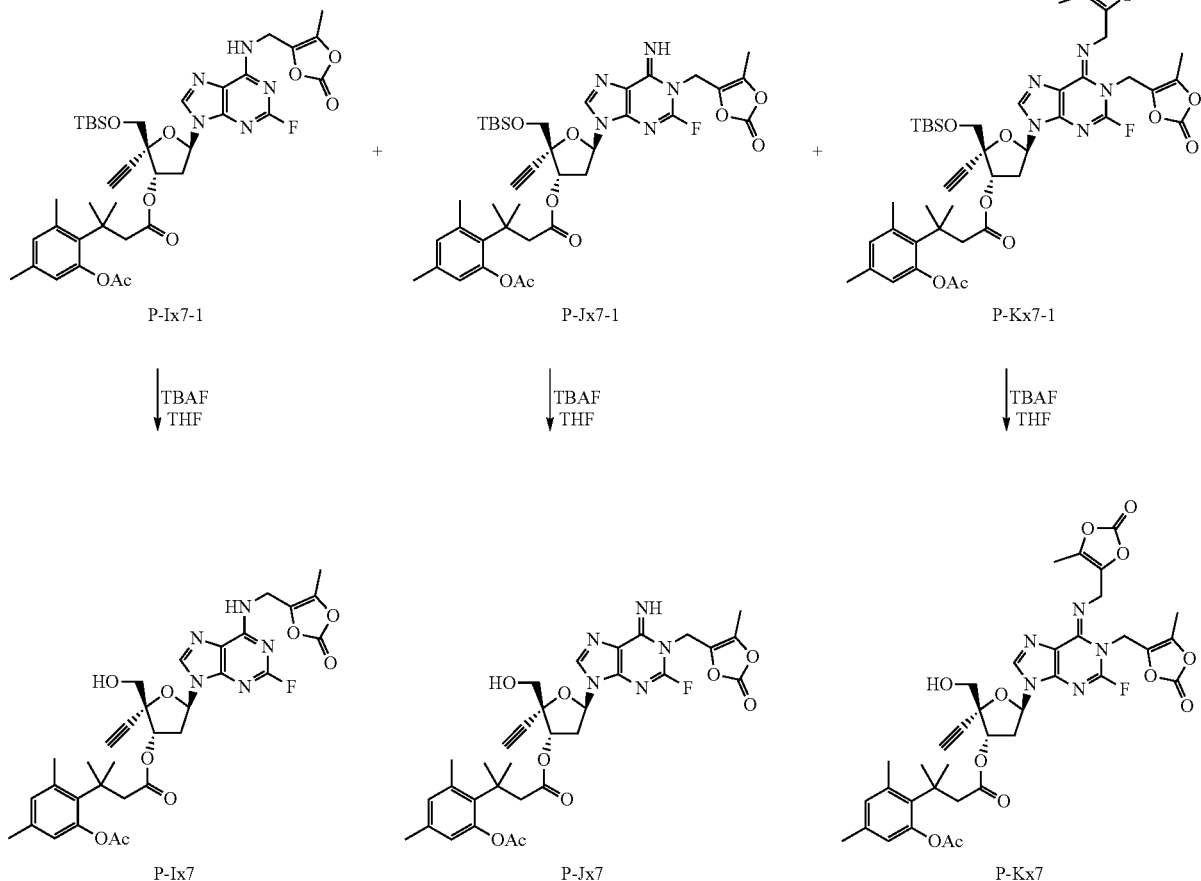

Synthesis of Compound P-Ix7—(2R,3S,5R)-2-ethynyl-5-(2-fluoro-6-(((5-methyl-2-oxo-1,3-dioxol-4-yl)methyl)amino)-9H-purin-9-yl)-2-(hydroxymethyl)tetrahydrofuran-3-yl 3-(2-acetoxy-4,6-dimethylphenyl)-3-methylbutanoate and Synthesis of Compound P-Jx7—(2R,3S,5R)-2-ethynyl-5-(2-fluoro-6-imino-1-((5-methyl-2-oxo-1,3-dioxol-4-yl)methyl)-1,6-dihydro-9H-purin-9-yl)-2-(hydroxymethyl)tetrahydrofuran-3-yl 3-(2-acetoxy-4,6-dimethylphenyl)-3-methylbutanoate and Synthesis of Compound P-Kx7—(2R,3S,5R)-2-ethynyl-5-((Z)-2-fluoro-1-((5-methyl-2-oxo-1,3-dioxol-4-yl)methyl)-6-(((5-methyl-2-oxo-1,3-dioxol-4-yl)methyl)imino)-1,6-dihydro-9H-purin-9-yl)-2-(hydroxymethyl)tetrahydrofuran-3-vi 3-(2-acetoxy-4,6-dimethylphenyl)-3-methylbutanoate Intermediates P-Ix7-1, P-Jx7-1 and P-Kx7-1 are made in the same manner as described for intermediates P-Wx6-1, P-Wx6-2 and P-Wx6-3 except intermediate P-GGG1 is used instead of intermediate B1.

Intermediate P-Ix7-1 is converted to example P-Ix7 in the same manner as that described for the conversion of intermediate B2 to example B. Intermediate P-Jx7-1 is similarly converted to example P-Jx7 and intermediate P-Kx7-1 is similarly converted to P-Kx7.

Examples P-Lx7, P-Mx7, and P-Nx7

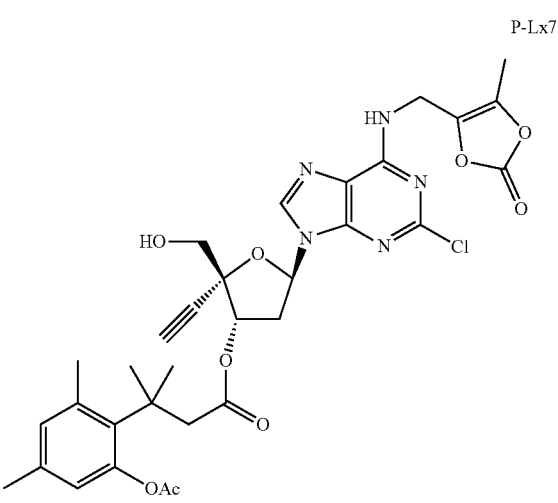

P-Lx7

-continued

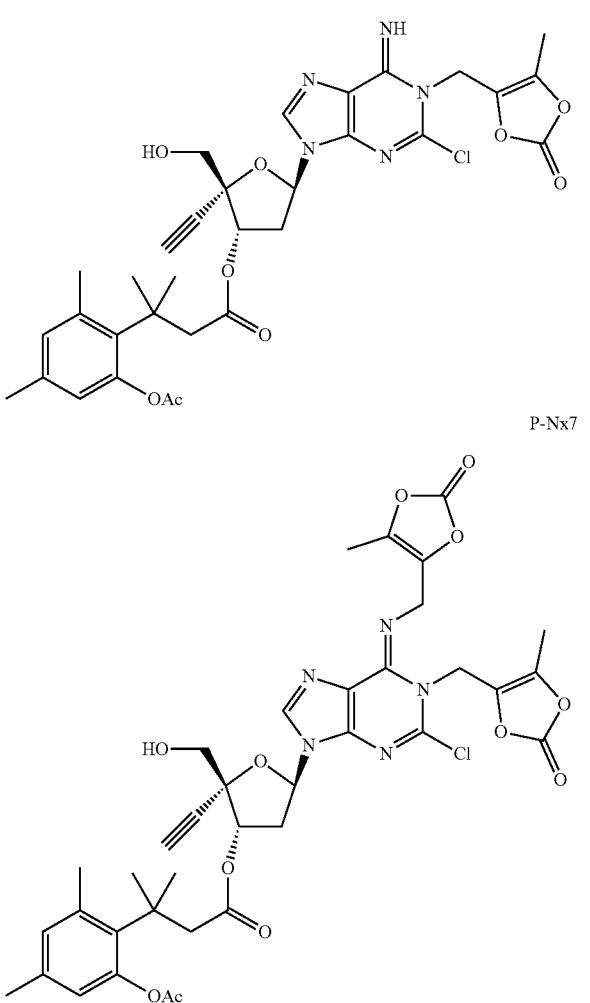

Synthesis of Compound P-Lx7—(2R,3S,5R)-5-(2-chloro-6-(((5-methyl-2-oxo-1,3-dioxol-4-yl)methyl)amino)-9H-purin-9-yl)-2-ethynyl-2-(hydroxymethyl)tetrahydrofuran-3-yl 3-(2-acetoxy-4,6-dimethylphenyl)-3-methylbutanoate and Synthesis of Compound P-Mx7—(2R,3S,5R)-5-(2-chloro-6-imino-1-((5-methyl-2-oxo-1,3-dioxol-4-yl)methyl)-1,6-dihydro-9H-purin-9-yl)-2-ethynyl-2-(hydroxymethyl)tetrahydrofuran-3-yl 3-(2-acetoxy-4,6-dimethylphenyl)-3-methylbutanoate and Synthesis of Compound P-Nx7—(2R,3S,5R)-5-((Z)-2-chloro-1-((5-methyl-2-oxo-1,3-dioxol-4-yl)methyl)-6-(((5-methyl-2-oxo-1,3-dioxol-4-yl)methyl)imino)-1,6-dihydro-9H-purin-9-yl)-2-ethynyl-2-(hydroxymethyl)tetrahydrofuran-3-yl 3-(2-acetoxy-4,6-dimethylphenyl)-3-methylbutanoate Compounds P-Lx7, P-Mx7, and P-Nx7 are prepared in the same manner as described for examples P-Ix7, P-Jx7, and P-Kx7 except ECldA is used instead of EFdA.

Although the foregoing has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula:

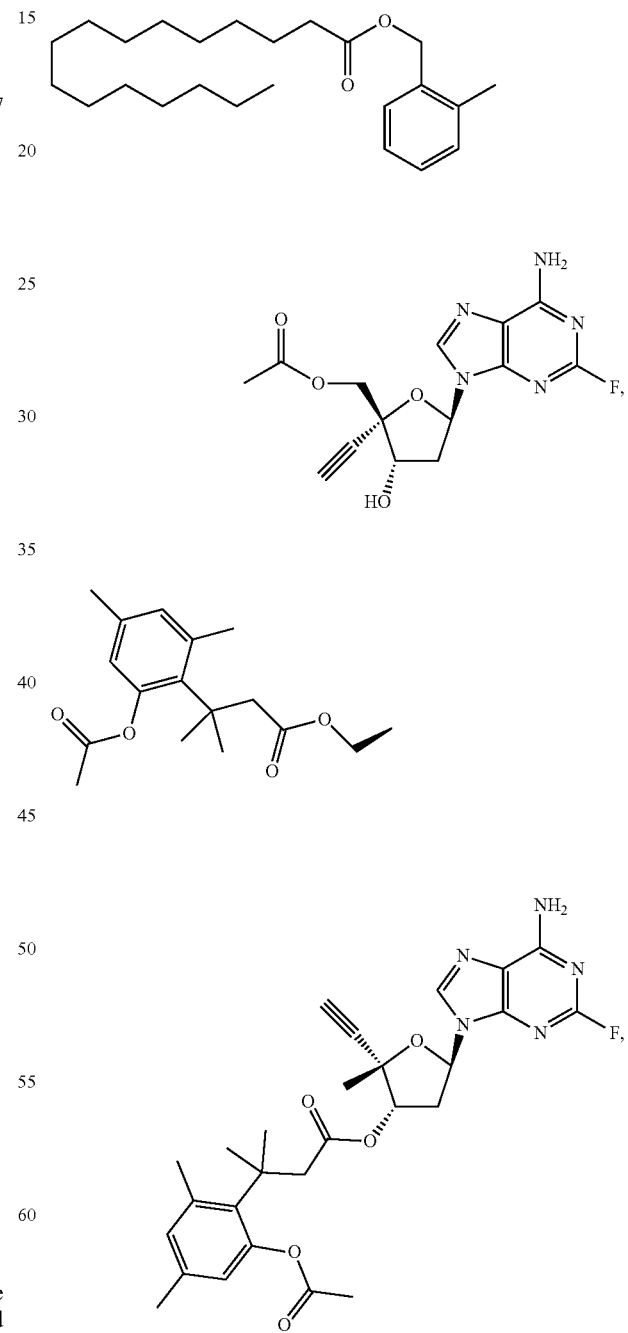

or a pharmaceutically acceptable salt thereof.

2. The compound of claim 1, or a pharmaceutically acceptable salt thereof, having the following formula:
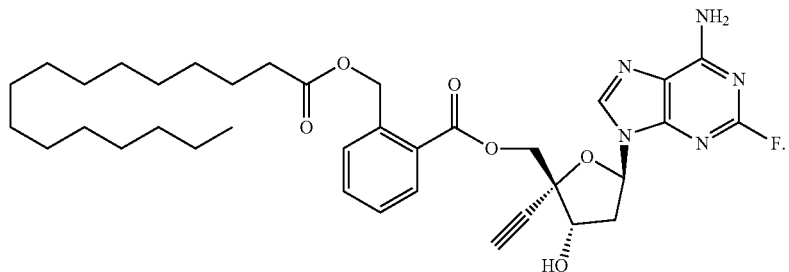 [SMILES: C#C[C@]1(COC(=O)c2ccccc2COC(=O)CCCCCCCCCCCCCCC)O[C@@H](n2cnc3c(N)nc(F)nc32)C[C@@H]1O]
3. The compound of claim 2, having the following formula:
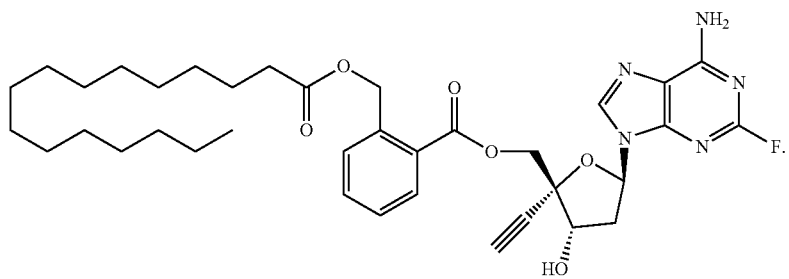 [SMILES: C#C[C@]1(COC(=O)c2ccccc2COC(=O)CCCCCCCCCCCCCCC)O[C@@H](n2cnc3c(N)nc(F)nc32)C[C@@H]1O]
4. The compound of claim 1, or a pharmaceutically acceptable salt thereof, having the following formula:
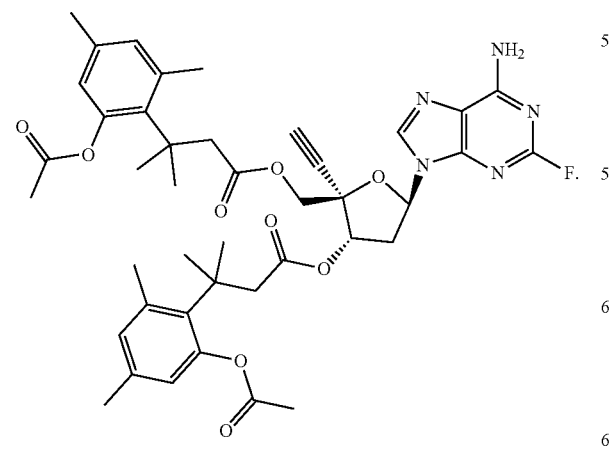
5. The compound of claim 4 having the following formula:
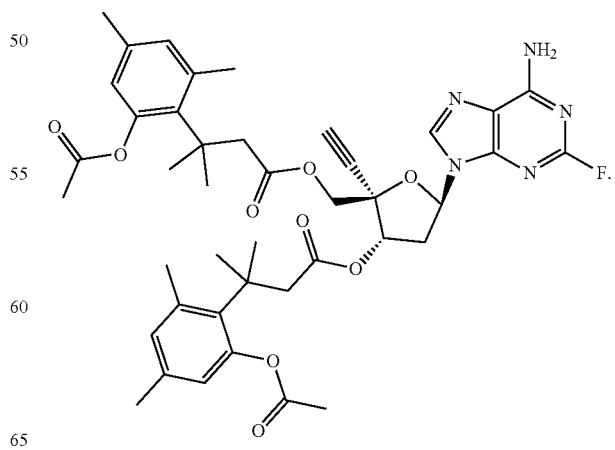

6. A compound of formula:
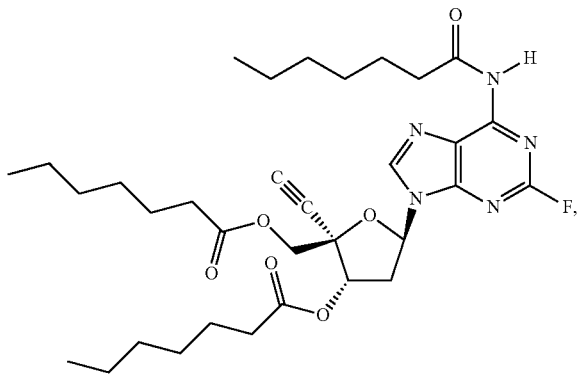
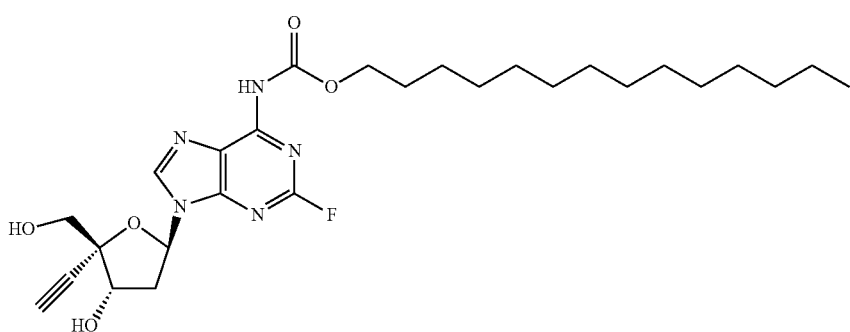
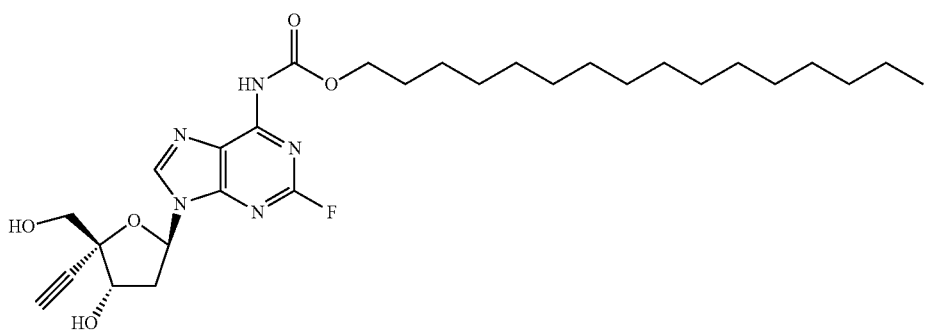
, or
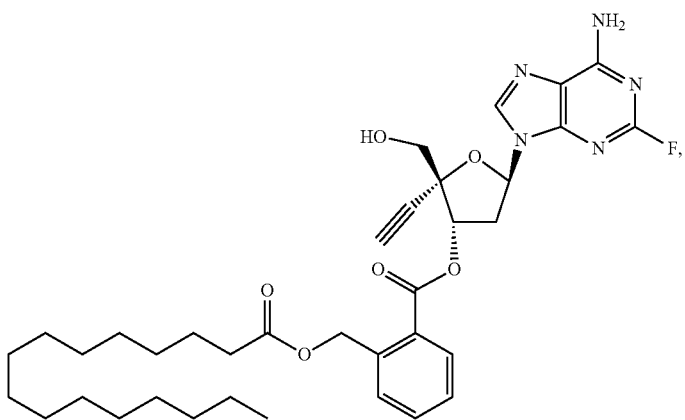
or a pharmaceutically acceptable salt thereof.

7. A compound of formula:

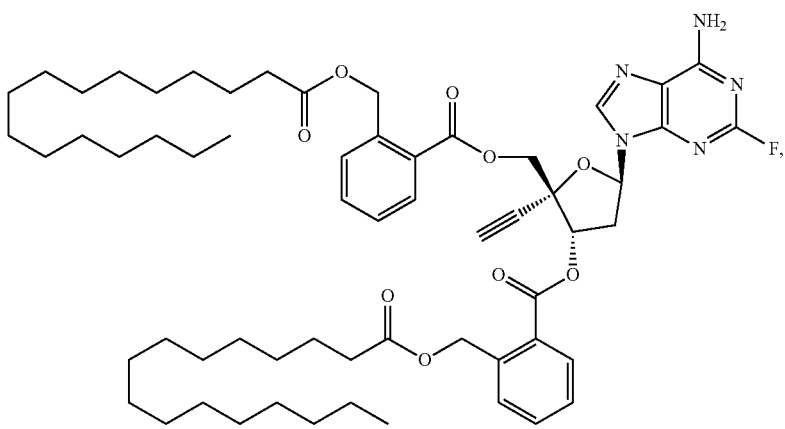 [SMILES: C#C[C@]1(COC(=O)c2ccccc2COC(=O)CCCCCCCCCCCCCCC)O[C@@H](n2cnc3c(N)nc(F)nc32)C[C@@H]1OC(=O)c1ccccc1COC(=O)CCCCCCCCCCCCCCC]

or a pharmaceutically acceptable salt thereof.

8. A compound of formula:

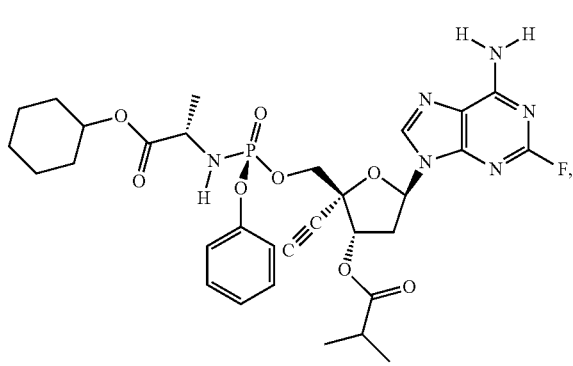

-continued

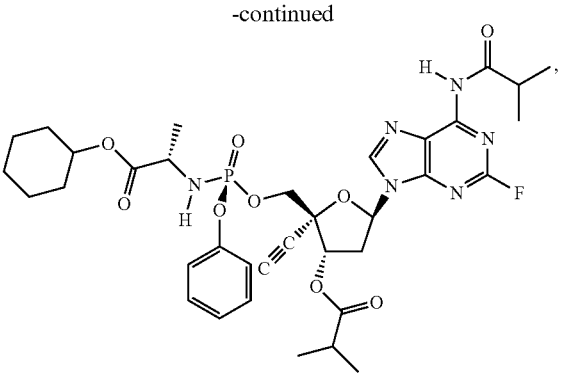

or a pharmaceutically acceptable salt thereof.

9. A pharmaceutical composition comprising a therapeutically effective amount of a compound of claim 1, or a pharmaceutically acceptable salt thereof, and a pharmaceutically acceptable excipient.

10. The pharmaceutical composition of claim 9, further comprising at least one additional therapeutic agent.

11. The pharmaceutical composition of claim 10, wherein the at least one additional therapeutic agent comprises abacavir, tenofovir alafenamide, tenofovir disoproxil, emtricitabine, bictegravir, dolutegravir, cabotegravir, N-((S)-1-(3-(4-chloro-3-(methylsulfonamido)-1-(2,2,2-trifluoroethyl)-1/-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, pharmaceutically acceptable salts thereof, or combinations thereof.

12. The pharmaceutical composition of claim 10, wherein the at least one additional therapeutic agent comprises adefovir, entecavir, telbivudine, lamivudine, or combinations thereof.

13. A method of treating an HIV infection in a human having the infection, comprising administering to the human a therapeutically effective amount of a compound of claim 1, or a pharmaceutically acceptable salt thereof.

14. A pharmaceutical composition comprising a therapeutically effective amount of a compound of claim 6, or a pharmaceutically acceptable salt thereof, and a pharmaceutically acceptable excipient.

15. The pharmaceutical composition of claim 14, further comprising at least one additional therapeutic agent.

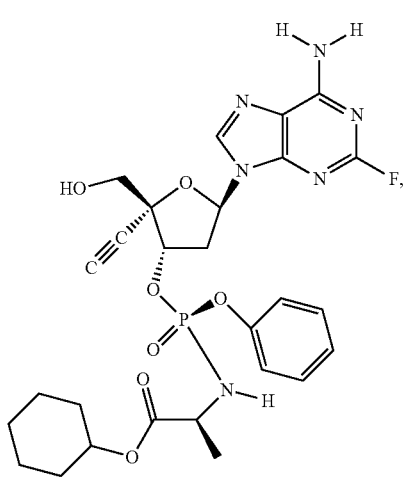

16. The pharmaceutical composition of claim 15, wherein the at least one additional therapeutic agent comprises abacavir, tenofovir alafenamide, tenofovir disoproxil, emtricitabine, bictegravir, dolutegravir, cabotegravir, N-((S)-1-(3-(4-chloro-3-(methylsulfonamido)-1-(2,2,2-trifluoroethyl)-1/-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, pharmaceutically acceptable salts thereof, or combinations thereof.

17. The pharmaceutical composition of claim 15, wherein the at least one additional therapeutic agent comprises adefovir, entecavir, telbivudine, lamivudine, or combinations thereof.

18. A method of treating an HIV infection in a human having the infection or preventing an HIV infection in a human at risk of having the infection, comprising administering to the human a therapeutically effective amount of a compound of claim 6, or a pharmaceutically acceptable salt thereof.

19. A pharmaceutical composition comprising a therapeutically effective amount of a compound of claim 7, or a pharmaceutically acceptable salt thereof, and a pharmaceutically acceptable excipient.

20. The pharmaceutical composition of claim 19, further comprising at least one additional therapeutic agent.

21. The pharmaceutical composition of claim 20, wherein the at least one additional therapeutic agent comprises abacavir, tenofovir alafenamide, tenofovir disoproxil, emtricitabine, bictegravir, dolutegravir, cabotegravir, N-((S)-1-(3-(4-chloro-3-(methylsulfonamido)-1-(2,2,2-trifluoroethyl)-1/-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, pharmaceutically acceptable salts thereof, or combinations thereof.

22. The pharmaceutical composition of claim 20, wherein the at least one additional therapeutic agent comprises adefovir, entecavir, telbivudine, lamivudine, or combinations thereof.

23. A method of treating an HIV infection in a human having the infection or preventing an HIV infection in a human at risk of having the infection, comprising administering to the human a therapeutically effective amount of a compound of claim 7, or a pharmaceutically acceptable salt thereof.

24. A pharmaceutical composition comprising a therapeutically effective amount of a compound of claim 8, or a pharmaceutically acceptable salt thereof, and a pharmaceutically acceptable excipient.

25. The pharmaceutical composition of claim 24, further comprising at least one additional therapeutic agent.

26. The pharmaceutical composition of claim 24, wherein the at least one additional therapeutic agent comprises abacavir, tenofovir alafenamide, tenofovir disoproxil, emtricitabine, bictegravir, dolutegravir, cabotegravir, N-((S)-1-(3-(4-chloro-3-(methylsulfonamido)-1-(2,2,2-trifluoroethyl)-1/-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, pharmaceutically acceptable salts thereof, or combinations thereof.

27. The pharmaceutical composition of claim 24, wherein the at least one additional therapeutic agent comprises adefovir, entecavir, telbivudine, lamivudine, or combinations thereof.

28. A method of treating an HIV infection in a human having the infection or preventing an HIV infection in a human at risk of having the infection, comprising administering to the human a therapeutically effective amount of a compound of claim 8, or a pharmaceutically acceptable salt thereof.

29. A compound of formula:

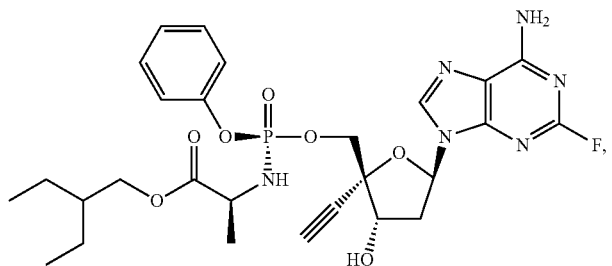

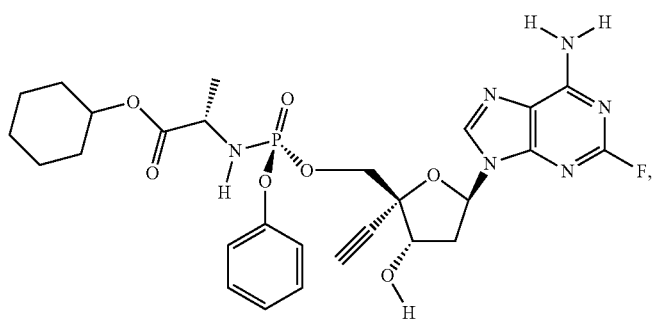

-continued

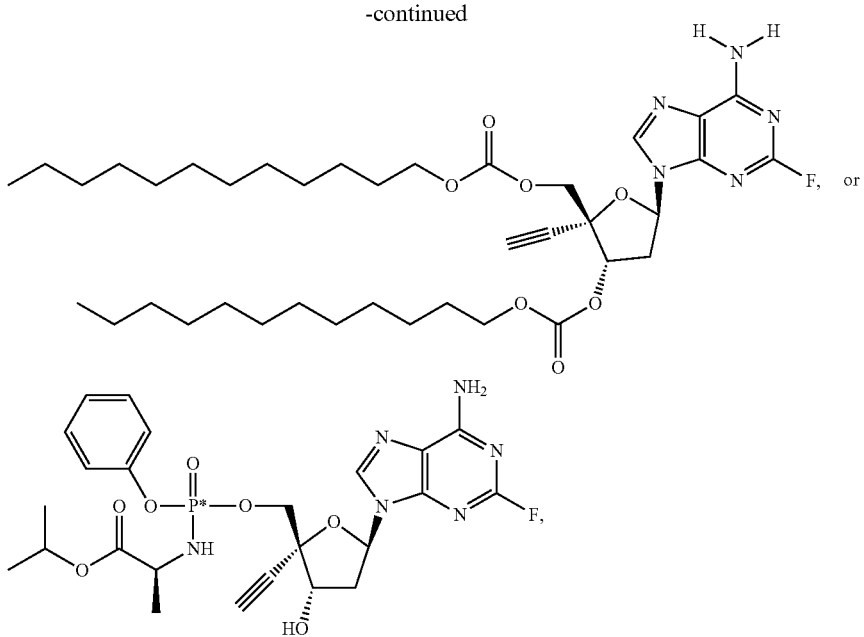

or a pharmaceutically acceptable salt thereof.

30. A pharmaceutical composition comprising a therapeutically effective amount of a compound of claim 29, or a pharmaceutically acceptable salt thereof, and a pharmaceutically acceptable excipient.

31. The pharmaceutical composition of claim 30, further comprising at least one additional therapeutic agent.

32. The pharmaceutical composition of claim 30, wherein the at least one additional therapeutic agent comprises abacavir, tenofovir alafenamide, tenofovir disoproxil, emtricitabine, bictegravir, dolutegravir, cabotegravir, N-((S)-1-(3-(4-chloro-3-(methylsulfonamido)-1-(2,2,2-trifluoroethyl)-1/-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, pharmaceutically acceptable salts thereof, or combinations thereof.

33. The pharmaceutical composition of claim 30, wherein the at least one additional therapeutic agent comprises adefovir, entecavir, telbivudine, lamivudine, or combinations thereof.

34. A method of treating an HIV infection in a human having the infection or preventing an HIV infection in a human at risk of having the infection, comprising administering to the human a therapeutically effective amount of a compound of claim 29, or a pharmaceutically acceptable salt thereof.

* * * * *